United States Patent
Han et al.

(10) Patent No.: US 9,611,224 B2
(45) Date of Patent: Apr. 4, 2017

(54) ANTIPROLIFERATIVE BENZO [B] AZEPIN-2-ONES

(71) Applicant: Hoffmann-La Roche Inc., Nutley, NJ (US)

(72) Inventors: Xiaochun Han, Cedar Grove, NJ (US); Yan Lou, Pleasanton, CA (US); Christophe Michoud, New York, NY (US); Steven Gregory Mischke, Florham Park, NJ (US); Stacy Remiszewski, Washington Township, NJ (US); Kenneth Carey Rupert, Bedminister, NJ (US)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 51 days.

(21) Appl. No.: 14/413,932

(22) PCT Filed: Jul. 11, 2013

(86) PCT No.: PCT/EP2013/064734
§ 371 (c)(1),
(2) Date: Jan. 9, 2015

(87) PCT Pub. No.: WO2014/009495
PCT Pub. Date: Jan. 16, 2014

(65) Prior Publication Data
US 2015/0353499 A1    Dec. 10, 2015

Related U.S. Application Data

(60) Provisional application No. 61/671,118, filed on Jul. 13, 2012.

(51) Int. Cl.
| | | |
|---|---|---|
| *A61K 31/55* | (2006.01) |
| *C07D 223/16* | (2006.01) |
| *C07D 401/06* | (2006.01) |
| *C07D 401/10* | (2006.01) |
| *C07D 403/06* | (2006.01) |
| *C07D 403/10* | (2006.01) |
| *C07D 405/10* | (2006.01) |
| *C07D 409/06* | (2006.01) |
| *C07D 413/06* | (2006.01) |
| *C07D 413/10* | (2006.01) |
| *C07D 407/06* | (2006.01) |
| *C07D 403/12* | (2006.01) |
| *C07D 405/12* | (2006.01) |
| *C07D 417/06* | (2006.01) |
| *C07D 417/10* | (2006.01) |
| *C07D 471/04* | (2006.01) |

(52) U.S. Cl.
CPC ......... *C07D 223/16* (2013.01); *C07D 401/06* (2013.01); *C07D 403/06* (2013.01); *C07D 403/10* (2013.01); *C07D 403/12* (2013.01); *C07D 405/10* (2013.01); *C07D 405/12* (2013.01); *C07D 409/06* (2013.01); *C07D 413/06* (2013.01); *C07D 413/10* (2013.01); *C07D 417/06* (2013.01); *C07D 417/10* (2013.01); *C07D 471/04* (2013.01)

(58) Field of Classification Search
CPC .... A61K 31/55; C07D 223/16; C07D 401/06; C07D 401/10; C07D 403/06; C07D 403/10; C07D 405/10; C07D 409/06; C07D 413/06; C07D 413/10; C07D 417/06
USPC ...................... 514/212.07; 540/523
See application file for complete search history.

(56) References Cited

U.S. PATENT DOCUMENTS 5,206,235 A    4/1993  Fisher et al.
5,843,941 A   12/1998  Marsters, Jr. et al.

FOREIGN PATENT DOCUMENTS

WO        9405634       3/1994
WO     2006133147      12/2006

OTHER PUBLICATIONS

The International Search Report and Written Opinion, mailed on Sep. 2, 2013, in the related PCT Appl. No. PCT/EP2013/064734.
The Chinese Office Action, mailed on Jan. 13, 2016, in the related Chinese Appl. No. 201380035991.0.
The Japanese Office Action, mailed on Feb. 23, 2016, in the related Japanese Appl. No. 2015-520998.

*Primary Examiner* — Brenda Coleman

(57) ABSTRACT

Disclosed are compounds of Formula (I) or pharmaceutically acceptable salts thereof, wherein W, X, Y, Z, $R^1$, $R^2$, $R^3$ and $R^4$ are described in this application, and methods of using said compounds in the treatment of cancer.

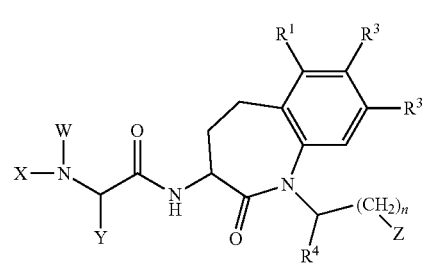

42 Claims, No Drawings

ANTIPROLIFERATIVE BENZO [B] AZEPIN-2-ONES

This application is a National Stage Application of PCT/EP2013/064734, filed Jul. 11, 2013, which claims priority from Provisional Application No. 61/671,118, filed on Jul. 13, 2012. Each of these applications is hereby incorporated by reference herein in its entirety.

SEQUENCE LISTING

The instant application contains a Sequence Listing which has been submitted electronically in ASCII format and is hereby incorporated by reference in its entirety. Said ASCII copy, created on Jun. 25, 2015, is named 111890-82999_SL.txt and is 3,583 bytes in size.

FIELD OF THE INVENTION

The present invention relates to substituted 1,3,4,5-tetrahydro-benzo[b]azepin-2-ones which act as inhibitors of SMAC protein binding to Inhibitor of Apoptosis Proteins (IAPs), and/or inhibitors of activated caspase protein binding to IAPs. These molecules are useful in the amelioration, treatment or control of cancer, especially solid tumors.

These compounds bind to the BIR2 and/or BIR3 regions of IAP proteins, including XIAP and cIAP, resulting in activation or reactivation of the caspase cascade and, as such, are useful for the treatment of proliferative diseases, including cancer.

BACKGROUND OF THE INVENTION

Cancer is a disease of uncontrolled cell growth causing local expansion of a tumor and, potentially, distant metastases. One mechanism by which cancer cells grow is by avoidance of apoptosis, or programmed cell death. Alterations in apoptotic pathways have been linked to cancer cells being resistant to standard treatments, e.g., chemotherapeutics or radiation, and to the incidence and progression of cancer. See, e.g., E. Dean et al., "X-linked inhibitor of apoptosis protein as a therapeutic target," Expert Opin. Ther. Targets (2007) 11(11):1459-1471

The two basic pathways for apoptotic cell death are the intrinsic pathway and the extrinsic pathway. The intrinsic apoptotic pathway can be initiated by various mechanisms including cellular stress and drug-induced DNA damage. The extrinsic pathway can be initiated by activation of the death receptors by a chemokine. Initiation of either pathway results in the activation of a family of proteases called caspases. Once activated, the caspases can act to cleave a variety of substrates creating a cascade of events that lead to the activation of the effector caspases 3 and 7 and eventual cell death. The IAP family of proteins can bind to and inhibit the activity of caspases thus inhibiting apoptosis. See, e.g., Dean, supra at 1460.

The IAPs can contain up to three copies of homologous structural domains called baculoviral IAP repeat (BIR) domains, BIR1, BIR2 and BIR3. The BIR3 domain of the prototypical IAPs, cIAP and XIAP, can bind to and inhibit activated caspase 9. The BIR2 domain, in contrast, binds to and inhibits caspases 3 and 7. The proapoptotic protein Smac (also known as DIABLO) can block the BIR2 and BIR3 domains of IAPs competing with activated caspases resulting in release of the activated caspases from the IAPs and completion of the apoptotic program. See, e.g., S. Wang, "Design of Small-Molecule Smac Mimetics as IAP Antagonists," Current Topics in Microbiology and Immunology 348, DOI 10.1007/82_2010_111, pp. 89-113.

Peptides and small molecules have been reported to bind to the BIR3 region of XIAP and cIAP, mimicking the action of Smac protein and releasing activated caspases. See, e.g., Dean, supra; and M. Gyrd-Hanse et al., "IAPs: From caspase inhibitors to modulators of NF-κB, inflammation and cancer," Nature Review/Cancer, August 2010, Vol 10:561-574.

SUMMARY OF THE INVENTION

One aspect of the present invention is a compound of Formula I

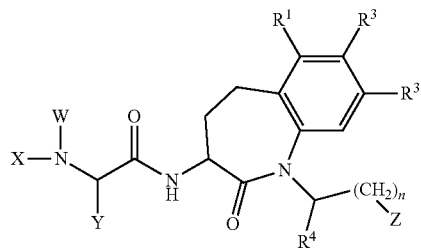

or pharmaceutically acceptable salts thereof, wherein W, X, Y, Z, $R^1$, $R^2$, $R^3$, $R^4$ and n are described in this application.

The present invention also relates to pharmaceutical compositions comprising one or more compounds of the invention, or a pharmaceutically acceptable salt thereof, and a pharmaceutically acceptable carrier or excipient.

The present invention further relates to a method of ameliorating, controlling or treating cancer, including specifically solid tumors, for example lung, pancreatic, colon, breast, bone and prostate cancers in a mammal, specifically a human, comprising administering to said mammal a therapeutically effective amount of a compound according to the invention or a pharmaceutically acceptable salt thereof.

DETAILED DESCRIPTION OF THE INVENTION

Definitions

Unless otherwise defined, all technical and scientific terms used herein have the same meaning as commonly understood by one of ordinary skill in the art to which this invention belongs.

As used herein, the following terms shall have the following definitions.

"Acyl" means a group of the formula —C(O)$R^{20}$ where, unless otherwise specified for a particular substituent, $R^{20}$ can be, for example, H, $C_{1-6}$-alkyl, aryl, arylalkyl, heterocyclyl, for example methyl, ethyl, isoxazolyl, pyrazinyl and the like.

"Alkyl" means a monovalent linear or branched saturated hydrocarbon of 1 to 12 carbon atoms. In particular embodiments, $C_{1-6}$-alkyl has 1 to 6 carbon atoms, and in more particular embodiments 1 to 4 carbon atoms. As used herein, "$C_{1-6}$-alkyl" denotes an alkyl group having from 1-6 carbon atoms. Examples of $C_{1-6}$-alkyl include methyl, ethyl, propyl, isopropyl, butyl (also known as n-butyl), iso-butyl, sec-butyl, tert-butyl, pentyl, hexyl, and the like. The $C_{1-6}$-alkyl group can be optionally enriched in deuterium, e.g., —$CD_3$, —$CD_2CD_3$ and the like.

"Alkenyl" means a monovalent linear or branched hydrocarbon group of 2 to 7 carbon atoms with at least one double bond. In particular embodiments, $C_{2-6}$-alkenyl has 2 to 6 carbon atoms with at least one double bond. Examples of $C_{2-6}$-alkenyl include ethenyl, propenyl, prop-2-enyl, isopropenyl, n-butenyl, iso-butenyl, and tert-butenyl.

"Alkynyl" means a monovalent linear or branched saturated hydrocarbon group of 2 to 7 carbon atoms comprising one, two or three triple bonds. In particular embodiments $C_{2-6}$-alkynyl has from 2 to 6 carbon atoms comprising one or two triple bonds. Examples of $C_{2-6}$-alkynyl include ethynyl, propynyl, prop-2-ynyl, isopropynyl, n-butynyl, and iso-butynyl.

"Alkoxy, alkoxyl or lower alkoxy" means any of the above $C_{1-6}$-alkyl groups which is attached to the remainder of the molecule by an oxygen atom (RO—). Typical $C_{1-6}$-alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylaminoethoxy, diethylamino ethoxy, dimethoxy-phosphoryl methoxy and the like.

"Aryl" means a monovalent aromatic carbocyclic mono-, bi- or tricyclic ring system comprising 6 to 19 carbon ring atoms. Examples of aryl moieties include, but are not limited to, phenyl, naphthyl (or naphathelenyl), tolyl, xylyl, pyridinyl, quinolinyl, pyrimidinyl, imidazolyl, thiazolyl, anthracenyl, tetrazolyl, and fluorenyl. A particular "aryl" group is phenyl.

"Aryloxy" means ($R^{30}O$—), wherein $R^{30}$ is aryl as defined herein. Examples of aryloxy moieties include benzyloxy.

"Cyano" means —CN (—C≡N)

"Cycloalkyl" means a substituted on unsubstituted stable monovalent saturated monocyclic, bicyclic or tricyclic system which consists of 3 to 10 ring carbon atoms. In particular embodiments $C_{3-7}$-cycloalkyl denotes a monovalent saturated monocyclic hydrocarbon group of 3 to 7 ring carbon atoms. Particular $C_{3-7}$-cycloalkyl groups are monocyclic. Examples for monocyclic $C_{3-7}$-cycloalkyl are cyclopropyl, cyclobutnyl, cyclopentyl, cyclohexyl or cycloheptyl. Bicyclic means consisting of two saturated carbocycles having one or more carbon atoms in common. Examples for bicyclic cycloalkyl are bicyclo[2.2.1]heptanyl, or bicyclo[2.2.2]octanyl. Tricyclic means consisting of three saturated carbocycles having two or more carbon atoms in common. Examples of tricyclic cycloalkyl include adamantane.

"Fused" when referring to two or more rings, e.g. aryl fused with cycloakyl, means that the rings have at least two atoms in common. An example of aryl fused with cycloalkyl is tetrahydronaphthalenyl.

"Halogen" or "Halo" means at atom selected from F, Cl, Br or I. In particular embodiments Halogen means F and Cl.

"Heteroatom" means at atom selected from N, O or S.

"Heteroaryl" means a substituted or unsubstituted aromatic heterocyclic ring system containing up to two rings, at least one ring of which includes 1, 2, or 3 heteroatoms, the remaining ring atoms being carbon. Examples of heteroaryl groups include, but are not limited to, thienyl (or thiophenyl), furyl (or furanyl), indolyl, pyrrolyl, pyridinyl, pyrazinyl, oxazolyl, isoxazolyl, oxadiazolyl, thiazolyl, quinolinyl, isoquinolinyl, indazolyl, pyrimidinyl, imidazolyl, triazolyl, tetrazolyl, triazinyl, pyrazolyl, benzo[d]isoxazolyl, 2-oxo-2H-chromen-4-yl, benzo[d]isoxazolyl, benzothiophenyl, naphthyrydinyl and cinnolinyl.

In the case of a heteroaryl that is bicyclic it should be understood that one ring may be aryl while the other is heteroaryl and both may be independently substituted or unsubstituted.

"Heterocyclyl," "heterocycle" or "heterocyclic ring" means a substituted or unsubstituted monovalent saturated or partly unsaturated mono- or bicyclic ring, non-aromatic hydrocarbon system of 3 to 9 ring atoms, comprising 1, 2, or 3 ring heteroatoms selected from N, O and S, the remaining ring atoms being carbon. In particular embodiments, heteroCcycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, tetrahydrofuranyl, piperazinyl, morpholinyl, thiomorpholinyl, 1,1-dioxo-thiomorpholin-4-yl, azepanyl, diazepanyl, homopiperazinyl, or oxazepanyl. Examples of partly unsaturated heterocycloalkyl are dihydrofuryl, imidazolinyl, dihydro-oxazolyl, dihydro-oxadiazolyl, dihydro-triazolyl, tetrahydro-pyridinyl, tetrahydro-triazinyl or dihydropyranyl.

In the case of a heterocycle that is bicyclic it should be understood that one ring may be heterocycle while the other is cycloalkyl, and either or both may be independently substituted. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl.

"$IC_{50}$" refers to the concentration of a particular compound required to inhibit 50% of a specific measured activity. $IC_{50}$ can be measured, inter alia, as is described subsequently in Example 71.

"Oxo" or ("Oxy") means =O.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoroacetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (1995) at pgs. 456-457.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

"Substituted," as in substituted $C_{1-6}$-alkyl, aryl or heteroaryl means that the substitution (i.e. replacement of one hydrogen atom) can occur at one or more positions and, unless otherwise indicated, that the substituents at each substitution site are independently selected from the specified options. The term "optionally substituted" refers to the fact that one or more hydrogen atoms of a chemical group (with one or more hydrogen atoms) can be, but does not necessarily have to be, substituted with another substituent.

"Sulfonyl" means a group of formula —$SO_2R^{20}$ where, unless otherwise specified for a specific substituent, $R^{20}$ may be as is previously defined in the definition of acyl.

The definitions described herein apply irrespective of whether the terms in question appear alone or in combination. It is contemplated that the definitions described herein can be appended to form chemically-relevant combinations, such as e.g. "heterocycloalkylaryl", "haloalkylheteroaryl", "arylalkylheterocycloalkyl", or "alkoxyalkyl". The last member of the combination is the radical which is binding to the rest of the molecule. The other members of the combination are attached to the binding radical in reversed order in respect of the literal sequence, e.g. the combination arylalkylheterocycloalkyl refers to a heterocycloalkyl-radical which is substituted by an $C_{1-6}$-alkyl which is substituted by an aryl.

As used in this application, if a formula or group appears to be missing a substituent, that is it appears the valence is not complete, it is presumed the missing substituent is an H.

In the structural formulae presented herein a broken bond (a) denotes that the substituent is below the plane of the paper and a wedged bond (b) denotes that the substituent is above the plane of the paper.

In one embodiment, the present invention relates to compounds of Formula I wherein: W and X are the same or different and each is independently selected from the group
H,
$C_{1-6}$-alkyl that optionally may be substituted with $OR^5$, aryl, $C_{2-6}$-alkenyl, $C_{2-6}$-alkynyl and $C_{3-7}$-cycloalkyl,
$C_{3-7}$-cycloalkyl, and
heterocycle,
or alternatively, X and W together with the nitrogen to which they are bound can form a $C_{2-9}$-heterocycle, or W together with the nitrogen to which it is bound and Y together with the carbon to which it is bound can form a $C_{3-9}$-heterocycle;
Y is selected from the group
$C_{1-6}$-alkyl that optionally may be substituted with $OR^5$ and $C_{3-7}$-cycloalkyl, and
$C_{3-7}$-cycloalkyl;
Z is selected from the group
$C_{1-6}$-alkyl that optionally may be substituted with aryl,
aryl that optionally may be substituted with
  $C_{1-6}$-alkyl that optionally may be substituted with $OR^5$, aryl and heterocyclyl,
  $OR^5$,
  halogen,
  $COOR^5$,
  $CONR^6R^7$,
  $NR^4C(O)R^5$,
  $C(O)R^5$,
  $CF_3$,
  $C_{2-6}$-alkenyl
  $C_{2-6}$-alkynyl that optionally may be substituted with heterocycle that optionally may be substituted with $OR^5$,
  heterocycle that optionally may be substituted with $C_{1-6}$-alkyl, oxo and $OR^5$,
  $NH_2C=N-NH_2$,
  $CONR^5SO_2R^4$,
  cyano that optionally may be substituted with heterocyclyl,
  $C_{3-7}$-cycloalkyl,
  aryl,
  heteroaryl that optionally may be substituted with $C_{1-6}$-alkyl, oxo and $CF_3$,
aryl fused with $C_{3-7}$-cycloalkyl, wherein the aryl may be substituted with $OR^5$
heteroaryl that optionally may be substituted with $C_{1-6}$-alkyl, $C_{2-6}$-alkynyl, $OR^5$, halogen, $COOR^5$, $CONR^6R^7$, oxo, $CF_3$, $C_{3-7}$-cycloalkyl, cyano and aryl, and
heterocyclyl;
$R^1$, $R^2$ and $R^3$ are the same or different and each is independently selected from the group
H,
halogen,
$C_{1-6}$-alkyl that optionally may be substituted with aryl,
cyano
aryl,
$C(O)R^5$,
$OR^5$,
N-acyl,
N-sulfonyl, and
$SO_2R^5$;
$R^4$ is selected from the group
H, and
$C_{1-6}$-alkyl;
$R^5$ is selected from the group
H,
$C_{1-6}$-alkyl that optionally may be substituted with aryl, $C_{3-7}$-cycloalkyl, and $CF_3$,
$C_{3-7}$-cycloalkyl,
$C_{2-6}$-alkenyl, aryl that optionally may be substituted with $NR^6R^7$, $C(O)R^7$, $CR^1OR^7$, $NO_2$ and $OR^7$,
heterocyclyl,
$CR^4F_2$, and
$NR^6R^7$;
$R^6$ and $R^7$ are the same or different and each is independently selected from the group
H, and
$C_{1-6}$-alkyl that optionally may be substituted with aryl, heteroaryl and $C_{3-7}$-cycloalkyl;
n is 0, 1 or 2;
or a pharmaceutically acceptable salt thereof.

One embodiment of the invention relates to a compound of Formula I, wherein
W is H;
X is selected from the group
H,
alkyl that optionally may be substituted with $OR^5$, aryl and $C_{3-7}$-cycloalkyl,
$C_{3-7}$-cycloalkyl, and
heterocycle,
Y is selected from the group
alkyl that optionally may be substituted with $OR^5$, and
$C_{3-7}$-cycloalkyl;
Z is selected from the group
aryl that optionally may be substituted with
  $C_{1-6}$-alkyl that optionally may be substituted with $OR^5$, aryl and heterocyclyl,
  $OR^5$,
  halogen,
  $COOR^5$,
  $CONR^6R^7$,
  $NR^4C(O)R^5$,
  $C(O)R^5$,
  $CF_3$,
  $C_{2-6}$-alkenyl
  $C_{2-6}$-alkynyl that optionally may be substituted with heterocycle that optionally may be substituted with $OR^5$,
  heterocycle
  $NH_2C=N-NH_2$,
  $CONR^5SO_2R^4$,
  cyano,
  $C_{3-7}$-cycloalkyl,
  aryl,
  heteroaryl that optionally may be substituted with $C_{1-6}$-alkyl, oxo and $CF_3$,
aryl fused with $C_{3-7}$-cycloalkyl, wherein the aryl may be substituted with $OR^5$, and
heteroaryl that optionally may be substituted with $C_{1-6}$-alkyl, $C_{2-6}$-alkynyl, $OR^5$, halogen, oxo, $CF_3$, cyano and aryl, and
$R^1$, $R^2$ and $R^3$ are the same or different and each is independently selected from the group
H,
aryl, and
$OR^5$,
$R^4$ is selected from the group
H, and
$C_{1-6}$-alkyl;
$R^5$ is selected from the group
H,
$C_{1-6}$-alkyl that optionally may be substituted with aryl, and $CF_3$, and
$C_{2-6}$-alkenyl,
$R^6$ and $R^7$ are H
n is 0, 1 or 2;
or a pharmaceutically acceptable salt thereof.

One embodiment of the invention relates to a compound of Formula I, wherein
W is H;
X is selected from the group
H,
alkyl that optionally may be substituted with $OR^5$, aryl and $C_{3-7}$-cycloalkyl,
$C_{3-7}$-cycloalkyl, and
heterocycle,
Y is selected from the group
alkyl that optionally may be substituted with $OR^5$, and
$C_{3-7}$-cycloalkyl;
Z is selected from the group
phenyl or naphthyl that optionally may be substituted with
  $C_{1-6}$-alkyl that optionally may be substituted with $OR^5$, aryl and heterocyclyl,
  $OR^5$,
  halogen,
  $COOR^5$,
  $CONR^6R^7$,
  $NR^4C(O)R^5$,
  $C(O)R^5$,
  $CF_3$,
  $C_{2-6}$-alkenyl
  $C_{2-6}$-alkynyl that optionally may be substituted with heterocycle that optionally may be substituted with $OR^5$,
  heterocycle
  $NH_2C=N-NH_2$,
  $CONR^5SO_2R^4$,
  cyano,
  $C_{3-7}$-cycloalkyl,
  aryl,
  heteroaryl that optionally may be substituted with $C_{1-6}$-alkyl, oxo and $CF_3$,
phenyl fused with $C_{3-7}$-cycloalkyl, wherein the aryl may be substituted with $OR^5$, and
heteroaryl that optionally may be substituted with $C_{1-6}$-alkyl, $C_{2-6}$-alkynyl, $OR^5$, halogen, oxo, $CF_3$, cyano and aryl, and
$R^1$, $R^2$ and $R^3$ are the same or different and each is independently selected from the group
H,
aryl, and
$OR^5$,
$R^4$ is selected from the group
H, and
$C_{1-6}$-alkyl;
$R^5$ is selected from the group
H,
$C_{1-6}$-alkyl that optionally may be substituted with aryl, and $CF_3$, and
$C_{2-6}$-alkenyl,
$R^6$ and $R^7$ are H
n is 0, 1 or 2;
or a pharmaceutically acceptable salt thereof.

One embodiment of the invention relates to compounds of Formula I where W is H, X and Y are both $CH_3$, n is 1 and $R^1$, $R^2$ and $R^3$ are H.

One embodiment of the invention relates to compounds of Formula I where W and X are independently selected from H, $C_{1-6}$-alkyl that optionally is substituted as defined above, $C_{3-7}$-cycloalkyl and heterocycle, or a pharmaceutically acceptable salt thereof.

Another embodiment of the invention relates to compounds of Formula I where X is $C_{1-6}$-alkyl and W is H, or a pharmaceutically acceptable salt thereof.

Another embodiment of the invention relates to compounds of Formula I where and X is methyl, ethyl, n-propyl, 2-hydroxyethyl or cyclobutyl and W is H, or a pharmaceutically acceptable salt thereof.

Another embodiment of the invention relates to compounds of Formula I where Y is $C_{1-6}$-alkyl that may be substituted as defined above, or a pharmaceutically acceptable salt thereof. A particular embodiment relates to compounds of Formula I where Y is methyl, ethyl, hydroxymethyl, 1-hydroxyethyl or cyclopropylmethyl, or a pharmaceutically acceptable salt thereof.

Another embodiment of the invention relates to compounds of Formula I where Z is $C_{1-6}$-alkyl. In a particular embodiment the $C_{1-6}$-alkyl group is $C_{1-6}$-alkyl that may be substituted with aryl or $OR^5$, or a pharmaceutically acceptable salt thereof. One such aryl substituent is phenyl.

Another embodiment of the invention relates to compounds of Formula I where Z is aryl that is not phenyl, and which aryl group optionally may be substituted as defined above for Formula I, or a pharmaceutically acceptable salt thereof. A particular example of an aryl group that is not phenyl is naphthalenyl, which optionally may be substituted with $C_{1-6}$-alkyl, $OR^5$, cyano, halogen, heterocycle, $C_{3-7}$-cycloalkyl, aryl, heteroaryl, $COOR^5$ and $CONR^5SO_2R^4$. An example of such aryl substituent is phenyl. Examples of such heteroaryl substituents include tetrazolyl, thiazolyl, oxazolyl, isoxazolyl, oxadiazolyl, triazolyl, triazinyl, pyrazolyl, and furanyl. Examples of $R^5$ and $R^4$ include $C_{1-6}$-alkyl. Examples of $C_{3-7}$-cycloalkyl substituents include cyclopropyl. In an embodiment the $C_{1-6}$-alkyl substituent is itself substituted with heterocycle, for example piperazinyl, morpholinyl, and piperidinyl.

Another embodiment of the invention relates to compounds of Formula I where Z is aryl fused with $C_{3-7}$-cycloalkyl, or a pharmaceutically acceptable salt thereof. An example of such a fused group is phenyl fused with cyclohexyl (or tetrahydro-naphthalen).

Another embodiment of the invention relates to compounds of Formula I where Z is heteroaryl that optionally may be substituted with for example $C_{1-6}$-alkyl, halogen, $OR^5$, oxo, $CF_3$, $C_{3-7}$-cycloalkyl and cyano, or a pharmaceutically acceptable salt thereof. Examples of such heteroaryl groups include thiophenyl, quinolinyl, indazolyl, oxazolyl, isoxazolyl, pyridinyl, imidazolyl, napththyridinyl, cinnolinyl and benzothiophenyl.

In another embodiment Z is heteroaryl that is bicyclic, and which may be substituted as immediately defined above. In a particular embodiment Z is quinolinyl, isoquinolinyl, benzo[b]thiophenyl, indazolyl, isoxazolyl, naphthyridinyl and cynnolinyl.

Another embodiment of the invention relates to compounds of Formula I where $R^1$, $R^2$ and $R^3$ are H, or a pharmaceutically acceptable salt thereof.

Another embodiment of the invention relates to compounds of Formula I where $R^3$ is H, phenyl, $OR^5$, cyano or Br, or a pharmaceutically acceptable salt thereof.

Another embodiment of the invention relates to compounds of Formula I where $R^4$ is H, or a pharmaceutically acceptable salt thereof.

Another embodiment of the invention relates to compounds of Formula I where $R^5$ is H or $C_{1-6}$-alkyl that optionally may be substituted with aryl, or a pharmaceutically acceptable salt thereof. In a particular embodiment, the $C_{1-6}$-alkyl is methyl or ethyl and either may be substituted with phenyl.

Another embodiment of the invention relates to compounds of Formula I where $R^6$ and $R^7$ are independently H or $C_{1-6}$-alkyl, or a pharmaceutically acceptable salt thereof.

Another embodiment of the invention relates to compounds of Formula I where n is 0, or a pharmaceutically acceptable salt thereof.

Another embodiment of the invention relates to compounds of Formula I where X is H or methyl, W is H, Y is methyl or ethyl, $R^1$, $R^2$, $R^3$ and $R^4$ are H, n is 0, and Z is phenyl that may be substituted with $C_{1-6}$-alkyl, $OCH_3$, F, Cl, Br, I or $CF_3$, or a pharmaceutically acceptable salt thereof.

Another embodiment of the invention relates to compounds of Formula I where X is H or methyl, W is H, Y is methyl or ethyl, $R^1$, $R^2$, $R^3$ and $R^4$ are H, n is 0, and Z is naphthalenyl that may be substituted with $OR^5$, halogen, $C_{1-6}$-alkyl that optionally is substituted with aryl or heterocyclyl, $CF_3$, $C_{2-6}$-alkynyl, $C_{2-6}$-alkenyl, heterocycle, $C(O)CH_3$, $COOR^5$, cyano, $C_{3-7}$-cycloalkyl, $CONHSO_2R^4$, and $CONH_2$, or a pharmaceutically acceptable salt thereof.

Another embodiment of the invention relates to compounds of Formula 1 where X is H or methyl, W is H, Y is methyl or ethyl, $R^1$, $R^2$, $R^3$ and $R^4$ are H, n is 0, and Z is isoquinolinyl or quinolinyl each of which optionally may be substituted with $C_{1-6}$-alkyl, $OR^5$, oxo, $C_{3-7}$-cycloalkyl, $CF_3$, cyano and halogen or a pharmaceutically acceptable salt thereof.

Another embodiment of the invention relates to compounds of Formula 1 where X is H or methyl, W is H, Y is methyl or ethyl, $R^1$, $R^2$, $R^3$ and $R^4$ are H, n is 0, and Z is selected from cinnolinyl, thiophenyl, benzothiophenyl, benzo[d]isoxazolyl, tetrahydronaphthalenyl, indazolyl, oxazolyl, thiazolyl, pyridinyl, imidazolyl or naphthyridinyl, each of which optionally may be substituted as permitted in the definitions of Formula I above, or a pharmaceutically acceptable salt thereof.

Compounds according to the invention wherein Z is $C_{1-6}$-alkyl include:
(S)-2-Methylamino-N-(2-oxo-1-phenethyl-2,3,4,5-tetrahydro-1H-benzo[b]azepin-3-yl)-propionamide hydrochloride (Example 55 g); and
(S)-2-Methylamino-N-[2-oxo-1-(3-phenyl-propyl)-2,3,4,5-tetrahydro-1H-benzo[b]azepin-3-yl]-propionamide hydrochloride (Example 55 h);
or a pharmaceutically acceptable salt of any of the foregoing compounds.

Compounds according to the invention wherein Z is aryl that is not phenyl include:
(S)-2-Amino-N—[(R)-1-(6-bromo-2-methoxy-naphthalen-1-ylmethyl)-2-oxo-2,3,4,5-tetrahydro-1H-benzo[b]azepin-3-yl]-butyramide hydrochloride (Example 5a)
(S)-2-Amino-N—[(S)-1-(6-bromo-2-methoxy-naphthalen-1-ylmethyl)-2-oxo-2,3,4,5-tetrahydro-1H-benzo[b]azepin-3-yl]-butyramide (Example 5b);
(S)—N—((S)-1-((6-Bromo-2-methoxynaphthalen-1-yl)methyl)-2-oxo-2,3,4,5-tetrahydro-1H-benzo[b]azepin-3-yl)-2-(2-hydroxyethylamino)butanamide (Example 6);
(S)—N—((S)-1-((6-Bromo-2-methoxynaphthalen-1-yl)methyl)-2-oxo-2,3,4,5-tetrahydro-1H-benzo[b]azepin-3-yl)-2-(cyclobutylamino)butanamide (Example 7);
(S)-2-(Benzylamino)-N—((S)-1-((6-bromo-2-methoxynaphthalen-1-yl)methyl)-2-oxo-2,3,4,5-tetrahydro-1H-benzo[b]azepin-3-yl)butanamide (Example 8);

(S)—N—((S)-1-((6-Bromo-2-methoxynaphthalen-1-yl)methyl)-2-oxo-2,3,4,5-tetrahydro-1H-benzo[b]azepin-3-yl)-2-(oxetan-3-ylamino)butanamide (Example 9);

(2S,3S)-2-Amino-N—((S)-1-((6-bromo-2-methoxynaphthalen-1-yl)methyl)-2-oxo-2,3,4,5-tetrahydro-1H-benzo[b]azepin-3-yl)-3-hydroxybutanamide hydrochloride (Example 10);

(2S,3R)-2-Amino-N—((S)-1-((6-bromo-2-methoxynaphthalen-1-yl)methyl)-2-oxo-2,3,4,5-tetrahydro-1H-benzo[b]azepin-3-yl)-3-hydroxybutanamide hydrochloride (Example 11);

(S)-2-Amino-N—[(S)-1-(6-bromo-2-methoxy-naphthalen-1-ylmethyl)-2-oxo-2,3,4,5-tetrahydro-1H-benzo[b]azepin-3-yl]-3-hydroxy-propionamide hydrochloride (Example 12);

{(S)-1-[(S)-1-(6-Bromo-2-methoxy-naphthalen-1-ylmethyl)-2-oxo-2,3,4,5-tetrahydro-1H-benzo[b]azepin-3-ylcarbamoyl]-2-hydroxy-ethyl}-carbamic acid tert-butyl ester hydrochloride (Example 13);

(S)—N—{(S)-1-[2-(3-Hydroxy-oxetan-3-ylethynyl)-naphthalen-1-ylmethyl]-2-oxo-2,3,4,5-tetrahydro-1H-benzo[b]azepin-3-yl}-2-methylamino-propionamide (Example 14);

(S)-2-Methylamino-N—[(S)-2-oxo-1-(2-propoxy-naphthalen-1-ylmethyl)-2,3,4,5-tetrahydro-1H-benzo[b]azepin-3-yl]-propionamide hydrochloride (Example 15);

(S)—N—[(S)-1-(2-Allyloxy-naphthalen-1-ylmethyl)-2-oxo-2,3,4,5-tetrahydro-1H-benzo[b]azepin-3-yl]-2-methylamino-propionamide (Example 16);

(S)—N—[(S)-1-(2-Hydroxy-naphthalen-1-ylmethyl)-2-oxo-2,3,4,5-tetrahydro-1H-benzo[b]azepin-3-yl]-2-methylamino-propionamide hydrochloride (Example 17);

(S)—N—[(S)-8-Benzyloxy-1-(2-methyl-naphthalen-1-ylmethyl)-2-oxo-2,3,4,5-tetrahydro-1H-benzo[b]azepin-3-yl]-2-methylamino-propionamide hydrochloride (Example 18);

(S)-2-Methylamino-N—[(S)-1-(2-methyl-naphthalen-1-ylmethyl)-2-oxo-8-phenyl-2,3,4,5-tetrahydro-1H-benzo[b]azepin-3-yl]-propionamide hydrochloride (Example 21);

(R)—N—[(S)-1-(6-Bromo-2-methoxy-naphthalen-1-ylmethyl)-2-oxo-2,3,4,5-tetrahydro-1H-benzo[b]azepin-3-yl]-2-methylamino-propionamide hydrochloride (Example 27);

(S)-2-Methylamino-N—{(S)-2-oxo-1-[7-(1H-tetrazol-5-yl)-naphthalen-1-ylmethyl]-2,3,4,5-tetrahydro-1H-benzo[b]azepin-3-yl}-propionamide (Example 28);

(S)—N—[(S)-1-(6-Bromo-2-methoxy-naphthalen-1-ylmethyl)-2-oxo-2,3,4,5-tetrahydro-1H-benzo[b]azepin-3-yl]-2-methylamino-propionamide hydrochloride (Example 29);

(S)—N—{(S)-1-[2-Methoxy-6-(4-methyl-thiazol-2-yl)-naphthalen-1-ylmethyl]-2-oxo-2,3,4,5-tetrahydro-1H-benzo[b]azepin-3-yl}-2-methylamino-propionamide hydrochloride (Example 30);

(S)—N—{(S)-1-[2-Methoxy-6-(5-oxo-4,5-dihydro-[1,2,4]oxadiazol-3-yl)-naphthalen-1-ylmethyl]-2-oxo-2,3,4,5-tetrahydro-1H-benzo[b]azepin-3-yl}-2-methylamino-propionamide hydrochloride (Example 31);

(S)—N—[(S)-1-(2-Methoxy-6-[1,2,4]oxadiazol-3-yl-naphthalen-1-ylmethyl)-2-oxo-2,3,4,5-tetrahydro-1H-benzo[b]azepin-3-yl]-2-methylamino-propionamide hydrochloride (Example 32);

(S)—N—{(S)-1-[6-(N-Aminocarbamimidoyl)-2-methoxy-naphthalen-1-ylmethyl]-2-oxo-2,3,4,5-tetrahydro-1H-benzo[b]azepin-3-yl}-2-methylamino-propionamide dihydrochloride (Example 33);

(S)—N—{(S)-1-[2-Methoxy-6-(5-oxo-4,5-dihydro-1H-[1,2,4]triazol-3-yl)-naphthalen-1-ylmethyl]-2-oxo-2,3,4,5-tetrahydro-1H-benzo[b]azepin-3-yl}-2-methylamino-propionamide hydrochloride (Example 34);

(S)—N—{(S)-1-[6-(5,6-Dioxo-1,4,5,6-tetrahydro-[1,2,4]triazin-3-yl)-2-methoxy-naphthalen-1-ylmethyl]-2-oxo-2,3,4,5-tetrahydro-1H-benzo[b]azepin-3-yl}-2-methylamino-propionamide hydrochloride (Example 35);

(S)—N—{(S)-1-[2-Methoxy-6-(5-trifluoromethyl-4H-[1,2,4]triazol-3-yl)-naphthalen-1-ylmethyl]-2-oxo-2,3,4,5-tetrahydro-1H-benzo[b]azepin-3-yl}-2-methylamino-propionamide hydrochloride (Example 36);

(S)—N—[(S)-1-(2-Methoxy-6-[1,2,4]triazin-3-yl-naphthalen-1-ylmethyl)-2-oxo-2,3,4,5-tetrahydro-1H-benzo[b]azepin-3-yl]-2-methylamino-propionamide hydrochloride (Example 37);

(S)—N—{(S)-1-[2-Methoxy-6-(1H-[1,2,4]triazol-3-yl)-naphthalen-1-ylmethyl]-2-oxo-2,3,4,5-tetrahydro-1H-benzo[b]azepin-3-yl}-2-methylamino-propionamide dihydrochloride (Example 38);

(S)—N—{(S)-1-[2-Methoxy-6-(1H-tetrazol-5-yl)-naphthalen-1-ylmethyl]-2-oxo-2,3,4,5-tetrahydro-1H-benzo[b]azepin-3-yl}-2-methylamino-propionamide hydrochloride (Example 39);

(S)—N—{(S)-1-[2-Methoxy-6-(2-methyl-2H-tetrazol-5-yl)-naphthalen-1-ylmethyl]-2-oxo-2,3,4,5-tetrahydro-1H-benzo[b]azepin-3-yl}-2-methylamino-propionamide hydrochloride (Example 40);

(S)—N—{(S)-1-[2-Methoxy-6-(1-methyl-1H-tetrazol-5-yl)-naphthalen-1-ylmethyl]-2-oxo-2,3,4,5-tetrahydro-1H-benzo[b]azepin-3-yl}-2-methylamino-propionamide hydrochloride (Example 41);

(S)—N—[(S)-1-(6-Acetylamino-2-methoxy-naphthalen-1-ylmethyl)-2-oxo-2,3,4,5-tetrahydro-1H-benzo[b]azepin-3-yl]-2-methylamino-propionamide hydrochloride (Example 42);

(S)—N—{(S)-1-[2-Methoxy-6-(1H-pyrazol-4-yl)-naphthalen-1-ylmethyl]-2-oxo-2,3,4,5-tetrahydro-1H-benzo[b]azepin-3-yl}-2-methylamino-propionamide hydrochloride (Example 43);

(S)—N—[(S)-1-(6-Acetyl-2-methoxy-naphthalen-1-ylmethyl)-2-oxo-2,3,4,5-tetrahydro-1H-benzo[b]azepin-3-yl]-2-methylamino-propionamide hydrochloride (Example 45);

(S)—N—[(S)-1-(2-Methoxy-6-vinyl-naphthalen-1-ylmethyl)-2-oxo-2,3,4,5-tetrahydro-1H-benzo[b]azepin-3-yl]-2-methylamino-propionamide hydrochloride (Example 46);

(S)—N—{(S)-1-[6-(1-Hydroxy-ethyl)-2-methoxy-naphthalen-1-ylmethyl]-2-oxo-2,3,4,5-tetrahydro-1H-benzo[b]azepin-3-yl}-2-methylamino-propionamide trifluoroacetate (Example 47a);

(S)-2-Methylamino-N—[(S)-1-(2-methyl-naphthalen-1-ylmethyl)-2-oxo-2,3,4,5-tetrahydro-1H-benzo[b]azepin-3-yl]-propionamide hydrochloride (Example 47b);

(S)—N—[(S)-1-(2-Methoxy-naphthalen-1-ylmethyl)-2-oxo-2,3,4,5-tetrahydro-1H-benzo[b]azepin-3-yl]-2-methylamino-propionamide hydrochloride (Example 47c);

(S)-2-Methylamino-N—[(S)-1-(4-methyl-naphthalen-1-ylmethyl)-2-oxo-2,3,4,5-tetrahydro-1H-benzo[b]azepin-3-yl]-propionamide hydrochloride (Example 47f);

(S)—N—[(S)-1-(4-Bromo-naphthalen-1-ylmethyl)-2-oxo-2,3,4,5-tetrahydro-1H-benzo[b]azepin-3-yl]-2-methylamino-propionamide hydrochloride (Example 47 g);

(S)-2-Methylamino-N—((S)-1-naphthalen-1-ylmethyl-2-oxo-2,3,4,5-tetrahydro-1H-benzo[b]azepin-3-yl)-propionamide hydrochloride (Example 47 h);

(S)—N—[(S)-1-(2-Ethynyl-naphthalen-1-ylmethyl)-2-oxo-2,3,4,5-tetrahydro-1H-benzo[b]azepin-3-yl]-2-methylamino-propionamide hydrochloride (Example 47i);

(S)—N—[(S)-1-(2-Cyclopropyl-naphthalen-1-ylmethyl)-2-oxo-2,3,4,5-tetrahydro-1H-benzo[b]azepin-3-yl]-2-methylamino-propionamide hydrochloride (Example 47k);

(S)—N—[(S)-1-(2-Methoxy-6-trifluoromethyl-naphthalen-1-ylmethyl)-2-oxo-2,3,4,5-tetrahydro-1H-benzo[b]azepin-3-yl]-2-methylamino-propionamide hydrochloride (Example 47l);

(S)—N—[(S)-1-(5-Bromo-2-methoxy-naphthalen-1-ylmethyl)-2-oxo-2,3,4,5-tetrahydro-1H-benzo[b]azepin-3-yl]-2-methylamino-propionamide hydrochloride (Example 47o);

(S)-2-Methylamino-N—{(S)-2-oxo-1-[2-(2,2,2-trifluoro-ethoxy)-naphthalen-1-ylmethyl]-2,3,4,5-tetrahydro-1H-benzo[b]azepin-3-yl}-propionamide hydrochloride (Example 47p);

(S)—N—[(S)-1-(2-Fluoro-naphthalen-1-ylmethyl)-2-oxo-2,3,4,5-tetrahydro-1H-benzo[b]azepin-3-yl]-2-methylamino-propionamide hydrochloride (Example 47s);

(S)—N—[(S)-1-(7-Bromo-2-methoxy-naphthalen-1-ylmethyl)-2-oxo-2,3,4,5-tetrahydro-1H-benzo[b]azepin-3-yl]-2-methylamino-propionamide hydrochloride (Example 47v);

(S)—N—[(S)-1-(2-Chloro-naphthalen-1-ylmethyl)-2-oxo-2,3,4,5-tetrahydro-1H-benzo[b]azepin-3-yl]-2-methylamino-propionamide hydrochloride (Example 47x);

(S)—N—[(S)-1-(2-Ethoxy-naphthalen-1-ylmethyl)-2-oxo-2,3,4,5-tetrahydro-1H-benzo[b]azepin-3-yl]-2-methylamino-propionamide hydrochloride (Example 47y);

(S)—N—[(S)-1-(2,4-Dimethyl-naphthalen-1-ylmethyl)-2-oxo-2,3,4,5-tetrahydro-1H-benzo[b]azepin-3-yl]-2-methylamino-propionamide hydrochloride (Example 47bb);

(S)—N—[(S)-1-(2-Isopropoxy-naphthalen-1-ylmethyl)-2-oxo-2,3,4,5-tetrahydro-1H-benzo[b]azepin-3-yl]-2-methylamino-propionamide hydrochloride (Example 47dd);

(S)—N—((S)-1-Anthracen-1-ylmethyl-2-oxo-2,3,4,5-tetrahydro-1H-benzo[b]azepin-3-yl)-2-methylamino-propionamide hydrochloride (Example 47ee);

(S)—N—[(S)-1-(7-Bromo-naphthalen-1-ylmethyl)-2-oxo-2,3,4,5-tetrahydro-1H-benzo[b]azepin-3-yl]-2-methylamino-propionamide hydrochloride (Example 47ff);

(S)—N—[(S)-1-(3-Bromo-naphthalen-1-ylmethyl)-2-oxo-2,3,4,5-tetrahydro-1H-benzo[b]azepin-3-yl]-2-methylamino-propionamide hydrochloride (Example 47gg);

(S)—N—[(S)-1-(8-Bromo-naphthalen-1-ylmethyl)-2-oxo-2,3,4,5-tetrahydro-1H-benzo[b]azepin-3-yl]-2-methylamino-propionamide hydrochloride (Example 47hh);

(S)—N—[(S)-1-(4-Cyano-naphthalen-1-ylmethyl)-2-oxo-2,3,4,5-tetrahydro-1H-benzo[b]azepin-3-yl]-2-methylamino-propionamide hydrochloride (Example 47kk);

(S)-2-Methylamino-N—((S)-1-naphthalen-2-ylmethyl-2-oxo-2,3,4,5-tetrahydro-1H-benzo[b]azepin-3-yl)-propionamide hydrochloride (Example 47nn);

(S)—N—[(S)-1-(5-Bromo-naphthalen-1-ylmethyl)-2-oxo-2,3,4,5-tetrahydro-1H-benzo[b]azepin-3-yl]-2-methylamino-propionamide hydrochloride (Example 47tt);

(S)—N—[(S)-1-(5-Furan-2-yl-2-methoxy-naphthalen-1-ylmethyl)-2-oxo-2,3,4,5-tetrahydro-1H-benzo[b]azepin-3-yl]-2-methylamino-propionamide (Example 49a);

(S)—N—[(S)-1-(6-Furan-2-yl-2-methoxy-naphthalen-1-ylmethyl)-2-oxo-2,3,4,5-tetrahydro-1H-benzo[b]azepin-3-yl]-2-methylamino-propionamide hydrochloride (Example 49b);

(S)—N—[(S)-1-(5-Furan-3-yl-2-methoxy-naphthalen-1-ylmethyl)-2-oxo-2,3,4,5-tetrahydro-1H-benzo[b]azepin-3-yl]-2-methylamino-propionamide hydrochloride (Example 49c);

(S)—N—[(S)-1-(6-Cyclopropyl-2-methoxy-naphthalen-1-ylmethyl)-2-oxo-2,3,4,5-tetrahydro-1H-benzo[b]azepin-3-yl]-2-methylamino-propionamide hydrochloride (Example 49d);

(S)—N—[(S)-1-(5-Cyclopropyl-naphthalen-1-ylmethyl)-2-oxo-2,3,4,5-tetrahydro-1H-benzo[b]azepin-3-yl]-2-methylamino-propionamide hydrochloride (Example 49e);

(S)—N—[(S)-1-(4-Benzyl-naphthalen-1-ylmethyl)-2-oxo-2,3,4,5-tetrahydro-1H-benzo[b]azepin-3-yl]-2-methylamino-propionamide hydrochloride (Example 49f);

(S)—N—[(S)-1-(3-Cyclopropyl-naphthalen-1-ylmethyl)-2-oxo-2,3,4,5-tetrahydro-1H-benzo[b]azepin-3-yl]-2-methylamino-propionamide hydrochloride (Example 49 g);

(S)-2-Methylamino-N—[(S)-2-oxo-1-(4-phenethyl-naphthalen-1-ylmethyl)-2,3,4,5-tetrahydro-1H-benzo[b]azepin-3-yl]-propionamide hydrochloride (Example 49 h);

(S)—N—[(S)-1-(6-Benzyl-2-methoxy-naphthalen-1-ylmethyl)-2-oxo-2,3,4,5-tetrahydro-1H-benzo[b]azepin-3-yl]-2-methylamino-propionamide hydrochloride (Example 49i);

(S)—N—[(S)-1-(3-Benzyl-naphthalen-1-ylmethyl)-2-oxo-2,3,4,5-tetrahydro-1H-benzo[b]azepin-3-yl]-2-methylamino-propionamide hydrochloride (Example 49j);

(S)—N—[(S)-1-(5-Benzyl-naphthalen-1-ylmethyl)-2-oxo-2,3,4,5-tetrahydro-1H-benzo[b]azepin-3-yl]-2-methylamino-propionamide hydrochloride (Example 49k);

(S)—N—[(S)-1-(4-Isopropoxymethyl-naphthalen-1-ylmethyl)-2-oxo-2,3,4,5-tetrahydro-1H-benzo[b]azepin-3-yl]-2-methylamino-propionamide hydrochloride (Example 49l);

(S)—N—[(S)-1-(4-Cyclopropyl-naphthalen-1-ylmethyl)-2-oxo-2,3,4,5-tetrahydro-1H-benzo[b]azepin-3-yl]-2-methylamino-propionamide hydrochloride (Example 49m);

(S)-2-Methylamino-N—[(S)-2-oxo-1-(5-piperazin-1-ylmethyl-naphthalen-1-ylmethyl)-2,3,4,5-tetrahydro-1H-benzo[b]azepin-3-yl]-propionamide hydrochloride (Example 49n);

(S)-2-Methylamino-N—[(S)-1-(4-morpholin-4-ylmethyl-naphthalen-1-ylmethyl)-2-oxo-2,3,4,5-tetrahydro-1H-benzo[b]azepin-3-yl]-propionamide hydrochloride (Example 49o);

(S)—N—{(S)-1-[6-(3,5-Dimethyl-isoxazol-4-ylmethyl)-2-methoxy-naphthalen-1-ylmethyl]-2-oxo-2,3,4,5-tetrahydro-1H-benzo[b]azepin-3-yl}-2-methylamino-propionamide hydrochloride (Example 49p);

(S)-2-Methylamino-N—[(S)-2-oxo-1-(4-piperidin-1-ylmethyl-naphthalen-1-ylmethyl)-2,3,4,5-tetrahydro-1H-benzo[b]azepin-3-yl]-propionamide hydrochloride (Example 49q);

(S)—N—[(S)-1-(2-Methoxy-6-piperazin-1-ylmethyl-naphthalen-1-ylmethyl)-2-oxo-2,3,4,5-tetrahydro-1H-benzo[b]azepin-3-yl]-2-methylamino-propionamide hydrochloride (Example 49r);

(S)-2-Methylamino-N—[(S)-1-(4-piperazin-1-ylmethyl-naphthalen-1-ylmethyl)-2-oxo-2,3,4,5-tetrahydro-1H-benzo[b]azepin-3-yl]-propionamide hydrochloride (Example 49s);

(S)—N—[(S)-1-(8-Cyclopropyl-naphthalen-1-ylmethyl)-2-oxo-2,3,4,5-tetrahydro-1H-benzo[b]azepin-3-yl]-2-methylamino-propionamide hydrochloride (Example 49t);

(S)—N—[(S)-1-(2-Methoxy-6-phenyl-naphthalen-1-ylmethyl)-2-oxo-2,3,4,5-tetrahydro-1H-benzo[b]azepin-3-yl]-2-methylamino-propionamide hydrochloride (Example 49u);

6-Methoxy-5-[(S)-3-((S)-2-methylamino-propionylamino)-2-oxo-2,3,4,5-tetrahydro-benzo[b]azepin-1-ylmethyl]-naphthalene-2-carboxylic acid methyl ester hydrochloride (Example 50);

6-Methoxy-5-[(S)-3-((S)-2-methylamino-propionylamino)-2-oxo-2,3,4,5-tetrahydro-benzo[b]azepin-1-ylmethyl]-naphthalene-2-carboxylic acid (Example 51);

(S)—N—[(S)-1-(6-Methanesulfonylaminocarbonyl-2-methoxy-naphthalen-1-ylmethyl)-2-oxo-2,3,4,5-tetrahydro-1H-benzo[b]azepin-3-yl]-2-methylamino-propionamide (Example 52a);

(S)—N—{(S)-1-[2-Methoxy-5-(propane-1-sulfonylaminocarbonyl)-naphthalen-1-ylmethyl]-2-oxo-2,3,4,5-tetrahydro-1H-benzo[b]azepin-3-yl}-2-methylamino-propionamide hydrochloride (Example 52b);

(S)—N—[(S)-1-(5-Methanesulfonylaminocarbonyl-2-methoxy-naphthalen-1-ylmethyl)-2-oxo-2,3,4,5-tetrahydro-1H-benzo[b]azepin-3-yl]-2-methylamino-propionamide hydrochloride (Example 52c);

(S)—N—{(S)-1-[2-Methoxy-6-(propane-1-sulfonylaminocarbonyl)-naphthalen-1-ylmethyl]-2-oxo-2,3,4,5-tetrahydro-1H-benzo[b]azepin-3-yl}-2-methylamino-propionamide hydrochloride (Example 52d);

6-Methoxy-5-[(S)-3-((S)-2-methylamino-propionylamino)-2-oxo-2,3,4,5-tetrahydro-benzo[b]azepin-1-ylmethyl]-naphthalene-1-carboxylic acid methyl ester hydrochloride (Example 52e);

5-[(S)-3-((S)-2-Methylamino-propionylamino)-2-oxo-2,3,4,5-tetrahydro-benzo[b]azepin-1-ylmethyl]-naphthalene-1-carboxylic acid hydrochloride (Example 52θ);

5-[(S)-3-((S)-2-Methylamino-propionylamino)-2-oxo-2,3,4,5-tetrahydro-benzo[b]azepin-1-ylmethyl]-naphthalene-1-carboxylic acid methyl ester hydrochloride (Example 52 g);

7-Methoxy-8-[(S)-3-((S)-2-methylamino-propionylamino)-2-oxo-2,3,4,5-tetrahydro-benzo[b]azepin-1-ylmethyl]-naphthalene-2-carboxylic acid methyl ester hydrochloride (Example 52 h);

(S)—N—[(S)-1-(5-Cyano-2-methoxy-naphthalen-1-ylmethyl)-2-oxo-2,3,4,5-tetrahydro-1H-benzo[b]azepin-3-yl]-2-methylamino-propionamide hydrochloride (Example 53);

5-[(S)-3-((S)-2-Methylamino-propionylamino)-2-oxo-2,3,4,5-tetrahydro-benzo[b]azepin-1-ylmethyl]-naphthalene-1-carboxylic acid amide (Example 54a);

6-Methoxy-5-[(S)-3-((S)-2-methylamino-propionylamino)-2-oxo-2,3,4,5-tetrahydro-benzo[b]azepin-1-ylmethyl]-naphthalene-2-carboxylic acid amide hydrochloride (Example 54b);

(S)—N—[(S)-1-(7-Cyano-2-methoxy-naphthalen-1-ylmethyl)-2-oxo-2,3,4,5-tetrahydro-1H-benzo[b]azepin-3-yl]-2-methylamino-propionamide hydrochloride (Example 54c);

(S)—N—[(S)-1-(6-Cyano-2-methoxy-naphthalen-1-ylmethyl)-2-oxo-2,3,4,5-tetrahydro-1H-benzo[b]azepin-3-yl]-2-methylamino-propionamide hydrochloride (Example 54d);

(S)—N—[(S)-1-(5-Cyano-naphthalen-1-ylmethyl)-2-oxo-2,3,4,5-tetrahydro-1H-benzo[b]azepin-3-yl]-2-methylamino-propionamide hydrochloride (Example 54e);

(S)—N—[(S)-1-(7-Cyano-naphthalen-1-ylmethyl)-2-oxo-2,3,4,5-tetrahydro-1H-benzo[b]azepin-3-yl]-2-methylamino-propionamide hydrochloride (Example 54f);

8-[(S)-3-((S)-2-Methylamino-propionylamino)-2-oxo-2,3,4,5-tetrahydro-benzo[b]azepin-1-ylmethyl]-naphthalene-2-carboxylic acid amide hydrochloride (Example 54 g);

(S)—N—[(S)-1-(8-Cyano-naphthalen-1-ylmethyl)-2-oxo-2,3,4,5-tetrahydro-1H-benzo[b]azepin-3-yl]-2-methylamino-propionamide hydrochloride (Example 54 h);

(S)—N—((S)-1-((6-Bromo-2-methoxynaphthalen-1-yl)methyl)-2-oxo-2,3,4,5-tetrahydro-1H-benzo[b]azepin-3-yl)-2-(methylamino)butanamide trifluoroacetate (Example 58);

(S)—N—((S)-1-((6-Bromo-2-methoxynaphthalen-1-yl)methyl)-2-oxo-2,3,4,5-tetrahydro-1H-benzo[b]azepin-3-yl)-2-(propylamino)propanamide (Example 59);

(S)—N—((S)-1-((6-Bromo-2-methoxynaphthalen-1-yl)methyl)-2-oxo-2,3,4,5-tetrahydro-1H-benzo[b]azepin-3-yl)-2-(isobutylamino)propanamide (Example 60);

(S)—N—((S)-1-((6-Bromo-2-methoxynaphthalen-1-yl)methyl)-2-oxo-2,3,4,5-tetrahydro-1H-benzo[b]azepin-3-yl)-2-(ethylamino)propanamide hydrochloride (Example 61);

(S)-2-(Azetidin-3-ylamino)-N—((S)-1-((6-bromo-2-methoxynaphthalen-1-yl)methyl)-2-oxo-2,3,4,5-tetrahydro-1H-benzo[b]azepin-3-yl)propanamide dihydrochloride (Example 62);

(S)—N—((S)-1-((6-Bromo-2-methoxynaphthalen-1-yl)methyl)-2-oxo-2,3,4,5-tetrahydro-1H-benzo[b]azepin-3-yl)-2-(ethylamino)butanamide hydrochloride (Example 63);

(S)—N—((S)-1-((5-Fluoro-2-methoxynaphthalen-1-yl)methyl)-2-oxo-2,3,4,5-tetrahydro-1H-benzo[b]azepin-3-yl)-2-(methylamino)propanamide hydrochloride (Example 64);

(S)—N—((S)-1-((6-Fluoro-2-methoxynaphthalen-1-yl)methyl)-2-oxo-2,3,4,5-tetrahydro-1H-benzo[b]azepin-3-yl)-2-(methylamino)propanamide hydrochloride (Example 65);

(S)—N—((S)-1-((6-Chloro-2-methoxynaphthalen-1-yl)methyl)-2-oxo-2,3,4,5-tetrahydro-1H-benzo[b]azepin-3-yl)-2-(methylamino)propanamide hydrochloride (Example 66);

(S)—N—((S)-1-((6-Bromo-2-methoxynaphthalen-1-yl)methyl)-2-oxo-2,3,4,5-tetrahydro-1H-benzo[b]azepin-3-yl)-2-(cyclopropylmethylamino)propanamide (Example 67);

(S)-2-Methylamino-N—{(S)-2-oxo-1-[5-(1H-tetrazol-5-yl)-naphthalen-1-ylmethyl]-2,3,4,5-tetrahydro-1H-benzo[b]azepin-3-yl}-propionamide hydrochloride (Example 69); and (S)—N—((S)-1-((5-Acetyl-2-methoxynaphthalen-1-yl)methyl)-2-oxo-2,3,4,5-tetrahydro-1H-benzo[b]azepin-3-yl)-2-(methylamino)propanamide hydrochloride (Example 70);

or a pharmaceutically acceptable salt of any of the foregoing compounds.

Compounds according to the invention wherein Z is aryl that is phenyl include:

(S)—N—[(S)-1-(5-Fluoro-2-methoxy-benzyl)-2-oxo-2,3,4,5-tetrahydro-1H-benzo[b]azepin-3-yl]-2-methylamino-propionamide hydrochloride (Example 1a);

(S)—N—[(S)-1-(2-Methoxy-5-trifluoromethyl-benzyl)-2-oxo-2,3,4,5-tetrahydro-1H-benzo[b]azepin-3-yl]-2-methylamino-propionamide hydrochloride (Example 1c);

(S)—N—[(S)-1-(4,5-Difluoro-2-methoxy-benzyl)-2-oxo-2,3,4,5-tetrahydro-1H-benzo[b]azepin-3-yl]-2-methylamino-propionamide hydrochloride (Example 1d);

(S)—N—[(S)-1-(5-Bromo-2-methoxy-benzyl)-2-oxo-2,3,4,5-tetrahydro-1H-benzo[b]azepin-3-yl]-2-methylamino-propionamide hydrochloride (Example 1e);

(S)—N—[(S)-1-(5-Chloro-2-methoxy-benzyl)-2-oxo-2,3,4,5-tetrahydro-1H-benzo[b]azepin-3-yl]-2-methylamino-propionamide hydrochloride (Example 1f);

(S)—N—[(S)-1-(2,5-Difluoro-benzyl)-2-oxo-2,3,4,5-tetrahydro-1H-benzo[b]azepin-3-yl]-2-methylamino-propionamide hydrochloride (Example 1 g);

(S)-2-Methylamino-N—((S)-2-oxo-1-pentafluorophenylmethyl-2,3,4,5-tetrahydro-1H-benzo[b]azepin-3-yl)-propionamide hydrochloride (Example 1 h);

(S)—N—[(S)-1-(4-Chloro-2-methoxy-benzyl)-2-oxo-2,3,4,5-tetrahydro-1H-benzo[b]azepin-3-yl]-2-methylamino-propionamide hydrochloride (Example 1i);

(S)—N—[(S)-1-(4-Bromo-2-methoxy-benzyl)-2-oxo-2,3,4,5-tetrahydro-1H-benzo[b]azepin-3-yl]-2-methylamino-propionamide hydrochloride (Example 1j);

(S)—N—[(S)-1-(2,5-Dichloro-benzyl)-2-oxo-2,3,4,5-tetrahydro-1H-benzo[b]azepin-3-yl]-2-methylamino-propionamide hydrochloride (Example 1l);

(S)—N—[(S)-1-(5-Chloro-2-fluoro-benzyl)-2-oxo-2,3,4,5-tetrahydro-1H-benzo[b]azepin-3-yl]-2-methylamino-propionamide hydrochloride (Example 1m);

(S)—N—[(S)-1-(5-Iodo-2-methoxy-benzyl)-2-oxo-2,3,4,5-tetrahydro-1H-benzo[b]azepin-3-yl]-2-methylamino-propionamide hydrochloride (Example 1n);

(S)—N—[(S)-1-(5-Isopropyl-2-methoxy-benzyl)-2-oxo-2,3,4,5-tetrahydro-1H-benzo[b]azepin-3-yl]-2-methylamino-propionamide hydrochloride (Example 1o);

(S)—N—((S)-1-Benzyl-8-benzyloxy-2-oxo-2,3,4,5-tetrahydro-1H-benzo[b]azepin-3-yl)-2-methylamino-propionamide hydrochloride (Example 22);

(S)—N—((S)-1-Benzyl-2-oxo-8-phenethyloxy-2,3,4,5-tetrahydro-1H-benzo[b]azepin-3-yl)-2-methylamino-propionamide hydrochloride (Example 23);

(S)—N—((S)-1-Benzyl-8-methoxy-2-oxo-2,3,4,5-tetrahydro-1H-benzo[b]azepin-3-yl)-2-methylamino-propionamide hydrochloride (Example 24);

(S)—N—[(S)-1-Benzyl-2-oxo-8-(3-phenyl-propoxy)-2,3,4,5-tetrahydro-1H-benzo[b]azepin-3-yl]-2-methylamino-propionamide hydrochloride (Example 25);

(S)-N-(1-Benzyl-8-bromo-2-oxo-2,3,4,5-tetrahydro-1H-benzo[b]azepin-3-yl)-2-methylamino-propionamide hydrochloride (Example 26);

(S)-2-Methylamino-N—[(S)-2-oxo-1-(2,3,5,6-tetramethyl-benzyl)-2,3,4,5-tetrahydro-1H-benzo[b]azepin-3-yl]-propionamide hydrochloride (Example 47ll);

(S)—N—[(S)-1-(2,3-Dimethyl-benzyl)-2-oxo-2,3,4,5-tetrahydro-1H-benzo[b]azepin-3-yl]-2-methylamino-propionamide hydrochloride (Example 47mm);

(S)—N—[(S)-1-(2-Chloro-benzyl)-2-oxo-2,3,4,5-tetrahydro-1H-benzo[b]azepin-3-yl]-2-methylamino-propionamide hydrochloride (Example 47oo);

(S)—N—[(S)-1-(2,6-Dimethyl-benzyl)-2-oxo-2,3,4,5-tetrahydro-1H-benzo[b]azepin-3-yl]-2-methylamino-propionamide hydrochloride (Example 47pp);

(S)—N—((S)-1-Benzyl-2-oxo-2,3,4,5-tetrahydro-1H-benzo[b]azepin-3-yl)-2-methylamino-propionamide hydrochloride (Example 47qq);

(S)—N—[(S)-1-(2,4-Dimethyl-benzyl)-2-oxo-2,3,4,5-tetrahydro-1H-benzo[b]azepin-3-yl]-2-methylamino-propionamide hydrochloride (Example 47a);

(S)-2-Methylamino-N—[(S)-1-(2-methyl-benzyl)-2-oxo-2,3,4,5-tetrahydro-1H-benzo[b]azepin-3-yl]-propionamide hydrochloride (Example 47ss);

(S)—N-(1-Biphenyl-2-ylmethyl-2-oxo-2,3,4,5-tetrahydro-1H-benzo[b]azepin-3-yl)-2-methylamino-propionamide hydrochloride (Example 55a);

(S)—N-(1-Biphenyl-3-ylmethyl-2-oxo-2,3,4,5-tetrahydro-1H-benzo[b]azepin-3-yl)-2-methylamino-propionamide hydrochloride (Example 55b);

(S)-2-Methylamino-N-[1-(6-methyl-biphenyl-3-ylmethyl)-2-oxo-2,3,4,5-tetrahydro-1H-benzo[b]azepin-3-yl]-propionamide hydrochloride (Example 55d);

(S)—N-(1-Benzyl-2-oxo-2,3,4,5-tetrahydro-1H-benzo[b]azepin-3-yl)-2-methylamino-propionamide hydrochloride (Example 55e); and (S)—N-(1-Biphenyl-4-ylmethyl-2-oxo-2,3,4,5-tetrahydro-1H-benzo[b]azepin-3-yl)-2-methylamino-propionamide hydrochloride (Example 55f);

or a pharmaceutically acceptable salt of any of the foregoing compounds.

Compounds according to the invention wherein Z is aryl fused with $C_{3-7}$-cycloalkyl include:

(S)—N—[(S)-1-(2-Methoxy-5,6,7,8-tetrahydro-naphthalen-1-ylmethyl)-2-oxo-2,3,4,5-tetrahydro-1H-benzo[b]azepin-3-yl]-2-methylamino-propionamide hydrochloride (Example 44), or a pharmaceutically acceptable salt of the foregoing compound.

Compounds according to the invention wherein Z is heteroaryl include:

(S)-2-Methylamino-N—[(S)-1-(1-methyl-1H-indazol-3-ylmethyl)-2-oxo-2,3,4,5-tetrahydro-1H-benzo[b]azepin-3-yl]-propionamide hydrochloride (Example 1b);

(S)—N—((S)-1-Benzo[d]isoxazol-3-ylmethyl-2-oxo-2,3,4,5-tetrahydro-1H-benzo[b]azepin-3-yl)-2-methylamino-propionamide hydrochloride (Example 1k);

(S)-2-(Methylamino)-N—((S)-2-oxo-1-(thiophen-2-ylmethyl)-2,3,4,5-tetrahydro-1H-benzo[b]azepin-3-yl)propanamide hydrochloride (Example 2a);

(S)-2-Methylamino-N—((S)-2-oxo-1-thiophen-3-ylmethyl-2,3,4,5-tetrahydro-1H-benzo[b]azepin-3-yl)-propionamide hydrochloride (Example 2b);

(S)-2-Methylamino-N—((S)-2-oxo-1-thiazol-5-ylmethyl-2,3,4,5-tetrahydro-1H-benzo[b]azepin-3-yl)-propionamide hydrochloride (Example 2c);

(S)-2-Methylamino-N—((S)-2-oxo-1-thiazol-2-ylmethyl-2,3,4,5-tetrahydro-1H-benzo[b]azepin-3-yl)-propionamide hydrochloride (Example 2d);

(S)-2-Methylamino-N—((S)-1-oxazol-5-ylmethyl-2-oxo-2,3,4,5-tetrahydro-1H-benzo[b]azepin-3-yl)-propionamide hydrochloride (Example 2e);

(S)-2-Methylamino-N—((S)-2-oxo-1-pyridin-3-ylmethyl-2,3,4,5-tetrahydro-1H-benzo[b]azepin-3-yl)-propionamide hydrochloride (Example 2f);

(S)-2-Methylamino-N—((S)-2-oxo-1-pyridin-2-ylmethyl-2,3,4,5-tetrahydro-1H-benzo[b]azepin-3-yl)-propionamide hydrochloride (Example 2 g);

(S)-2-Methylamino-N—((S)-2-oxo-1-pyridin-4-ylmethyl-2,3,4,5-tetrahydro-1H-benzo[b]azepin-3-yl)-propionamide hydrochloride (Example 2 h);

(S)-2-Methylamino-N—[(S)-1-(3-methyl-3H-imidazol-4-ylmethyl)-2-oxo-2,3,4,5-tetrahydro-1H-benzo[b]azepin-3-yl]-propionamide hydrochloride (Example 2i);

(S)-2-Amino-N—((S)-1-((3-methoxyquinolin-4-yl)methyl)-2-oxo-2,3,4,5-tetrahydro-1H-benzo[b]azepin-3-yl)butanamide (Example 3);

(S)-2-(2-Hydroxyethylamino)-N—((S)-1-((3-methoxyquinolin-4-yl)methyl)-2-oxo-2,3,4,5-tetrahydro-1H-benzo[b]azepin-3-yl)butanamide (Example 4);

(S)—N—[(S)-1-(5-Bromo-benzo[b]thiophen-3-ylmethyl)-2-oxo-2,3,4,5-tetrahydro-1H-benzo[b]azepin-3-yl]-2-methylamino-propionamide hydrochloride (Example 19);

(S)—N—((S)-1-Benzo[b]thiophen-3-ylmethyl-2-oxo-2,3,4,5-tetrahydro-1H-benzo[b]azepin-3-yl)-2-methylamino-propionamide (Example 20);

(S)-2-Methylamino-N—((S)-2-oxo-1-quinolin-4-ylmethyl-2,3,4,5-tetrahydro-1H-benzo[b]azepin-3-yl)-propionamide hydrochloride (Example 47d);

(S)-2-Methylamino-N—((S)-2-oxo-1-quinolin-5-ylmethyl-2,3,4,5-tetrahydro-1H-benzo[b]azepin-3-yl)-propionamide hydrochloride (Example 47e);

(S)—N—[(S)-1-(3-Ethynyl-quinolin-4-ylmethyl)-2-oxo-2,3,4,5-tetrahydro-1H-benzo[b]azepin-3-yl]-2-methylamino-propionamide hydrochloride (Example 47j);

(S)—N—[(S)-1-(3-Methoxy-[1,8]naphthyridin-4-ylmethyl)-2-oxo-2,3,4,5-tetrahydro-1H-benzo[b]azepin-3-yl]-2-methylamino-propionamide hydrochloride (Example 47m);

(S)—N—[(S)-1-(2-Chloro-3-methyl-quinolin-4-ylmethyl)-2-oxo-2,3,4,5-tetrahydro-1H-benzo[b]azepin-3-yl]-2-methylamino-propionamide hydrochloride (Example 47n);

(S)-2-Methylamino-N—[(S)-1-(3-methyl-quinolin-4-ylmethyl)-2-oxo-2,3,4,5-tetrahydro-1H-benzo[b]azepin-3-yl]-propionamide hydrochloride (Example 47q);

(S)—N—[(S)-1-(3-Chloro-[1,8]naphthyridin-4-ylmethyl)-2-oxo-2,3,4,5-tetrahydro-1H-benzo[b]azepin-3-yl]-2-methylamino-propionamide hydrochloride (Example 47r);

(S)-2-Methylamino-N—{(S)-2-oxo-1-[3-(2,2,2-trifluoro-ethoxy)-quinolin-4-ylmethyl]-2,3,4,5-tetrahydro-1H-benzo[b]azepin-3-yl}-propionamide hydrochloride (Example 47t);

(S)-2-Methylamino-N—[(S)-1-(3-methyl-isoquinolin-4-ylmethyl)-2-oxo-2,3,4,5-tetrahydro-1H-benzo[b]azepin-3-yl]-propionamide hydrochloride (Example 47u);

(S)—N—((S)-1-Isoquinolin-4-ylmethyl-2-oxo-2,3,4,5-tetrahydro-1H-benzo[b]azepin-3-yl)-2-methylamino-propionamide hydrochloride (Example 47z);

(S)—N—((S)-1-Cinnolin-4-ylmethyl-2-oxo-2,3,4,5-tetrahydro-1H-benzo[b]azepin-3-yl)-2-methylamino-propionamide hydrochloride (Example 47aa);

(S)-2-Methylamino-N—((S)-1-[1,8]naphthyridin-4-ylmethyl-2-oxo-2,3,4,5-tetrahydro-1H-benzo[b]azepin-3-yl)-propionamide hydrochloride (Example 47cc);

(S)—N—[(S)-1-(3-Methoxy-quinolin-4-ylmethyl)-2-oxo-2,3,4,5-tetrahydro-1H-benzo[b]azepin-3-yl]-2-methylamino-propionamide hydrochloride (Example 47ii);

(S)—N—((S)-1-Benzo[b]thiophen-7-ylmethyl-2-oxo-2,3,4,5-tetrahydro-1H-benzo[b]azepin-3-yl)-2-methylamino-propionamide hydrochloride (Example 47jj);

(S)-2-Methylamino-N—[(S)-2-oxo-1-(1-oxy-quinolin-4-ylmethyl)-2,3,4,5-tetrahydro-1H-benzo[b]azepin-3-yl]-propionamide hydrochloride (Example 48);

(S)-2-Methylamino-N-[2-oxo-1-(3-phenyl-isoxazol-5-ylmethyl)-2,3,4,5-tetrahydro-1H-benzo[b]azepin-3-yl]-propionamide hydrochloride (Example 55c);

(S)—N—((S)-1-((3-Cyclopropylquinolin-4-yl)methyl)-2-oxo-2,3,4,5-tetrahydro-1H-benzo[b]azepin-3-yl)-2-(methylamino)propanamide dihydrochloride (Example 56); and (S)—N—((S)-1-((2,6-Bis(trifluoromethyl)quinolin-4-yl)methyl)-2-oxo-2,3,4,5-tetrahydro-1H-benzo[b]azepin-3-yl)-2-(methylamino)propanamide hydrochloride (Example 57);

or a pharmaceutically acceptable salt of any of the foregoing compounds.

In a particular embodiment, the invention relates to compounds wherein Z is naphthalenyl, said compounds being selected from the following group:

(S)—N—[(S)-1-(6-Bromo-2-methoxy-naphthalen-1-ylmethyl)-2-oxo-2,3,4,5-tetrahydro-1H-benzo[b]azepin-3-yl]-2-methylamino-propionamide hydrochloride (Example 29);

(S)—N—[(S)-1-(2-Ethoxy-naphthalen-1-ylmethyl)-2-oxo-2,3,4,5-tetrahydro-1H-benzo[b]azepin-3-yl]-2-methylamino-propionamide hydrochloride (Example 47y);

(S)—N—[(S)-1-(5-Bromo-2-methoxy-naphthalen-1-ylmethyl)-2-oxo-2,3,4,5-tetrahydro-1H-benzo[b]azepin-3-yl]-2-methylamino-propionamide hydrochloride (Example 47o);

(S)—N—[(S)-1-(5-Cyano-2-methoxy-naphthalen-1-ylmethyl)-2-oxo-2,3,4,5-tetrahydro-1H-benzo[b]azepin-3-yl]-2-methylamino-propionamide hydrochloride (Example 53);

(S)-2-Methylamino-N—{(S)-2-oxo-1-[2-(2,2,2-trifluoro-ethoxy)-naphthalen-1-ylmethyl]-2,3,4,5-tetrahydro-1H-benzo[b]azepin-3-yl}-propionamide hydrochloride (Example 47p);

(S)—N—[(S)-1-(2-Methoxy-6-trifluoromethyl-naphthalen-1-ylmethyl)-2-oxo-2,3,4,5-tetrahydro-1H-benzo[b]azepin-3-yl]-2-methylamino-propionamide hydrochloride (Example 47l);

(S)—N—[(S)-1-(2-Chloro-naphthalen-1-ylmethyl)-2-oxo-2,3,4,5-tetrahydro-1H-benzo[b]azepin-3-yl]-2-methylamino-propionamide hydrochloride (Example 47x);

(S)—N—((S)-1-((5-Fluoro-2-methoxynaphthalen-1-yl)methyl)-2-oxo-2,3,4,5-tetrahydro-1H-benzo[b]azepin-3-yl)-2-(methylamino)propanamide (Example 64);

(S)—N—((S)-1-((6-Fluoro-2-methoxynaphthalen-1-yl)methyl)-2-oxo-2,3,4,5-tetrahydro-1H-benzo[b]azepin-3-yl)-2-(methylamino)propanamide (Example 65); and (S)—N—((S)-1-((6-Chloro-2-methoxynaphthalen-1-yl)methyl)-2-oxo-2,3,4,5-tetrahydro-1H-benzo[b]azepin-3-yl)-2-(methylamino)propanamide hydrochloride (Example 66);

or a pharmaceutically acceptable salt of any of the foregoing compounds.

In a particular embodiment, the invention relates to compounds wherein Z is quinolinyl,
said compounds being selected from the following group:

(S)-2-Methylamino-N—((S)-2-oxo-1-quinolin-4-ylmethyl-2,3,4,5-tetrahydro-1H-benzo[b]azepin-3-yl)-propionamide hydrochloride (Example 47d);

(S)-2-Methylamino-N—((S)-2-oxo-1-quinolin-5-ylmethyl-2,3,4,5-tetrahydro-1H-benzo[b]azepin-3-yl)-propionamide hydrochloride (Example 47e);

(S)—N—[(S)-1-(3-Methoxy-quinolin-4-ylmethyl)-2-oxo-2,3,4,5-tetrahydro-1H-benzo[b]azepin-3-yl]-2-methylamino-propionamide hydrochloride (Example 47ii);

(S)—N—((S)-1-Isoquinolin-4-ylmethyl-2-oxo-2,3,4,5-tetrahydro-1H-benzo[b]azepin-3-yl)-2-methylamino-propionamide hydrochloride (Example 47z);

(S)-2-Methylamino-N—{(S)-2-oxo-1-[3-(2,2,2-trifluoro-ethoxy)-quinolin-4-ylmethyl]-2,3,4,5-tetrahydro-1H-benzo[b]azepin-3-yl}-propionamide hydrochloride (Example 47t);

(S)-2-Methylamino-N—[(S)-1-(3-methyl-quinolin-4-ylmethyl)-2-oxo-2,3,4,5-tetrahydro-1H-benzo[b]azepin-3-yl]-propionamide hydrochloride (Example 47q);

(S)—N—[(S)-1-(3-Ethynyl-quinolin-4-ylmethyl)-2-oxo-2,3,4,5-tetrahydro-1H-benzo[b]azepin-3-yl]-2-methyl-amino-propionamide hydrochloride (Example 47j);

(S)-2-Methylamino-N—[(S)-1-(3-methyl-isoquinolin-4-yl-methyl)-2-oxo-2,3,4,5-tetrahydro-1H-benzo[b]azepin-3-yl]-propionamide hydrochloride (Example 47u);

(S)—N—[(S)-1-(2-Chloro-3-methyl-quinolin-4-ylmethyl)-2-oxo-2,3,4,5-tetrahydro-1H-benzo[b]azepin-3-yl]-2-methylamino-propionamide hydrochloride (Example 47n); and (S)—N—((S)-1-((3-Cyclopropylquinolin-4-yl)methyl)-2-oxo-2,3,4,5-tetrahydro-1H-benzo[b]azepin-3-yl)-2-(methylamino)propanamide dihydrochloride (Example 56);

or a pharmaceutically acceptable salt of any of the foregoing compounds.

In a particular embodiment, the invention relates to compounds wherein Z is indazolyl, cinnolinyl, naphthyridinyl, benzoisoxazolyl or benzothiophenyl, said compounds being selected from the following group:

(S)-2-Methylamino-N—[(S)-1-(1-methyl-1H-indazol-3-yl-methyl)-2-oxo-2,3,4,5-tetrahydro-1H-benzo[b]azepin-3-yl]-propionamide hydrochloride (Example 1b);

(S)—N—((S)-1-Cinnolin-4-ylmethyl-2-oxo-2,3,4,5-tetrahydro-1H-benzo[b]azepin-3-yl)-2-methylamino-propionamide hydrochloride (Example 47aa);

(S)-2-Methylamino-N—((S)-1-[1,8]naphthyridin-4-ylmethyl-2-oxo-2,3,4,5-tetrahydro-1H-benzo[b]azepin-3-yl)-propionamide hydrochloride (Example 47cc);

(S)—N—[(S)-1-(3-Methoxy-[1,8]naphthyridin-4-ylmethyl)-2-oxo-2,3,4,5-tetrahydro-1H-benzo[b]azepin-3-yl]-2-methylamino-propionamide hydrochloride (Example 47m);

(S)—N—[(S)-1-(3-Chloro-[1,8]naphthyridin-4-ylmethyl)-2-oxo-2,3,4,5-tetrahydro-1H-benzo[b]azepin-3-yl]-2-methylamino-propionamide hydrochloride (Example 47r);

(S)—N—((S)-1-Benzo[d]isoxazol-3-ylmethyl-2-oxo-2,3,4,5-tetrahydro-1H-benzo[b]azepin-3-yl)-2-methylamino-propionamide hydrochloride (Example 1k); and (S)—N—((S)-1-Benzo[b]thiophen-3-ylmethyl-2-oxo-2,3,4,5-tetrahydro-1H-benzo[b]azepin-3-yl)-2-methylamino-propionamide (Example 20);

or a pharmaceutically acceptable salt of any of the foregoing compounds.

The compounds of Formula I as well as their salts have at least one asymmetric carbon atom and therefore may be present as mixtures of different stereoisomers. The various isomers can be isolated by known separation methods, e.g., chromatography.

Compounds disclosed herein and covered by formula I above may exhibit tautomerism (e.g. Example 33) or structural isomerism. It is intended that the invention encompasses any tautomeric or structural isomeric form of these compounds, or mixtures of such forms, and is not limited to any one tautomeric or structural isomeric form depicted in the formulas above.

Dosages

The compounds of the invention preferably bind to BIR domains of an IAP preventing the IAP from binding to other proteins. Examples of Bir binding proteins include, but are not limited to, caspase 3, caspase 7, caspase 9, Smac and the like. Examples of IAPs include, but are not limited to, XIAP, cIAP1, cIAP2 or NAIP. In one aspect, the compound of the invention bind to the BIR2 and/or BIR3 domains of XIAP, cIAP1 and/or cIAP2. In another aspect, the compounds of the invention bind to the BIR2 domain of XIAP, cIAP1 and/or cIAP2.

Compounds of the invention are useful for inducing apoptosis in cells or sensitizing cells to apoptotic signals, in particular cancer cells. Apoptotic signals can be induced in cancer cells by, e.g., radiation therapy or antineoplastic chemotherapy. Alternatively, apoptotic signals can be induced in cancer cells by activation of the death receptors by death receptor agonists. Death receptor agonists can be naturally occurring, e.g., tumor necrosis factor α, (TNF-α) or non-naturally occurring, e.g., a synthetic antibody such as a DR4 or DR5 antibody.

The compounds of the present invention are thus useful in the amelioration, control or treatment of cell proliferative disorders such as, in particular, oncological disorders. These compounds and formulations containing said compounds are anticipated to be useful in the treatment or control of blood cancers, such as, for example, acute myeloid leukemia, or solid tumors, such as, for example, breast, colon, lung and prostate tumors.

A "therapeutically effective amount" or "effective amount" of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as one or more bolus injections or as a continuous infusion.

Pharmaceutical preparations useful in the practice of the invention, i.e., comprising the compounds of the invention can be administered internally, such as orally (e.g. in the form of tablets, coated tablets, dragees, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions). Moreover, administration can be effected topically (e.g. in the form of ointments, creams or oils).

Compositions/Formulations

In an alternative embodiment, the present invention includes pharmaceutical compositions comprising at least one compound of formula I, or a pharmaceutically acceptable salt thereof, and a pharmaceutically acceptable excipient and/or carrier.

These pharmaceutical compositions can be suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

The compounds of Formula I and their pharmaceutically acceptable salts and esters can be processed with pharmaceutically inert, inorganic or organic adjuvants for the production of tablets, coated tablets, dragees and hard gelatin capsules. Lactose, polyvinylpyrrolidone, hydroxypropylmethylcellulose, hydroxypropylcellulose, microcrystalline cellulose, corn starch or derivatives thereof, talc, stearic acid or its salts etc. can be used, for example, as such adjuvants for tablets, dragees and hard gelatin capsules.

Suitable adjuvants for soft gelatin capsules, are, for example, vegetable oils, waxes, fats, semi-solid substances and liquid polyols, etc. Suitable adjuvants for the production of solutions and syrups are, for example, H$_2$O, polyols, saccharose, invert sugar, glucose, etc. Suitable adjuvants for injection solutions are, for example, H$_2$O, alcohols, polyols, glycerol, vegetable oils, etc. Suitable adjuvants for suppositories are, for example, natural or hardened oils, waxes, fats, semi-solid or liquid polyols, etc. Suitable adjuvants for topical preparations are glycerides, semi-synthetic and synthetic glycerides, hydrogenated oils, liquid waxes, liquid paraffins, liquid fatty alcohols, sterols, polyethylene glycols and cellulose derivatives.

Moreover, the pharmaceutical preparations can contain preservatives, solubilizers, viscosity-increasing substances, stabilizers, wetting agents, emulsifiers, sweeteners, colorants, flavors, salts for varying the osmotic pressure, buffers, masking agents or antioxidants. They can also contain other therapeutic substances.

The compounds in the present invention (compounds of general Formula I) can be prepared using the general reaction scheme set out in Scheme 1 below.

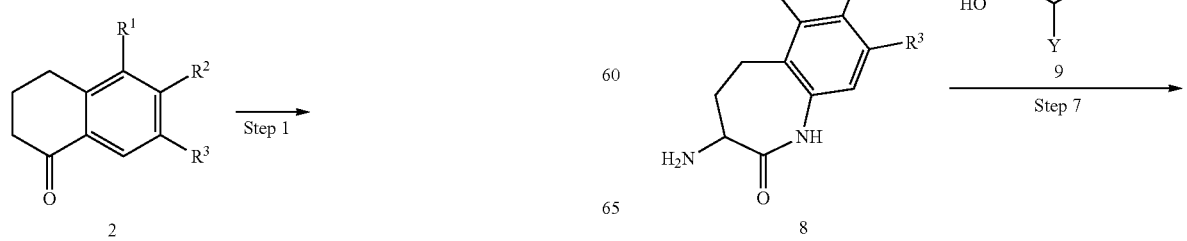

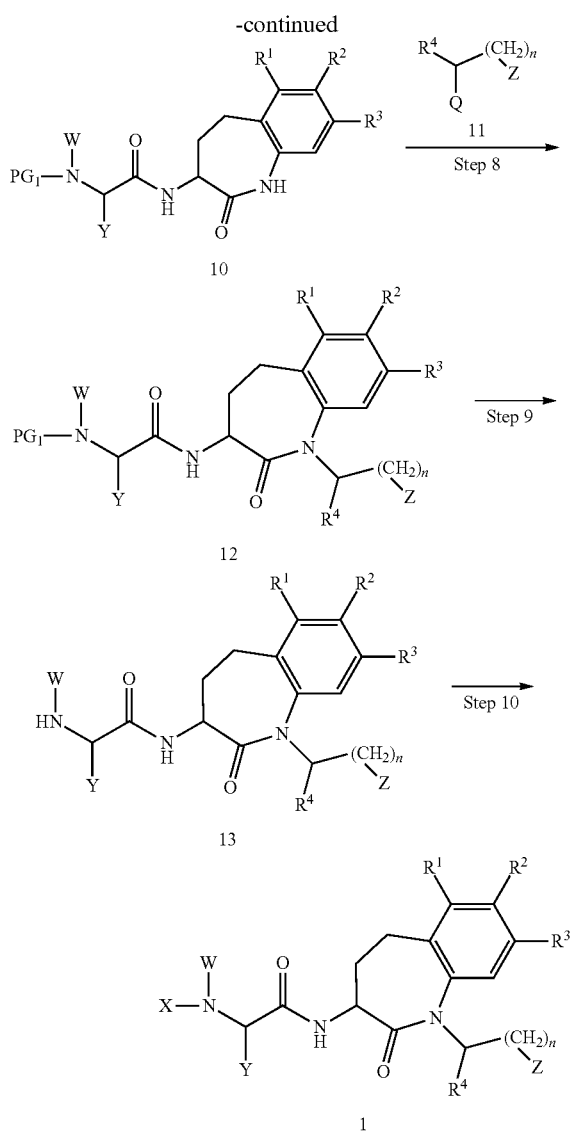

Step 1: A substituted or unsubstituted 3,4-dihydro-2H-naphthalen-1-one of general formula 2 can be converted to an oxime of general formula 3. Those skilled in the art will recognize there are several methods to achieve this conversion including, but not limited to, treating ketone 2 with hydroxylamine hydrochloride in an appropriate solvent, e.g., methanol or ethanol, at an appropriate temperature ranging from about −20° C. to about 120° C., for an amount of time sufficient to carry out this transformation. Additional methods have been described in a recent review: Synthesis of oximes and hydroxamic acids by Porcheddu and Giacomelli in Chemistry of Hydroxylamines, Oximes and Hydroxamic Acids (2009), (Pt. 1), 163-231, published by John Wiley & Sons Ltd., Chichester, UK.

Step 2: Those skilled in the art will recognize there are several methods to convert compounds of general formula 3 to compounds of general formula 4, where $A_1$ is a sulfonyl group. These include, but are not limited to, treating compounds of general formula 3 with a sulfonating agent, e.g., mesyl chloride or tosyl chloride, and a base, e.g., pyridine, in an appropriate solvent, e.g., dichloromethane (DCM) at an appropriate temperature, ranging from about −20° C. to about 120° C. for an amount of time sufficient to carry out this transformation.

Step 3: Those skilled in the art will recognize there are several methods to convert compounds of general formula 4 to compounds of general formula 5. These include, but are not limited to, treating compounds of general formula 4 with a base, e.g., KOAc or NaOAc, in an appropriate solvent or solvent mixture, e.g., 95%, EtOH or MeOH or a mixture of water and an alcohol, at an appropriate temperature ranging from about 20° C. to about 150° C., for an amount of time sufficient to carry out this transformation.

For a review of transformations described in Steps 2 and 3, see Gawley, The Beckmann Reactions: Rearrangements, Elimination-Additions, Fragmentations, and Rearrangement-Cyclizations, Organic Reactions 1988, 35, 1-420.

Those skilled in the art will also recognize that compounds of general formula 3 can also be converted directly to compounds of general formula 5. Methods to achieve this conversion include, but are not limited to, treating compounds of general formula 3 with an acid, e.g., sulfuric acid or polyphosphoric acid, at an appropriate temperature ranging from about 20° C. to about 150° C., for an amount of time sufficient to carry out this transformation. This type of transformation has been reviewed (Gawley, cited above).

Step 4: A leaving group such as a halogen, e.g., Br or I, can be added to compounds of general formula 5 resulting in the formation of compounds of general formula 6 where $A_2$ is a leaving group, such as Br or I. For example, compounds of general formula 5 can be treated with a base, such as triethylamine (TEA), in an appropriate solvent or solvent mixture, e.g., DCM or tetrahydrofuran (THF) or a mixture of DCM and THF, followed by adding trimethylsilyl iodide (TMSI) and a halogenating agent, e.g., $I_2$, at an appropriate temperature ranging from about −20° C. to about 120° C., for an amount of time sufficient to carry out this transformation.

Step 5: Compounds of general formula 6 can be converted to compounds of general formula 7. Step 5 is most conveniently performed by treating compounds of general formula 6 with, e.g., sodium azide in an in an appropriate solvent, e.g., dimethylformamide (DMF) at an appropriate temperature, ranging from about −20° C. to about 120° C. for an amount of time sufficient to carry out this transformation.

Step 6: This step involves the reduction of the azido group in compounds of general formula 7. Those skilled in the art will recognize there are several methods to accomplish this reduction including catalytic hydrogenation and chemical reduction. The choice of reduction method will be influenced by the substitution on the phenyl ring indicated by $R^1$, $R^2$ and $R^3$ so that unwanted side reactions do not occur. For example, compounds of general formula 7 can treated with an appropriate hydrogenation catalyst, e.g., 10% Pd/C, in an appropriate solvent, e.g., EtOH, and subjected to hydrogenation at pressures ranging from atmospheric pressure to elevated pressure, up to about 50 PSI for an amount of time sufficient to carry out this transformation. Alternatively, compounds of general formula 7 can treated with an appropriate chemical reducing agent, e.g. triphenylphosphine, in an appropriate solvent or solvent mixture, e.g., THF or a mixture of water and THF, at an appropriate temperature ranging from about 0° C. to about 150° C., for an amount of time sufficient to carry out this transformation.

Step 7: This step entails the coupling of a suitably protected α-amino-acid of general formula 9 to compounds of general formula 8, where $PG_1$ is a group that renders the α-amine Nitrogen inert to reaction conditions used in the rest of the synthetic sequence and W is defined as described above. Preferred choices for protecting group $PG_1$ may be made by reference to organic chemistry text books (e.g.

Protective Groups in Organic Synthesis, Theodora W. Greene et al.), general chemistry literature, or would be generally known to one knowledgeable in the art of organic synthesis. In particular, carbamate-based protecting groups, e.g. tert-butyloxycarbonyl and benzyloxycarbonyl, are preferred but other amine-protecting groups may also be effective. Those skilled in the art will recognize there are several methods using known peptide coupling reaction techniques to convert compounds of general formula 8 and compounds of general formula 9 to compounds of general formula 10. Typical peptide coupling reagents which may be employed include diimide based reagents, e.g. dicyclohexylcarbodiimide, (3-dimethylamino-propyl)-ethylcarbodiimide hydrochloride; or naphtha based reagents, e.g. O-benzotriazol-1-yl-N,N,N',N'-tetramethyluronium hexaflurorophosphate or O-benzotriazol-1-yl-N,N,N',N'-bis(tetramethylene)naphtha hexaflurorophosphate. Additionally, a catalyst can be optionally added to the reaction, e.g., 1-hydroxybenzotriazole or N-hydroxysuccinimide.

Alternative peptide coupling reagents may also effective in performing this conversion. Selection of alternative peptide coupling reagents may be made by reference to general chemistry literature or would be generally known to one knowledgeable in the art of organic synthesis.

Step 8: This step involves the reaction of compounds of general formula 10 with compounds of general formula 11 to form compounds of general formula 12, where Q is a suitable leaving group, e.g., a halogen such as Br or I, or a sulfonate ester, such as methanesulfonate ester. Step 8 can be accomplished by treating compounds of general formula 10 with a base and compounds of general formula 11 in a suitable solvent for an amount of time sufficient to carry out this transformation. The base used can be inorganic, e.g., $Cs_2CO_3$, or organic, e.g., lithium bis(trimethylsilyl)amide. Solvents are chosen to be compatible with the base and other reaction conditions, such as temperature, and include, but are not limited to, e.g., THF or DMF. Temperatures suitable for this reaction can range from −78° C. to 100° C. Those skilled in the art will recognize that a catalyst can be added to the mixture. Such catalysts can include, but are not limited to, e.g., NaI or tetrabutylammonium iodide.

Step 9: This step in the synthetic sequence entails the removal of protecting group $PG_1$ from compounds of general formula 12 to form amine-containing compounds of general formula 13. The choice of protecting group $PG_1$ and conditions used during step 10 for removal of $PG_1$ is influenced by what other potentially reactive functional groups are present in compounds of general formula 12 and the requirement of avoiding undesired reactions elsewhere in the starting material or product of the reaction, i.e., compounds of general formulae 12 and 13, respectively. In the case where the amine-protecting group $PG_1$ present in compounds of general formula 12 is tert-butyloxycarbonyl, the protecting group can be removed under acidic conditions such as trifluoroacetic acid in dichloromethane or hydrochloric acid in p-dioxane. Removal of the tert-butyloxycarbonyl group under acidic conditions initially liberates the corresponding salt of the compound of general formula 13, from which the free amine of general formula 13 can be liberated after treatment with base. Alternatively, if the protecting group $PG_1$ is benzyloxycarbonyl removal can be accomplished by catalytic hydrogenation using a suitable catalyst, e.g., 10% Pd/C and treating the mixture with a hydrogen source, e.g., $H_2$ or ammonium formate, in an appropriate solvent, e.g., EtOH.

Those skilled in the art will recognize that there are a variety of conditions for removing protecting groups from nitrogen atoms which may be identified by reference to organic chemistry text books (e.g. Protective Groups in Organic Synthesis, Theodora W. Greene et al.) or general chemistry literature.

In cases where X in general Formula I is desired to be H no further reactions are needed as compounds of general formula 13 are equivalent to compounds of general Formula 1, where X=H.

Step 10 involves the introduction of an additional substitution to the nitrogen atom bearing group W. Those skilled in the art will recognize there are several ways to accomplish this transformation. These include, but are not limited to, reductive amination or C1-6-alkyl ation. For example, compounds of general formula 13 can be treated with an aldehyde, e.g., acetaldehyde, benzaldehyde or 3-pyridinecarboxaldehyde, and a reducing agent, e.g., $NaBH_4$ or $NaBH_3CN$, in a suitable solvent, e.g., MeOH or EtOH, at an appropriate temperature ranging from about −20° C. to about 100° C., for an amount of time sufficient to carry out this transformation. Alternatively, compounds can be treated with an C1-6-alkylating agent, e.g., methyl iodide, benzyl bromide or allyl bromide, and a base, e.g., pyridine or TEA, in a suitable solvent, e.g., DCM or THF at an appropriate temperature ranging from about −20° C. to about 100° C. for an amount of time sufficient to carry out this transformation.

Those skilled in the art will recognize that a catalyst can be added to the mixture. Such catalysts can include, but are not limited to, e.g., NaI or tetrabutylammonium iodide.

It will be apparent to one knowledgeable in the art of organic synthesis that when one or more of the substituents labeled W, Y or $R^1$ through $R^4$, or substituents included in their definitions, in the compounds shown in Scheme 1 are in and of themselves chemically reactive groups, or contain chemically reactive groups, then additional modification of the compounds of general formulas 2 through 13 which contain those reactive groups may be possible. The point in the synthetic sequence at which modification of the chemically reactive groups takes place may be chosen such that the newly elaborated group is chemically inert to the reagents to be employed during the remaining steps of the synthetic sequence and does not interfere with the remaining steps in the synthetic sequence shown in Scheme 1.

Alternatively, if the newly elaborated group is not chemically inert or can interfere with the remaining steps in the synthetic sequence, it may be necessary to temporarily mask the reactive functional group with an appropriate protecting group or to derivatize the functional group into a moiety which is stable to the remaining transformations in the synthetic sequence and will be present in the final product of the reaction sequence. If a protecting group is introduced which is not required in the final compound of general Formula 1 then it may either be removed under the conditions remaining in the synthetic sequence shown in Scheme 1 or by introduction of an additional deprotection step into the synthetic sequence depending upon the nature of the protecting group employed.

The reaction conditions for the above reactions can vary to a certain extent. Those skilled in the art will recognize that the sequence of some reaction steps described in Scheme 1 can vary, as shown in Scheme 2 below.

Scheme 2

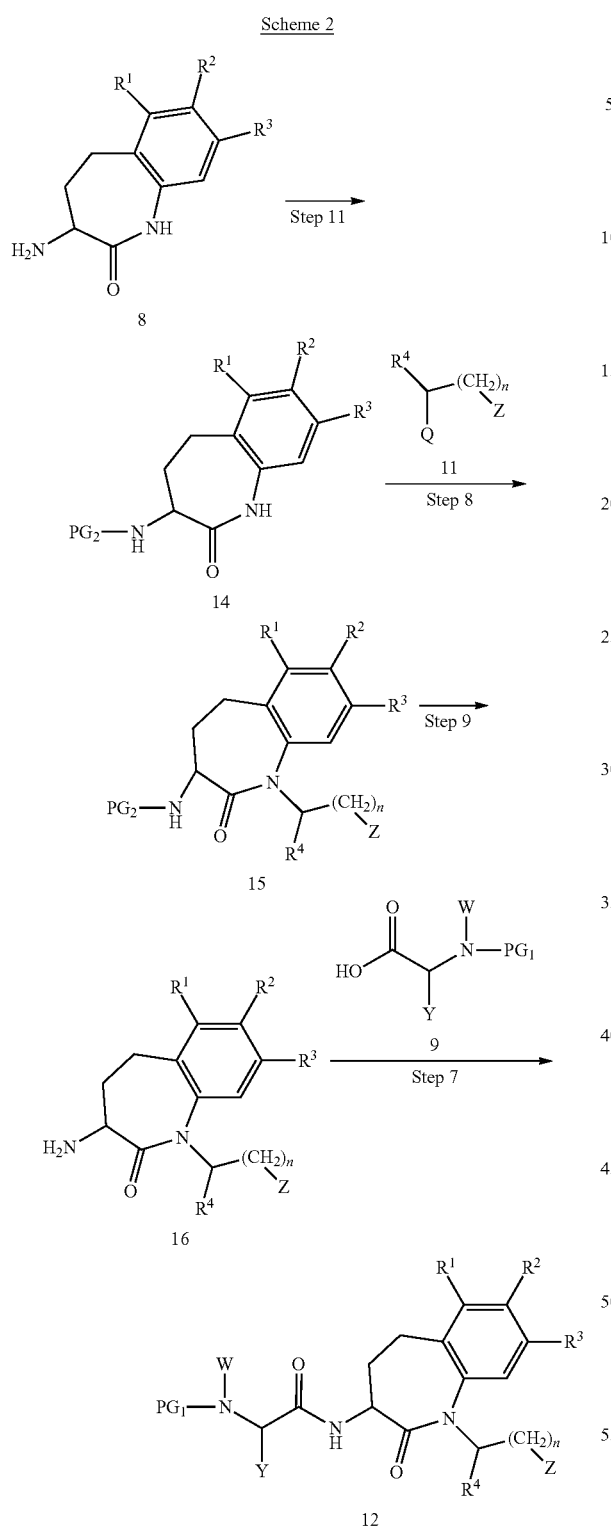

Scheme 3

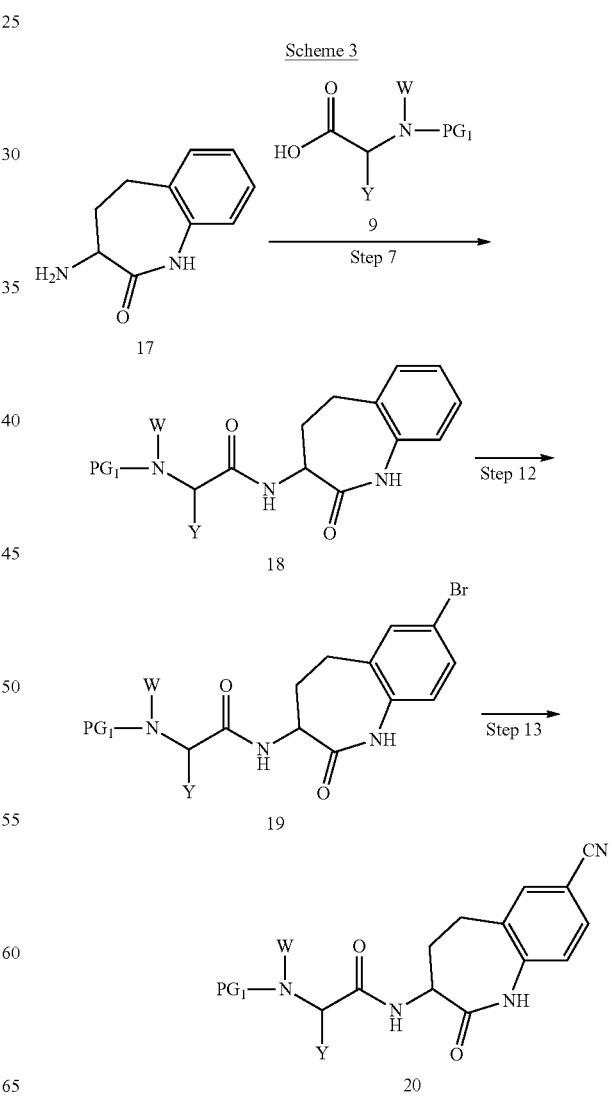

zyloxycarbonyl, are preferred but other amine-protecting groups may also be effective. For example, compounds of general formula 8 can be treated with a carbamoylating agent, e.g., di-tert-butyl-dicarbonate, in an appropriate solvent, e.g., DCM, at an appropriate temperature ranging from about −20° C. to about 100° C., for an amount of time sufficient to carry out this transformation to provide compounds of general formula 14.

Compounds of general formula 14 can be treated as described above in Step 8 to provide compounds of general formula 15.

Compounds of general formula 15 can be treated above as described for Step 9 to provide compounds of general formula 16.

Compounds of general formula 16 can be treated above as described for Step 11 to provide compounds of general formula 12.

If a suitably substituted compound of general formula 8 is not commercially available or known in the literature to provide the desired compounds of general formula 10, compounds of general formula 10 can be synthesized from known or commercial starting materials as exemplified in Scheme 3 below.

Step 11: This step involves introduction of a protecting group on the basic Nitrogen of compounds of general formula 8. The choice of protecting group is dependent on the reaction steps to be completed after introduction of the protecting group and preferred protecting groups can be made as described above for Step 7. In particular carbamate-based protecting groups, e.g. tert-butyloxycarbonyl and ben- Thus, for example, compound 17 can be treated as described in Step 7 to afford compounds of general formula 18.

Step 12: Compounds of general formula 18 can then be treated with a brominating reagent, e.g., N-bromosuccinimide, in the presence of a base, e.g., $Cs_2CO_3$ or $Na_2CO_3$, in a suitable solvent, e.g., DMF, at an appropriate temperature ranging from about 0° C. to about 120° C., to provide compounds of general formula 19.

Step 13: Compounds of general formula 19 can then be cyanated using methods known to those skilled in the art. For example, compounds of general formula 19 can be treated with a cyanide salt, e.g., $Zn(CN)_2$, and a catalyst, e.g., $Pd(P(Ph)_3)_4$, in a suitable solvent, e.g., DMF, at an appropriate temperature ranging from about 0° C. to about 120° C., to provide compounds of general formula 20. Those skilled in the art will recognize that compounds of general formula 20 are equivalent to compounds of general formula 10 where $R^1$ and $R^3$ are both hydrogen and $R^2$ is cyano.

Methods to perform the above described reactions and processes would be apparent to those of ordinary skill in the art based on the present disclosure, or can be deduced in analogy from the examples. Starting materials are commercially available or can be made by methods analogous to those described in the Examples below.

Crystal Forms

When the compounds of the invention are solids, it is understood by those skilled in the art that these compounds, and their salts, may exist in different crystal or polymorphic forms, all of which are intended to be within the scope of the present invention and specified formulas.

EXAMPLES

The compounds of the present invention may be synthesized according to known techniques. The following examples and references are provided to aid the understanding of the present invention. The examples are not intended, however, to limit the invention, the true scope of which is set forth in the appended claims. The names of the final products in the examples were generated using AutoNom 2000 Add-in v4.0 SP2 (function in ISIS Draw, Elsevier/MDL), or AutoNom 2000 TT v4.01.305 (Elsevier/MDL), or functions available in ChemDraw Pro Control 11.0.2 (CambridgeSoft Corp.), or Struct=Name feature of electronic notebooks.

Preparation of Intermediates

5-Bromo-2-methoxybenzyl methanesulfonate

To a mixture of triethylamine (TEA, 128 µL, 0.92 mmol) and (5-bromo-2-methoxyphenyl)methanol (100 mg, 0.46 mmol) in dichloromethane (DCM, 5 mL) at 0° C. MsCl (43 µL, 0.55 mmol) was added dropwise. The mixture was stirred at 0° C. for 30 min. and diluted with DCM. The mixture was washed with sat. $NH_4Cl$, sat. $NaHCO_3$, water, and dried over $MgSO_4$. Concentration gave the title compound as a yellow oil that was used without further purification.

5-Chloro-2-methoxybenzyl methanesulfonate

In a similar manner to that described for the preparation of 5-bromo-2-methoxybenzyl methanesulfonate, (5-chloro-2-methoxyphenyl)methanol (100 mg, 0.58 mmol) was converted to the title compound which was used without purification.

4-Chloro-2-methoxybenzyl methanesulfonate

In a similar manner to that described for the preparation of 5-bromo-2-methoxybenzyl methanesulfonate, (4-chloro-2-methoxyphenyl)methanol (100 mg, 0.58 mmol) was converted to the title compound which was used without purification.

4-Bromo-2-methoxybenzyl methanesulfonate

In a similar manner to that described for the preparation of 5-bromo-2-methoxybenzyl methanesulfonate, (4-bromo-2-methoxyphenyl)methanol (100 mg, 0.46 mmol) was converted to the title compound which was used without purification.

5-Chloro-2-fluorobenzyl methanesulfonate

In a similar manner to that described for the preparation of 5-bromo-2-methoxybenzyl methanesulfonate, (5-chloro-2-fluorophenyl)methanol (50 mg, 0.31 mmol) was converted to the title compound which was used without purification.

5-Iodo-2-methoxybenzyl methanesulfonate

Step 1: 2-Hydroxy-5-iodobenzaldehyde (500 mg, 2.02 mmol), iodomethane (188 µL, 3.02 mmol), and $K_2CO_3$ (1.39 g, 10.0 mmol) were combined in DMF (10 mL) and stirred for 16 h at room temperature (RT). The mixture was partitioned between EtOAc and $H_2O$. The organic layer was separated, washed with $H_2O$, brine and dried over $MgSO_4$. Concentration gave 5-iodo-2-methoxybenzaldehyde (445 mg, 1.7 mmol, 84%, white solid) which was used without purification.

Step 2: To a solution of 5-iodo-2-methoxybenzaldehyde (445 mg, 1.7 mmol) in EtOH (3 mL) at 0° C. was added $NaBH_4$ (64 mg, 1.7 mmol). The mixture was stirred at RT for 1 h, cooled to 0° C. and sat. $NH_4Cl$ was added dropwise. After 15 min., the mixture was partitioned between EtOAc and $H_2O$. The organic layer was separated and washed with $H_2O$, brine and dried over $MgSO_4$. Concentration gave (5-iodo-2-methoxyphenyl)methanol (400 mg, 1.51 mmol, 89%, white solid) which was used without purification.

Step 3: To a mixture of TEA (53 µL, 0.78 mmol) and (5-iodo-2-methoxyphenyl)methanol (50 mg, 0.31 mmol) in DCM (5 mL) at 0° C. was added MsCl (22 µL, 0.28 mmol) dropwise. The mixture was stirred at 0° C. for 30 min diluted with DCM, washed with sat. $NH_4Cl$, sat. $NaHCO_3$, $H_2O$, and dried over $MgSO_4$. Concentration gave the title compound as a yellow oil that was used without purification.

5-Isopropyl-2-methoxybenzyl methanesulfonate

Step 1: To a 0° C. solution of 5-isopropyl-2-methoxybenzaldehyde (500 mg, 2.81 mmol) in EtOH (3 mL) was added $NaBH_4$ (106 mg, 2.81 mmol). The mixture was warmed to RT, stirred for 1 h, cooled to 0° C. and diluted with sat. $NH_4Cl$. After 15 min., the mixture was partitioned between EtOAc and $H_2O$. The organic layer was separated and washed with $H_2O$, brine and dried over $MgSO_4$. Concentration gave (5-isopropyl-2-methoxyphenyl)methanol (460 mg, 2.55 mmol, 91%, white solid) which was used without purification.

Step 2: To a mixture of TEA (77 µL, 0.56 mmol) and (5-isopropyl-2-methoxyphenyl)methanol (50 mg, 0.28 mmol) in DCM (5 mL) at 0° C. was added MsCl (32 µL, 0.42 mmol) dropwise. The mixture was stirred at 0° C. for 30 min., diluted with DCM and the organic layer was washed with sat. NH₄Cl, sat. NaHCO₃, H₂O, and dried over MgSO₄. Concentration gave 5-isopropyl-2-methoxybenzyl methanesulfonate as a yellow oil that was used without purification.

2-(Chloromethyl)thiophene

A solution of thiophen-2-ylmethanol (200 mg, 1.75 mmol), diisopropylethylamine (DIEA, 453 mg, 612 μL, 3.5 mmol) in DCM (5 mL) was cooled to 0° C., MsCl (163 μL, 2.1 mmol) was added and the mixture warmed to RT. After 2 h H₂O and DCM were added, the organic layer separated and washed with sat. NH₄Cl, H₂O, sat. NaHCO₃, dried with MgSO₄ and concentrated to give the title compound (203 mg, light brown oil) which was used without purification MS m/z 133 (MH⁺).

3-(Chloromethyl)thiophene

In a similar manner to that described for 2-(chloromethyl)thiophene, thiophen-3-ylmethanol (200 mg, 1.75 mmol) and MsCl (163 μL, 2.1 mmol) gave 3-(chloromethyl)thiophene (212 mg, 91%, light brown oil). MS m/z 133 (MH⁺)

5-Chloromethyl-thiazole

In a similar manner to that described for 2-(chloromethyl)thiophene, thiazol-5-ylmethanol (200 mg, 1.74 mmol) and MsCl (163 μL, 2.1 mmol) gave 5-chloromethyl-thiazole (200 mg, 86%, light brown oil). MS m/z 134 (MH⁺)

2-Chloromethyl-thiazole

In a similar manner to that described for 2-(chloromethyl)thiophene, thiazol-2-ylmethanol (200 mg, 1.74 mmol) and MsCl (163 μL, 2.1 mmol) gave 2-chloromethyl-thiazole (205 mg, 88%, light brown oil). MS m/z 134 (MH⁺)

5-Chloromethyl-oxazole

In a similar manner to that described for 2-(chloromethyl)thiophene, thiazol-5-ylmethanol (200 mg, 2.02 mmol) and MsCl (187 μL, 2.42 mmol) gave 5-chloromethyl-thiazole (193 mg, 81%, light brown oil). MS m/z 118 (MH⁺)

5-(Chloromethyl)-1-methyl-1H-imidazole hydrochloride

Methyl-1H-imidazol-5-yl)methanol (100 mg, 892 μmol) was combined with thionyl chloride (1 mL). The mixture was refluxed for 2 h and concentrated. The residue was dissolved in minimum amount of EtOH and ether was added. The mixture was sonicated to give 5-(chloromethyl)-1-methyl-1H-imidazole hydrochloride (128 mg, 86%, light yellow solid) which was used without purification. MS m/z 131 (MH⁺)

4-(Chloromethyl)-3-methoxyquinoline

Step 1: 3-Hydroxyquinoline-4-carboxylic acid (3.39 g, 17.9 mmol, Eq: 1.00) and K₂CO₃ (9.91 g, 71.7 mmol, Eq: 4) were combined with acetone (125 mL) to give a light brown suspension. After 10 min iodomethane (6.36 g, 2.8 mL, 44.8 mmol, Eq: 2.5) was added dropwise. After 18 h at RT, the mixture was concentrated, poured into H₂O and extracted with EtOAc. The combined extracts were washed with H₂O, brine, dried over Na₂SO₄ and concentrated. The residue was purified by flash chromatography to give 3-methoxy-quinoline-4-carboxylic acid methyl ester (1.1605 g red oil that solidified).

Step 2: 3-Methoxy-quinoline-4-carboxylic acid methyl ester (1.3227 g, 6.09 mmol, Eq: 1.00) was combined with toluene (12 mL), the solution was cooled to −78° C. and DIBAL-H 1.0 M in hexanes (18.9 mL, 18.9 mmol, Eq: 3.1) was added. After 30 min the mixture was diluted with H₂O, MgSO₄ was added and EtOAc was added. The solid was filtered and washed with excess EtOAc and the filtrate was purified by flash chromatography to give 4-hydroxymethylquinolin-3-ol (0.7323 g, light brown solid).

Step 3: 4-Hydroxymethyl-quinolin-3-ol (0.7323 g, 3.87 mmol, Eq: 1.00) was combined with DCM (20 mL) and the solution cooled to 0° C. Thionyl chloride (921 mg, 565 μL, 7.74 mmol, Eq: 2) was added dropwise. The mixture was warmed to RT stirred for 18 h, diluted with DCM and sat. NaHCO₃. The organic layer was washed with sat. NaHCO₃ and H₂O, dried over Na₂SO₄ and concentrated to give the title compound as a light brown solid which was used without purification. (0.73 g).

Methanesulfonic acid 2-ethynyl-naphthalen-1-ylmethyl ester

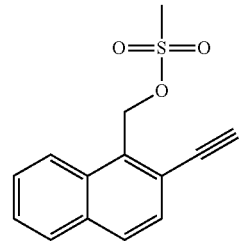 [SMILES: C#Cc1ccc2ccccc2c1COS(C)(=O)=O]

Step 1: 2-Hydroxynaphthalene-1-carboxylic acid methyl ester (2.2 g, 10.9 mmol, Eq: 1.00) was combined with pyridine (9 mL) and the solution cooled to 0° C. Triflic anhydride (3.38 g, 2.02 mL, 12.0 mmol, Eq: 1.1) was added slowly. After 5 min mixture was warmed to RT. After 18 h, the mixture was poured into H₂O and extracted with Et₂O. The combined extracts were washed with H₂O, 0.5 M HCl, brine, dried over Na₂SO₄ and concentrated. The resulting material was purified by flash chromatography to give 2-trifluoromethanesulfonyloxy-naphthalene-1-carboxylic acid methyl ester (3.31 g, nearly colorless oil).

Step 2: 2-Trifluoromethanesulfonyloxy-naphthalene-1-carboxylic acid methyl ester (0.5 g, 1.5 mmol, Eq: 1.00) was combined with DMF (4 mL), the solution was cooled to 0° C. and degassed. Trimethylsilylacetylene (250 mg, 332 μL, 2.54 mmol, Eq: 1.7) and TEA (257 mg, 354 μL, 2.54 mmol, Eq: 1.7) were added and the mixture was degassed. Copper (I) iodide (26.8 mg, 299 μmol, Eq: 0.2) and tetrakis(triphenylphosphine)palladium(0) (173 mg, 150 μmol, Eq: 0.1) were added and the mixture warmed to RT. After 18 h, the mixture was poured into EtOAc and washed with sat. NH₄Cl and brine. The organic layer was dried over Na₂SO₄ and concentrated. The resulting material was purified by flash chromatography to give 2-trimethylsilanylethynyl-naphthalene-1-carboxylic acid methyl ester (0.38 g, brown oil).

Step 3: 2-Trimethylsilanylethynyl-naphthalene-1-carboxylic acid methyl ester (0.38 g, 1.35 mmol, Eq: 1.00) was combined with THF (12 mL) and 1.0 M tetrabutylammonium fluoride (TBAF) in THF (1.55 mL, 1.55 mmol, Eq: 1.15) was added dropwise. After 30 min., the mixture was poured into H₂O and extracted with Et₂O. The extracts were combined, washed with H₂O and brine, dried over Na₂SO₄ and concentrated. The resulting material was purified by flash chromatography to give 2-ethynyl-naphthalene-1-carboxylic acid methyl ester (0.228 g, light brown solid).

Step 4: 2-Ethynyl-naphthalene-1-carboxylic acid methyl ester (0.4875 g, 2.32 mmol, Eq: 1.00) was combined with THF (25 mL) and the solution cooled to −78° C. Lithium aluminum hydride (LAH) 1.0 M in THF (2.9 mL, 2.9 mmol, Eq: 1.25) was added and the mixture was warmed to RT. After 2.5 h, the mixture was diluted with brine, the resulting precipitate was filtered and washed with Et₂O. The filtrate was concentrated, diluted with brine and extracted with EtOAc. The extracts were combined, washed with H₂O and brine. The extracts were dried over Na₂SO₄ and concentrated to give (2-ethynyl-naphthalen-1-yl)-methanol (0.305 g, yellow solid) which was used without purification.

Step 5: (2-Ethynyl-naphthalen-1-yl)-methanol (0.1 g, 549 µmol, Eq: 1.00) and TEA (111 mg, 153 µL, 1.1 mmol, Eq: 2) were combined with DCM (3.00 mL) and MsCl (75.4 mg, 51.3 µL, 659 µmol, Eq: 1.2) was added. After 75 min., the mixture was poured into DCM and washed with brine. The mixture was concentrated to give the title compound as a yellow residue which used immediately without purification.

(2-((3-hydroxyoxetan-3-yl)ethynyl)naphthalene-1-yl)methyl methanesulfonate

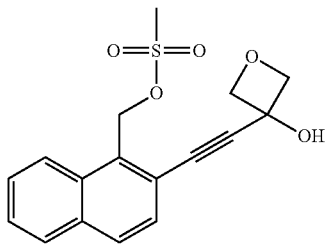 [SMILES: CS(=O)(=O)OCc1c(C#CC2(O)COC2)ccc2ccccc12]

Step 1: (2-Ethynyl-naphthalen-1-yl)-methanol (186 mg, 1.02 mmol, Eq: 1.00) and imidazole (104 mg, 1.53 mmol, Eq: 1.50) were combined with THF (10 mL), tert-butyldimethylchlorosilane (185 mg, 1.22 mmol, Eq: 1.20) was added and the mixture was stirred overnight. Additional amounts of imidazole (104 mg, 1.53 mmol, Eq: 1.50) and tert-butyldimethylchlorosilane (185 mg, 1.22 mmol, Eq: 1.20) were added and the mixture was stirred for 2.5 h. The reaction was diluted with sat. NH₄Cl and extracted with EtOAc. The combined extracts were concentrated and the resulting material was purified by flash chromatography to afford tert-butyl-(2-ethynyl-naphthalen-1-ylmethoxy)-dimethyl-silane (275 mg, 91%).

Step 2: tert-Butyl-(2-ethynyl-naphthalen-1-ylmethoxy)-dimethyl-silane (275 mg, 928 µmol, Eq: 1.00) was combined with THF (8 mL), the mixture was flushed with N₂ and cooled to −78° C. 1.6 M n-BuLi in hexane (754 µL, 1.21 mmol, Eq: 1.30) was added and the mixture was stirred for 30 min Oxetan-3-one (134 mg, 1.86 mmol, Eq: 2.00) was added and the mixture was stirred at −78° C. for 5 min and warmed to RT. After 40 min., the solution was diluted with sat. NH₄Cl and extracted with EtOAc. The organic extracts were washed with brine, dried over Na₂SO₄ and concentrated. The resulting material was purified by flash chromatography to afford 3-[1-(tert-butyl-dimethyl-silanyloxymethyl)-naphthalen-2-ylethynyl]-oxetan-3-ol (248 mg, 72%, yellow solid).

Step 3: 3-[1-(tert-Butyl-dimethyl-silanyloxymethyl)-naphthalen-2-ylethynyl]-oxetan-3-ol (248 mg, 673 µmol, Eq: 1.00) was combined with THF (5 mL) cooled to 0° C. and 1.0 M TBAF in THF (2.02 mL, 2.02 mmol, Eq: 3.00) was added. The mixture was stirred at 0° C. for 45 min then at RT for 4 h. The solution was diluted with sat. NH₄Cl and extracted with EtOAc. The organic solution was washed with brine, dried over Na₂SO₄ and concentrated. The resulting material was purified by flash chromatography to afford 3-(1-hydroxymethyl-naphthalen-2-ylethynyl)-oxetan-3-ol (150 mg, 88%).

Step 4: 3-(1-Hydroxymethyl-naphthalen-2-ylethynyl)-oxetan-3-ol (150 mg, 590 µmol, Eq: 1.00) was combined with DCM (5 mL) to give a suspension. TEA (119 mg, 164 µL, 1.18 mmol, Eq: 2.00) and MsCl (71.0 mg, 47.9 µL, 619 µmol, Eq: 1.05) were added and the mixture was stirred at RT for 1.5 h. The mixture was diluted with ice-H₂O and extracted with DCM. The organic layer was separated and concentrated to afford the title compound which was used without purification (185 mg, 94%).

2-Allyloxy-1-chloromethyl-naphthalene

Step 1: 2-Allyloxy-naphthalene-1-carbaldehyde (5.73 g, 27 mmol) was dissolved in MeOH (140 mL) and THF (30 mL), the solution cooled to 0° C. and NaBH₄ (1.02 g, 27 mmol) was added. After 2.5 h, the mixture was diluted with H₂O and concentrated. The residue was diluted with EtOAc, washed with H₂O, dried over Na₂SO₄, filtered and concentrated to give (2-allyloxy-naphthalen-1-yl)-methanol (5.65 g, 98%).

Step 2: (2-Allyloxy-naphthalen-1-yl)-methanol (1.0 g, 4.67 mmol) was dissolved in toluene (15 mL) and pyridine (0.4 mL), the mixture cooled to 0° C. and thionyl chloride (0.83 g, 7 mmol) added. After 18 h, the mixture was diluted with H₂O and extracted with EtOAc. The combined extracts were washed with H₂O, sat. NaHCO₃, brine, dried over Na₂SO₄, filtered and concentrated to give the title compound which was used without purification (1.08 g, 99%).

4-Bromomethyl-2-methyl-biphenyl

Step 1: A mixture of methyl 3-bromo-4-methylbenzoate (2.29 g, 10 mmol), phenyl boronic acid (1.22 g, 10 mmol), Pd(PPh₃)₄ (0.35 g, 0.3 mmol), 2.5 M Na₂CO₃ (7.5 mL), and toluene (30 mL) was heated at 90° C. for 18 h. The mixture was concentrated, diluted with EtOAc, washed with H₂O, brine, dried over Na₂SO₄ and concentrated. The resulting material was purified by flash chromatography to give 2-methyl-biphenyl-4-carboxylic acid methyl ester (2.26 g, 99%, colorless oil).

Step 2: 1.0 M LiAlH₄ in THF (5 mL, 5 mmol) was added to a solution of 2-methyl-biphenyl-4-carboxylic acid methyl ester (2.26 g, 9.99 mmol, Eq: 1.00) THF (25 mL) at 0° C. The mixture was stirred for 60 min at 0° C., warmed to RT and diluted with brine. MgSO₄ was added followed by EtOAc. Insoluble material was removed by filtration and the filter cake washed with EtOAc. The filtrate was washed with H₂O, dried over Na₂SO₄, and concentrated to afford (2-methyl-biphenyl-4-yl)-methanol (1.93 g, 97%, white solid) which was used without purification.

Step 3: (2-Methyl-biphenyl-4-yl)-methanol (1.0 g, 5.04 mmol) was cooled to 0° C. and PBr₃ (0.61 mL, 6.6 mmol) was added. After 40 min. at RT the mixture was diluted with 100 mL DCM and washed with H$_2$O, brine, dried over Na$_2$SO$_4$ and concentrated. The resulting material was purified by flash chromatography to give the title compound (0.67 g, 51%, white solid).

5-Bromo-1-(chloromethyl)-2-methoxynaphthalene

Step 1: 1.0 M TiCl$_4$ in DCM (11.8 mL, 11.8 mmol, Eq: 2.2) and dichloromethyl methyl ether (677 mg, 525 μL, 5.89 mmol, Eq: 1.1) were added to 30 mL DCM and the mixture cooled to 0° C. A solution of 1-bromo-6-methoxynaphthalene (1.27 g, 5.36 mmol, Eq: 1.00) in DCM 10 mL was added and the mixture warmed to RT. Approx. 10 mL additional DCM was added. After 1 h at RT, the mixture was diluted with 1 M HCl and extracted with DCM. The extracts were combined, washed with H$_2$O, brine, dried over Na$_2$SO$_4$ and concentrated. The resulting material was purified by flash chromatography to give 5-bromo-2-methoxy-1-naphthaldehyde (1.29 g).

Step 2: 5-bromo-2-methoxy-1-naphthaldehyde (1.52 g, 5.73 mmol, Eq: 1.00) was combined with EtOH (50 mL) and NaBH$_4$ (217 mg, 5.73 mmol, Eq: 1.00) was added. After 18 h, the mixture was diluted with H$_2$O and extracted with EtOAc. The combined extracts were washed with H$_2$O, dried over Na$_2$SO$_4$, filtered and concentrated to give (5-bromo-2-methoxynaphthalen-1-yl)methanol (1.7 g, off-white solid) which was used without purification.

Step 3: Thionyl chloride (1.14 g, 697 μL, 9.55 mmol, Eq: 1.5) was added to a mixture of (5-bromo-2-methoxynaphthalen-1-yl)methanol (1.7 g, 6.36 mmol, Eq: 1.00) and pyridine (755 mg, 772 μL, 9.55 mmol, Eq: 1.5) in DCM (40 mL) at 0° C. The mixture was warmed to RT. After 18 h, the mixture was diluted with sat. NaHCO$_3$ and DCM. The organic layer was separated, washed with sat. NaHCO$_3$, H$_2$O, brine, dried over Na$_2$SO$_4$, filtered and concentrated to afford the title compound (1.33 g beige solid) which was used without purification.

1-(Chloromethyl)-2-(2,2,2-trifluoroethoxy)naphthalene

Step 1: To a 25 mL microwave vial was added 2-hydroxy-1-naphthaldehyde (1 g, 5.81 mmol, Eq: 1.00), Cs$_2$CO$_3$ (2.84 g, 8.71 mmol, Eq: 1.5) and 2-iodo-1,1,1-trifluoroethane (1.46 g, 687 μL, 6.97 mmol, Eq: 1.2) in DMF (8.00 mL). The vial was capped and heated in the microwave at 125° C. for 60 min. The naphtha was poured into brine and extracted with EtOAc. The combined extracts were washed with brine, dried over Na$_2$SO$_4$ and concentrated. The resulting material was purified by flash chromatography to give 2-(2,2,2-trifluoroethoxy)-1-naphthaldehyde (0.8768 g, yellow-brown solid).

Step 2: 2-(2,2,2-Trifluoroethoxy)-1-naphthaldehyde (0.8768 g, 3.45 mmol, Eq: 1.00) was combined with EtOH (30.0 mL) to give a brown solution. NaBH$_4$ (130 mg, 3.45 mmol, Eq: 1.00) was added. After 90 min., the mixture was poured into 1 M HCl and extracted with EtOAc. The extracts were combined, washed with brine, dried over Na$_2$SO$_4$ and concentrated. The resulting material was purified by flash chromatography to give (2-(2,2,2-trifluoroethoxy)naphthalene-1-yl)methanol (0.6036 g, light brown oil).

Step 3: (2-(2,2,2-Trifluoroethoxy)naphthalene-1-yl)methanol (0.6036 g, 2.36 mmol, Eq: 1.00) was combined with DCM (40 mL) to give a light yellow solution. Thionyl chloride (561 mg, 344 μL, 4.71 mmol, Eq: 2) was added. After 18 h, the mixture was poured into sat. NaHCO$_3$ and extracted with DCM. The extracts were combined, washed with sat. NaHCO$_3$, H$_2$O, and brine, dried over Na$_2$SO$_4$ and concentrated to afford the title compound (0.5558 g light brown solid) which was used without purification.

(3-((Trimethylsilyl)ethynyl)quinolin-4-yl)methyl methanesulfonate

Step 1: 3-Hydroxyquinoline-4-carboxylic acid (1.75 g, 9.25 mmol, Eq: 1.00), N-(3-dimethylaminopropyl)-N'-ethylcarbodiimide hydrochloride (EDCI, 1.95 g, 10.2 mmol, Eq: 1.1) and methanol (14.8 g, 18.7 mL, 463 mmol, Eq: 50) were combined with DCM (56.0 mL) and 4-(dimethylamino)pyridine (DMAP) (113 mg, 925 μmol, Eq: 0.1) was added. After 18 h, the mixture was concentrated, poured into H$_2$O and extracted with EtOAc. The extracts were combined, washed with H$_2$O, brine, dried over Na$_2$SO$_4$ and concentrated. The resulting material was purified by flash chromatography to give methyl 3-hydroxyquinoline-4-carboxylate (0.5110 g, white solid).

Step 2: Methyl 3-hydroxyquinoline-4-carboxylate (1.85 g, 9.1 mmol, Eq: 1.00) was combined with pyridine (26 mL) and the solution cooled to 0° C. Triflic anhydride (5.65 g, 3.38 mL, 20.0 mmol, Eq: 2.2) was added at 0° C. After 5 min. the mixture was warmed to RT and stirred for 18 h. The mixture was poured into H$_2$O and extracted with ether. The extracts were combined and washed with H$_2$O, 0.5 M HCl, brine, dried over Na$_2$SO$_4$ and concentrated. The resulting material was purified by flash chromatography to afford methyl 3-(trifluoromethylsulfonyloxy)naphthale-4-carboxylate (2.6997 g, light yellow oil).

Step 3: Methyl 3-(trifluoromethylsulfonyloxy)naphthale-4-carboxylate (0.7825 g, 2.33 mmol, Eq: 1.00) was combined with DMF (7 mL) to give a light yellow solution. The solution was cooled to 0° C., degassed and trimethylsilylacetylene (390 mg, 518 μL, 3.97 mmol, Eq: 1.7) and TEA (402 mg, 553 μL, 3.97 mmol, Eq: 1.7) were added. The solution was degassed, tetrakis(triphenylphosphine)palladium(0) (270 mg, 233 μmol, Eq: 0.1), copper (I) iodide (41.8 mg, 467 μmol, Eq: 0.2) were added and after 10 min the mixture warmed to RT After 6 h, the mixture was poured into EtOAc and washed with sat. NH$_4$Cl, brine, dried over Na$_2$SO$_4$ and concentrated. The resulting material was purified by flash chromatography to afford methyl 3-((trimethylsilypethynyl)naphthale-4-carboxylate (0.6555 g, brown oil) MS m/z 284.0 (MH$^+$)

Step 3: Methyl 3-((trimethylsilyl)ethynyl)naphthale-4-carboxylate (0.244 g, 861 μmol, Eq: 1.00) was combined with THF (5 mL) and the solution cooled to −78° C. and LAH 1.0 M in THF (947 μL, 947 μmol, Eq: 1.1) was added dropwise. After 1 h the mixture was warmed to 0° C. The reaction was diluted with a solution of 2 mL AcOH, 2 mL H$_2$O, and 4 mL THF. The mixture was poured into H$_2$O and extracted with EtOAc. The extracts were combined, washed with brine, dried over Na$_2$SO$_4$ and concentrated. The resulting material was purified by flash chromatography to give (3-((trimethylsilyl)ethynyl)quinolin-4-yl)methanol (21.8 mg, light brown oil).

Step 5: (3-((Trimethylsilyl)ethynyl)quinolin-4-yl)methanol (21.6 mg, 84.6 μmol, Eq: 1.00) and TEA (17.1 mg, 23.6 μL, 169 μmol, Eq: 2) were combined with DCM (2 mL) and MsCl (14.5 mg, 9.89 μL, 127 μmol, Eq: 1.5) was added. After 1 h, the mixture was poured into DCM and washed with H$_2$O and brine. The mixture was concentrated to give the title compound (17.5 mg, yellow oil) which was used immediately without purification.

(2-Cyclopropylnaphthalen-1-yl)methyl methanesulfonate

Step 1: A 20 mL microwave vial was charged with methyl 2-(trifluoromethylsulfonyloxy)-1-naphthoate (0.9862 g, 2.9 mmol), potassium cyclopropyltrifluoroborate (42.9 mg, 2.9 mmol), 2-dicyclohexylphosphino-2',4',6'-triisopropylbiphenyl (X-PHOS, 166 mg, 348 µmol), palladium(II) acetate (39 mg, 174 µmol) and $K_2CO_3$ (1.21 g, 8.69 mmol). The reaction vessel was capped, evacuated and purged with $N_2$. Toluene (12 mL 0 and $H_2O$ (1.2 mL) were added and the vessel purged with $N_2$. The mixture was heated to 80° C. for 18 h, cooled and diluted with EtOAc. The mixture was washed with brine, dried over $Na_2SO_4$ and concentrated. The resulting material was purified by flash chromatography to give methyl 2-cyclopropyl-1-naphthoate (0.3634 g, yellow oil).

Step 2: Methyl 2-cyclopropyl-1-naphthoate (0.2738 g, 1.21 mmol, Eq: 1.00) was combined with THF (10 mL), the solution cooled to −78° C. and LAH 1.0 M in THF (1.51 mL, 1.51 mmol, Eq: 1.25) was added. The mixture was warmed to RT, stirred for 1 h and diluted with brine. The resulting precipitate was filtered and the filter cake washed with ether. The filtrate was washed with $H_2O$ and brine, dried over $Na_2SO_4$ and concentrated to give (2-cyclopropylnaphthalen-1-yl)methanol (0.2242 g, colorless oil) which was used without purification.

Step 3: In a similar manner to that described for the preparation of (3-((trimethylsilyl)ethynyl)quinolin-4-yl)methyl methanesulfonate Step 5, (2-cyclopropylnaphthalen-1-yl)methanol (87 mg, 439 µmol) was converted to the title compound (52.2 mg, yellow oil) which was used immediately without purification.

(2-Methoxy-6-(trifluoromethyl)naphthalene-1-yl) methyl methanesulfonate

Step 1: 2-Iodo-6-methoxynaphthalene (2.91 g, 10.2 mmol, Eq: 1.00), copper (I) iodide (2.34 g, 12.3 mmol, Eq: 1.2) and potassium fluoride (714 mg, 12.3 mmol, Eq: 1.2) were combined with DMF (20 mL) and methyl chlorodifluoroacetate (3.55 g, 2.59 mL, 24.6 mmol, Eq: 2.4) was added. The mixture was heated to 120° C. for 18 h, cooled to RT and partitioned between $H_2O$ and ether. The biphasic mixture was filtered through Celite. The aqueous layer was separated, diluted with 50 mL brine and extracted with ether. The combined extracts were dried over $Na_2SO_4$, concentrated and the residue purified by flash chromatography to give 2-methoxy-6-(trifluoromethyl)naphthalene contaminated with 10%, of unreacted starting material (1.66 g total material) which was used without further purification.

Step 2: In a similar manner to that described for the preparation of 5-bromo-1-(chloromethyl)-2-methoxynaphthalene Step 1, 2-methoxy-6-(trifluoromethyl)naphthalene (1.0 g, 4.42 mmol) was converted to 2-methoxy-6-(trifluoromethyl)-1-naphthaldehyde (0.4228 g, light yellow solid).

Step 3: In a similar manner to that described for the preparation of 5-bromo-1-(chloromethyl)-2-methoxynaphthalene Step 2, 2-methoxy-6-(trifluoromethyl)-1-naphthaldehyde (0.4226 g, 1.66 mmol) was converted to (2-methoxy-6-(trifluoromethyl)naphthalene-1-yl)methanol (0.3643 g, white solid).

Step 4: In a similar manner to that described for the preparation of (3-((trimethylsilyl)ethynyl)quinolin-4-yl)methyl methanesulfonate Step 5, (2-methoxy-6-(trifluoromethyl)naphthalene-1-yl)methanol (75 mg, 293 µmol) was converted to the title compound (49.6 mg, off white waxy solid) which was used immediately without purification.

(3-Methoxy-1,8-naphthyridin-4-yl)methyl methanesulfonate

Step 1: 3-Methoxy-1,8-naphthyridine-4-carbaldehyde (100 mg, 531 µmol, Eq: 1.00, *J. Med. Chem.* 2009, 52, 7446) was combined with EtOH (4.00 mL) and $NaBH_4$ (20.1 mg, 531 µmol, Eq: 1.00) was added. After 1 h, the mixture was poured into $H_2O$ and extracted with DCM and EtOAc. The extracts were combined, washed with $H_2O$, dried over $Na_2SO_4$ and concentrated to afford (3-methoxy-1,8-naphthyridin-4-yl)methanol (34.6 mg, yellow solid) which was used without purification.

Step 2: In a similar manner to that described for the preparation of (3-((trimethylsilyl)ethynyl)quinolin-4-yl) methyl methanesulfonate Step 5, (3-methoxy-1,8-naphthyridin-4-yl)methanol (34.6 mg, 182 µmol) was converted to the title compound (32.2 mg, light brown solid) which was used without purification.

(2-Chloro-3-methylquinolin-4-yl)methyl methanesulfonate

Step 1: 2-chloro-3-methylquinoline-4-carbonyl chloride (200 mg, 833 µmol, Eq: 1.00, US 20060135447 A1) and $NaBH_4$ (189 mg, 5.00 mmol, Eq: 6) were combined with THF (4 mL) to give a suspension. After 2 h, the mixture was diluted with $H_2O$ and extracted with DCM. The combined extracts were dried over $Na_2SO_4$ and concentrated to afford (2-chloro-3-methylquinolin-4-yl)methanol (0.1105 g, off-white solid) which was used without purification.

Step 2: In a similar manner to that described for the preparation of (3-((trimethylsilyl)ethynyl)quinolin-4-yl) methyl methanesulfonate Step 5, (2-chloro-3-methylquinolin-4-yl)methanol (107.5 mg, 518 µmol) was converted to the title compound which was used immediately without purification.

(3-Methylquinolin-4-yl)methyl methanesulfonate

Step 1: Methyl 3-methylquinoline-4-carboxylate (0.2229 g, 1.11 mmol, *J. Med. Chem.* 1991, 34, 367) was combined with THF (12 mL). EtOH (1.2 mL) and lithium borohydride (145 mg, 6.65 mmol, Eq: 6) were added. After 18 h the mixture was poured into $H_2O$ and extracted with EtOAc. The extracts were combined, washed with brine, dried over $Na_2SO_4$ and concentrated. The resulting material was purified by flash chromatography to give (3-methylquinolin-4-yl)methanol (18 mg).

Step 2: In a similar manner to that described for the preparation of (3-((trimethylsilyl)ethynyl)quinolin-4-yl) methyl methanesulfonate Step 5, (3-methylquinolin-4-yl)methanol (39.2 mg, 226 µmol) was converted to the title compound (45 mg, yellow oil) which was used immediately without purification.

(3-Chloro-1,8-naphthyridin-4-yl)methyl methanesulfonate

Step 1: In a similar manner to that described for the preparation of 5-bromo-1-(chloromethyl)-2-methoxynaphthalene Step 2 except the reaction was stirred 30 min., 3-chloro-1,8-naphthyridine-4-carbaldehyde (96 mg, 498 µmol, *J. Med. Chem.* 2009, 52, 7446) was converted to (3-chloro-1,8-naphthyridin-4-yl)methanol (15.4 mg, light brown solid) which was used without purification.

Step 2: In a similar manner to that described for the preparation of (3-((trimethylsilypethynyl)quinolin-4-yl)methyl methanesulfonate Step 5, (3-chloro-1,8-naphthyridin-4-yl)methanol (15.4 mg, 79.1 μmol) was converted to the title compound (18.7 mg, light brown oil) which was used without purification.

(2-Fluoronaphthalen-1-yl)methyl methanesulfonate

Step 1: In a similar manner to that described for the preparation of 5-bromo-1-(chloromethyl)-2-methoxynaphthalene Step 2 except the reaction was stirred 60 min., 2-fluoro-1-naphthaldehyde (0.5016 g, 2.88 mmol) was converted to (2-fluoronaphthalen-1-yl)methanol which was purified by flash chromatography (0.2941 g, waxy white solid).

Step 2: In a similar manner to that described for the preparation of (3-((trimethylsilypethynyl)quinolin-4-yl)methyl methanesulfonate Step 5, (2-fluoronaphthalen-1-yl)methanol (96.6 mg, 548 μmol) was converted to the title compound (85.1 mg, light yellow oil) which was used immediately without purification.

(3-(2,2,2-Trifluoroethoxy)quinolin-4-yl)methyl methanesulfonate

Step 1: Methyl 3-hydroxyquinoline-4-carboxylate (0.5578 g, 2.75 mmol, Eq: 1.00), 2,2,2-trifluoroethyl 4-methylbenzenesulfonate (1.05 g, 4.12 mmol, Eq: 1.5) and $K_2CO_3$ (948 mg, 6.86 mmol, Eq: 2.5) were combined with DMF (30 mL) and the mixture heated to 80° C. for 15 h. The mixture was poured into brine and extracted with EtOAc. The extracts were combined, washed with brine, dried over $Na_2SO_4$ and concentrated. The resulting material was purified by flash chromatography to give methyl 3-(2,2,2-trifluoroethoxy)naphthale-4-carboxylate (0.4584 g, light yellow solid)

Step 2: Methyl 3-(2,2,2-trifluoroethoxy)naphthale-4-carboxylate (0.1487 g, 521 μmol, Eq: 1.00) and LiCl (133 mg, 3.13 mmol, Eq: 6) were combined with EtOH (3 mL) and THF (9 mL) and $NaBH_4$ (118 mg, 3.13 mmol, Eq: 6) was added. After 18 h, 120 mg of $LiBH_4$ was added to the mixture. After 3 h, the mixture was poured into $H_2O$ and extracted with EtOAc. The extracts were combined, washed with $H_2O$, brine and dried over $Na_2SO_4$ and concentrated. The resulting material was purified by flash chromatography to give (3-(2,2,2-trifluoroethoxy)quinolin-4-yl)methanol (68.0 mg, white solid).

Step 3: In a similar manner to that described for the preparation of (3-((trimethylsilypethynyl)quinolin-4-yl)methyl methanesulfonate Step 5, (3-(2,2,2-trifluoroethoxy)quinolin-4-yl)methanol (0.1164 g, 453 μmol) was converted to the title compound which was used immediately without purification.

(3-Methylisoquinolin-4-yl)methyl methanesulfonate

Step 1: 3-methylisoquinoline-4-carbaldehyde (45.6 mg, 266 μmol, Eq: 1.00, WO1998046572) was combined with EtOH (3 mL) and $NaBH_4$ (10.1 mg, 266 μmol, Eq: 1.00) was added. After 4 h, the reaction was diluted with $H_2O$, acidified with 1 N HCl and extracted with DCM. The aqueous layer was made basic with sat. $NaHCO_3$ and extracted with EtOAc. The combined extracts were washed with $H_2O$, dried over $Na_2SO_4$, filtered and concentrated to give (3-methylisoquinolin-4-yl)methanol (24.1 mg, yellow solid) which was used without purification.

Step 2: In a similar manner to that described for the preparation of (3-((trimethylsilypethynyl)quinolin-4-yl)methyl methanesulfonate Step 5, (3-methylisoquinolin-4-yl)methanol (24.1 mg, 139 μmol) was converted to the title compound (20.5 mg yellow oil) which was used immediately without purification.

7-Bromo-1-(chloromethyl)-2-methoxynaphthalene

Step 1: In a similar manner to that described for the preparation of 5-bromo-1-(chloromethyl)-2-methoxynaphthalene Step 2 except the reaction was stirred for 1 h, 7-bromo-2-methoxy-1-naphthaldehyde (1 g, 3.77 mmol, *J. Materials Chem.* 2009, 19, 3153) was converted to (7-bromo-2-methoxynaphthalen-1-yl)methanol (0.94 g, light yellow solid) which was used without purification.

Step 2: In a similar manner to that described in the preparation of 5-bromo-1-(chloromethyl)-2-methoxynaphthalene Step 3, (7-bromo-2-methoxynaphthalen-1-yl)methanol (0.94 g, 3.52 mmol) was converted to the title compound (0.72 g, light brown solid) which was used without purification.

(2-Chloronaphthalen-1-yl)methyl methanesulfonate

Step 1: In a similar manner to that described for the preparation of 5-bromo-1-(chloromethyl)-2-methoxynaphthalene Step 2 except the reaction was stirred for 40 min., 2-chloro-1-naphthaldehyde (0.5 g, 2.62 mmol) was converted to (2-chloronaphthalen-1-yl)methanol which was purified by flash chromatography (0.1940 g, white solid).

Step 2: In a similar manner to that described for the preparation of (3-((trimethylsilypethynyl)quinolin-4-yl)methyl methanesulfonate Step 5, (2-chloronaphthalen-1-yl)methanol (90 mg, 467 μmol) was converted to the title compound (71.9 mg, light brown oil) which was used without purification.

Chloromethyl-2-ethoxy-naphthalene

Step 1: 2-Ethoxy-1-naphthoic acid (1.0 g, 4.62 mmol) was combined with THF (5 mL) and the solution cooled to 0° C.-1.0 M $BH_3$ in THF (11.6 mL, 11.6 mmol) was added and the mixture warmed to RT. After 18 h the mixture was diluted with $H_2O$ and DCM. The organic layer was washed with brine, dried over $Na_2SO_4$ and concentrated. The resulting material was purified by flash chromatography to give (2-ethoxy-naphthalen-1-yl)-methanol (0.66 g, 71%, colorless oil).

Step 2: (2-Ethoxy-naphthalen-1-yl)-methanol (0.38 g, 1.88 mmol) in toluene (5 mL) was cooled to 0° C. and thionyl chloride (0.21 mL, 2.82 mmol) was added. After 187 h at RT the reaction was diluted with $H_2O$ and EtOAc. The organic layer was washed with $H_2O$, sat. $NaHCO_3$, brine, dried over $Na_2SO_4$ and concentrated to afford the title compound (0.33 g, yellow solid) which was used without purification.

4-(Bromomethyl)isoquinoline hydrobromide

Isoquinolin-4-ylmethanol (0.2 g, 1.26 mmol, Eq: 1.00) was combined with AcOH (5 mL). 33%, HBr in AcOH (11.9 g, 8 mL, 48.6 mmol, Eq: 38.7) was added. The mixture was heated at reflux for 2 h during which time a precipitate formed. The mixture was cooled, diluted with ether and Cinnolin-4-ylmethyl methanesulfonate Step 1: Methyl cinnoline-4-carboxylate (1.68 g, 8.93 mmol, Eq: 1.00) was combined with MeOH (40 mL), cooled to 0° C. and NaBH$_4$ (675 mg, 17.9 mmol, Eq: 2) added in portions. The mixture was warmed to RT stirred 1.5 h, diluted with sat. NH$_4$Cl and concentrated. The resulting mixture was triturated with EtOAc and filtered, the filtrate was concentrated and the residue purified by flash chromatography. The resulting material was triturated with ether to give cinnolin-4-ylmethanol (0.9566 g, blue solid).

Step 2: In a similar manner to that described for the preparation of (3-((trimethylsilyl)ethynyl)quinolin-4-yl) methyl methanesulfonate Step 5 except the reaction was stirred at 0° C. for 1 h, cinnolin-4-ylmethanol (0.15 g, 936 µmol) was converted to the title compound (177 mg, dark blue oil) which was used without purification.

Bromo-5-(bromomethyl)naphthalene

Step 1: 5-Bromo-1-naphthoic acid (1.32 g, 5.26 mmol, Eq: 1.00) was combined with THF (5 mL), the mixture cooled to 0° C. and borane tetrahydrofuran complex (13.1 mmol, Eq: 2.5) was added. The mixture was stirred at RT for 18 h, diluted with H$_2$O and concentrated. The residue was diluted with EtOAc and washed with brine. The organic layer was dried over Na$_2$SO$_4$, concentrated and the residue purified by flash chromatography to afford (5-bromonaphthalen-1-yl)methanol (1.13 g, white solid).

Step 2: (5-Bromonaphthalen-1-yl)methanol (1.13 g, 4.77 mmol, Eq: 1.00) and pyridine (377 mg, 4.77 mmol, Eq: 1) were combined with DCM (20 mL), cooled to 0° C. and PBr$_3$ (1.29 g, 4.77 mmol, Eq: 1) in 10 mL DCM was added. After 2 h, the mixture was diluted with an ice/H$_2$O mixture and DCM. The layers were separated and the aqueous layer was extracted with DCM. The combined organic layers were washed with NaHCO$_3$, brine, dried over Na$_2$SO$_4$ and concentrated. The residue was purified by flash chromatography to afford the title compound (0.4698 g, white solid).

(1,8-Naphthyridin-4-yl)methyl methanesulfonate

Step 1: 1,8-naphthyridine-4-carboxylic acid (1.5 g, 8.61 mmol, Eq: 1.00) was dissolved in DMF (5 mL), the solution cooled to 0° C. and thionyl chloride (8.15 g, 5 mL, 68.5 mmol, Eq: 7.95) added. After 20 min., mixture was warmed to RT. After 60 min., the mixture was concentrated, the residue cooled to 0° C. and MeOH (39.6 g, 50 mL, 1.24 mol, Eq: 143) added. The mixture was heated to 70° C. After 18 h, the mixture was cooled, concentrated, diluted with sat. NaHCO$_3$ and extracted with EtOAc. The extracts were combined, washed with H$_2$O, brine, dried over Na$_2$SO$_4$ and concentrated. The resulting material was purified by flash chromatography to afford methyl 1,8-naphthyridine-4-carboxylate (0.98 g, yellow solid).

Step 2: Methyl 1,8-naphthyridine-4-carboxylate (0.9779 g, 5.2 mmol, Eq: 1.00) was dissolved in MeOH (25 mL), the solution cooled to 0° C. and NaBH$_4$ (590 mg, 15.6 mmol, Eq: 3) added in portions. The mixture was warmed to RT and stirred overnight. The mixture was diluted with sat. NH$_4$Cl and concentrated. The residue was triturated with a naphtha of 25% MeOH in EtOAc, filtered and the filtrate passed through a silica gel plug and concentrated to give a yellow solid that was triturated with ether to afford (1,8-naphthyridin-4-yl)methanol (0.64 g) which was used without purification.

Step 3: In a similar manner to that described for the preparation of (3-((trimethylsilyl)ethynyl)quinolin-4-yl) methyl methanesulfonate Step 5, (1,8-naphthyridin-4-yl) methanol (0.1 g, 624 µmol) was converted to the title compound which was used immediately without purification.

1-(Chloromethyl)-2-isopropoxynaphthalene

Step 1: 2-Isopropoxy-1-naphthaldehyde (0.83 g, 3.87 mmol) was combined with THF (4 mL) and MeOH (20 mL), the solution cooled to 0° C., NaBH$_4$ (147 mg, 3.87 mmol) was added and the mixture warmed to RT. After 3 h the mixture was diluted with H$_2$O and extracted with EtOAc. The organic extracts were washed with H$_2$O, dried over Na$_2$SO$_4$ and concentrated to give (2-isopropoxynaphthalen-1-yl)methanol (0.8128 g, yellow oil).

Step 2: (2-Isopropoxynaphthalen-1-yl)methanol (0.81 g, 3.76 mmol) and pyridine (0.3 mL, 3.76 mmol) in THF 10 mL was cooled to 0° C. and thionyl chloride (0.21 mL, 2.82 mmol) was added. After 18 h at RT, the reaction was diluted with EtOAc and washed with H$_2$O, brine, dried over Na$_2$SO$_4$ and concentrated to afford the title compound (0.75 g, 85%, beige solid) which was used without purification.

2-(Benzyloxy)-1-(chloromethyl)naphthalene

Step 1: In a similar manner to that described for the preparation of 1-(chloromethyl)-2-isopropoxynaphthalene, 2-(benzyloxy)-1-naphthaldehyde (1.5 g, 5.72 mmol) was converted to the title compound (1.14 g, 77%, beige solid) which was used without purification.

1-(Bromomethyl)anthracene

Anthracen-1-ylmethanol (0.36 g, 1.73 mmol, Eq: 1.00) was combined with CHCl$_3$ (7 mL) and pyridine, the mixture cooled to 0° C., PBr$_3$ (234 mg, 864 µmol, Eq: 0.5) added and the mixture warmed to RT. After 1 h, the mixture was diluted with H$_2$O. The organic layer was separated, washed with H$_2$O, dried over Na$_2$SO$_4$ and concentrated to afford the title compound (0.303 g, yellow solid) which was used without purification.

7-Bromo-1-(bromomethyl)naphthalene

7-Bromo-1-methylnaphthalene (0.4158 g, 1.88 mmol, Eq: 1.00), N-bromosuccinimide (335 mg, 1.88 mmol, Eq: 1.00) and benzoyl peroxide (4.56 mg, 18.8 µmol, Eq: 01) were combined with CCl$_4$ (10 mL) in a 20 mL sealed tube to give a light yellow suspension which was heated to 80° C. for 15 h. The mixture was cooled, concentrated and the resulting material was purified by flash chromatography to afford the title compound (0.3627 g white solid).

Methyl-[(S)-1-((S)-2-oxo-2,3,4,5-tetrahydro-1H-benzo[b]azepin-3-ylcarbamoyl)-ethyl]-carbamic acid tert-butyl ester

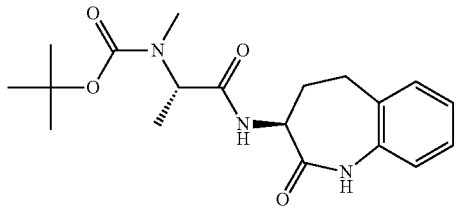 [SMILES: C[C@@H](C(=O)N[C@H]1CCc2ccccc2NC1=O)N(C)C(=O)OC(C)(C)C]

(S)-3-Amino-1,3,4,5-tetrahydro-benzo[b]azepin-2-one (0.4186 g, 2.38 mmol, Eq: 1.00), BOC-N-Me-Ala-OH (579 mg, 2.85 mmol, Eq: 1.2) and TEA (721 mg, 993 μL, 7.13 mmol, Eq: 3) were combined with DMF (8 mL) to give an off-white solution. O-benzotriazol-1-yl-N,N,N'N'-tetramethyluronium hexafluorophosphate (HBTU, 1.08 g, 2.85 mmol, Eq: 1.2) and 1-hydroxybenzotriazole hydrate (HOBT.H$_2$O, 437 mg, 2.85 mmol, Eq: 1.2) in 8 mL DMF were added. After 18 h, the mixture was poured into 100 mL brine and extracted with EtOAc. The extracts were combined, washed with 1:1 sat. NaHCO$_3$/brine and brine. The extracts were dried over Na$_2$SO$_4$ and concentrated. The resulting material was purified by flash chromatography to give the title compound (0.808 g, 94%, white foam).

(S)-3-Amino-1-((3-methoxyquinolin-4-yl)methyl)-4,5-dihydro-1H-benzo[b]azepin-2 (3H)-one dihydrochloride

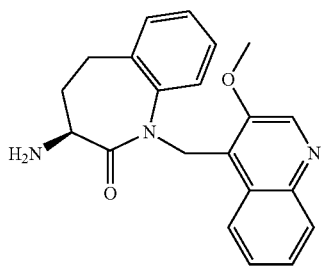 [SMILES: COc1cnc2ccccc2c1CN1C(=O)[C@@H](N)CCc2ccccc21]

Step 1: (S)-3-Amino-4,5-dihydro-1H-benzo[b]azepin-2 (3H)-one (169 mg, 959 μmol, Eq: 1.00) was combined with DCM (5 mL), di-tert-butyl dicarbonate (230 mg, 1.05 mmol, Eq: 1.10) was added and the mixture was stirred at RT for 3 h. The mixture was diluted with 1 N HCl and extracted with EtOAC. The combined extracts were washed with sat. NaHCO$_3$, brine, dried over Na$_2$SO$_4$ and concentrated to afford (S)-tert-butyl 2-oxo-2,3,4,5-tetrahydro-1H-benzo[b]azepin-3-ylcarbamate which was used without purification (265 mg, 100%, white solid).

Step 2: (S)-tert-Butyl 2-oxo-2,3,4,5-tetrahydro-1H-benzo[b]azepin-3-ylcarbamate (185 mg, 669 μmol, Eq: 1.00) and 4-(chloromethyl)-3-methoxyquinoline (209 mg, 1.00 mmol, Eq: 1.5) were combined with DMF (6 mL) and Cs$_2$CO$_3$ (327 mg, 1.00 mmol, Eq: 1.5) and NaI (151 mg, 1.00 mmol, Eq: 1.5) were added. The mixture was stirred at 50° C. for 3 h, cooled, diluted with H$_2$O and extracted with EtOAc. The combined extracts were dried over Na$_2$SO$_4$, filtered and concentrated. The resulting material was purified by flash chromatography to afford [(S)-1-(3-methoxy-quinolin-4-yl-methyl)-2-oxo-2,3,4,5-tetrahydro-1H-benzo[b]azepin-3-yl]-carbamic acid tert-butyl ester (188 mg, 63%, pale yellow foam).

Step 3: 2 N HCl in ether (1.00 mL, 2.00 mmol, Eq: 4.76) was added to a solution of [(S)-1-(3-methoxy-quinolin-4-ylmethyl)-2-oxo-2,3,4,5-tetrahydro-1H-benzo[b]azepin-3-yl]-carbamic acid tert-butyl ester (188 mg, 420 μmol, Eq: 1.00) in MeOH (0.5 mL). After 3 h the mixture was concentrated to afford the title compound (177 mg, 100%). MS m/z 348.0 (MH$^+$)

(3-Cyclopropylquinolin-4-yl)methyl methanesulfonate

Step 1: A mixture of methyl 3-(trifluoromethylsulfonyloxy)naphthale-4-carboxylate (1.26 g, 3.76 mmol, Eq: 1.00), potassium cyclopropyltrifluoroborate (612 mg, 4.13 mmol, Eq: 1.1), 2-dicyclohexylphosphino-2',6'-di-1-propoxy-1,1'-biphenyl (210 mg, 451 μmol, Eq: 0.12), Pd(Oac)$_2$ (50.6 mg, 225 μmol, Eq: 06) and K$_2$CO$_3$ (519 mg, 3.76 mmol, Eq: 1.00) in toluene (8 mL) and H$_2$O (800 μL) was purged with N$_2$ and heated to 80° C. After 15 h the mixture was poured into EtOAc, washed with brine, dried over Na$_2$SO$_4$ and concentrated. The residue was purified by flash chromatography to afford the methyl 3-cyclopropylquinoline-4-carboxylate (0.6861 g, 80.3%, yellow oil). MS m/z 228.0 (MH$^+$)

Step 2: DIBAL-H 1 M in DCM (3.53 mL, 3.53 mmol, Eq: 3.3) was added to a solution of methyl 3-cyclopropylquinoline-4-carboxylate (0.2429 g, 1.07 mmol, Eq: 1.00) in DCM (20 mL) at −78° C. After 2 h the mixture was diluted with MeOH and a small amount of H$_2$O and solid Na$_2$SO$_4$ was added. The mixture was warmed to RT, filtered through Celite and the filtrate washed with brine and concentrated. The residue was purified by flash chromatography to afford (3-cyclopropylquinolin-4-yl)methanol (96.2 mg, 45.2%, white solid). MS m/z 200.0 (MH$^+$)

Step 3: Methanesulfonyl chloride (43.1 mg, 29.3 μL, 376 μmol, Eq: 1.5) was added to a mixture of (3-cyclopropylquinolin-4-yl)methanol (50 mg, 251 μmol, Eq: 1.00) and TEA (50.8 mg, 70.0 μL, 502 μmol, Eq: 2) in DCM (4 mL). After 45 min the mixture was diluted with DCM and washed with H$_2$O. and brine. The organic layer was dried over Na$_2$SO$_4$ and concentrated to afford the title compound (53.1 mg, 76.3%, light yellow solid) which was used without purification. MS m/z 277.9 (MH$^+$)

(2,6-Bis(trifluoromethyl)quinolin-4-yl)methyl methanesulfonate

In a similar manner to that described for (3-cyclopropylquinolin-4-yl)methyl methanesulfonate Step 3, (2,6-bis(trifluoromethyl)quinolin-4-yl)methanol (75 mg, 254 μmol) was converted to the title compound (63.2 mg, 66.6%, off-white solid) which was used without purification. MS m/z 373.9 (MH$^+$)

tert-Butyl methyl((S)-1-oxo-1-((S)-2-oxo-2,3,4,5-tetrahydro-1H-benzo[b]azepin-3-ylamino)butan-2-yl)carbamate

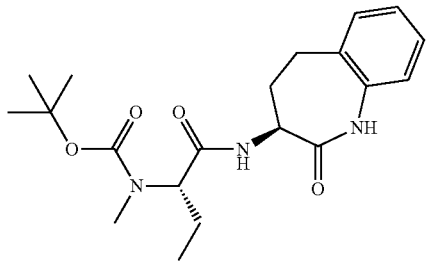 [SMILES: CC[C@@H](C(=O)N[C@H]1CCc2ccccc2NC1=O)N(C)C(=O)OC(C)(C)C]

A solution of HBTU (209 mg, 552 μmol, Eq: 1.2) and HOBT.H$_2$O (84.6 mg, 552 μmol, Eq: 1.2) in DMF (5 mL) was added to a mixture of (S)-3-amino-4,5-dihydro-1H-benzo[b]azepin-2(3H)-one (81.1 mg, 460 μmol, Eq: 1.00), (S)-2-(tert-butoxycarbonyl(methyl)amino)butanoic acid (Helv. Chim. Acta 1994, 1138, 100 mg, 460 μmol, Eq: 1.00) and TEA (140 mg, 192 μL, 1.38 mmol, Eq: 3) in DMF (5 mL). After 1 h, the mixture was diluted with EtOAc and washed with 1:1 sat NaHCO$_3$/brine and brine. The organic layer was dried over Na$_2$SO$_4$ and concentrated. The residue was purified by flash chromatography to afford the title compound (121.0 mg, 70.0%) as a white foam. MS m/z 376.0 (MH$^+$)

(5-Fluoro-2-methoxynaphthalen-1-yl)methyl methanesulfonate

Step 1: Sodium nitrite (1.13 g, 16.3 mmol, Eq: 1.3) in 4 mL H$_2$O was added dropwise to a mixture of 5-aminonaphthalen-2-ol (2 g, 12.6 mmol, Eq: 1.00) and tetrafluoroboric acid (48%, in H$_2$O) (11.8 g, 10.0 mL, 64.5 mmol, Eq: 5.13) in H$_2$O (10.0 mL) at 0° C. After 30 min the mixture was filtered, the filter cake washed with H$_2$O, ether and dried under vacuum to afford 6-hydroxynaphthalene-1-diazonium tetrafluoroborate 92.07 g, 63.9%, brown solid) which was used without purification.

Step 2: 6-Hydroxynaphthalene-1-diazonium tetrafluoroborate (2.07 g, 8.02 mmol, Eq: 1.00) in toluene (70 mL) was heated at 110° C. for 3 h. The mixture was cooled, filtered and the filter cake washed with toluene. The filtrate was concentrated and purified by flash chromatography to give 5-fluoronaphthalen-2-ol (0.4945 g, 38%, yellow-brown oil that solidified) which was used without purification.

Step 3: Iodomethane (866 mg, 381 μL, 6.1 mmol, Eq: 2) was added to a mixture of 5-fluoronaphthalen-2-ol (494.5 mg, 3.05 mmol, Eq: 1.00) and K$_2$CO$_3$ (1.26 g, 9.15 mmol, Eq: 3) in acetone (20 mL) and the mixture heated to 40° C. After 15 h., the mixture was cooled, diluted with EtOAc, washed with H$_2$O, dried over Na$_2$SO$_4$ and concentrated. The residue was purified by flash chromatography to give 1-fluoro-6-methoxynaphthalene (0.4245 g, 79%, nearly colorless oil).

Step 4: A solution of 1-fluoro-6-methoxynaphthalene (0.5077 g, 2.88 mmol, Eq: 1.00) in DCM (10 mL) was added to a mixture 1 M TiCl$_4$ in DCM (6.34 mL, 6.34 mmol, Eq: 2.2) and dichloromethyl methyl ether (364 mg, 282 μL, 3.17 mmol, Eq: 1.1) in DCM (10 mL) at 0° C. The mixture was warmed to RT. After 1 h, the mixture was poured into 1 M HCl and extracted with DCM. The combined extracts were washed with H$_2$O, brine, dried over Na$_2$SO$_4$ and concentrated. The residue was purified by flash chromatography to give 5-fluoro-2-methoxy-1-naphthaldehyde (0.4376 g, 74.4%, yellow solid). MS m/z 204.9 (MH$^+$)

Step 5: NaBH$_4$ (37.1 mg, 979 μmol, Eq: 1.00) was added to a suspension of 5-fluoro-2-methoxy-1-naphthaldehyde (0.2 g, 979 μmol, Eq: 1.00) in EtOH (4 mL). After 1 h the mixture was diluted with 1 N HCl and extracted with EtOAc. The combined extracts were washed with H$_2$O, dried over Na$_2$SO$_4$ and concentrated to give (5-fluoro-2-methoxynaphthalen-1-yl)methanol (175.5 mg, 86.9%, light yellow solid). MS m/z 188.9 (M–H$_2$O)

Step 6: In a similar manner to that described for (3-cyclopropylquinolin-4-yl)methyl methanesulfonate Step 3, (5-fluoro-2-methoxynaphthalen-1-yl)methanol (60 mg, 291 μmol) was converted to the title compound (35.1 mg, light yellow solid) which was used without purification.

(6-Fluoro-2-methoxynaphthalen-1-yl)methyl methanesulfonate

Step 1: In a similar manner to that described for 5-fluoro-2-methoxy-1-naphthaldehyde, 2-fluoro-6-methoxynaphthalene (WO 2002024619 A1, 0.35 g, 1.99 mmol) was converted to 6-fluoro-2-methoxy-1-naphthaldehyde (157.5 mg, 38.8%, off-white solid). MS m/z 205.0 (MH$^+$)

Step 2: In a similar manner to that described for (5-fluoro-2-methoxynaphthalen-1-yl)methyl methanesulfonate Step 5 except the mixture was stirred for 3 h, 6-fluoro-2-methoxy-1-naphthaldehyde (157.5 mg, 771 μmol) was converted to a material that was purified by flash chromatography. The purified material was lyophilized from MeCN/H$_2$O to afford (6-fluoro-2-methoxynaphthalen-1-yl)methanol (132.7 mg, white solid).

Step 3: In a similar manner to that described for (3-cyclopropylquinolin-4-yl)methyl methanesulfonate Step 3, (6-fluoro-2-methoxynaphthalen-1-yl)methanol (68 mg, 330 μmol) was converted to the title compound (49.5 mg, light yellow solid) which was used without purification.

(6-chloro-2-methoxynaphthalen-1-yl)methyl methanesulfonate

In a similar manner to that described for (6-fluoro-2-methoxynaphthalen-1-yl)methyl methanesulfonate, 2-chloro-6-methoxynaphthalene (WO 2002024619 A1, 1.1823 g, 6.14 mmol) was converted to the title compound (38.1 mg, off-white solid) which was used without purification.

The compounds of the invention may form a salt with an acid, for example hydrochloric acid, hydrobromic acid or trifluoroacetic acid. In the following examples, most of the compounds are reported in the hydrochloride salt form.

Example 1a (S)—N—[(S)-1-(5-Fluoro-2-methoxy-benzyl)-2-oxo-2,3,4,5-tetrahydro-1H-benzo[b]azepin-3-yl]-2-methylamino-propionamide hydrochloride

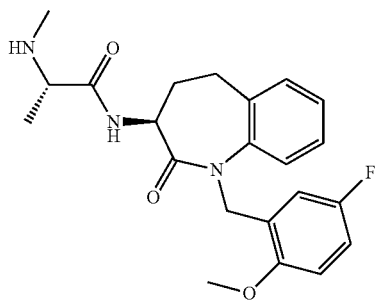 [SMILES: CN[C@@H](C)C(=O)N[C@H]1CCc2ccccc2N(Cc2cc(F)ccc2OC)C1=O]

Step 1: Methyl-[(S)-1-((S)-2-oxo-2,3,4,5-tetrahydro-1H-benzo[b]azepin-3-ylcarbamoyl)-ethyl]-carbamic acid tert-butyl ester (50 mg, 0.14 mmol), 2-(bromomethyl)-4-fluoro-1-methoxybenzene (36 mg, 0.17 mmol), and $Cs_2CO_3$ (135 mg, 0.42 mmol) were combined in DMF (2 mL) and stirred for 16 h at RT. The mixture was partitioned between EtOAc (30 mL) and $H_2O$ (30 mL). The aqueous layer was separated, and the organic layer was washed with $H_2O$, brine and dried over $MgSO_4$. The mixture was filtered and the filtrate concentrated to give purified by silica gel chromatography to afford {(S)-1-[(S)-1-(5-fluoro-2-methoxy-benzyl)-2-oxo-2,3,4,5-tetrahydro-1H-benzo[b]azepin-3yl carbamoyl]-ethyl}-methyl-carbamic acid tert-butyl ester (53 mg, 77%, colorless oil).

Step 2: {(S)-1-[(S)-1-(5-fluoro-2-methoxy-benzyl)-2-oxo-2,3,4,5-tetrahydro-1H-benzo[b]azepin-3yl carbamoyl]-ethyl}-methyl-carbamic acid tert-butyl ester (53 mg, 0.11 mmol) was dissolved in methanol (2 mL) and acetyl chloride (50 µL, 0.70 mmol) was added dropwise. The mixture was kept overnight at RT then was concentrated to give the title compound (42 mg, 91%, white solid). MS m/z 400 (MH$^+$)

In a similar manner to that described for Example 1a, methyl-[(S)-1-((S)-2-oxo-2,3,4,5-tetrahydro-1H-benzo[b]azepin-3-ylcarbamoyl)-ethyl]-carbamic acid tert-butyl ester can be converted to the following compounds as hydrochloride salts.

TABLE 1

| Examples | Final Product | m/z (MH$^+$) |
|---|---|---|
| 1b | | 406 |
| 1c | | 450 |
| 1d | | 418 |
| 1e | | 460 |
| 1f | | 416 |
| 1g | | 388 |

TABLE 1-continued

| Examples | Final Product | m/z (MH+) |
|---|---|---|
| 1h | (structure) | 442 |
| 1i | (structure) | 416 |
| 1j | (structure) | 460 |
| 1k | (structure) | 393 |
| 1l | (structure) | 420 |
| 1m | (structure) | 404 |
| 1n | (structure) | 508 |
| 1o | (structure) | 424 |

Example 2a (S)-2-(Methylamino)-N—((S)-2-oxo-1-(thiophen-2-ylmethyl)-2,3,4,5-tetrahydro-1H-benzo[b]azepin-3-yl)propanamide hydrochloride

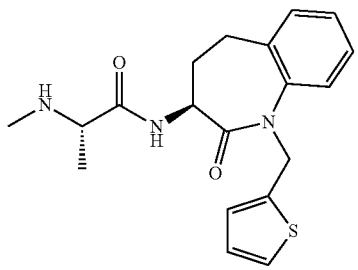 [SMILES: CN[C@@H](C)C(=O)N[C@H]1CCc2ccccc2N(Cc2cccs2)C1=O]

Step 1: To the mixture of methyl-[(S)-1-((S)-2-oxo-2,3,4,5-tetrahydro-1H-benzo[b]azepin-3-ylcarbamoyl)-ethyl]-carbamic acid tert-butyl ester (40 mg, 111 µmol) and Cs$_2$CO$_3$ (108 mg, 332 µmol) in DMF (1 mL) was added 2-(chloromethyl)thiophene (17.6 mg, 133 µmol) The suspension was stirred at ambient temperature for 2 h. The reaction was diluted with H$_2$O (10 mL) and extracted with EtOAc. The combined organics were washed with H$_2$O, brine, dried with MgSO$_4$ and concentrated. The resulting material was purified by flash chromatography to give methyl-[(S)-1-((S)-2-oxo-1-thiophen-2-ylmethyl-2,3,4,5-tetrahydro-1H-benzo[b]azepin-3-ylcarbamoyl)-ethyl]-carbamic acid tert-butyl ester (42 mg, 83%, colorless oil). MS m/z 458 (MH$^+$)

Step 2: Methyl-[(S)-1-((S)-2-oxo-1-thiophen-2-ylmethyl-2,3,4,5-tetrahydro-1H-benzo[b]azepin-3-ylcarbamoyl)-ethyl]-carbamic acid tert-butyl ester (40 mg, 87.4 µmol) was combined with 4 N HCl in 1,4-dioxane (3 mL). The mixture was stirred at ambient temperature for 1 h. The mixture was concentrated to give an oil that was lyophilized from MeCN/H$_2$O to afford the title compound (31 mg, 90%, off white solid). MS m/z 358 (MH$^+$)

In a similar manner to that described for Example 2a, methyl-[(S)-1-((S)-2-oxo-2,3,4,5-tetrahydro-1H-benzo[b]azepin-3-ylcarbamoyl)-ethyl]-carbamic acid tert-butyl ester can be converted to the following compounds.

TABLE 2

| Entry | Final Product | m/z (MH$^+$) |
|---|---|---|
| 2b | | 358 |
| 2c | | 359 |
| 2d | | 359 |
| 2e | | 343 |
| 2f | | 353 |
| 2g | | 353 |

TABLE 2-continued

| Entry | Final Product | m/z (MH+) |
|---|---|---|
| 2h | | 353 |
| 2i | | 356 |

Example 3

(S)-2-amino-N—((S)-1-((3-methoxyquinolin-4-yl)methyl)-2-oxo-2,3,4,5-tetrahydro-1H-benzo[b]azepin-3-yl)butanamide

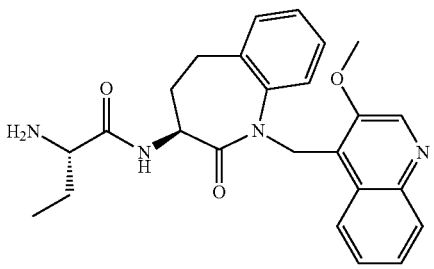 [SMILES: CC[C@H](N)C(=O)N[C@H]1CCc2ccccc2N(Cc2c(OC)cnc3ccccc23)C1=O]

Step 1: (S)-3-Amino-1-((3-methoxyquinolin-4-yl)methyl)-4,5-dihydro-1H-benzo[b]azepin-2(3H)-one dihydrochloride (65 mg, 155 μmol, Eq: 1.00), TEA (78.2 mg, 108 μL, 773 μmol, Eq: 5.00) and (S)-2-(tert-butoxycarbonylamino)butanoic acid (37.7 mg, 186 μmol, Eq: 1.20) were combined with DMF (1.5 mL), HOBT.H₂O (20.9 mg, 155 μmol, Eq: 1.00) and HBTU (70.4 mg, 186 μmol, Eq: 1.20) were added and the mixture was stirred for 1 h. The mixture was diluted with sat. NaHCO₃ and extracted with EtOAc. The combined extracts were washed with brine, dried over Na₂SO₄ and concentrated. The resulting material was purified by flash chromatography to provide {(S)-1-[(S)-1-(3-methoxy-quinolin-4-ylmethyl)-2-oxo-2,3,4,5-tetrahydro-1H-benzo[b]azepin-3-ylcarbamoyl]-propyl}-carbamic acid tert-butyl ester (62 mg, 75%).

Step 2: 2.0 M HCl in ether (2 mL, 4.00 mmol, Eq: 34.4) was added to a solution of {(S)-1-[(S)-1-(3-methoxy-quinolin-4-ylmethyl)-2-oxo-2,3,4,5-tetrahydro-1H-benzo[b]azepin-3-ylcarbamoyl]-propyl}-carbamic acid tert-butyl ester (62 mg, 116 μmol, Eq: 1.00) in MeOH (1 mL). After 1.5 h the mixture was concentrated. The residue was partitioned between 1 N NaOH/brine and EtOAc. The organic layer was dried over Na₂SO₄ and concentrated to afford the title compound (47 mg, 93%). MS m/z 433.0 (MH+)

Example 4

(S)-2-(2-Hydroxyethylamino)-N—((S)-1-((3-methoxyquinolin-4-yl)methyl)-2-oxo-2,3,4,5-tetrahydro-1H-benzo[b]azepin-3-yl)butanamide

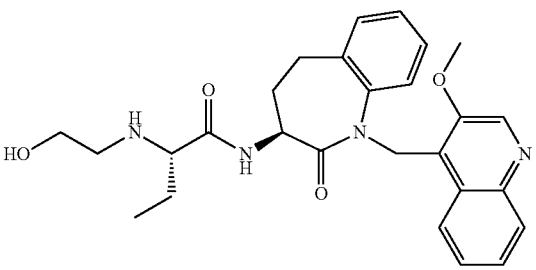 [SMILES: CC[C@H](NCCO)C(=O)N[C@H]1CCc2ccccc2N(Cc2c(OC)cnc3ccccc23)C1=O]

(S)-2-Amino-N—((S)-1-((3-methoxyquinolin-4-yl)methyl)-2-oxo-2,3,4,5-tetrahydro-1H-benzo[b]azepin-3-yl)butanamide (20 mg, 46.2 μmol, Eq: 1.00) and glycolaldehyde dimer (3.05 mg, 25.4 μmol, Eq: 0.55) were dissolved MeOH (0.5 mL), acetic acid (2.78 mg, 2.67 μL, 46.2 μmol, Eq: 1.00) and sodium cyanoborohydride (4.36 mg, 69.4 μmol, Eq: 1.50) were successively added and the mixture was stirred overnight. The mixture was diluted with 1 N HCl, made basic by adding 1 N NaOH and extracted with EtOAc. The resulting material was purified by flash chromatography to afford the title compound contaminated with ~30%, of an epimeric isomer (5.5 mg, 63%). MS m/z 477.1 (MH+)

Examples 5(a) & 5(b)

(S)-2-Amino-N—[(R)-1-(6-bromo-2-methoxy-naphthalen-1-ylmethyl)-2-oxo-2,3,4,5-tetrahydro-1H-benzo[b]azepin-3-yl]-butyramide hydrochloride (Example 5a)

and (S)-2-Amino-N—[(S)-1-(6-bromo-2-methoxy-naphthalen-1-ylmethyl)-2-oxo-2,3,4,5-tetrahydro-1H-benzo[b]azepin-3-yl]-butyramide (Example 5b)

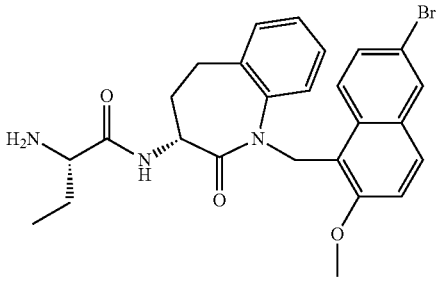

5(a)

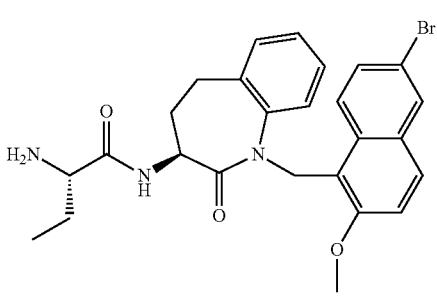

5(b)

Step 1: 3-Amino-1,3,4,5-tetrahydro-benzo[b]azepin-2-one (416 mg, 2.36 mmol, Eq: 1.00), (S)-2-(BOC-amino)butyric acid (578 mg, 2.84 mmol, Eq: 1.2) and TEA (717 mg, 987 μL, 7.08 mmol, Eq: 3.00) were combined with DMF (10 mL) and HOBT.H$_2$O (383 mg, 2.83 mmol, Eq: 1.20) and HBTU (1.34 g, 3.54 mmol, Eq: 1.50) were added. After 1 h 20 min., the mixture was diluted with 1 N HCl and extracted with EtOAc. The combined extracts were washed with 1 N NaOH and brine, dried over Na$_2$SO$_4$ and concentrated to afford [(S)-1-(2-oxo-2,3,4,5-tetrahydro-1H-benzo[b]azepin-3-ylcarbamoyl)-propyl]-carbamic acid tert-butyl ester (860 mg) as a mixture of diastereomers which was used without purification.

Step 2: [(S)-1-(2-Oxo-2,3,4,5-tetrahydro-1H-benzo[b]azepin-3-ylcarbamoyl)-propyl]-carbamic acid tert-butyl ester (300 mg, 830 μmol, Eq: 1.00), 6-bromo-1-(chloromethyl)-2-methoxynaphthalene (332 mg, 1.16 mmol, Eq: 1.40) and NaI (187 mg, 1.25 mmol, Eq: 1.50) were combined with DMF (10 mL) and Cs$_2$CO$_3$ (406 mg, 1.25 mmol, Eq: 1.50) was added. The mixture was stirred at 60° C. overnight, diluted with H$_2$O and extracted with EtOAc. The combined extracts were washed with brine, dried over Na$_2$SO$_4$ and concentrated. The resulting material was purified by flash chromatography to afford {(S)-1-[1-(6-bromo-2-methoxy-naphthalen-1-ylmethyl)-2-oxo-2,3,4,5-tetrahydro-1H-benzo[b]azepin-3-ylcarbamoyl]-propyl}-carbamic acid tert-butyl ester as a mixture of diastereomers.

Step 3: The diastereomers were separated by supercritical fluid chromatography (SFC) on a chiral column to give one diastereomer that eluted first, Diastereomer 1 (5a), and one that eluted second, Diastereomer 2 (5b).

Step 4: In two separate flasks, each diastereomer was combined with MeOH (1 mL) to give colorless solutions and treated with 2.0 M HCl in ether (3 mL, 6.00 mmol, Eq: 29.5) at RT for 6 h. Each mixture was separately concentrated and the individual products were lyophilized from MeCN/H$_2$O. Diastereomer 1 (5a): 106 mg, MS m/z 511.9 (MH$^+$) Diastereomer 2 (5a): 110 mg, MS m/z 511.9 (MH$^+$). Both diastereomers were tested separately in the BIR2 TR-FRET assay with Diastereomer 2 (5b) being more potent. By analogy from known analogs, the (S,S) stereochemistry was assigned to Diastereomer 2 (5b).

Example 6

(S)—N—((S)-1-((6-Bromo-2-methoxynaphthalen-1-yl)methyl)-2-oxo-2,3,4,5-tetrahydro-1H-benzo[b]azepin-3-yl)-2-(2-hydroxyethylamino)butanamide

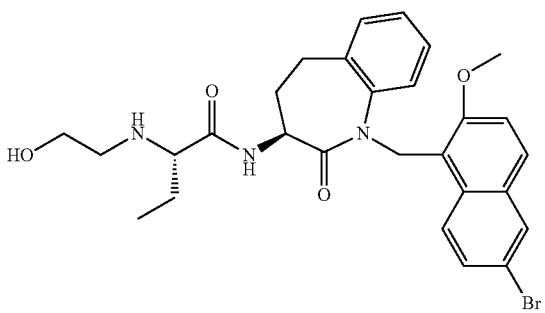 [SMILES: CC[C@H](NCCO)C(=O)N[C@H]1CCc2ccccc2N(Cc2c(OC)ccc3cc(Br)ccc23)C1=O]

Step 1: (S)-2-Amino-N—[(S)-1-(6-bromo-2-methoxy-naphthalen-1-ylmethyl)-2-oxo-2,3,4,5-tetrahydro-1H-benzo[b]azepin-3-yl]-butyramide hydrochloride (90 mg, 165 μmol, Eq: 1.00) was dissolved in H$_2$O and the pH of the solution was adjusted to 10 with 10% NaOH and the solution extracted with EtOAC. The organic extracts were dried with Na$_2$SO$_4$, filtered and concentrated to afford 83 mg of (S)-2-amino-N—[(S)-1-(6-bromo-2-methoxy-naphthalen-1-ylmethyl)-2-oxo-2,3,4,5-tetrahydro-1H-benzo[b]azepin-3-yl]-butyramide.

Step 2: (S)-2-Amino-N—[(S)-1-(6-bromo-2-methoxy-naphthalen-1-ylmethyl)-2-oxo-2,3,4,5-tetrahydro-1H-benzo[b]azepin-3-yl]-butyramide was dissolved in MeOH (2 mL) and glycolaldehyde dimer (10.9 mg, 90.5 μmol, Eq: 0.55), acetic acid (9.5 μL, 165 μmol, Eq: 1.0) and sodium cyanoborohydride (15.5 mg, 247 μmol, Eq: 1.5) were successively added. The mixture was stirred at RT overnight. The mixture was diluted with 1 N HCl, 1 N NaOH added to adjust the pH to ca. 11. The mixture was extracted with EtOAc, the extracts washed with brine, dried over Na$_2$SO$_4$, concentrated and the resulting material purified by flash chromatography to afford the title compound which was lyophilized from MeCN/H$_2$O (55 mg, 60%). MS m/z 556.0 (MH$^+$)

Example 7

(S)—N—((S)-1-((6-Bromo-2-methoxynaphthalen-1-yl)methyl)-2-oxo-2,3,4,5-tetrahydro-1H-benzo[b]azepin-3-yl)-2-(cyclobutylamino)butanamide

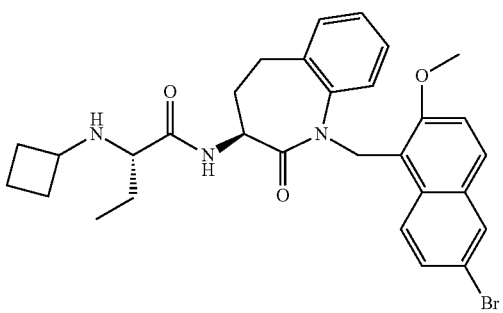 [SMILES: CC[C@H](NC1CCC1)C(=O)N[C@H]1CCc2ccccc2N(Cc2c(OC)ccc3cc(Br)ccc23)C1=O]

Following the procedure described in Example 6, (S)-2-amino-N—[(S)-1-(6-bromo-2-methoxy-naphthalen-1-ylmethyl)-2-oxo-2,3,4,5-tetrahydro-1H-benzo[b]azepin-3-yl]-butyramide hydrochloride (37 mg) and cyclubutanone (5 mg) were converted to the title compound (29 mg, 70%). MS m/z 565.8 (MH+)

Example 8

(S)-2-(Benzylamino)-N—((S)-1-((6-bromo-2-methoxynaphthalen-1-yl)methyl)-2-oxo-2,3,4,5-tetrahydro-1H-benzo[b]azepin-3-yl)butanamide

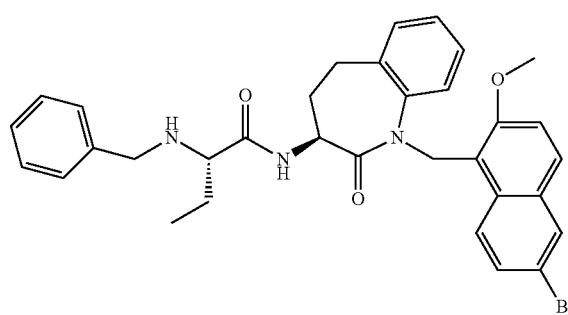

Following the procedure described in Example 6, (S)-2-amino-N—[(S)-1-(6-bromo-2-methoxy-naphthalen-1-ylmethyl)-2-oxo-2,3,4,5-tetrahydro-1H-benzo[b]azepin-3-yl]-butyramide hydrochloride (36 mg) and benzaldehyde (7.5 mg) were converted to the title compound (34 mg, 80%). MS m/z 602.0 (MH+)

Example 9

(S)—N—((S)-1-((6-Bromo-2-methoxynaphthalen-1-yl)methyl)-2-oxo-2,3,4,5-tetrahydro-1H-benzo[b]azepin-3-yl)-2-(oxetan-3-ylamino)butanamide

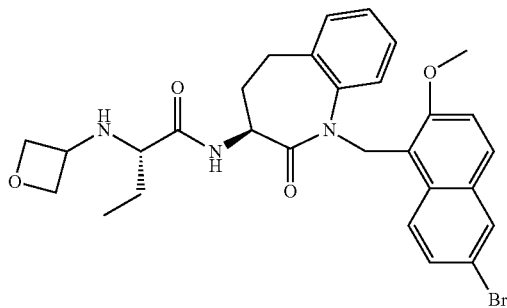 [SMILES: CC[C@H](NC1COC1)C(=O)N[C@H]1CCc2ccccc2N(Cc2c(OC)ccc3cc(Br)ccc23)C1=O]

Following the procedure described in Example 6, (S)-2-amino-N—[(S)-1-(6-bromo-2-methoxy-naphthalen-1-ylmethyl)-2-oxo-2,3,4,5-tetrahydro-1H-benzo[b]azepin-3-yl]-butyramide hydrochloride (35 mg) and oxetan-3-one (5 mg) were converted to the title compound (22 mg, 57%). MS m/z 568.0 (MH+

Example 10

(2S,3S)-2-Amino-N—((S)-1-((6-bromo-2-methoxynaphthalen-1-yl)methyl)-2-oxo-2,3,4,5-tetrahydro-1H-benzo[b]azepin-3-yl)-3-hydroxybutanamide hydrochloride

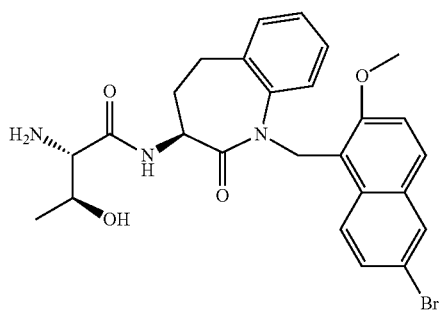 [SMILES: COc1ccc2cc(Br)ccc2c1CN1C(=O)[C@@H](NC(=O)[C@@H](N)[C@H](C)O)CCc2ccccc21]

Step 1: In a similar manner to that described for Example 5 Step 1, except 6 Eq. of TEA were used (S)-3-amino-4,5-dihydro-1H-benzo[b]azepin-2(3H)-one (123 mg, 698 µmol, Eq: 1.00), BOC-allo-threonine dicyclohexylamine salt (336 mg, 838 µmol, Eq: 1.20) were converted to [(1S,2S)-2-hydroxy-1-((S)-2-oxo-2,3,4,5-tetrahydro-1H-benzo[b]azepin-3-ylcarbamoyl)-propyl]-carbamic acid tert-butyl ester (263 mg, white foam).

Step 2: In a similar manner to that described for Example 5 Step 2 except the mixture was heated at 65° C. for 5 h, [(1S,2S)-2-hydroxy-1-((S)-2-oxo-2,3,4,5-tetrahydro-1H-benzo[b]azepin-3-ylcarbamoyl)-propyl]-carbamic acid tert-butyl ester (104 mg, 276 µmol, Eq: 1.00) and 6-bromo-1-(chloromethyl)-2-methoxynaphthalene (102 mg, 358 µmol, Eq: 1.30) were converted to {(1S,2S)-1-[(S)-1-(6-bromo-2-methoxy-naphthalen-1-ylmethyl)-2-oxo-2,3,4,5-tetrahydro-1H-benzo[b]azepin-3-ylcarbamoyl]-2-hydroxy-propyl}-carbamic acid tert-butyl ester (70 mg, 41%).

Step 3: 2.0 M HCl in ether (3 mL, 6.00 mmol, Eq: 55.3) was added to a solution of {(1S,2S)-1-[(S)-1-(6-bromo-2-methoxy-naphthalen-1-ylmethyl)-2-oxo-2,3,4,5-tetrahydro-1H-benzo[b]azepin-3-ylcarbamoyl]-2-hydroxy-propyl}-carbamic acid tert-butyl ester (68 mg, 109 µmol, Eq: 1.00) in MeOH (3 mL). After 2 h the mixture was concentrated and the residue was lyophilized from MeCN/H2O to afford the title compound (61 mg, 100%, white powder). MS m/z 528.0 (MH+)

Example 11

(2S,3R)-2-Amino-N—((S)-1-((6-bromo-2-methoxynaphthalen-1-yl)methyl)-2-oxo-2,3,4,5-tetrahydro-1H-benzo[b]azepin-3-yl)-3-hydroxybutanamide hydrochloride

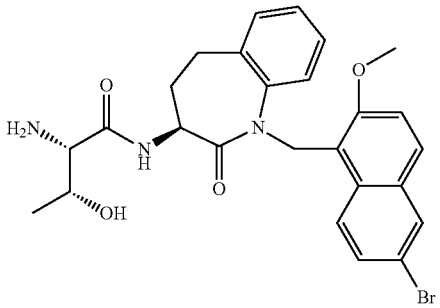 [SMILES: COc1ccc2cc(Br)ccc2c1CN1C(=O)[C@@H](NC(=O)[C@@H](N)[C@@H](C)O)CCc2ccccc21]

Step 1: In a similar manner to that described for Example 5 Step 1, (S)-3-amino-4,5-dihydro-1H-benzo[b]azepin-2 (3H)-one (123 mg, 698 µmol, Eq: 1.00) and BOC-Thr-OH (184 mg, 838 µmol, Eq: 1.20) were converted to [(1S,2R)-2-hydroxy-1-((S)-2-oxo-2,3,4,5-tetrahydro-1H-benzo[b]azepin-3-ylcarbamoyl)-propyl]-carbamic acid tert-butyl ester (249 mg, 95%) which was used without purification.

Step 2: In a similar manner to that described for Example 5 Step 2 except the mixture was heated at 65° C. for 5 h, [(1S,2R)-2-hydroxy-1-((S)-2-oxo-2,3,4,5-tetrahydro-1H-benzo[b]azepin-3-ylcarbamoyl)-propyl]-carbamic acid tert-butyl ester (104 mg, 276 µmol, Eq: 1.00) and 6-bromo-1-(chloromethyl)-2-methoxynaphthalene (102 mg, 358 µmol, Eq: 1.30) were converted to {(1S,2R)-1-[(S)-1-(6-bromo-2-methoxy-naphthalen-1-ylmethyl)-2-oxo-2,3,4,5-tetrahydro-1H-benzo[b]azepin-3-ylcarbamoyl]-2-hydroxy-propyl}-carbamic acid tert-butyl ester which was purified by flash chromatography (66 mg, 38%).

Step 3: In a similar manner to that described for Example 10 Step 3, {(1S,2R)-1-[(S)-1-(6-bromo-2-methoxy-naphthalen-1-ylmethyl)-2-oxo-2,3,4,5-tetrahydro-1H-benzo[b]azepin-3-ylcarbamoyl]-2-hydroxy-propyl}-carbamic acid tert-butyl ester (68 mg, 109 µmol) was converted to the title compound (61 mg, 100%, white powder). MS m/z 528.0 (MH$^+$)

Example 12

(S)-2-Amino-N—[(S)-1-(6-bromo-2-methoxy-naphthalen-1-ylmethyl)-2-oxo-2,3,4,5-tetrahydro-1H-benzo[b]azepin-3-yl]-3-hydroxy-propionamide hydrochloride

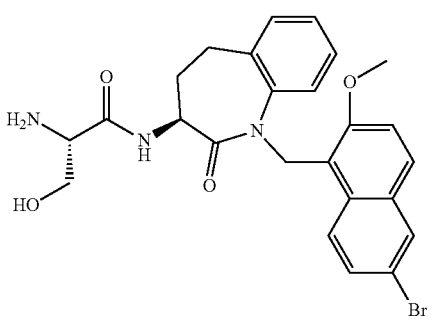 [SMILES: COc1ccc2cc(Br)ccc2c1CN1C(=O)[C@@H](NC(=O)[C@@H](N)CO)CCc2ccccc21]

Step 1: In a similar manner to that described for Example 5 Step 1, (S)-3-amino-4,5-dihydro-1H-benzo[b]azepin-2 (3H)-one (150 mg, 851 µmol, Eq: 1.00), BOC-Ser-OH (210 mg, 1.02 mmol, Eq: 1.20) were converted to [(S)-2-hydroxy-1-((S)-2-oxo-2,3,4,5-tetrahydro-1H-benzo[b]azepin-3-yl-carbamoyl)-ethyl]-carbamic acid tert-butyl ester (254 mg) which was used without purification.

Step 2: [(S)-2-Hydroxy-1-((S)-2-oxo-2,3,4,5-tetrahydro-1H-benzo[b]azepin-3-ylcarbamoyl)-ethyl]-carbamic acid tert-butyl ester (107 mg, 294 µmol, Eq: 1.00), 6-bromo-1-(chloromethyl)-2-methoxynaphthalene (92.5 mg, 324 µmol, Eq: 1.10) and Cs$_2$CO$_3$ (106 mg, 324 µmol, Eq: 1.10) were combined with DMF (4 mL) and NaI (44.1 mg, 294 µmol, Eq: 1.00) was added. The mixture was stirred at 50° C. for 5 h and additional 6-bromo-1-(chloromethyl)-2-methoxynaphthalene (17 mg, 0.2 eq) was added and the mixture was stirred at 65° C. for 4.5 h. The mixture was cooled to RT. After 60 h the mixture was diluted with H$_2$O and extracted with EtOAc. The combined extracts were dried over Na$_2$SO$_4$, concentrated and the residue purified by flash chromatography to afford {(S)-1-[(S)-1-(6-bromo-2-methoxy-naphthalen-1-ylmethyl)-2-oxo-2,3,4,5-tetrahydro-1H-benzo[b]azepin-3-ylcarbamoyl]-2-hydroxy-ethyl}-carbamic acid tert-butyl ester (71 mg, 39%).

Step 3: In a similar manner to that described for Example 10 Step 3, {(S)-1-[(S)-1-(6-bromo-2-methoxy-naphthalen-1-ylmethyl)-2-oxo-2,3,4,5-tetrahydro-1H-benzo[b]azepin-3-ylcarbamoyl]-2-hydroxy-ethyl}-carbamic acid tert-butyl ester (70 mg, 114 µmol, Eq: 1.00) was converted to the title compound (61 mg, 97%, white foam). MS m/z 513.7 (MH$^+$)

Example 13

{(S)-1-[(S)-1-(6-Bromo-2-methoxy-naphthalen-1-ylmethyl)-2-oxo-2,3,4,5-tetrahydro-1H-benzo[b]azepin-3-ylcarbamoyl]-2-hydroxy-ethyl}-carbamic acid tert-butyl ester hydrochloride

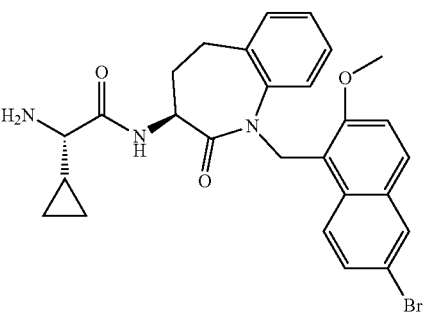 [SMILES: COc1ccc2cc(Br)ccc2c1CN1C(=O)[C@@H](NC(=O)[C@@H](N)C2CC2)CCc2ccccc21]

Step 1: In a similar manner to that described for Example 5 Step 1, (S)-3-amino-4,5-dihydro-1H-benzo[b]azepin-2 (3H)-one (150 mg, 851 µmol, Eq: 1.00) and (S)-2-(tert-butoxycarbonylamino)-2-cyclopropylacetic acid (220 mg, 1.02 mmol, Eq: 1.20) were converted to [(S)-cyclopropyl-((S)-2-oxo-2,3,4,5-tetrahydro-1H-benzo[b]azepin-3-ylcarbamoyl)-methyl]-carbamic acid tert-butyl ester (318 mg) which was used without purification.

In a similar manner to that described for Example 5 Step 2 the mixture was heated at 65° C. for 4 h, [(S)-cyclopropyl-((S)-2-oxo-2,3,4,5-tetrahydro-1H-benzo[b]azepin-3-ylcarbamoyl)-methyl]-carbamic acid tert-butyl ester (120 mg, 321 µmol, Eq: 1.00) and 6-bromo-1-(chloromethyl)-2-methoxynaphthalene (119 mg, 418 µmol, Eq: 1.30)

were converted to {(S)—[(S)-1-(6-bromo-2-methoxy-naphthalen-1-ylmethyl)-2-oxo-2,3,4,5-tetrahydro-1H-benzo[b]azepin-3-ylcarbamoyl]-cyclopropyl-methyl}-carbamic acid tert-butyl ester (120 mg, 60%) after purification by flash chromatography.

In a similar manner to that described for Example 10 Step 3, {(S)—[(S)-1-(6-bromo-2-methoxy-naphthalen-1-ylmethyl)-2-oxo-2,3,4,5-tetrahydro-1H-benzo[b]azepin-3-ylcarbamoyl]-cyclopropyl-methyl}-carbamic acid tert-butyl ester (115 mg, 185 µmol, Eq: 1.00) was converted to the title compound (92 mg, 92%). MS m/z 524.0 (MH$^+$)

Example 14

(S)—N—{(S)-1-[2-(3-Hydroxy-oxetan-3-ylethynyl)-naphthalen-1-ylmethyl]-2-oxo-2,3,4,5-tetrahydro-1H-benzo[b]azepin-3-yl}-2-methylamino-propionamide

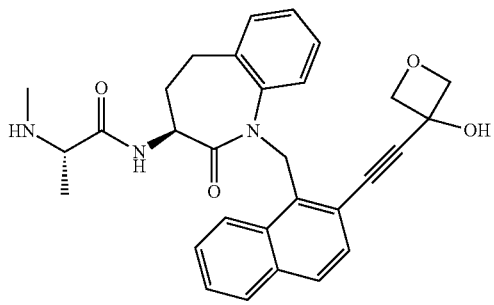 [SMILES: CN[C@@H](C)C(=O)N[C@H]1CCc2ccccc2N(Cc2c(C#CC3(O)COC3)ccc3ccccc23)C1=O]

Step 1: In a similar manner to that described for Example 5 Step 2 except the mixture was heated at 50° C., methyl-[(S)-1-((S)-2-oxo-2,3,4,5-tetrahydro-1H-benzo[b]azepin-3-ylcarbamoyl)-ethyl]-carb amic acid tert-butyl ester (67 mg, 185 µmol, Eq: 1.00) and (2-((3-hydroxyoxetan-3-yl)ethynyl)naphthalene-1-yl)methyl methanesulfonate (185 mg, 556 µmol, Eq: 3.00) were converted to ((S)-1-{(S)-1-[2-(3-hydroxy-oxetan-3-ylethynyl)-naphthalen-1-ylmethyl]-2-oxo-2,3,4,5-tetrahydro-1H-benzo[b]azepin-3-ylcarbamoyl}-ethyl)-methyl-carbamic acid tert-butyl ester. The material obtained was purified twice by flash naphthalenehy afford ((S)-1-{(S)-1-[2-(3-hydroxy-oxetan-3-ylethynyl)-naphthalen-1-ylmethyl]-2-oxo-2,3,4,5-tetrahydro-1H-benzo[b]azepin-3-ylcarbamoyl}-ethyl)-methyl-carbamic acid tert-butyl ester (11 mg), contaminated with 10% of starting azepinone.

Step 2: ((S)-1-{(S)-1-[2-(3-Hydroxy-oxetan-3-yl ethynyl)-naphthalen-1-ylmethyl]-2-oxo-2,3,4,5-tetrahydro-1H-benzo[b]azepin-3-ylcarbamoyl}-ethyl)-methyl-carbamic acid tert-butyl ester (10 mg, 16.7 µmol, Eq: 1.00) was combined with DCM (10 mL) and TFA (5 mL, 16.7 µmol, Eq: 1.00) was added. After 10 min., the mixture was concentrated and the residue was lyophilized from MeCN/H$_2$O. The lyophilized powder was partitioned between 1 N HCl and ether. The layers were separated. The pH of the aqueous layer was adjusted to 12 with 10 N NaOH and extracted with EtOAc. The extracts were washed with brine and concentrated to afford the title compound with 90% purity (7.5 mg, 90 mg). MS m/z 497.9 (MH$^+$)

Example 15

(S)-2-Methylamino-N—[(S)-2-oxo-1-(2-propoxy-naphthalen-1-ylmethyl)-2,3,4,5-tetrahydro-1H-benzo[b]azepin-3-yl]-propionamide hydrochloride

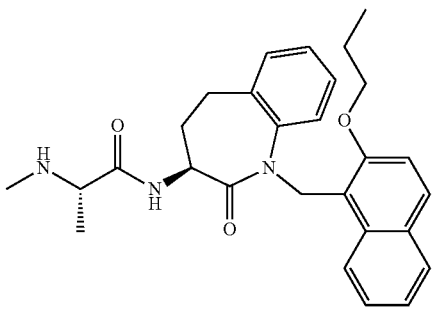 [SMILES: CCCOc1ccc2ccccc2c1CN1C(=O)[C@@H](NC(=O)[C@H](C)NC)CCc2ccccc21]

Step 1: In a similar manner to that described for Example 5 Step 2 except the mixture was heated at 65° C. for 18 h, methyl-[(S)-1-((S)-2-oxo-2,3,4,5-tetrahydro-1H-benzo[b]azepin-3-ylcarbamoyl)-ethyl]-carbamic acid tert-butyl ester (112 g, 309 mmol) and 2-allyloxy-1-chloromethyl-naphthalene (1.08 g, 4.64 mmol, Eq: 1.5) were converted to {(S)-1-[(S)-1-(2-allyloxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (904.4 mg, 52%, white solid) after purification by flash chromatography.

Step 2: A mixture of {(S)-1-[(S)-1-(2-allyloxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (0.14 g, 0.25 mmol) and 10% Pd/C in EtOH (10 mL) was stirred under H$_2$. After 3 h, the mixture was filtered through Celite and the filtrate concentrated. The resulting material was purified by flash chromatography to afford methyl-{(S)-1-[(S)-2-oxo-1-(2-propoxy-naphthalen-1-ylmethyl)-2,3,4,5-tetrahydro-1H-benzo[b]azepin-3-ylcarbamoyl]-ethyl}-carbamic acid tert-butyl ester as a (39.7 mg, 28%, white solid).

Step 3: In a similar manner to that described for Example 10 Step 3, methyl-{(S)-1-[(S)-2-oxo-1-(2-prop oxy-naphthalen-1-ylmethyl)-2,3,4,5-tetrahydro-1H-benzo[b]azepin-3-ylcarbamoyl]-ethyl}-carbamic acid tert-butyl ester (39.7 mg, 71.0 µmol) was converted to the title compound (28.3 mg, off-white solid, 80%). MS m/z 460.1 (MH$^+$)

Example 16

(S)—N—[(S)-1-(2-Allyloxy-naphthalen-1-ylmethyl)-2-oxo-2,3,4,5-tetrahydro-1H-benzo[b]azepin-3-yl]-2-methylamino-propionamide

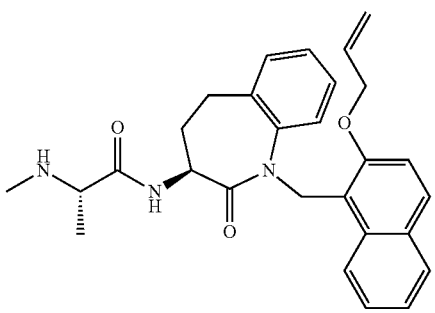 [SMILES: C=CCOc1ccc2ccccc2c1CN1C(=O)[C@@H](NC(=O)[C@H](C)NC)CCc2ccccc21]

A mixture of {(S)-1-[(S)-1-(2-allyloxy-naphthalen-1-yl-methyl)-2-oxo-2,3,4,5-tetrahydro-1H-benzo[b]azepin-3-yl-carbamoyl]-ethyl}-methyl-carbamic acid tert-butyl ester (0.14 g, 0.25 mmol), NaCNBH$_3$ (16 mg, 0.25 mmol) and TMS-Cl (27 mg, 0.25 mmol) in MeCN (1 mL) was stirred at 40° C. After 18 h TMS-I (0.1 mL) was added. After 30 min., the mixture was diluted with EtOAc, washed with brine, dried over Na$_2$SO$_4$ and concentrated to afford the title compound (57.7 mg, white solid, 45%). MS m/z 458.0 (MH$^+$)

Example 17

(S)—N—[(S)-1-(2-Hydroxy-naphthalen-1-ylm-ethyl)-2-oxo-2,3,4,5-tetrahydro-1H-benzo[b]azepin-3-yl]-2-methylamino-propionamide hydrochloride

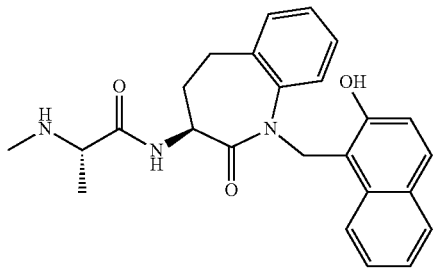 [SMILES: CN[C@@H](C)C(=O)N[C@H]1CCc2ccccc2N(Cc2c(O)ccc3ccccc23)C1=O]

Step 1: To {(S)-1-[(S)-1-(2-Allyloxy-naphthalen-1-ylm-ethyl)-2-oxo-2,3,4,5-tetrahydro-1H-benzo[b]azepin-3-yl-carbamoyl]-ethyl}-methyl-carbamic acid tert-butyl ester (0.14 g, 0.25 mmol) in THF (2 mL) was added polymethylhydrosilane (30 mg), Pd(PPh$_3$)$_4$ (10 mg) and ZnCl$_2$ (25 mg). The mixture was stirred at RT for 2 h, diluted with H$_2$O and brine and extracted with EtOAc. The extracts were washed with brine, dried over Na$_2$SO$_4$ and concentrated. The resulting material was purified by flash chromatography to give {(S)-1-[(S)-1-(2-hydroxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester as a. (38.3 mg, 30%, light solid).

Step 2: In a similar manner to that described for Example 10 Step 3, (S)-1-[(S)-1-(2-hydroxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (38.3 mg, 74.0 µmol) was converted to the title compound (29.1 mg, off-white solid, 87%). MS m/z 418.0 (MH$^+$)

Example 18

(S)—N—[(S)-8-Benzyloxy-1-(2-methyl-naphthalen-1-ylmethyl)-2-oxo-2,3,4,5-tetrahydro-1H-benzo[b]azepin-3-yl]-2-methylamino-propionamide hydrochloride

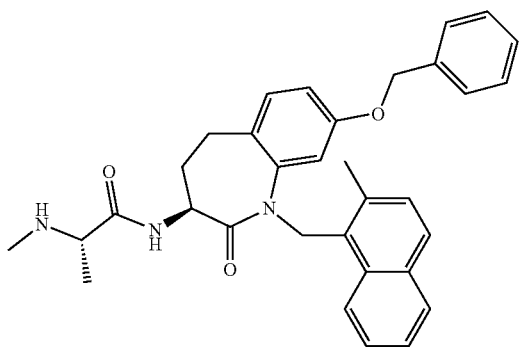 [SMILES: CN[C@@H](C)C(=O)N[C@H]1CCc2ccc(OCc3ccccc3)cc2N(Cc2c(C)ccc3ccccc23)C1=O]

Step 1: A mixture of 7-benzyloxy-3,4-dihydro-2H-naphthalen-1-one (1.17 g, 4.63 mmol), sodium acetate (0.46 g, 5.56 mmol) and hydroxylamine hydrochloride (0.39 g, 5.56 mmol) in MeOH (15 mL) was heated at 65° C. for 1.5 h, cooled, diluted with H$_2$O and extracted with DCM. The combined extracts were washed with H$_2$O, brine, dried over Na$_2$SO$_4$ and concentrated to afford 7-benzyloxy-3,4-dihydro-2H-naphthalen-1-one oxime (1.17 g, 95%, light yellow solid) which was used without purification.

Step 2: A mixture of 7-benzyloxy-3,4-dihydro-2H-naphthalen-1-one oxime (1.17 g, 7.38 mmol), p-toluenesulfonyl chloride (0.92 g, 4.82 mmol) and pyridine (0.39 mL, 4.82 mmol) in DCM (20 mL) was stirred for 2 days, diluted with DCM and washed with H$_2$O. The organic layer was washed with brine, dried over Na$_2$SO$_4$ and concentrated to afford 7-benzyloxy-3,4-dihydro (2H)-naphthalen-1-one-O-[(4-methylphenyl)sulfonyl]oxime (1.65 g, 89%, off-white solid) which was used without purification.

Step 3: A mixture of 7-benzyloxy-3,4-dihydro (2H)-naphthalen-1-one-O-[(4-methylphenyl)sulfonyl]oxime (1.0 g, 2.37 mmol) and KOAc (4.66 g, 47.4 mmol) in H$_2$O (8 mL) and EtOH (5 mL) was heated in a microwave at 130° C. for 30 min. The mixture was cooled to RT, diluted with H$_2$O and extracted with EtOAc. The combined extracts were washed with H$_2$O, brine, dried over Na$_2$SO$_4$ and concentrated to afford 8-benzyloxy-1,3,4,5-tetrahydro-benzo[b]azepin-2-one (0.45 g, 71%, beige solid).

Step 4: A mixture of 8-benzyloxy-1,3,4,5-tetrahydro-benzo[b]azepin-2-one (0.45 g, 1.69 mmol) and TEA (1.18 mL, 8.45 mmol) in DCM (10 mL) and THF (1 mL) was cooled to −15° C. TMS-I (0.48 mL, 3.38 mmol) and I$_2$ (0.86 g, 3.38 mmol) were added and the mixture warmed to RT. After 15 min., the mixture was diluted with 50% Na$_2$S$_2$O$_3$ and extracted with DCM. The combined extracts were washed with H$_2$O, brine, dried over Na$_2$SO$_4$ and concentrated. The resulting material was purified by flash chromatography to give 8-benzyloxy-3-iodo-1,3,4,5-tetrahydro-benzo[b]azepin-2-one (0.60 g, 90%, beige solid).

Step 5: A mixture of 8-benzyloxy-3-iodo-1,3,4,5-tetrahydro-benzo[b]azepin-2-one (0.60 g, 1.53 mmol) and NaN$_3$ (0.12 g, 1.84 mmol) in DMF (10 mL) was stirred for 2 h, diluted with EtOAc (50 mL), washed with H$_2$O, brine, dried over Na$_2$SO$_4$ and concentrated. The resulting material was purified by flash chromatography to afford 3-azido-8-benzyloxy-1,3,4,5-tetrahydro-benzo[b]azepin-2-one. (0.35 g, 75%, off-white solid).

Step 6: Triphenylphosphine (0.84 g, 3.19 mmol) was added to a solution of 3-azido-8-benzyloxy-1,3,4,5-tetrahydro-benzo[b]azepin-2-one (0.35 g, 1.14 mmol) in THF (12 mL) and H$_2$O (12 mL). After 2 h, the mixture was diluted with 1 N HCl and extracted with ether. The aqueous layer was made basic with 1 N NaOH and extracted with DCM. The combined extracts were washed with H$_2$O, dried over Na$_2$SO$_4$ and concentrated to give 3-amino-8-benzyloxy-1,3,4,5-tetrahydro-benzo[b]azepin-2-one (0.30 g, 93%).

Step 7: In a similar manner to that described for Example 5 Step 1 except the mixture was stirred for 4 h, 3-amino-8-benzyloxy-1,3,4,5-tetrahydro-benzo[b]azepin-2-one (0.30 g, 1.06 mmol, Eq: 1.00) and BOC-N-Me-Ala-OH (260 mg, 1.27 mmol) were reacted to give a material which was purified by flash chromatography to afford two diastereomers whose absolute stereochemistries were assigned based on the biological activities after conversion to the target compounds. Less polar isomer: [(S)-1-(I-8-benzyloxy-2-oxo-2,3,4,5-tetrahydro-1H-benzo[b]azepin-3-ylcarbamoyl)-ethyl]-methyl-carbamic acid tert-butyl ester 0.22 g. More polar isomer: [(S)-1-((S)-8-benzyloxy-2-oxo-2,3,4,5-tetrahydro-1H-benzo[b]azepin-3-ylcarbamoyl)-ethyl]-methyl-carbamic acid tert-butyl ester 0.20 g.

Step 8: In a similar manner to that described for Example 5 Step 2 except the mixture was heated at 65° C. for 6 h, [(S)-1-((S)-8-benzyloxy-2-oxo-2,3,4,5-tetrahydro-1H-benzo[b]azepin-3-ylcarbamoyl)-ethyl]-methyl-carbamic acid tert-butyl ester (103 mg, 220 μmol) and 1-chloromethyl-2-methyl naphthalene (63 mg, 330 μmol), Cs₂CO3 (108 mg, 330 μmol, Eq: 1.5) were reacted to give a material which was purified by flash chromatography to give {(S)-1-[(S)-8-benzyloxy-1-(2-methyl-naphthalen-1-ylmethyl)-2-oxo-2,3,4,5-tetrahydro-1H-benzo[b]azepin-3-ylcarbamoyl]-ethyl}-methyl-carbamic acid tert-butyl ester (56.9 mg, 41%, light yellow solid).

Step 9: In a similar manner to that described for Example 10 Step 3, {(S)-1-[(S)-8-benzyloxy-1-(2-methyl-naphthalen-1-ylmethyl)-2-oxo-2,3,4,5-tetrahydro-1H-benzo[b]azepin-3-ylcarbamoyl]-ethyl}-methyl-carbamic acid tert-butyl ester (69.9 mg, 92 μmol) was converted to the title compound (39.9 mg, 78%, white solid). MS m/z 522.0 (MH⁺)

Example 19

(S)—N—[(S)-1-(5-Bromo-benzo[b]thiophen-3-ylmethyl)-2-oxo-2,3,4,5-tetra hydro-1H-benzo[b]azepin-3-yl]-2-methylamino-propionamide hydrochloride

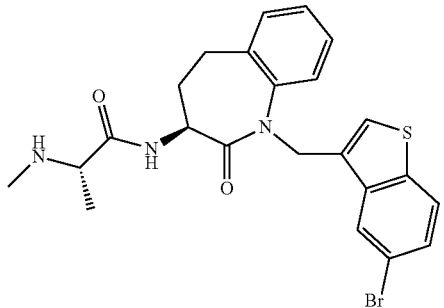 [SMILES: CN[C@@H](C)C(=O)N[C@H]1CCc2ccccc2N(Cc2csc3ccc(Br)cc23)C1=O]

Step 1: In a similar manner to that described for Example 5 Step 2, methyl-[(S)-1-((S)-2-oxo-2,3,4,5-tetrahydro-1H-benzo[b]azepin-3-ylcarbamoyl)-ethyl]-carbamic acid tert-butyl ester (100 mg, 277 μmol), 5-bromo-3-chloromethyl-benzo[b]thiophene (108 mg, 415 μmol) were reacted to give a material which was purified by flash chromatography to afford {(S)-1-[(S)-1-(5-bromo-benzo[b]thiophen-3-ylmethyl)-2-oxo-2,3,4,5-tetrahydro-1H-benzo[b]azepin-3-ylcarbamoyl]-ethyl}-methyl-carbamic acid tert-butyl ester (90.5 mg, 56%, light yellow solid).

Step 2: In a similar manner to that described for Example 10 Step 3, {(S)-1-[(S)-1-(5-bromo-benzo[b]thiophen-3-ylmethyl)-2-oxo-2,3,4,5-tetrahydro-1H-benzo[b]azepin-3-ylcarbamoyl]-ethyl}-methyl-carbamic acid tert-butyl ester (90.5 mg, 154 μmol) was converted to the title compound (64.8 mg, white solid, 80%). MS m/z 487.8 (MH⁺).

Example 20

(S)—N—((S)-1-Benzo[b]thiophen-3-ylmethyl-2-oxo-2,3,4,5-tetrahydro-1H-benzo[b]azepin-3-yl)-2-methylamino-propionamide

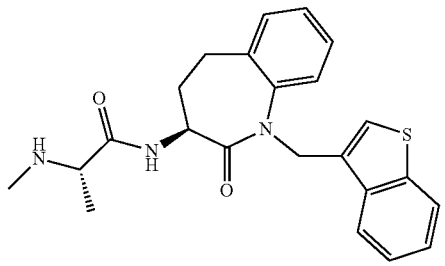 [SMILES: CN[C@@H](C)C(=O)N[C@H]1CCc2ccccc2N(Cc2csc3ccccc23)C1=O]

A mixture of (S)—N—[(S)-1-(5-bromo-benzo[b]thiophen-3-ylmethyl)-2-oxo-2,3,4,5-tetrahydro-1H-benzo[b]azepin-3-yl]-2-methylamino-propionamide hydrochloride (30 mg, 0.057 mmol), 10% Pd/C (10 mg) and EtOH (15 mL) was hydrogenated at 50 psi (Parr apparatus) for 18 h, filtered through Celite, the filtrate concentrated, diluted with 1 N NaOH (15 mL) and extracted with DCM. The organic extracts were washed with H₂O, brine, dried over Na₂SO₄ and concentrated. The residue was taken up in MeCN/H₂O and lyophilized to afford the title compound. (10.4 mg, 44%, white solid) MS m/z 408.3 (MH⁺).

Example 21

(S)-2-Methylamino-N—[(S)-1-(2-methyl-naphthalen-1-ylmethyl)-2-oxo-8-phenyl-2,3,4,5-tetrahydro-1H-benzo[b]azepin-3-yl]-propionamide hydrochloride

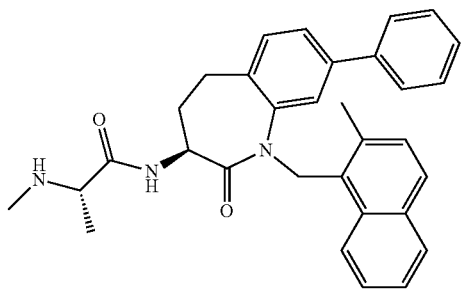 [SMILES: CN[C@@H](C)C(=O)N[C@H]1CCc2ccc(-c3ccccc3)cc2N(Cc2c(C)ccc3ccccc23)C1=O]

Step 1: A mixture of 8-bromo-1,3,4,5-tetrahydro-benzo[b]azepin-2-one (0.68 g, 2.83 mmol), phenyl boronic acid (0.43 g, 3.54 mmol), Pd(PPh₃)₄ (0.33 g, 0.283 mmol), 2 M Na₂CO₃ (9 mL) and toluene (9 mL) was heated in a microwave at 110° C. for 30 min. The reaction was diluted with EtOAc (100 mL) and washed with brine. The organic solution was dried over Na₂SO₄ and concentrated. The resulting material was purified by flash chromatography to give 8-phenyl-1,3,4,5-tetrahydro-benzo[b]azepin-2-one (0.41 g, 61%) which was used without purification.

Step 2: Following the procedure described in Example 18 Step 4,8-phenyl-1,3,4,5-tetrahydro-benzo[b]azepin-2-one (0.69 g, 2.91 mmol) was converted to 3-iodo-8-phenyl-1,3, 4,5-tetrahydro-benzo[b]azepin-2-one (0.82 g, 78%, beige solid) after purification by flash chromatography.

Step 3: Following the procedure described in Example 18 Step 5, 3-iodo-8-phenyl-1,3,4,5-tetrahydro-benzo[b]azepin-2-one (0.82 g, 2.26 mmol) was converted to 3-azido-8-phenyl-1,3,4,5-tetrahydro-benzo[b]azepin-2-one (0.52 g, 83%, off-white solid) after purification by flash chromatography.

Step 4: Following the procedure described in Example 18 Step 6, 3-azido-8-phenyl-1,3,4,5-tetrahydro-benzo[b]azepin-2-one (0.52 g, 1.89 mmol) was converted to 3-amino-8-phenyl-1,3,4,5-tetrahydro-benzo[b]azepin-2-one which was used without purification (0.46 g, 98%).

Step 5: In a similar manner to that described for Example 5 Step 1 except the mixture was stirred for 2 d, 3-amino-8-phenyloxy-1,3,4,5-tetrahydro-benzo[b]azepin-2-one (0.46 g, 1.84 mmol, Eq: 1.00), BOC-N-Me-Ala-OH (450 mg, 2.21 mmol, Eq: 1.2) were reacted to give a material which was purified by flash chromatography to afford two diastereomers whose absolute stereochemistries were assigned based on the biological activities after conversion to the target compounds. The less polar isomer was assigned as methyl-[(S)-1-(I-2-oxo-8-phenyl-2,3,4,5-tetrahydro-1H-benzo[b]azepin-3-ylcarbamoyl)-ethyl]-carbamic acid tert-butyl ester (0.26 g); the more polar isomer was assigned as methyl-[(S)-1-((S)-2-oxo-8-phenyl-2,3,4,5-tetrahydro-1H-benzo[b]azepin-3-ylcarbamoyl)-ethyl]-carbamic acid tert-butyl ester (0.32 g).

Step 6: In a similar manner to that described for Example 5 Step 2 except the mixture was heated at 65° C. for 5 h, methyl-[(S)-1-((S)-2-oxo-8-phenyl-2,3,4,5-tetrahydro-1H-benzo[b]azepin-3-ylcarbamoyl)ethyl]-carbamic acid tert-butyl ester (150 mg, 340 µmol), 1-chloromethyl-2-methyl naphthalene (98 mg, 510 µmol) were reacted to give a material which was purified by flash chromatography to give methyl-{(S)-1-[(S)-1-(2-methyl-naphthalen-1-ylmethyl)-2-oxo-8-phenyl-2,3,4,5-tetrahydro-1H-benzo[b]azepin-3-ylcarbamoyl]-ethyl}-carbamic acid tert-butyl ester (103.4 mg, 51%, light yellow solid).

Step 7: In a similar manner to that described for Example 10 Step 3, methyl-{(S)-1-[(S)-1-(2-methyl-naphthalen-1-ylmethyl)-2-oxo-8-phenyl-2,3,4,5-tetrahydro-1H-benzo[b]azepin-3-ylcarbamoyl]-ethyl}-carbamic acid tert-butyl ester (103 mg, 175 µmol) was converted to the title compound (82.1 mg, 89%, off-white solid). MS m/z 492.0 (MH$^+$)

Example 22

(S)—N—((S)-1-Benzyl-8-benzyloxy-2-oxo-2,3,4,5-tetrahydro-1H-benzo[b]azepin-3-yl)-2-methylamino-propionamide hydrochloride

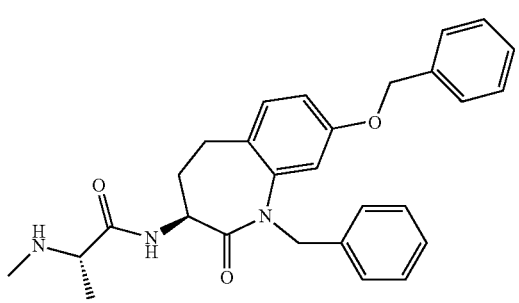 [SMILES: CN[C@@H](C)C(=O)N[C@H]1CCc2ccc(OCc3ccccc3)cc2N(Cc2ccccc2)C1=O]

Step 1: [(S)-1-((S)-8-Benzyloxy-2-oxo-2,3,4,5-tetrahydro-1H-benzo[b]azepin-3-ylcarbamoyl)-ethyl]-methyl-carbamic acid tert-butyl ester (100 mg, 214 µmol), benzyl bromide (55 mg, 320 µmol) and Cs$_2$CO$_3$ (104 mg, 320 µmol, Eq: 1.5) were combined with DMF (4 mL) and the mixture was heated to 60° C. After 18 h, the mixture was cooled, poured into EtOAc, washed with brine, dried over Na$_2$SO$_4$ and concentrated. The resulting material was purified by flash chromatography to give [(S)-1-((S)-1-benzyl-8-benzyloxy-2-oxo-2,3,4,5-tetrahydro-1H-benzo[b]azepin-3-ylcarbamoyl)-ethyl]-methyl-carbamic acid tert-butyl ester as a white solid (85.3 mg, 71%).

Step 2: In a similar manner to that described for Example 10 Step 3, [(S)-1-((S)-1-benzyl-8-benzyloxy-2-oxo-2,3,4,5-tetrahydro-1H-benzo[b]azepin-3-ylcarbamoyl)-ethyl]-methyl-carbamic acid tert-butyl ester (85.3 mg, 152 µmol) was converted to the title compound (53.9 mg, yellow solid, 72%). MS m/z 458.0 (MH$^+$)

Example 23

(S)—N—((S)-1-Benzyl-2-oxo-8-phenethyloxy-2,3,4,5-tetrahydro-1H-benzo[b]azepin-3-yl)-2-methyl-amino-propionamide hydrochloride

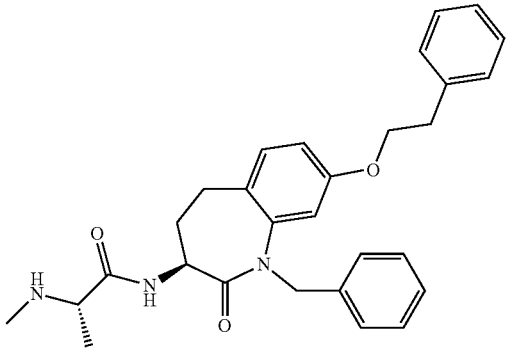 [SMILES: CN[C@@H](C)C(=O)N[C@H]1CCc2ccc(OCCc3ccccc3)cc2N(Cc2ccccc2)C1=O]

Step 1: A solution of 7-hydroxy-1-tetralone (0.53 g, 3.27 mmol) and diisopropyl azodicarboxylate (0.66 g, 3.27 mmol) in THF (30 mL) was added to a solution of 2-phenylethanol (0.40 g, 3.27 mmol) and triphenylphosphine (0.86 g, 3.27 mmol) in THF (30 mL) over 15 min. After 18 h, the mixture was poured into 200 mL H$_2$O and extracted with EtOAc. The combined extracts were washed with brine, dried over Na$_2$SO$_4$ and concentrated. The resulting material was purified by flash chromatography to give 7-phenethyloxy-3,4-dihydro-2H-naphthalen-1-one (0.83 g, 74%, white solid).

Step 2: In a similar manner to that described in Example 18 Steps 2-6 except in Step 2 the mixture was stirred for 18 h and in Step 3 the mixture was heated to 150° C. in a microwave, 7-phenethyloxy-3,4-dihydro-2H-naphthalen-1-one (0.83 g, 3.12 mmol) was converted to 3-amino-8-phenethyloxy-1,3,4,5-tetrahydro-benzo[b]azepin-2-one (0.25 g) which was used without purification.

Step 3: In a similar manner to that described in Example 5 except the reaction was stirred for 18 h, 3-amino-8-phenethyloxy-1,3,4,5-tetrahydro-benzo[b]azepin-2-one (0.25 g, 0.86 mmol) and BOC-N-Me-Ala-OH (210 mg, 1.03 mmol) were reacted to give a material which was purified by flash chromatography to afford two diastereomers whose absolute stereochemistries were assigned based on the biological activities after conversion to the target compounds. Less polar isomer: methyl-[(S)-1-(I-2-oxo-8-phenethyloxy-2,3,4,5-tetrahydro-1H-benzo[b]azepin-3-ylcarbamoyl)-ethyl]-carbamic acid tert-butyl (0.17 g). More polar isomer: methyl-[(S)-1-((S)-2-oxo-8-phenethyloxy-2,3,4,5-tetrahydro-1H-benzo[b]azepin-3-ylcarbamoyl)-ethyl]-carbamic acid tert-butyl ester (0.20 g).

Step 4: In a similar manner to that described for Example 5 Step 2 except NaI was omitted, methyl-[(S)-1-((S)-2-oxo-8-phenethyloxy-2,3,4,5-tetrahydro-1H-benzo[b]azepin-3-ylcarbamoyl)-ethyl]-carbamic acid tert-butyl ester (90 mg, 186 μmol) and benzyl bromide (48 mg, 280 μmol) were reacted to give a material which was purified by flash chromatography to afford [(S)-1-((S)-1-benzyl-2-oxo-8-phenethyloxy-2,3,4,5-tetrahydro-1H-benzo[b]azepin-3-ylcarbamoyl)-ethyl]-methyl-carbamic acid tert-butyl ester (75.4 mg, 71%, white solid). MS m/z 472.1 (MH$^+$)

Step 5: In a similar manner to that described for Example 10 Step 3, methyl-[(S)-1-((S)-2-oxo-8-phenethyloxy-2,3,4,5-tetrahydro-1H-benzo[b]azepin-3-ylcarbamoyl)-ethyl]-carbamic acid tert-butyl ester (85.3 mg, 152 μmol) was converted to the title compound (55.7 mg, 72%, yellow solid). MS m/z 472.1 (MH$^+$)

Example 24

(S)—N—((S)-1-Benzyl-8-methoxy-2-oxo-2,3,4,5-tetrahydro-1H-benzo[b]azepin-3-yl)-2-methylamino-propionamide hydrochloride

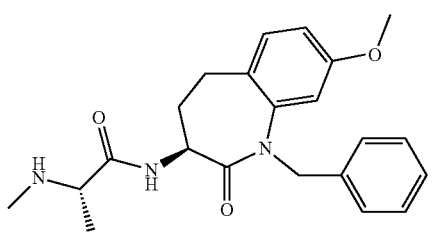 [SMILES: CN[C@@H](C)C(=O)N[C@H]1CCc2ccc(OC)cc2N(Cc2ccccc2)C1=O]

Step 1: In a similar manner to that described for Example 18 Step 4 except 1.8 eq. TEA was used, 8-methoxy-1,3,4,5-tetrahydro-benzo[b]azepin-2-one (0.88 g, 4.6 mmol) was converted to a material which was purified by flash chromatography to give of 3-iodo-8-methoxy-1,3,4,5-tetrahydro-benzo[b]azepin-2-one (1.41 g, 90%, beige solid).

Step 2: In a similar manner to that described for Example 18 Step 5, 3-iodo-8-methoxy-1,3,4,5-tetrahydro-benzo[b]azepin-2-one (1.41 g, 4.45 mmol) was converted to a material which was purified by flash chromatography to give 3-azido-8-methoxy-1,3,4,5-tetrahydro-benzo[b]azepin-2-one (0.94 g, 91%, white solid).

Step 3: 3-Azido-8-methoxy-1,3,4,5-tetrahydro-benzo[b]azepin-2-one (0.89 g, 3.82 mmol), 10% Pd/C (1 g), and EtOH (100 mL) was hydrogenated at 50 psi (Parr apparatus) for 48 h, the mixture filtered through Celite and the filtrate concentrated to give 3-amino-8-methoxy-1,3,4,5-tetrahydro-benzo[b]azepin-2-one as a white solid (0.78 g, 99%).

Step 4: In a similar manner to that described for Example 5 Step 1 except the mixture was stirred for 18 h, 3-amino-8-methoxy-1,3,4,5-tetrahydro-benzo[b]azepin-2-one (0.78 g, 3.77 mmol, Eq: 1.00), and BOC-N-Me-Ala-OH (920 mg, 4.52 mmol, Eq: 1.2) were reacted to give a material which was purified by flash chromatography to afford two diastereomers whose absolute stereochemistries were assigned based on the biological activities after conversion to the target compounds. Less polar isomer: [(S)-1-(8-methoxy-2-oxo-2,3,4,5-tetrahydro-1H-benzo[b]azepin-3-ylcarbamoyl)-ethyl]-methyl-carbamic acid tert-butyl ester (0.53 g). More polar isomer: [(S)-1-((S)-8-methoxy-2-oxo-2,3,4,5-tetrahydro-1H-benzo[b]azepin-3-ylcarbamoyl)-ethyl]-methyl-carbamic acid tert-butyl ester (0.22 g)

Step 5: In a similar manner to that described in Example 5 Step 2 except NaI was omitted, [(S)-1-((S)-8-methoxy-2-oxo-2,3,4,5-tetrahydro-1H-benzo[b]azepin-3-ylcarbamoyl)-ethyl]-methyl-carbamic acid tert-butyl ester (90 mg, 186 μmol) and benzyl bromide (48 mg, 280 μmol) were reacted to give a material which was purified by flash chromatography to afford [(S)-1-((S)-1-benzyl-2-oxo-8-phenethyloxy-2,3,4,5-tetrahydro-1H-benzo[b]azepin-3-ylcarbamoyl)-ethyl]-methyl-carbamic acid tert-butyl ester (75.4 mg 71%, white solid).

Step 6: In a similar manner to that described for Example 10 Step 3, [(S)-1-((S)-1-benzyl-2-oxo-8-phenethyloxy-2,3,4,5-tetrahydro-1H-benzo[b]azepin-3-ylcarbamoyl)-ethyl]-methyl-carbamic acid tert-butyl ester (75.4 mg, 132 μmol) was converted to the title compound (55.7 mg, 72%, yellow solid). MS m/z 382.3 (MH$^+$)

Example 25

(S)—N—[(S)-1-Benzyl-2-oxo-8-(3-phenyl-propoxy)-2,3,4,5-tetrahydro-1H-benzo[b]azepin-3-yl]-2-methylamino-propionamide hydrochloride

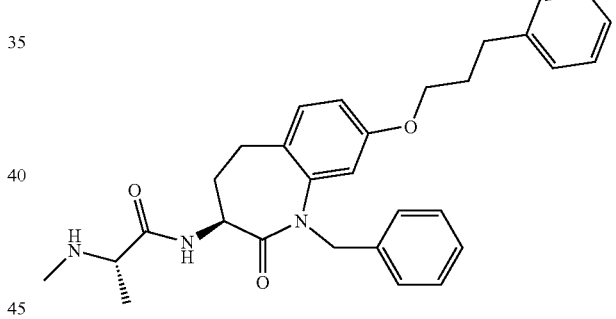

Step 1: In a similar manner to that described in RO5468989 Step 1, 7-hydroxy-1-tetralone (0.81 g, 5.0 mmol) and 3-phenyl-1-propanol (0.75 g, 5.5 mmol) were reacted to give a material which was purified by flash chromatography to afford 7-(3-phenyl-propoxy)-3,4-dihydro-2H-naphthalen-1-one (1.22 g, 87%, yellow oil).

Step 2: In a similar manner to that described in Example 18 Steps 1-6 except in Step 1 the reaction was heated for 18 h, in Step 2 the reaction was stirred for 18 h and in Step 3 the reaction was heated to 150° C. for 60 min., 7-(3-phenyl-propoxy)-3,4-dihydro-2H-naphthalen-1-one (1.22 g, 4.36 mmol) was converted to 3-amino-8-(3-phenyl-propoxy)-1,3,4,5-tetrahydro-benzo[b]azepin-2-one (0.27 g) which was used without purification.

Step 3: In a similar manner to that described for Example 5 Step 1 except the reaction was stirred for 18 h, 3-amino-8-(3-phenyl-prop oxy)-1,3,4,5-tetrahydro-benzo[b]azepin-2-one (0.27 g, 0.88 mmol, Eq: 1.00), BOC-N-Me-Ala-OH (210 mg, 1.06 mmol, Eq: 1.2) were reacted to give a material which was purified by flash chromatography to afford two diastereomers whose absolute stereochemistries were assigned based on the biological activities after conversion to the target compounds. Less polar isomer: Methyl-{(S)-1-[I-2-oxo-8-(3-phenyl-propoxy)-2,3,4,5-tetrahydro-1H-benzo[b]azepin-3-ylcarbamoyl]-ethyl}-carbamic acid tert-butyl ester (0.14 g). More polar isomer: methyl-{(S)-1-[(S)-2-oxo-8-(3-phenyl-propoxy)-2,3,4,5-tetrahydro-1H-benzo[b]azepin-3-ylcarbamoyl]-ethyl}-carbamic acid tert-butyl ester (0.14 g).

Step 4: In a similar manner to that described for Example 5 Step 2 except the mixture was heated at 60° C. for 2 d and NaI was omitted, methyl-{(S)-1-[(S)-2-oxo-8-(3-phenyl-propoxy)-2,3,4,5-tetrahydro-1H-benzo[b]azepin-3-ylcarbamoyl]-ethyl}-carbamic acid tert-butyl ester (20 mg, 186 µmol) and benzyl bromide (48 mg, 280 µmol) were converted to a material which was purified by flash chromatography to afford {(S)-1-[(S)-1-benzyl-2-oxo-8-(3-phenyl-prop oxy)-2,3,4,5-tetrahydro-1H-benzo[b]azepin-3-ylcarbamoyl]-ethyl}-methyl-carbamic acid tert-butyl ester (70.2 mg, 64%, white solid).

Step 5: In a similar manner to that described for Example 10 Step 3, {(S)-1-[(S)-1-benzyl-2-oxo-8-(3-phenyl-propoxy)-2,3,4,5-tetrahydro-1H-benzo[b]azepin-3-ylcarbamoyl]-ethyl}-methyl-carbamic acid tert-butyl ester (70.2 mg, 120 µmol) was converted to the title compound (54.6 mg, 87%, white solid). MS m/z 486.1 (MH$^+$)

Example 26

(S)—N-(1-Benzyl-8-bromo-2-oxo-2,3,4,5-tetrahydro-1H-benzo[b]azepin-3-yl)-2-methylamino-propionamide hydrochloride

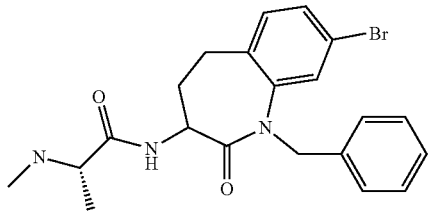 [SMILES: CN[C@@H](C)C(=O)NC1CCc2ccc(Br)cc2N(Cc2ccccc2)C1=O]

Step 1: In a similar manner to that described for Example 18 Steps 4-6 except that in Step 5 the mixture was stirred for 18 h and in Step 6 the mixture was stirred for 1 h, 8-bromo-1,3,4,5-tetrahydro-benzo[b]azepin-2-one (0.55 g, 2.3 mmol) was converted to 3-amino-8-bromo-1,3,4,5-tetrahydro-benzo[b]azepin-2-one (0.32 g).

Step 2: In a similar manner to that described for Example 5 Step 1 except the reaction was stirred for 18 h, 3-amino-8-bromo-1,3,4,5-tetrahydro-benzo[b]azepin-2-one (0.32 g, 1.27 mmol) and BOC-N-Me-Ala-OH (310 mg, 1.52 mmol, Eq: 1.2) was converted to [(S)-1-(8-bromo-2-oxo-2,3,4,5-tetrahydro-1H-benzo[b]azepin-3-ylcarbamoyl)-ethyl]-methyl-carbamic acid tert-butyl ester (0.54 g, 96%, white powder) as a mixture of diastereomers.

Step 3: In a similar manner to that described for Example 5 Step 2 except the mixture was heated for 1.5 h and NaI was omitted, [(S)-1-(8-bromo-2-oxo-2,3,4,5-tetrahydro-1H-benzo[b]azepin-3-ylcarbamoyl)-ethyl]-methyl-carbamic acid tert-butyl ester (127 mg, 290 µmol) and benzyl bromide (74 mg, 430 µmol) was converted to a material that was purified by flash chromatography to afford [(S)-1-((S)-1-benzyl-8-bromo-2-oxo-2,3,4,5-tetrahydro-1H-benzo[b]azepin-3-ylcarbamoyl)-ethyl]-methyl-carbamic acid tert-butyl ester as a mixture of diastereomers (117 mg, 76%, white solid).

Step 4: [(S)-1-((S)-1-Benzyl-8-bromo-2-oxo-2,3,4,5-tetrahydro-1H-benzo[b]azepin-3-yl-carbamoyl)-ethyl]-methyl-carbamic acid tert-butyl ester (117 mg, 220 µmol) and 2.0 M HCl in ether (5 mL, 6.00 mmol) were combined with MeOH (1.0 mL). After 1.5 h, the reaction was filtered, the precipitate washed with ether and dried to afford the title compound as a mixture of diastereomers (81.5 mg, 79%, white solid). MS m/z 431.8 (M+H$^+$)

Example 27

(R)—N—[(S)-1-(6-Bromo-2-methoxy-naphthalen-1-ylmethyl)-2-oxo-2,3,4,5-tetrahydro-1H-benzo[b]azepin-3-yl]-2-methylamino-propionamide hydrochloride

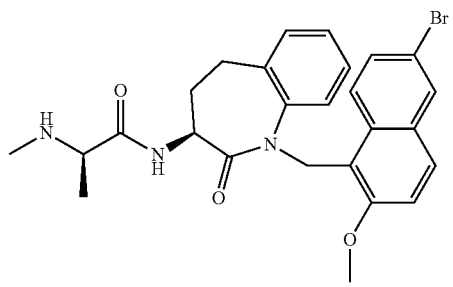 [SMILES: CN[C@H](C)C(=O)N[C@H]1CCc2ccccc2N(Cc2c(OC)ccc3cc(Br)ccc23)C1=O]

A solution of HBTU (1.29 g, 3.4 mmol, Eq: 1.2) and HOBT.H$_2$O (521 mg, 3.4 mmol, Eq: 1.2) in DMF (10 mL) was added to a mixture of 3-amino-1,3,4,5-tetrahydro-benzo[b]azepin-2-one (0.5 g, 2.84 mmol, Eq: 1.00), BOC-N-Me-D-Ala-OH (692 mg, 3.4 mmol, Eq: 1.2) and TEA (861 mg, 1.19 mL, 8.51 mmol, Eq: 3) in DMF (10 mL). After 1 h the mixture was diluted with EtOAC, washed with brine, sat. NaHCO$_3$, brine, dried over Na$_2$SO$_4$ and concentrated. The residue was purified by flash chromatography to afford two diastereomers whose absolute stereochemistries were assigned based on the biological activities after conversion to the target compounds. Less polar isomer: I-2-methyl-amino-N—((S)-2-oxo-2,3,4,5-tetrahydro-1H-benzo[b]azepin-3-yl)-propionamide (0.409 g, white solid). More polar isomer: I-2-methylamino-N—(I-2-oxo-2,3,4,5-tetrahydro-1H-benzo[b]azepin-3-yl)-propionamide (0.383 g, white solid).

Step 2: In a similar manner to that described for Example 5 Step 2 except the mixture was heated at 65° C., I-2-methylamino-N—((S)-2-oxo-2,3,4,5-tetrahydro-1H-benzo[b]azepin-3-yl)-propionamide (0.2 g, 553 µmol, Eq: 1.00) and 6-bromo-1-chloromethyl-2-methoxynaphthalene (237 mg, 830 µmol, Eq: 1.5) were converted to a material that was purified by flash chromatography to afford tert-butyl I-1-((S)-1-((6-bromo-2-methoxynaphthalen-1-yl)methyl)-2-oxo-2,3,4,5-tetrahydro-1H-benzo[b]azepin-3-ylamino)-1-oxopropan-2-yl(methyl)carbamate after lyophilization from MeCN/H$_2$O (174.1 mg, 52%, white solid).

Step 3: In a similar manner to that described for Example 10 Step 3, tert-butyl I-1-((S)-1-((6-bromo-2-methoxynaphthalen-1-yl)methyl)-2-oxo-2,3,4,5-tetrahydro-1H-benzo[b]azepin-3-ylamino)-1-oxopropan-2-yl(methyl)carbamate (60 mg, 98.3 µmol) was converted to the title compound (50.0 mg, 93%, white solid). MS m/z 511.9 (MH$^+$)

Example 28

(S)-2-Methylamino-N—{(S)-2-oxo-1-[7-(1H-tetrazol-5-yl)-naphthalen-1-ylmethyl]-2,3,4,5-tetrahydro-1H-benzo[b]azepin-3-yl}-propionamide

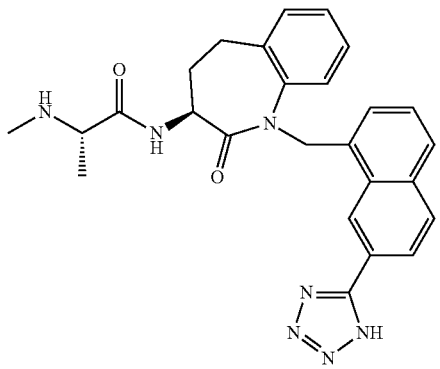 [SMILES: CN[C@@H](C)C(=O)N[C@H]1CCc2ccccc2N(Cc2cccc3ccc(-c4nnn[nH]4)cc23)C1=O]

Step 1: In a similar manner to that described for Example 5 Step 2 except the mixture was heated for 2 d, methyl-[(S)-1-((S)-2-oxo-2,3,4,5-tetrahydro-1H-benzo[b]azepin-3-ylcarbamoyl)-ethyl]-carbamic acid tert-butyl ester (350 mg, 967 μmol, Eq: 0.8) and 7-bromo-1-bromomethyl-naphthalene (0.363 g, 1.21 mmol, Eq: 1.00) were reacted to give a material which was purified by flash chromatography to afford {(S)-1-[(S)-1-(7-bromo-naphthalen-1-ylmethyl)-2-oxo-2,3,4,5-tetrahydro-1H-benzo[b]azepin-3-ylcarbamoyl]-ethyl}-methyl-carbamic acid tert-butyl ester (0.403 g, 58%, white solid)

Step 2: A mixture of {(S)-1-[(S)-1-(7-bromo-naphthalen-1-ylmethyl)-2-oxo-2,3,4,5-tetrahydro-1H-benzo[b]azepin-3-ylcarbamoyl]-ethyl}-methyl-carbamic acid tert-butyl ester (0.28 g, 482 μmol, Eq: 1.00), zinc cyanide (85.0 mg, 723 μmol, Eq: 1.5) and tetrakis(triphenylphosphine)palladium (0) (167 mg, 145 μmol, Eq: 3) in DMF (4.6 mL) was degassed, purged with N₂, heated at 80° C. for 18 h. the mixture was cooled, diluted with EtOAc, washed with brine, dried over Na₂SO₄ and concentrated. The resulting material was purified by flash chromatography to give {(S)-1-[(S)-1-(7-cyano-naphthalen-1-ylmethyl)-2-oxo-2,3,4,5-tetrahydro-1H-benzo[b]azepin-3-ylcarbamoyl]-ethyl}-methyl-carbamic acid tert-butyl ester after lyophilization from MeCH/H₂O (0.190 g, white solid, 75%). MS m/z 427.1 (M−BOC+H)

Step 3: A mixture of {(S)-1-[(S)-1-(7-cyano-naphthalen-1-ylmethyl)-2-oxo-2,3,4,5-tetrahydro-1H-benzo[b]azepin-3-ylcarbamoyl]-ethyl}-methyl-carbamic acid tert-butyl ester (0.12 g, 228 μmol, Eq: 1.00) and trimethylsilyl azide (TMS-N₃, 82.9 mg, 684 μmol, Eq: 3) in DMF (410 μL) and MeOH was stirred at RT for 10 min then heated to 80° C. After 18 h, the mixture was cooled, diluted with EtOAc and washed with 1 N HCl, H₂O and brine, the organic layer dried over Na₂SO₄ and concentrated. The resulting material was purified by flash chromatography to give methyl-((S)-1-{(S)-2-oxo-1-[7-(1H-tetrazol-5-yl)-naphthalen-1-ylmethyl]-2,3,4,5-tetrahydro-1H-benzo[b]azepin-3-ylcarbamoyl}-ethyl)-carbamic acid tert-butyl ester after lyophilization from MeCH/H₂O to give the title compound (58.3 mg, white solid, 45%).

Step 4: In a similar manner to that described for Example 10 Step 3, methyl-((S)-1-{(S)-2-oxo-1-[7-(1H-tetrazol-5-yl)-naphthalen-1-ylmethyl]-2,3,4,5-tetrahydro-1H-benzo[b]azepin-3-ylcarbamoyl}-ethyl)-carbamic acid tert-butyl ester (20 mg, 35.1 μmol) was converted to the title compound (14.2 mg, white solid, 80%). MS m/z 470.1 (MH⁺)

Example 29

(S)—N—[(S)-1-(6-Bromo-2-methoxy-naphthalen-1-ylmethyl)-2-oxo-2,3,4,5-tetrahydro-1H-benzo[b]azepin-3-yl]-2-methylamino-propionamide hydrochloride

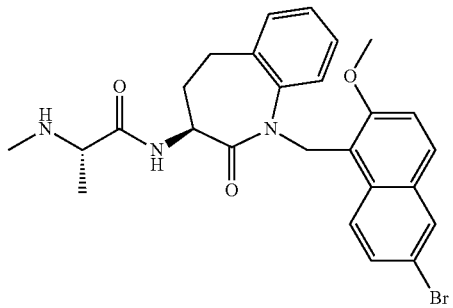 [SMILES: CN[C@@H](C)C(=O)N[C@H]1CCc2ccccc2N(Cc2c(OC)ccc3cc(Br)ccc23)C1=O]

Step 1: In a similar manner to that described for Example 5 Step 2 except the mixture was heated at 65° C. for 4.5 h, methyl-[(S)-1-((S)-2-oxo-2,3,4,5-tetrahydro-1H-benzo[b]azepin-3-ylcarbamoyl)-ethyl]-carbamic acid tert-butyl ester (220 mg, 609 μmol, Eq: 1.00) and 6-bromo-1-chloromethyl-2-methoxynaphthalene (261 mg, 913 μmol, Eq: 1.50) were reacted to give a material which was purified by flash chromatography to give {(S)-1-[(S)-1-(6-bromo-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (304 mg, 82%).

Step 2: In a similar manner to that described for Example 10 Step 3, {(S)-1-[(S)-1-(6-bromo-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (304 mg, 498 μmol, Eq: 1.00) was converted to the title compound (190 mg, 70%, white solid). MS m/z 511.9 (MH⁺)

Example 30

(S)—N—{(S)-1-[2-Methoxy-6-(4-methyl-thiazol-2-yl)-naphthalen-1-ylmethyl]-2-oxo-2,3,4,5-tetrahydro-1H-benzo[b]azepin-3-yl}-2-methylamino-propionamide hydrochloride

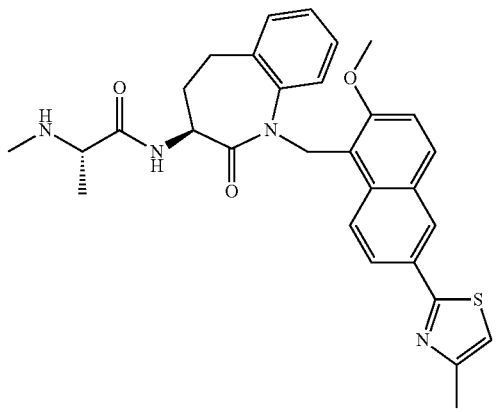 [SMILES: CN[C@@H](C)C(=O)N[C@H]1CCc2ccccc2N(Cc2c(OC)ccc3cc(-c4nc(C)cs4)ccc23)C1=O]

Step 1: A mixture of {(S)-1-[(S)-1-(6-bromo-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (335 mg, 549 μmol, Eq: 1.00), zinc cyanide (96.7 mg, 823 μmol, Eq: 1.50) and tetrakis(triphenylphosphine)palladium(0) (190 mg, 165 μmol, Eq: 0.3) in DMF (6 mL) was degassed, purged with N₂ and heated at 80° C. overnight. The mixture was diluted with EtOAc and washed with H₂O/brine, the organic layer dried over Na₂SO₄ and concentrated. The resulting material was purified by flash chromatography to afford {(S)-1-[(S)-1-(6-cyano-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (94 mg, 31%). MS m/z 457.1 (M BOC+H⁺)

Step 2: To a 20 mL microwave vial was added {(S)-1-[(S)-1-(6-cyano-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (94 mg, 169 μmol, Eq: 1.00), and 20 wt. % ammonium sulfide (1 mL, 3.00 mmol, Eq: 17.8) in DMF (5 mL). The vial was capped and heated in the microwave at 100° C. for 5 min. The mixture was diluted with 0.1 N HCl and extracted with EtOAc. The combined extracts were washed with brine, dried over Na₂SO₄ and concentrated. The resulting material was purified by flash chromatography to afford {(S)-1-[(S)-1-(2-methoxy-6-thiocarbamoyl-naphthalen-1-ylmethyl)-2-oxo-2,3,4,5-tetrahydro-1H-benzo[b]azepin-3-ylcarbamoyl]-ethyl}-methyl-carbamic acid tert-butyl ester (90 mg, 90%).

Step 3: {(S)-1-[(S)-1-(2-Methoxy-6-thiocarbamoyl-naphthalen-1-ylmethyl)-2-oxo-2,3,4,5-tetrahydro-1H-benzo[b]azepin-3-ylcarbamoyl]-ethyl}-methyl-carbamic acid tert-butyl ester (63 mg, 107 μmol, Eq: 1.00) was combined with EtOH (2.00 mL) chloroacetone (11.8 mg, 128 μmol, Eq: 1.20) was added at RT and the mixture was stirred at RT for 1.5 h, heated to 50° C. for 1 h and heated to 70° C. for 1.5 h. K₂CO₃ (29.5 mg, 213 μmol, Eq: 2.00) was added and the mixture was stirred at 70° C. overnight. The mixture was diluted with H₂O and extracted with EtOAc. The combined extracts were dried over Na₂SO₄, concentrated and the resulting material purified by flash chromatography to give a material that was purified by reverse phase HPLC to afford (S)—N—{(S)-1-[2-methoxy-6-(4-methyl-thiazol-2-yl)-naphthalen-1-ylmethyl]-2-oxo-2,3,4,5-tetrahydro-1H-benzo[b]azepin-3-yl}-2-methylamino-propionamide (12 mg, 18%).

Step 4: In a similar manner to that described for Example 10 Step 3, (S)—N—{(S)-1-[2-methoxy-6-(4-methyl-thiazol-2-yl)-naphthalen-1-ylmethyl]-2-oxo-2,3,4,5-tetrahydro-1H-benzo[b]azepin-3-yl}-2-methylamino-propionamide (12 mg, 19.1 μmol, Eq: 1.00) was converted to the title compound as a white powder (10.8 mg, 100%). MS m/z 529.1 (MH⁺)

Example 31

(S)—N—{(S)-1-[2-Methoxy-6-(5-oxo-4,5-dihydro-[1,2,4]oxadiazol-3-yl)-naphthalen-1-ylmethyl]-2-oxo-2,3,4,5-tetrahydro-1H-benzo[b]azepin-3-yl}-2-methylamino-propionamide hydrochloride

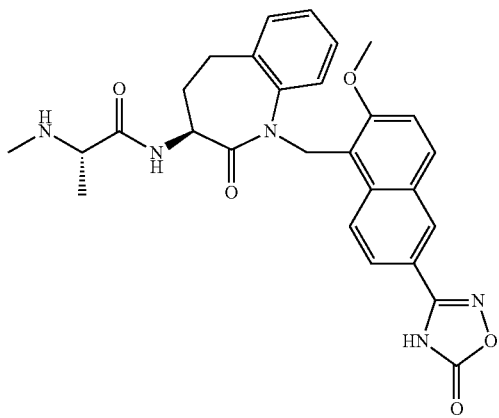 [SMILES: CN[C@@H](C)C(=O)N[C@H]1CCc2ccccc2N(Cc2c(OC)ccc3cc(-c4noc(=O)[nH]4)ccc23)C1=O]

Step 1: {(S)-1-[(S)-1-(2-methoxy-6-thiocarbamoyl-naphthalen-1-ylmethyl)-2-oxo-2,3,4,5-tetrahydro-1H-benzo[b]azepin-3-ylcarbamoyl]-ethyl}-methyl-carbamic acid tert-butyl ester (90 mg, 152 μmol, Eq: 1.00), NH₂OH.HCl (529 mg, 7.62 mmol, Eq: 50) and TEA (771 mg, 1.06 mL, 7.62 mmol, Eq: 50) were combined with DMF (6 mL) and the mixture stirred at RT overnight. The mixture was diluted with sat. NaHCO₃/brine and extracted with EtOAc. The combined extracts were dried over Na₂SO₄ and concentrated to afford {(S)-1-[(S)-1-(6-(N-hydroxycarbamimidoyl)-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester which was used without purification (90 mg, 100%).

Step 2: To a 10 mL microwave vial was added {(S)-1-[(S)-1-(6-(N-hydroxycarbamimidoyl)-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (43 mg, 72.9 μmol, Eq: 1.00), and N,N'-carbonyldiimidazole (14.2 mg, 87.5 μmol, Eq: 1.2) in dioxane (3 mL). The vial was capped and heated in the microwave at 120° C. for 10 min. The solution was concentrated and the residue was adsorbed on silica gel and purified by flash chromatography to afford ((S)-1-{(S)-1-[2-methoxy-6-(5-oxo-4,5-dihydro-[1,2,4]oxadiazol-3-yl)-naphthalen-1-ylmethyl]-2-oxo-2,3,4,5-tetrahydro-1H-benzo[b]azepin-3-ylcarbamoyl}-ethyl)-methyl-carbamic acid tert-butyl ester (30 mg, 67%).

Step 3: In a similar manner to that described for Example 10 Step 3, ((S)-1-{(S)-1-[2-methoxy-6-(5-oxo-4,5-dihydro-[1,2,4]oxadiazol-3-yl)-naphthalen-1-ylmethyl]-2-oxo-2,3,4,5-tetrahydro-1H-benzo[b]azepin-3-ylcarbamoyl}-ethyl)-methyl-carbamic acid tert-butyl ester (28 mg, 45.5 μmol) was converted to the title compound (25 mg, 100%). MS m/z 516.1 (MH⁺)

Example 32

(S)—N—[(S)-1-(2-Methoxy-6-[1,2,4]oxadiazol-3-yl-naphthalen-1-ylmethyl)-2-oxo-2,3,4,5-tetrahydro-1H-benzo[b]azepin-3-yl]-2-methylamino-propionamide hydrochloride

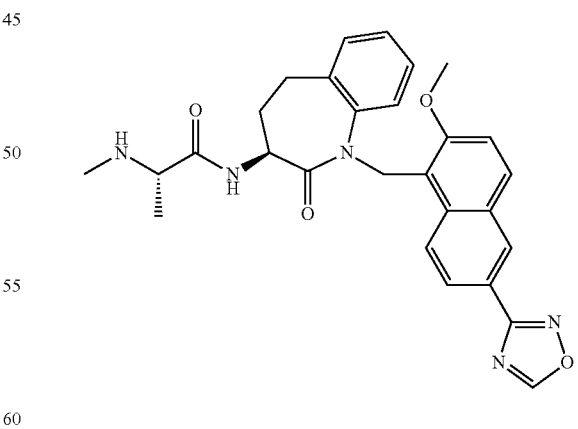

Step 1: To a 10 mL microwave vial was added {(S)-1-[(S)-1-(6-(N-hydroxycarbamimidoyl)-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (42 mg, 71.2 μmol, Eq: 1.00), triethyl orthoformate (528 mg, 592 μL, 3.56 mmol, Eq: 50) and AcOH (21.4 mg, 20.4 μL, 356 μmol, Eq: 5.00) in EtOH (2.5 mL). The vial was capped and heated in the microwave at 120° C. for 10 min then heated in the microwave at 140° C. for 40 min. The mixture was diluted with H₂O/brine and extracted with EtOAc. The combined organic extracts were dried over Na₂SO₄, concentrated and the resulting material was purified by flash chromatography to afford {(S)-1-[(S)-1-(2-methoxy-6-[1,2,4]oxadiazol-3-yl-naphthalen-1-ylmethyl)-2-oxo-2,3,4,5-tetrahydro-1H-benzo[b]azepin-3-ylcarbamoyl]-ethyl}-methyl-carbamic acid tert-butyl ester (22 mg, 52%).

Step 2: {(S)-1-[(S)-1-(2-Methoxy-6-[1,2,4]oxadiazol-3-yl-naphthalen-1-ylmethyl)-2-oxo-2,3,4,5-tetrahydro-1H-benzo[b]azepin-3-ylcarbamoyl]-ethyl}-methyl-carbamic acid tert-butyl ester (20 mg, 33.4 µmol, Eq: 1.00) was combined with dioxane (0.5 mL) and MeOH (0.5 mL). 2.0 M HCl in ether (2.0 mL, 4.00 mmol, Eq: 120) was added at RT and the mixture was stirred overnight. The mixture was concentrated and the residue was triturated with acetonitrile. The supernatant was concentrated and the residue was lyophilized to afford the title compound (15 mg, 84%, white solid). MS m/z 500.0 (MH⁺)

Example 33

(S)—N—{(S)-1-[6-(N-Aminocarbamimidoyl)-2-methoxy-naphthalen-1-ylmethyl]-2-oxo-2,3,4,5-tetrahydro-1H-benzo[b]azepin-3-yl}-2-methyl-amino-propionamide dihydrochloride

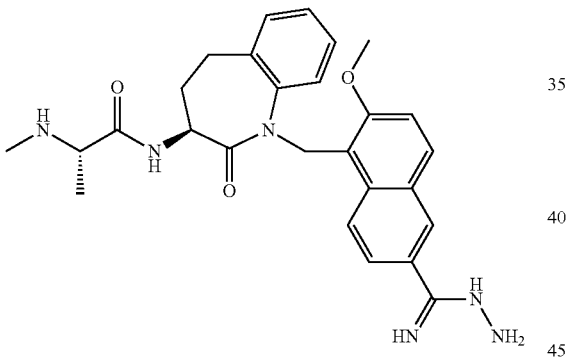

Step 1: {(S)-1-[(S)-1-(2-Methoxy-6-thiocarbamoyl-naphthalen-1-ylmethyl)-2-oxo-2,3,4,5-tetrahydro-1H-benzo[b]azepin-3-ylcarbamoyl]-ethyl}-methyl-carbamic acid tert-butyl ester (220 mg, 372 µmol, Eq: 1.00) and hydrazine monohydrate (1.86 g, 1.84 mL, 37.2 mmol, Eq: 100) were combined with DMF (15.0 mL) and the mixture stirred at RT. After 40 min the mixture was diluted with H₂O/brine and extracted with EtOAc. The combined extracts were dried over Na₂SO₄ and concentrated to give {(S)-1-[(S)-1-(6-(N-aminocarbamimidoyl)-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester which was used without purification (240 mg).

Step 2: In a similar manner to that described for Example 10 Step 3 except the mixture was stirred for 1 h 10 min., {(S)-1-[(S)-1-(6-(N-aminocarbamimidoyl)-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (12 mg, 20.4 µmol, Eq: 1.00) was converted to the title compound (11 mg, 96%, white powder). MS m/z 489.0 (MH⁺)

Example 34

(S)—N—{(S)-1-[2-Methoxy-6-(5-oxo-4,5-dihydro-1H-[1,2,4]triazol-3-yl)-naphthalen-1-ylmethyl]-2-oxo-2,3,4,5-tetrahydro-1H-benzo[b]azepin-3-yl}-2-methylamino-propionamide hydrochloride

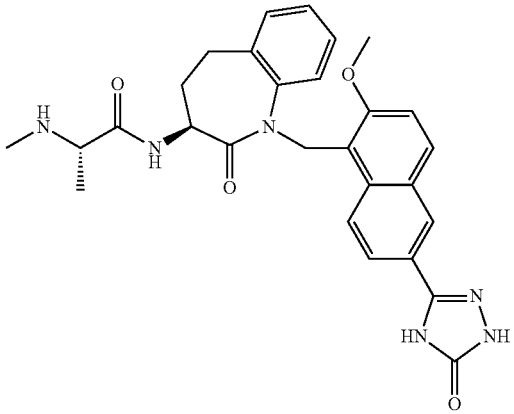 [SMILES: CN[C@@H](C)C(=O)N[C@H]1CCc2ccccc2N(Cc2c(OC)ccc3cc(-c4n[nH]c(=O)[nH]4)ccc23)C1=O]

Step 1: N,N'-Carbonyldiimidazole (12.6 mg, 77.5 µmol, Eq: 1.2) was added to a solution of {(S)-1-[(S)-1-(6-(N-aminocarbamimidoyl)-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (38 mg, 64.5 µmol, Eq: 1.00) in THF (1 mL) and the mixture was stirred for 4 days. The mixture was adsorbed on silica and purified by flash chromatography to afford ((S)-1-{(S)-1-[2-ethoxy-6-(5-oxo-4,5-dihydro-1H-[1,2,4]triazol-3-yl)-naphthalen-1-ylmethyl]-2-oxo-2,3,4,5-tetrahydro-1H-benzo[b]azepin-3-ylcarbamoyl}-ethyl)-methyl-carbamic acid tert-butyl ester (10 mg, 25%).

Step 2: In a similar manner to that described for Example 10 Step 3, ((S)-1-{(S)-1-[2-Methoxy-6-(5-oxo-4,5-dihydro-1H-[1,2,4]triazol-3-yl)-naphthalen-1-ylmethyl]-2-oxo-2,3,4,5-tetrahydro-1H-benzo[b]azepin-3-ylcarbamoyl}-ethyl)-methyl-carbamic acid tert-butyl ester (10 mg, 16.3 µmol) was converted to the title compound (9 mg, 100%, white powder). MS m/z 515.1 (MH⁺)

Example 35

(S)—N—{(S)-1-[6-(5,6-Dioxo-1,4,5,6-tetrahydro-[1,2,4]triazin-3-yl)-2-methoxy-naphthalen-1-ylmethyl]-2-oxo-2,3,4,5-tetrahydro-1H-benzo[b]azepin-3-yl}-2-methylamino-propionamide hydrochloride

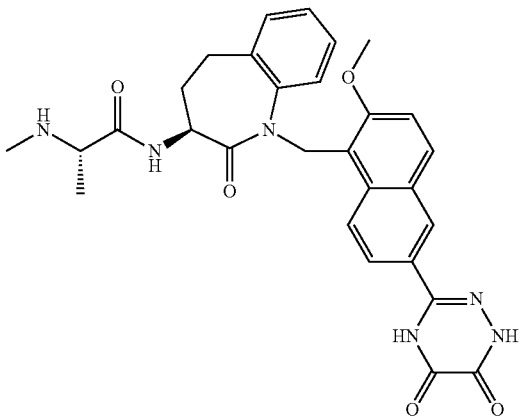 [SMILES: CN[C@@H](C)C(=O)N[C@H]1CCc2ccccc2N(Cc2c(OC)ccc3cc(-c4n[nH]c(=O)c(=O)[nH]4)ccc23)C1=O]

Step 1: 1,1'-Oxalyldiimidazole (10.1 mg, 53.0 µmol, Eq: 1.2) was added to {(S)-1-[(S)-1-(6-(N-aminocarbamimidoyl)-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (26 mg, 44.2 µmol, Eq: 1.00) in THF (1 mL). After 24 h at RT, 1,1'-oxalyldiimidazole (10 mg) was added and the mixture stirred at RT overnight. The mixture was adsorbed on silica and purified by flash chromatography to give a substance that was purified by reverse phase HPLC to afford ((S)-1-{(S)-1-[6-(5,6-dioxo-1,4,5,6-tetrahydro-[1,2,4]triazin-3-yl)-2-methoxy-naphthalen-1-ylmethyl]-2-oxo-2,3,4,5-tetrahydro-1H-benzo[b]azepin-3-ylcarbamoyl}-ethyl)-methyl-carbamic acid tert-butyl ester (4 mg, 14%).

Step 2: In a similar manner to that described for Example 10 Step 3 except MeOH was replaced by dioxane and the mixture stirred overnight, ((S)-1-{(S)-1-[6-(5,6-dioxo-1,4,5,6-tetrahydro-[1,2,4]triazin-3-yl)-2-methoxy-naphthalen-1-ylmethyl]-2-oxo-2,3,4,5-tetrahydro-1H-benzo[b]azepin-3-ylcarbamoyl}-ethyl)-methyl-carbamic acid tert-butyl ester (4 mg, 6.22 µmol) was converted to the title compound (3.6 mg, white powder). MS m/z 543.1 (MH$^+$)

Example 36

(S)—N—{(S)-1-[2-Methoxy-6-(5-trifluoromethyl-4H-[1,2,4]triazol-3-yl)-naphthalen-1-ylmethyl]-2-oxo-2,3,4,5-tetrahydro-1H-benzo[b]azepin-3-yl}-2-methylamino-propionamide hydrochloride

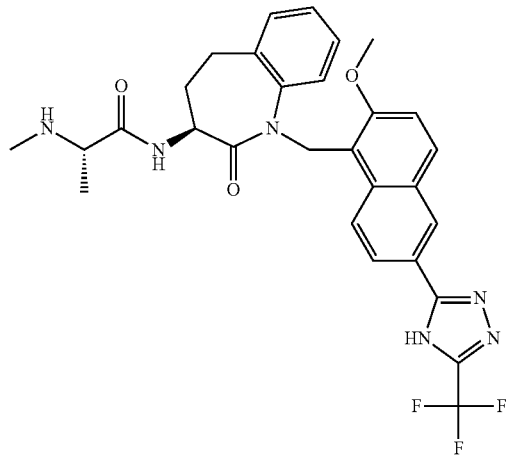 [SMILES: CN[C@@H](C)C(=O)N[C@H]1CCc2ccccc2N(Cc2c(OC)ccc3cc(-c4nnc(C(F)(F)F)[nH]4)ccc23)C1=O]

Step 1: {(S)-1-[(S)-1-(6-(N-Aminocarbamimidoyl)-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (85 mg, 144 µmol, Eq: 1.00) and TEA (43.8 mg, 60.9 µL, 433 µmol, Eq: 3.00) were combined with DCM (4 mL), the solution cooled to 0° C. and trifluoroacetic anhydride (36.4 mg, 24.5 µL, 173 µmol, Eq: 1.20) added. The mixture was stirred overnight with warming to RT. The mixture was diluted with brine/H$_2$O, extracted with EtOAc, the extracts dried over Na$_2$SO$_4$, concentrated and the resulting material purified by flash chromatography to afford ((S)-1-{(S)-1-[2-methoxy-6-(5-trifluoromethyl-4H-[1,2,4]triazol-3-yl)-naphthalen-1-ylmethyl]-2-oxo-2,3,4,5-tetrahydro-1H-benzo[b]azepin-3-ylcarbamoyl}-ethyl)-methyl-carbamic acid tert-butyl ester (31 mg, 32%).

Step 2: In a similar manner to that described for Example 10 Step 3 except the mixture was stirred 1 h, ((S)-1-{(S)-1-[2-methoxy-6-(5-trifluoromethyl-4H-[1,2,4]triazol-3-yl)-naphthalen-1-ylmethyl]-2-oxo-2,3,4,5-tetrahydro-1H-benzo[b]azepin-3-ylcarbamoyl}-ethyl)-methyl-carbamic acid tert-butyl ester (31 mg, 46.5 µmol) was converted to the title compound (28 mg, 100%, white powder). MS m/z 567.1 (MH$^+$)

Example 37

(S)—N—[(S)-1-(2-Methoxy-6-[1,2,4]triazin-3-yl-naphthalen-1-ylmethyl)-2-oxo-2,3,4,5-tetrahydro-1H-benzo[b]azepin-3-yl]-2-methylamino-propionamide hydrochloride

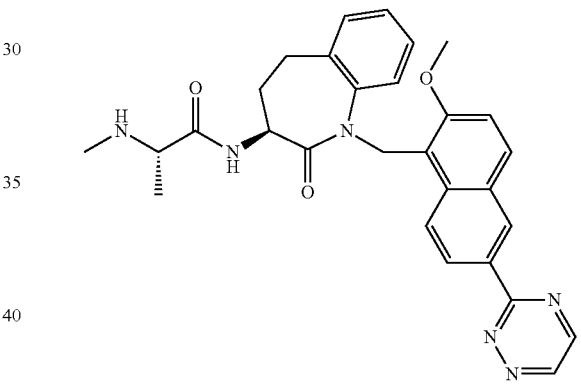

Step 1: To a 10 mL microwave vial was added {(S)-1-[(S)-1-(6-(N-aminocarbamimidoyl)-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (28 mg, 47.6 µmol, Eq: 1.00), glyoxal hydrate trimer (50.0 mg, 238 µmol, Eq: 5.0) and AcOH (5 mg, 83.3 µmol, Eq: 1.75) in EtOH (1.5 mL). The vial was capped and heated in the microwave at 160° C. for 5 min., the mixture diluted with H$_2$O/brine and extracted with EtOAc. The combined organic extracts were dried over Na$_2$SO$_4$, concentrated and the resulting material purified by flash chromatography to afford {(S)-1-[(S)-1-(2-methoxy-6-[1,2,4]triazin-3-yl-naphthalen-1-ylmethyl)-2-oxo-2,3,4,5-tetrahydro-1H-benzo[b]azepin-3-ylcarbamoyl]-ethyl}-methyl-carbamic acid tert-butyl ester (14 mg, 48%).

Step 2: In a similar manner to that described for Example 10 Step 3 except the mixture was stirred 1 h, {(S)-1-[(S)-1-(2-methoxy-6-[1,2,4]triazin-3-yl-naphthalen-1-ylmethyl)-2-oxo-2,3,4,5-tetrahydro-1H-benzo[b]azepin-3-ylcarbamoyl]-ethyl}-methyl-carbamic acid tert-butyl ester (14 mg, 22.9 µmol was converted to the title compound (12 mg, 97%, white powder). MS m/z 511.1 (MH$^+$)

Example 38

(S)—N—{(S)-1-[2-Methoxy-6-(1H-[1,2,4]triazol-3-yl)-naphthalen-1-ylmethyl]-2-oxo-2,3,4,5-tetrahydro-1H-benzo[b]azepin-3-yl}-2-methylamino-propionamide dihydrochloride

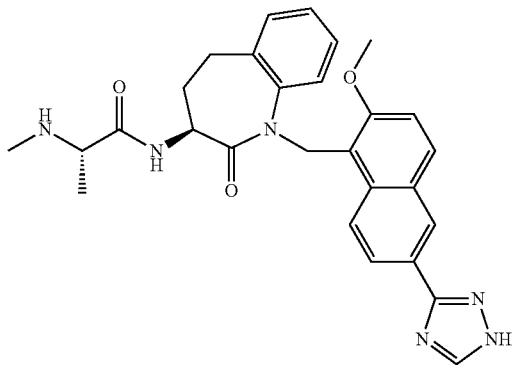 [SMILES: CN[C@@H](C)C(=O)N[C@H]1CCc2ccccc2N(Cc2c(OC)ccc3cc(-c4nc[nH]n4)ccc23)C1=O]

Step 1: To a 20 mL microwave vial were added {(S)-1-[(S)-1-(6-(N-aminocarbamimidoyl)-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (33 mg, 56.1 μmol, Eq: 1.00), and triethyl orthoformate (831 mg, 5.61 mmol, Eq: 100) in DMF (2.5 mL). The vial was capped and heated in the microwave at 140° C. for 5 min., the mixture diluted with 2 M Na$_2$CO$_3$ and partitioned between H$_2$O and EtOAc. The combined organic extracts were dried over Na$_2$SO$_4$ and concentrated. The resulting material was adsorbed on silica and purified by flash chromatography to afford [(S)-1-((S)-1-{6-[formylamino-(formyl-hydrazono)-methyl]-2-methoxy-naphthalen-1-ylmethyl}-2-oxo-2,3,4,5-tetrahydro-1H-benzo[b]azepin-3-ylcarbamoyl)-ethyl]-methyl-carbamic acid tert-butyl ester containing trace amounts of ((S)-1-{(S)-1-[2-methoxy-6-(1H-[1,2,4]triazol-3-yl)-naphthalen-1-ylmethyl]-2-oxo-2,3,4,5-tetrahydro-1H-benzo[b]azepin-3-ylcarbamoyl}-ethyl)-methyl-carbamic acid tert-butyl ester (18 mg).

Step 2: The mixture of products from Step 1 (18 mg) was dissolved in EtOH (2.5 mL), 100 μL of AcOH was added and the mixture was microwaved at 120° C. for 10 min. The solution was concentrated to afford ((S)-1-{(S)-1-[2-methoxy-6-(1H-[1,2,4]triazol-3-yl)-naphthalen-1-ylmethyl]-2-oxo-2,3,4,5-tetrahydro-1H-benzo[b]azepin-3-ylcarbamoyl}-ethyl)-methyl-carbamic acid tert-butyl ester which was used without purification (18 mg, 54%).

Step 3: In a similar manner to that described for Example 10 Step 3 except the mixture was stirred 1.3 h and lyophilization from MeCN/H$_2$O was omitted, ((S)-1-{(S)-1-[2-methoxy-6-(1H-[1,2,4]triazol-3-yl)-naphthalen-1-ylmethyl]-2-oxo-2,3,4,5-tetrahydro-1H-benzo[b]azepin-3-ylcarbamoyl}-ethyl)-methyl-carbamic acid tert-butyl ester (18 mg, 30.1 μmol) was converted to the title compound (16.5 mg, 96%, white powder). MS m/z 499.2 (MH$^+$)

Example 39

(S)—N—{(S)-1-[2-Methoxy-6-(1H-tetrazol-5-yl)-naphthalen-1-ylmethyl]-2-oxo-2,3,4,5-tetrahydro-1H-benzo[b]azepin-3-yl}-2-methylamino-propionamide hydrochloride

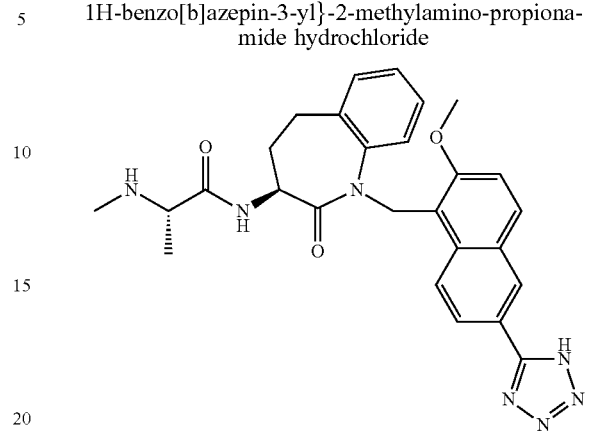

Step 1: TMS-N$_3$ (32.7 mg, 269 μmol, Eq: 1.5) was added to a mixture of {(S)-1-[(S)-1-(6-cyano-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (100 mg, 180 μmol, Eq: 1.00) and copper(I) oxide (2.57 mg, 18.0 μmol, Eq: 0.1) in DMF (323 μL) and MeOH. After 10 min the mixture was heated to 80° C. After 18 h, the mixture was diluted with EtOAc, washed with 1 N HCl, brine, dried over Na$_2$SO$_4$ and concentrated. The resulting material was purified by flash chromatography give ((S)-1-{(S)-1-[2-methoxy-6-(1H-tetrazol-5-yl)-naphthalen-1-ylmethyl]-2-oxo-2,3,4,5-tetrahydro-1H-benzo[b]azepin-3-ylcarbamoyl}-ethyl)-methyl-carbamic acid tert-butyl ester (36.5 mg, 34%, white solid). MS m/z 600.1 (MH$^+$)

Step 2: ((S)-1-{(S)-1-[2-Methoxy-6-(1H-tetrazol-5-yl)-naphthalen-1-ylmethyl]-2-oxo-2,3,4,5-tetrahydro-1H-benzo[b]azepin-3-ylcarbamoyl}-ethyl)-methyl-carbamic acid tert-butyl ester (36.5 mg, 60.9 μmol, Eq: 1.00) and 2.0 M HCl in Et$_2$O (3 mL) were combined with MeOH (1 mL). After 2 h the naphtha was concentrated, the residue dissolved in MeCN/H$_2$O and the resulting solution lyophilized to afford the title compound (22.3 mg, 68%, yellow solid). MS m/z 500.1 (MH$^+$)

Example 40

(S)—N—{(S)-1-[2-Methoxy-6-(2-methyl-2H-tetrazol-5-yl)-naphthalen-1-ylmethyl]-2-oxo-2,3,4,5-tetrahydro-1H-benzo[b]azepin-3-yl}-2-methyl-amino-propionamide hydrochloride

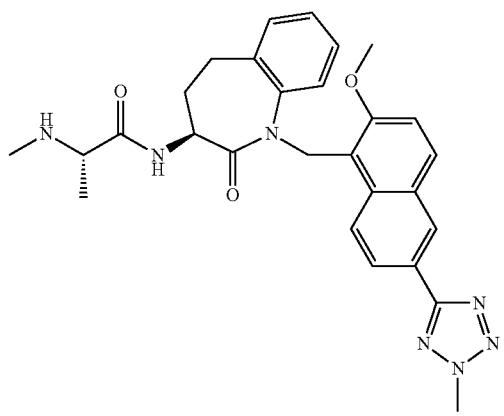 [SMILES: CN[C@@H](C)C(=O)N[C@H]1CCc2ccccc2N(Cc2c(OC)ccc3cc(-c4nnn(C)n4)ccc23)C1=O]

Step 1: ((S)-1-{(S)-1-[2-Methoxy-6-(1H-tetrazol-5-yl)-naphthalen-1-ylmethyl]-2-oxo-2,3,4,5-tetrahydro-1H-benzo[b]azepin-3-ylcarbamoyl}-ethyl)-methyl-carbamic acid tert-butyl ester (0.3989 g, 665 µmol, Eq: 1.00), K₂CO₃ (460 mg, 3.33 mmol, Eq: 5) and CH₃I (472 mg, 3.33 mmol, Eq: 5) were combined with DMF (5 mL). After 18 h, the mixture was diluted with EtOAc, washed with brine, dried over Na₂SO₄ and concentrated. The resulting material was purified by flash chromatography to afford ((S)-1-{(S)-1-[2-methoxy-6-(2-methyl-2H-tetrazol-5-yl)-naphthalen-1-ylmethyl]-2-oxo-2,3,4,5-tetrahydro-1H-benzo[b]azepin-3-ylcarbamoyl}-ethyl)-methyl-carbamic acid tert-butyl ester (184.1 mg, white solid) and ((S)-1-{(S)-1-[2-methoxy-6-(1-methyl-1H-tetrazol-5-yl)-naphthalen-1-ylmethyl]-2-oxo-2,3,4,5-tetrahydro-1H-benzo[b]azepin-3-ylcarbamoyl}-ethyl)-methyl-carbamic acid tert-butyl ester (46.9 mg, white solid) whose structures were elucidated by nOe NMR experiments.

Step 2: In a similar manner to that described for Example 10 Step 3, ((S)-1-{(S)-1-[2-methoxy-6-(2-methyl-2H-tetrazol-5-yl)-naphthalen-1-ylmethyl]-2-oxo-2,3,4,5-tetrahydro-1H-benzo[b]azepin-3-ylcarbamoyl}-ethyl)-methyl-carbamic acid tert-butyl ester (184.1 g, 300 mmol) was converted to the title compound (143.2 mg, 87%, white solid). MS m/z 514.1 (MH⁺)

Example 41

(S)—N—{(S)-1-[2-Methoxy-6-(1-methyl-1H-tetrazol-5-yl)-naphthalen-1-ylmethyl]-2-oxo-2,3,4,5-tetrahydro-1H-benzo[b]azepin-3-yl}-2-methyl-amino-propionamide hydrochloride

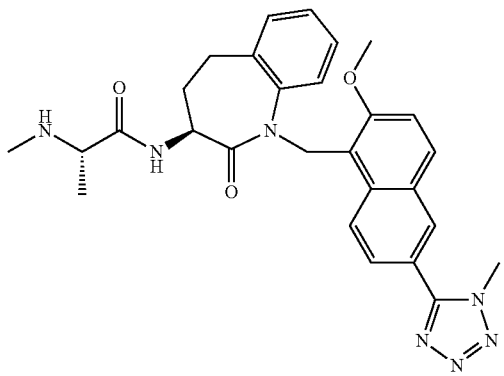

In a similar manner to that described for Example 10 Step 3, ((S)-1-{(S)-1-[2-methoxy-6-(1-methyl-1H-tetrazol-5-yl)-naphthalen-1-ylmethyl]-2-oxo-2,3,4,5-tetrahydro-1H-benzo[b]azepin-3-ylcarbamoyl}-ethyl)-methyl-carbamic acid tert-butyl ester (46.9 mg, 76.4 µmol) was converted to the title compound (33.5 mg, 80%, off-white solid). MS m/z 514.1 (MH⁺)

Example 42

(S)—N—[(S)-1-(6-Acetylamino-2-methoxy-naphthalen-1-ylmethyl)-2-oxo-2,3,4,5-tetrahydro-1H-benzo[b]azepin-3-yl]-2-methylamino-propionamide hydrochloride

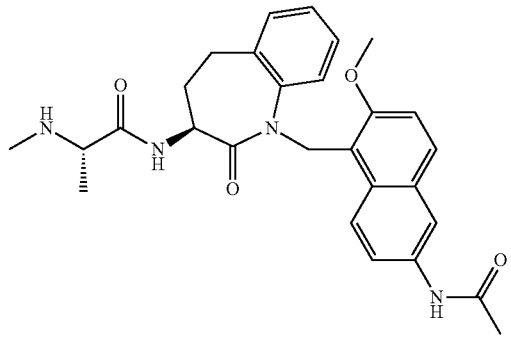 [SMILES: CN[C@@H](C)C(=O)N[C@H]1CCc2ccccc2N(Cc2c(OC)ccc3cc(NC(C)=O)ccc23)C1=O]

Step 1: {(S)-1-[(S)-1-(6-Bromo-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (100 mg, 164 µmol), acetamide (11.6 mg, 197 µmol), tris(dibenzylideneacetone)dipalladium(0) chloroform adduct (6 mg, 5.73 µmol), 4,5-bis(diphenylphosphino)-9,9-dimethylxanthene (Xantphos, 10 mg, 17.2 µmol) and Cs₂CO₃ (75 mg, 230 µmol) were placed in a 5 mL microwave vessel and capped. The vessel was evacuated and purged with N₂. Dioxane (2 mL) was added and the vessel heated to 100° C. After 18 h the mixture was cooled, diluted with EtOAc, washed with brine, dried over Na₂SO₄ and concentrated. The resulting material was purified by flash chromatography to give a substance that was lyophilized from MeCN/H₂O to afford {(S)-1-[(S)-1-(6-acetylamino-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (58.2 mg, yellow solid, 60%).

Step 2: In a similar manner to that described for Example 10 Step 3, {(S)-1-[(S)-1-(6-acetylamino-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (58.2 mg, 98.9 µmol) was converted to the title compound (43.9 mg, 85%, yellow solid). MS m/z 489.1 (MH⁺)

Example 43

(S)—N—{(S)-1-[2-Methoxy-6-(1H-pyrazol-4-yl)-naphthalen-1-ylmethyl]-2-oxo-2,3,4,5-tetrahydro-1H-benzo[b]azepin-3-yl}-2-methylamino-propionamide hydrochloride

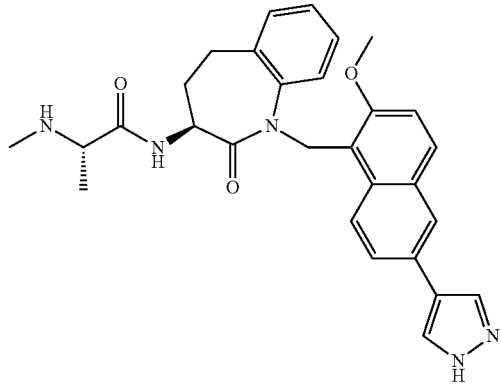 [SMILES: CN[C@@H](C)C(=O)N[C@H]1CCc2ccccc2N(Cc2c(OC)ccc3cc(-c4cn[nH]c4)ccc23)C1=O]

Step 1: {(S)-1-[(S)-1-(6-Bromo-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (100 mg, 164 µmol), 1-tert-butoxycarbonyl-1h-pyrazole-4-boronic acid, pinacol ester (72.3 mg, 246 ummol), bis (triphenylphosphine) palladium(II) dichloride (5.75 mg, 8.2 µmol) were placed in a 20 mL microwave vessel and capped. The vessel was evacuated, purged with N$_2$, DMF (6 mL) and 2 M Na$_2$CO$_3$ solution (2 mL) was added and the vessel heated to 100° C. After 18 h, the mixture was diluted with EtOAc, washed with brine, dried over Na$_2$SO$_4$ and concentrated. The resulting material was purified by flash chromatography to afford ((S)-1-{(S)-1-[2-methoxy-6-(1H-pyrazol-4-yl)-naphthalen-1-ylmethyl]-2-oxo-2,3,4,5-tetrahydro-1H-benzo[b]azepin-3-ylcarbamoyl}-ethyl)-methyl-carbamic acid tert-butyl ester after lyophilization from MeCN/H$_2$O (43.3 mg, 44%, white solid).

Step 2: In a similar manner to that described for Example 10 Step 3, ((S)-1-{(S)-1-[2-methoxy-6-(1H-pyrazol-4-yl)-naphthalen-1-ylmethyl]-2-oxo-2,3,4,5-tetrahydro-1H-benzo[b]azepin-3-ylcarbamoyl}-ethyl)-methyl-carbamic acid tert-butyl ester (43.3 mg, 72.4 µmol) was converted to the title compound (33.7 mg, 87%, white solid). MS m/z 498.0 (MO.

Example 44

(S)—N—[(S)-1-(2-Methoxy-5,6,7,8-tetrahydro-naphthalen-1-ylmethyl)-2-oxo-2,3,4,5-tetrahydro-1H-benzo[b]azepin-3-yl]-2-methylamino-propionamide hydrochloride

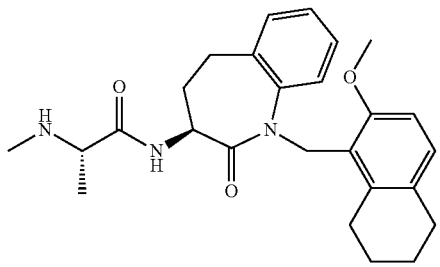 [SMILES: CN[C@@H](C)C(=O)N[C@H]1CCc2ccccc2N(Cc2c(OC)ccc3c2CCCC3)C1=O]

Step 1: A mixture of {(S)-1-[(S)-1-(6-bromo-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (52.8 mg, 0.086 mmol), 10% Pd/C (25 mg) and EtOH (15 mL) was hydrogenated at 50 psi (Parr apparatus) for 18 h, the mixture filtered through Celite and the filtrate concentrated. The resulting material was purified by flash chromatography to afford {(S)-1-[(S)-1-(2-methoxy-5,6,7,8-tetrahydro-naphthalen-1-ylmethyl)-2-oxo-2,3,4,5-tetrahydro-1H-benzo[b]azepin-3-ylcarbamoyl]-ethyl}-methyl-carbamic acid tert-butyl ester (21.6 mg, white solid).

Step 2: In a similar manner to that described for Example 10 Step 3, {(S)-1-[(S)-1-(2-methoxy-5,6,7,8-tetrahydro-naphthalen-1-ylmethyl)-2-oxo-2,3,4,5-tetrahydro-1H-benzo[b]azepin-3-ylcarbamoyl]-ethyl}-methyl-carbamic acid tert-butyl ester (21.6 mg, 40 µmol) was converted to the title compound (11.3 mg, white solid, 60%). MS m/z 436.0 (MH$^+$).

Example 45

(S)—N—[(S)-1-(6-Acetyl-2-methoxy-naphthalen-1-ylmethyl)-2-oxo-2,3,4,5-tetrahydro-1H-benzo[b]azepin-3-yl]-2-methylamino-propionamide hydrochloride

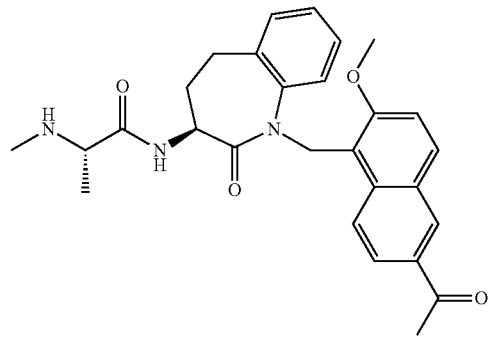 [SMILES: CN[C@@H](C)C(=O)N[C@H]1CCc2ccccc2N(Cc2c(OC)ccc3cc(C(C)=O)ccc23)C1=O]

Step 1: {(S)-1-[(S)-1-(6-Bromo-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (0.38 g, 622 µmol, Eq: 1.00), 1-(vinyloxy)butane (156 mg, 197 µL, 1.56 mmol, Eq: 2.5), palladium(II) acetate (8.38 mg, 37.3 µmol, Eq: 0.06) 1,3-bis(diphenylphosphino)propane (30.8 mg, 74.7 µmol, Eq: 0.12) and K$_2$CO$_3$ (103 mg, 747 µmol, Eq: 1.2) were combined with DMF (3.04 mL) and H$_2$O (0.3 mL). The mixture was heated to 80° C. for 18 h, cooled, poured into 50 mL H$_2$O and extracted with EtOAc. The combined organic extracts were washed with brine, dried over Na$_2$SO$_4$ and concentrated. The resulting material was purified by flash chromatography to give ((S)-1-{(S)-1-[6-(1-butoxy-vinyl)-2-methoxy-naphthalen-1-ylmethyl]-2-oxo-2,3,4,5-tetrahydro-1H-benzo[b]azepin-3-ylcarbamoyl}-ethyl)-methyl-carbamic acid tert-butyl ester (0.251 g, 64%, white foam).

Step 2: ((S)-1-{(S)-1-[6-(1-Butoxy-vinyl)-2-methoxy-naphthalen-1-ylmethyl]-2-oxo-2,3,4,5-tetrahydro-1H-benzo[b]azepin-3-ylcarbamoyl}-ethyl)-methyl-carbamic acid tert-butyl ester (0.252 g, 399 µmol, Eq: 1.00) and 1 N HCl (5 mL, 5.00 mmol, Eq: 12.5) were combined with THF (10 mL) to give a colorless solution. After 2 h the mixture was poured into 50 mL H$_2$O and extracted with EtOAc. The combined organic extracts were washed with brine, dried over Na$_2$SO$_4$ and concentrated. The resulting material was purified by flash chromatography to give {(S)-1-[(S)-1-(6-acetyl-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester as a white solid after lyophilazation from MeCN/H$_2$O (111.5 mg, 49%, white solid).

Step 3: {(S)-1-[(S)-1-(6-Acetyl-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (26.6 mg, 46.4 µmol, Eq: 1.00) and 4.0 M HCl in dioxane (1.5 mL, 6.00 mmol, Eq: 129) were combined to give a light yellow solution. After 1 h, the mixture was concentrated and the residue lyophilized from MeCN/H$_2$O to afford the title compound (20.9 mg, 88%, off-white solid). MS m/z 474.0 (MH$^+$)

Example 46

(S)—N—[(S)-1-(2-Methoxy-6-vinyl-naphthalen-1-ylmethyl)-2-oxo-2,3,4,5-tetrahydro-1H-benzo[b]azepin-3-yl]-2-methylamino-propionamide hydrochloride

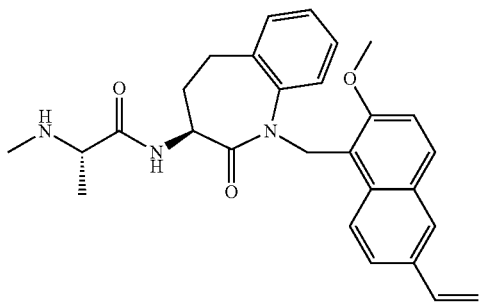 [SMILES: C=Cc1ccc2c(CN3C(=O)[C@@H](NC(=O)[C@H](C)NC)CCc4ccccc43)c(OC)ccc2c1]

Example 47a (S)—N—{(S)-1-[6-(1-Hydroxy-ethyl)-2-methoxy-naphthalen-1-ylmethyl]-2-oxo-2,3,4,5-tetrahydro-1H-benzo[b]azepin-3-yl}-2-methylamino-propionamide trifluoroacetate, mixture of diastereomers

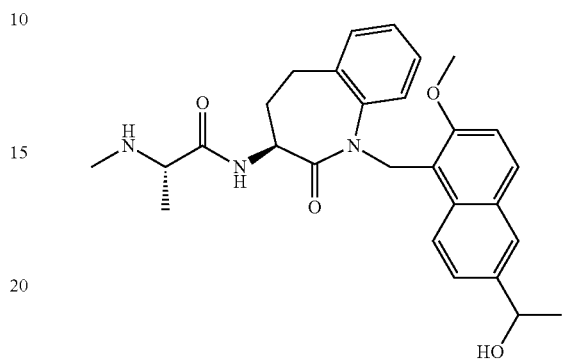

Step 1: {(S)-1-[(S)-1-(6-Acetyl-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (50 mg, 87.2 μmol, Eq: 1.00) and NaBH$_4$ (3.3 mg, 87.2 μmol, Eq: 1.00) were combined with EtOH (1 mL). After 5 h, the mixture was poured into 20 mL H$_2$O and extracted with EtOAc. The combined organic extracts were washed with H$_2$O, dried over Na$_2$SO$_4$ and concentrated. The resulting material was purified by flash chromatography to give (S)—N—{(S)-1-[6-(1-hydroxy-ethyl)-2-methoxy-naphthalen-1-ylmethyl]-2-oxo-2,3,4,5-tetrahydro-1H-benzo[b]azepin-3-yl}-2-methylamino-propionamide (32.2 mg, 64%, white foam).

Step 2: In a similar manner to that described for Example 45 Step 3 except the mixture was stirred 2 h, (S)—N—{(S)-1-[6-(1-hydroxy-ethyl)-2-methoxy-naphthalen-1-ylmethyl]-2-oxo-2,3,4,5-tetrahydro-1H-benzo[b]azepin-3-yl}-2-methylamino-propionamide (32.2 mg, 55.9 μmol, Eq: 1.00) was converted to the title compound (23.9 mg, white solid, 86%). MS m/z 458.0 (MH$^+$)

(S)—N—[(S)-1-(6-Acetyl-2-methoxy-naphthalen-1-ylmethyl)-2-oxo-2,3,4,5-tetrahydro-1H-benzo[b]azepin-3-yl]-2-methylamino-propionamide (117 mg, 247 μmol, Eq: 1.00) was combined with EtOH (4 mL) to give a yellow solution. NaBH$_4$ (9.35 mg, 247 μmol, Eq: 1.00) was added. After 2.5 h the reaction was diluted with 20 mL H$_2$O and extracted with EtOAc. The combined organic extracts were washed with H$_2$O, brine, dried over Na$_2$SO$_4$ and concentrated. The resulting material was purified by preparative reverse phase HPLC to afford the title compound after lyophilization (115.1 mg, 79%, white solid). MS m/z 458.1 (MH$^+$).

In a similar manner to that described for Example 5 Step 2 where the conditions can be varied so that the temperature can range from 50° C.-70° C. and the reaction time can range from 2-24 h and NaI can be optionally omitted, and in a similar manner to that described for Example 10 Step 3 except the reaction time can range from 30 min to 24 h, methyl-[(S)-1-((S)-2-oxo-2,3,4,5-tetrahydro-1H-benzo[b]azepin-3-ylcarbamoyl)-ethyl]-carbamic acid tert-butyl ester can be converted to the following compounds as hydrochloride salts.

TABLE 3

| Example | Final Product | m/z (MH$^+$) |
|---|---|---|
| 47b |  | 416.0 |

TABLE 3-continued

| Example | Final Product | m/z (MH⁺) |
|---|---|---|
| 47c | | 432.0 |
| 47d | | 403.1 |
| 47e | | 403.1 |
| 47f | | 416.0 |
| 47g | | 481.8 |

TABLE 3-continued

| Example | Final Product | m/z (MH+) |
|---|---|---|
| 47h | | 402.0 |
| 47i | | 426.1 |
| 47j | | 427.0 |
| 47k | | 442.1 |
| 47l | | 500.0 |

TABLE 3-continued

| Example | Final Product | m/z (MH⁺) |
|---------|---------------|-----------|
| 47m | | 434.0 |
| 47n | | 451.0 |
| 47o | | 511.9 |
| 47p | | 500.2 |
| 47q | | 417.0 |

TABLE 3-continued

| Example | Final Product | m/z (MH+) |
|---|---|---|
| 47r | | 438.0 |
| 47s | | 420.1 |
| 47t | | 501.0 |
| 47u | | 417.0 |
| 47v | | 511.9 |

TABLE 3-continued

| Example | Final Product | m/z (MH+) |
|---------|---------------|-----------|
| 47x | | 435.9 |
| 47y | | 446.0 |
| 47z | | 403.1 |
| 47aa | | 404.2 |
| 47bb | | 430.0 |

TABLE 3-continued

| Example | Final Product | m/z (MH⁺) |
|---|---|---|
| 47cc | | 404.1 |
| 47dd | | 460.1 |
| 47ee | | 452.1 |
| 47ff | | 481.9 |
| 47gg | | 481.9 |

TABLE 3-continued

| Example | Final Product | m/z (MH+) |
|---|---|---|
| 47hh | | 482.0 |
| 47ii | | 433.0 |
| 47jj | | 407.9 |
| 47kk | | 427.0 |
| 47ll | | 408.0 |
| 47mm | | 434.0 |

TABLE 3-continued

| Example | Final Product | m/z (MH+) |
|---|---|---|
| 47nn | | 402.0 |
| 47oo | | 385.9 |
| 47pp | | 380.0 |
| 47qq | | 352.4 |
| 47rr | | 380.0 |
| 47ss | | 366.0 |

TABLE 3-continued

| Example | Final Product | m/z (MH+) |
|---|---|---|
| 47tt | | 481.9 |

Intermediates obtained in the course of preparing the products listed in Table 3 can be derivatized further to afford additional compounds, as exemplified below.

Example 48

(S)-2-Methylamino-N—[(S)-2-oxo-1-(1-oxy-quinolin-4-ylmethyl)-2,3,4,5-tetrahydro-1H-benzo[b]azepin-3-yl]-propionamide hydrochloride

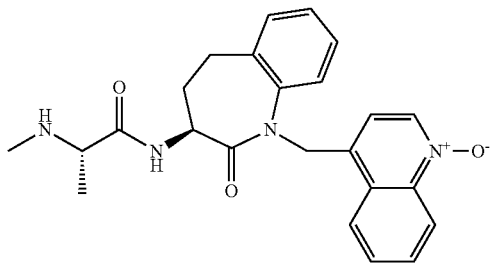 [SMILES: CN[C@@H](C)C(=O)N[C@H]1CCc2ccccc2N(Cc2cc[n+]([O-])c3ccccc23)C1=O]

Step 1: Methyl-[(S)-1-((S)-2-oxo-1-quinolin-4-ylmethyl-2,3,4,5-tetrahydro-1H-benzo[b]azepin-3-ylcarbamoyl)-ethyl]-carbamic acid tert-butyl ester (0.1 g, 199 μmol, Eq: 1.00) was dissolved in DCM (4 mL) and 3-chloroperbenzoic acid (93.6 mg, 418 μmol, Eq: 2.1) was added. After 18 h, the mixture was poured into DCM, washed with 1 M NaOH, brine, dried over Na$_2$SO$_4$ and concentrated to afford methyl-{(S)-1-[(S)-2-oxo-1-(1-oxy-quinolin-4-ylmethyl)-2,3,4,5-tetrahydro-1H-benzo[b]azepin-3-ylcarbamoyl]-ethyl}-carbamic acid tert-butyl ester (78.9 mg, light yellow solid, 77%)

Step 2: In a similar manner to that described for Example 10 Step 3, methyl-{(S)-1-[(S)-2-oxo-1-(1-oxy-quinolin-4-ylmethyl)-2,3,4,5-tetrahydro-1H-benzo[b]azepin-3-ylcarbamoyl]-ethyl}-carbamic acid tert-butyl ester (78.9 mg, 152 μmol) was converted to the title compound (59.1 mg, 85%, yellow solid). MS m/z 419.0 (MH+)

Example 49a (S)—N—[(S)-1-(5-Furan-2-yl-2-methoxy-naphthalen-1-ylmethyl)-2-oxo-2,3,4,5-tetrahydro-1H-benzo[b]azepin-3-yl]-2-methylamino-propionamide

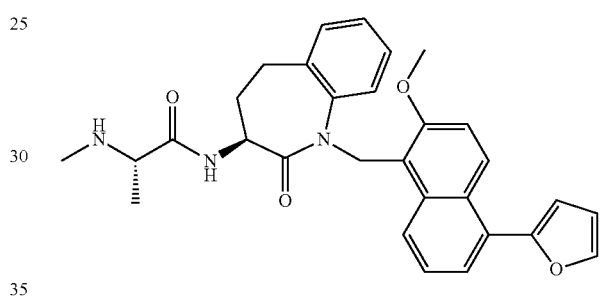

Step 1: A mixture of {(S)-1-[(S)-1-(5-bromo-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (100 mg, 164 μmol), potassium 2-furantrifluoroborate (42.7 mg, 246 μmol), Pd(Oac)$_2$ (1.1 mg, 4.91 μmmol), 2-dicyclohexylphosphino-2',6'-diisopropoxybiphenyl (4.59 mg, 9.83 μmol), Na$_2$CO$_3$ (34.7 mg, 328 μmol) and EtOH (1.5 mL) was purged with N$_2$ then heated at 85° C. for 18 h. The mixture was cooled, diluted with EtOAc and washed with brine, dried over Na$_2$SO$_4$ and concentrated. The resulting material was purified by flash chromatography to give {(S)-1-[(S)-1-(5-furan-2-yl-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (67.7 mg, 69%, light solid). MS m/z 598.1 (MH+)

Step 2: In a similar manner to that described for Example 45 Step 3, {(S)-1-[(S)-1-(5-furan-2-yl-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (67.7 mg, 113 μmol) was converted to the title compound (53.8 mg, 89%, gray solid). MS m/z 498.0 (MH+)

Following the procedures described in Example 49a, intermediates obtained in the preparation of the products described in Examples 47g, 47p, 47x, 47gg, 47ii and 47nn of Table 3 and Example 30, Step 1, were converted to the following compound listed in Table 4.

TABLE 4
| Example | Reagent | Product | m/z (MH+) |
|---|---|---|---|
| 49b | 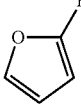 | 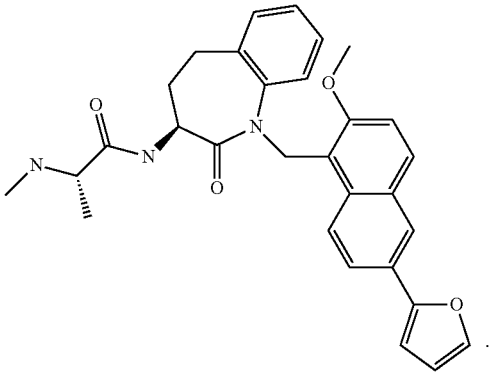 [SMILES: CN[C@@H](C)C(=O)N[C@H]1CCc2ccccc2N(Cc2c(OC)ccc3cc(-c4ccco4)ccc23)C1=O] | 498.1 |
| 49c | 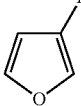 | 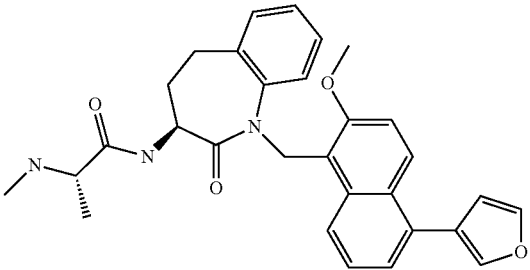 [SMILES: CN[C@@H](C)C(=O)N[C@H]1CCc2ccccc2N(Cc2c(OC)ccc3c(-c4ccoc4)cccc23)C1=O] | 498.0 |
| 49d |  | 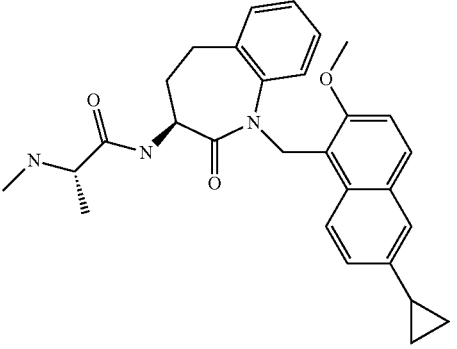 [SMILES: CN[C@@H](C)C(=O)N[C@H]1CCc2ccccc2N(Cc2c(OC)ccc3cc(C4CC4)ccc23)C1=O] | 472.0 |
| 49e |  | 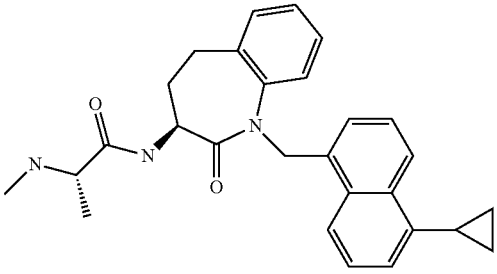 [SMILES: CN[C@@H](C)C(=O)N[C@H]1CCc2ccccc2N(Cc2cccc3c(C4CC4)cccc23)C1=O] | 442.1 |
| 49f | 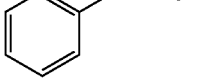 | 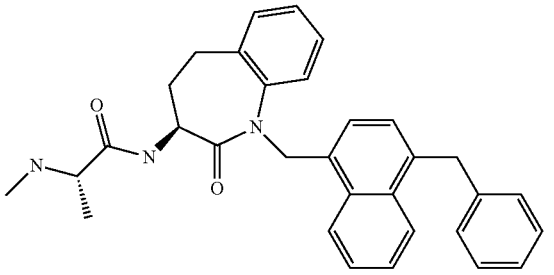 [SMILES: CN[C@@H](C)C(=O)N[C@H]1CCc2ccccc2N(Cc2ccc(Cc3ccccc3)c3ccccc23)C1=O] | 492.1 |

TABLE 4-continued

| Example | Reagent | Product | m/z (MH+) |
|---|---|---|---|
| 49g | ▷—BF₃K | (structure) | 442.1 |
| 49h | PhCH₂CH₂—BF₃K | (structure) | 506.4 |
| 49i | PhCH₂—BF₃K | (structure) | 522.2 |
| 49j | PhCH₂—BF₃K | (structure) | 492.1 |
| 49k | PhCH₂—BF₃K | (structure) | 492.1 |

TABLE 4-continued
| Example | Reagent | Product | m/z (MH+) |
|---|---|---|---|
| 49l | 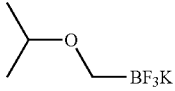 | 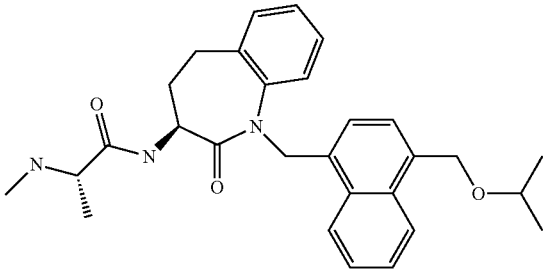 [SMILES: CN[C@@H](C)C(=O)N[C@H]1CCc2ccccc2N(Cc2ccc(COC(C)C)c3ccccc23)C1=O] | 574.1 |
| 49m | 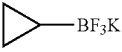 | 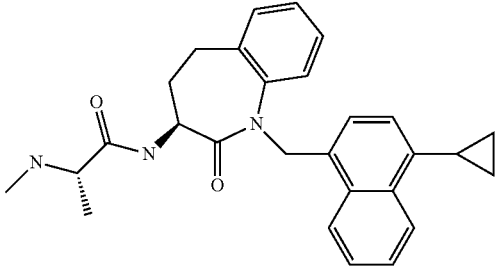 [SMILES: CN[C@@H](C)C(=O)N[C@H]1CCc2ccccc2N(Cc2ccc(C3CC3)c3ccccc23)C1=O] | 442.0 |
| 49n | 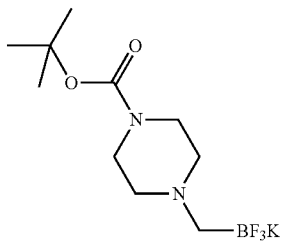 | 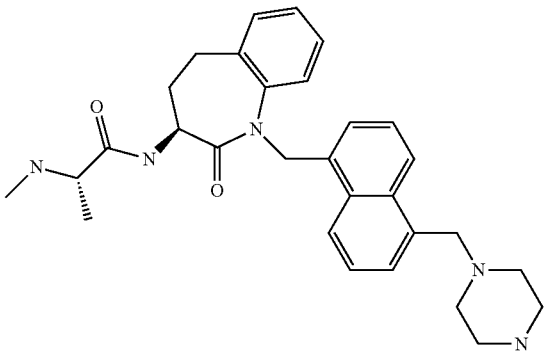 [SMILES: CN[C@@H](C)C(=O)N[C@H]1CCc2ccccc2N(Cc2cccc3c(CN4CCNCC4)cccc23)C1=O] | 500.1 |
| 49o | 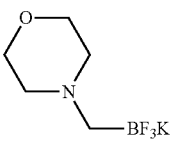 | 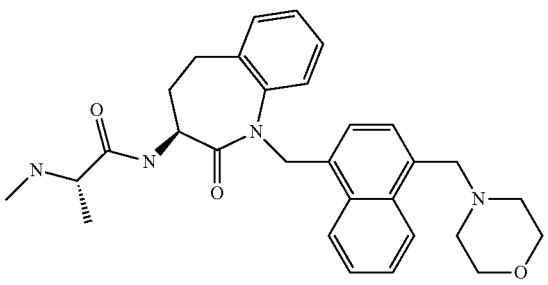 | 501.0 |
| 49p | 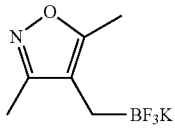 | 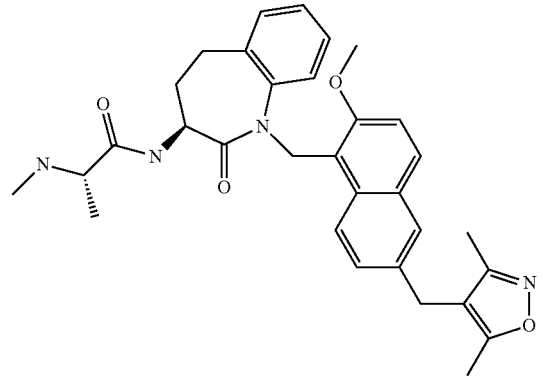 [SMILES: CN[C@@H](C)C(=O)N[C@H]1CCc2ccccc2N(Cc2c(OC)ccc3cc(Cc4c(C)noc4C)ccc23)C1=O] | 527.1 |

TABLE 4-continued
| Example | Reagent | Product | m/z (MH+) |
|---|---|---|---|
| 49q | 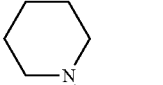 | 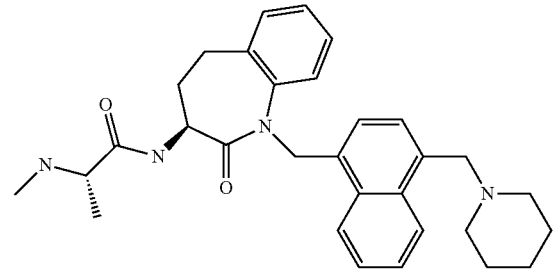 [SMILES: CN[C@@H](C)C(=O)N[C@H]1CCc2ccccc2N(Cc2ccc(CN3CCCCC3)c3ccccc23)C1=O] | 499.0 |
| 49r | 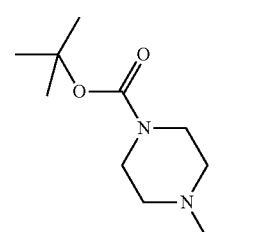 | 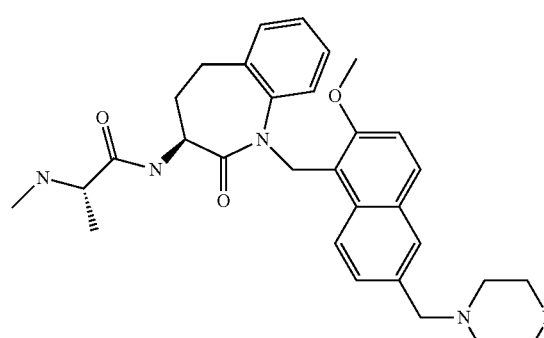 | 530.2 |
| 49s | 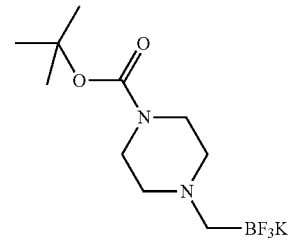 | 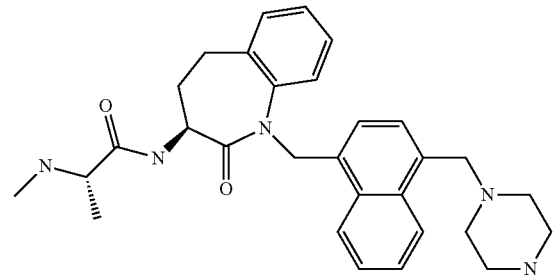 [SMILES: CN[C@@H](C)C(=O)N[C@H]1CCc2ccccc2N(Cc2ccc(CN3CCNCC3)c3ccccc23)C1=O] | 500.1 |
| 49t | 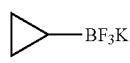 | 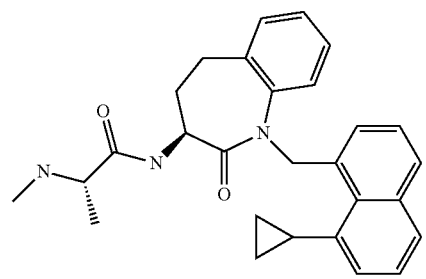 [SMILES: CN[C@@H](C)C(=O)N[C@H]1CCc2ccccc2N(Cc2cccc3cccc(C4CC4)c23)C1=O] | 442.1 |
| 49u | 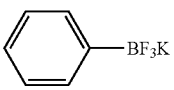 | 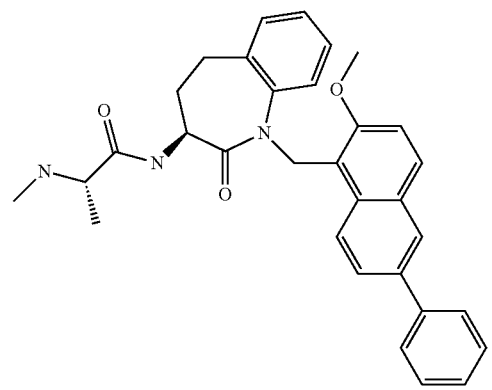 [SMILES: CN[C@@H](C)C(=O)N[C@H]1CCc2ccccc2N(Cc2c(OC)ccc3cc(-c4ccccc4)ccc23)C1=O] | 508.1 |

Example 50

6-Methoxy-5-[(S)-3-((S)-2-methylamino-propionylamino)-2-oxo-2,3,4,5-tetrahydro-benzo[b]azepin-1-ylmethyl]-naphthalene-2-carboxylic acid methyl ester hydrochloride

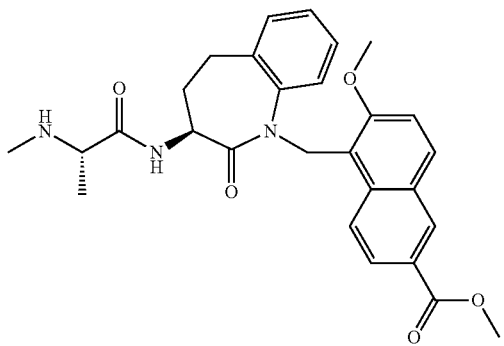

Step 1: {(S)-1-[(S)-1-(6-Bromo-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (153 mg, 0.25 mmol, Eq: 1.00), palladium(II) acetate (2.25 mg, 10.0 µmol, Eq: 0.04) and Xantphos (11.6 mg, 20.0 µmol, Eq: 0.08) were combined. The vessel was evacuated and purged with $N_2$. MeOH (80.1 mg, 2.5 mmol, Eq: 10) and TEA were added, the vessel was purged with CO gas and heated to 70° C. After 18 h, the mixture was cooled, diluted with EtOAc, washed with 1 N HCl, $H_2O$, brine, dried over $Na_2SO_4$ and concentrated. The resulting material was purified by flash chromatography to give 5-{(S)-3-[(S)-2-(tert-butoxycarbonyl-methyl-amino)-propionylamino]-2-oxo-2,3,4,5-tetrahydro-benzo[b]azepin-1-ylmethyl}-6-methoxy-naphthalene-2-carboxylic acid methyl ester (110.8 mg, 75%, white solid).

Step 2: In a similar manner to that described for Example 10 Step 3, 5-{(S)-3-[(S)-2-(tert-butoxycarbonyl-methyl-amino)-propionylamino]-2-oxo-2,3,4,5-tetrahydro-benzo[b]azepin-1-ylmethyl}-6-methoxy-naphthalene-2-carboxylic acid methyl ester (44 mg, 74.6 µmol) was converted to the title compound (29.0 mg, 74%, white solid). MS m/z 490.1 (MH$^+$)

Example 51

6-Methoxy-5-[(S)-3-((S)-2-methylamino-propionylamino)-2-oxo-2,3,4,5-tetrahydro-benzo[b]azepin-1-ylmethyl]-naphthalene-2-carboxylic acid

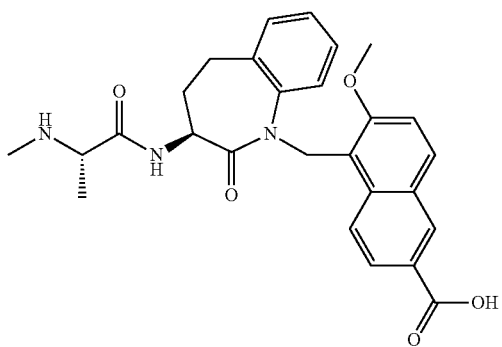 [SMILES: CN[C@@H](C)C(=O)N[C@H]1CCc2ccccc2N(Cc2c(OC)ccc3cc(C(=O)O)ccc23)C1=O]

Step 1: 5-{(S)-3-[(S)-2-(tert-Butoxycarbonyl-methyl-amino)-propionylamino]-2-oxo-2,3,4,5-tetrahydro-benzo[b]azepin-1-ylmethyl}-6-methoxy-naphthalene-2-carboxylic acid methyl ester (377.5 mg, 640 µmol, Eq: 1.00) was combined with THF (10 mL) and LiOH.$H_2O$ (134 mg, 3.2 mmol, Eq: 5) in $H_2O$ (15 mL) was added. After 18 h, the mixture was diluted with 1 N HCl and extracted with EtOAc. The combined extracts were washed with $H_2O$, brine, dried over $Na_2SO_4$, and concentrated to give 5-{(S)-3-[(S)-2-(tert-butoxycarbonyl-methyl-amino)-propionylamino]-2-oxo-2,3,4,5-tetrahydro-benzo[b]azepin-1-ylmethyl}-6-methoxy-naphthalene-2-carboxylic acid which was used without purification (0.35 g light yellow foam).

Step 2: 5-{(S)-3-[(S)-2-(tert-Butoxycarbonyl-methyl-amino)-propionylamino]-2-oxo-2,3,4,5-tetrahydro-benzo[b]azepin-1-ylmethyl}-6-methoxy-naphthalene-2-carboxylic acid (66.4 mg, 115 µmol, Eq: 1.00) and 2.0 M HCl in diethyl ether (4 mL, 8.00 mmol, Eq: 69.4) were combined and a precipitate formed. After 2 h, 2 mL dioxane was added and the mixture stirred for 18 h. The mixture was concentrated and the residue lyophilized from MeCN/$H_2O$ to afford the title compound (50.4 mg, 85%, white solid). MS m/z 476.0 (MH$^+$)

Example 52a (S)—N—[(S)-1-(6-Methanesulfonylaminocarbonyl-2-methoxy-naphthalen-1-ylmethyl)-2-oxo-2,3,4,5-tetrahydro-1H-benzo[b]azepin-3-yl]-2-methylamino-propionamide

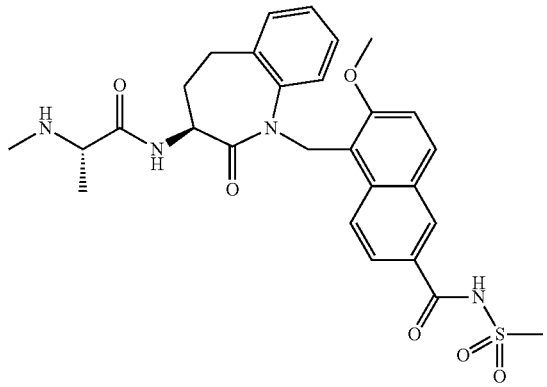

Step 1: 5-{(S)-3-[(S)-2-(tert-Butoxycarbonyl-methyl-amino)-propionylamino]-2-oxo-2,3,4,5-tetrahydro-benzo[b]azepin-1-ylmethyl}-6-methoxy-naphthalene-2-carboxylic acid (100 mg, 174 µmol, Eq: 1.00), EDCI (41.6 mg, 217 µmol, Eq: 1.25) and DMAP (26.5 mg, 217 µmol, Eq: 1.25) were combined with DCM (6.00 mL) and methanesulfonamide (20.7 mg, 217 µmol, Eq: 1.25) was added. After 2 h, the mixture was diluted with DCM, washed with 0.5 M HCl, brine, dried over $Na_2SO_4$ and concentrated. The resulting material was purified by preparative HPLC to give a material that was lyophilized from MeCN/$H_2O$ to afford {(S)-1-[(S)-1-(6-methanesulfonylaminocarbonyl-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (27.6 mg, 23%, white solid).

Step 2: In a similar manner to that described for Example 10 Step 3, {(S)-1-[(S)-1-(6-methanesulfonylaminocarbonyl-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (27.6 mg, 42.3 µmol) was converted to the title compound (18.5 mg, 74%, white solid). (MS m/z 553.1 MH$^+$)

In a similar manner to that described in Example 50, Example 51 and Example 52a the following compounds were prepared.

TABLE 5

| Example | Product | m/z (MH+) |
|---|---|---|
| 52b | | 581.0 |
| 52c | | 553.0 |
| 52d | | 581.1 |
| 52e | | 490.0 |

TABLE 5-continued

| Example | Product | m/z (MH+) |
|---|---|---|
| 52f | | 446.0 |
| 52g | | 460.0 |
| 52h | | 490.1 |

Example 53

(S)—N—[(S)-1-(5-Cyano-2-methoxy-naphthalen-1-ylmethyl)-2-oxo-2,3,4,5-tetrahydro-1H-benzo[b]azepin-3-yl]-2-methylamino-propionamide hydrochloride

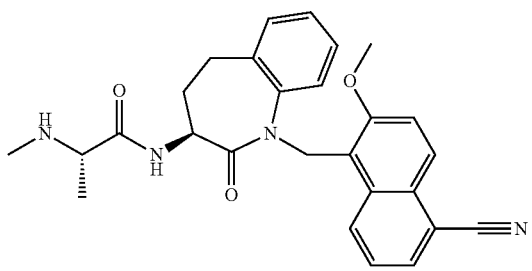 [SMILES: CN[C@@H](C)C(=O)N[C@H]1CCc2ccccc2N(Cc2c(OC)ccc3c(C#N)cccc23)C1=O]

Step 1: In a similar manner to that described for Example 30 Step 1, (S)—N—[(S)-1-(5-bromo-2-methoxy-naphthalen-1-ylmethyl)-2-oxo-2,3,4,5-tetrahydro-1H-benzo[b]azepin-3-yl]-2-methylamino-propionamide (0.3 g, 491 µmol, Eq: 1.00) was converted to {(S)-1-[(S)-1-(5-cyano-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (0.229 g, 83%, light yellow solid).

Step 2: In a similar manner to that described for Example 45 Step 3 except 1 mL MeOH was added to the mixture, {(S)-1-[(S)-1-(5-cyano-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (69.9 mg, 126 µmol was converted to the title compound (60.1 mg, 97%, white solid). (MS m/z 457.1 MH+).

Example 54a

5-[(S)-3-((S)-2-Methylamino-propionylamino)-2-oxo-2,3,4,5-tetrahydro-benzo[b]azepin-1-ylmethyl]-naphthalene-1-carboxylic acid amide

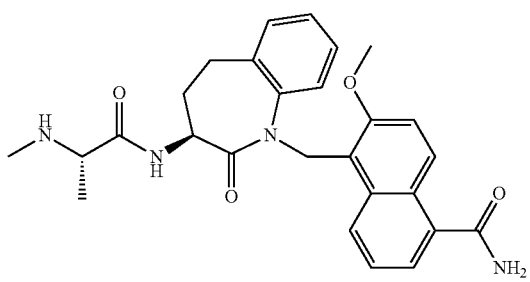 [SMILES: CN[C@@H](C)C(=O)N[C@H]1CCc2ccccc2N(Cc2c(OC)ccc3c(C(N)=O)cccc23)C1=O]

Step 1: {(S)-1-[(S)-1-(5-Cyano-2-methoxy-naphthalen-1-ylmethyl)-2-oxo-2,3,4,5-tetrahydro-1H-benzo[b]azepin-3-ylcarbamoyl]-ethyl}-methyl-carbamic acid tert-butyl ester (50 mg, 94.9 μmol, Eq: 1.00) and $K_2CO_3$ (6.56 mg, 47.5 μmol, Eq: 0.5) were combined with DMSO (1.25 mL) to give a white suspension and 30% $H_2O_2$ (832 mg, 7.34 mmol, Eq: 77.3) was added. After 1 h, the mixture was diluted with $H_2O$ resulting in a precipitate. The precipitate was collected by filtration, washed with $H_2O$ and petroleum ether, dissolved in MeCN/$H_2O$ and lyophilized to give {(S)-1-[(S)-1-(5-carbamoyl-naphthalen-1-ylmethyl)-2-oxo-2,3,4,5-tetrahydro-1H-benzo[b]azepin-3-ylcarbamoyl]-ethyl}-methyl-carbamic acid tert-butyl ester which was used without purification (26.2 mg, 51%, white solid).

Step 2: In a similar manner to that described for Example 10 Step 3, {(S)-1-[(S)-1-(5-carbamoyl-naphthalen-1-ylmethyl)-2-oxo-2,3,4,5-tetrahydro-1H-benzo[b]azepin-3-ylcarbamoyl]-ethyl}-methyl-carbamic acid tert-butyl ester (26.2 mg, 48.1 μmol) was converted to the title compound (29.5 mg, light yellow oil). MS m/z 445.1 ($MH^+$)

Following the procedures described in Examples 53 and 54a, the following compounds were prepared as hydrochloride salts.

TABLE 6

| Example | Product | m/z ($MH^+$) |
| --- | --- | --- |
| 54b | 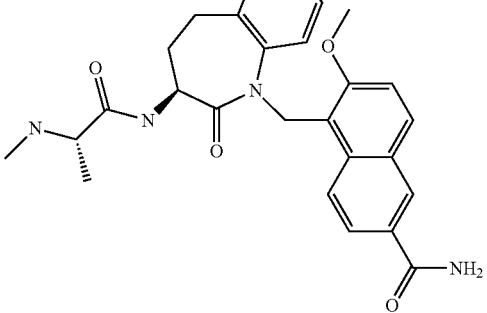 | 475.1 |
| 54c | 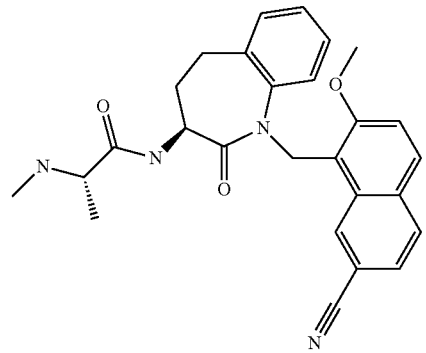 [SMILES: CN[C@@H](C)C(=O)N[C@H]1CCc2ccccc2N(Cc2c(OC)ccc3ccc(C#N)cc23)C1=O] | 457.1 |

TABLE 6-continued

| Example | Product | m/z (MH+) |
|---------|---------|-----------|
| 54d | | 457.0 |
| 54e | | 427.0 |
| 54f | | 427.0 |

TABLE 6-continued

| Example | Product | m/z (MH+) |
|---|---|---|
| 54g | | 445.1 |
| 54h | | 427.0 |

Example 55

Methyl-[(S)-1-(2-oxo-2,3,4,5-tetrahydro-1H-benzo[b]azepin-3-ylcarbamoyl)-ethyl]-carbamic acid tert-butyl ester

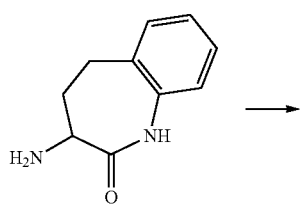 →

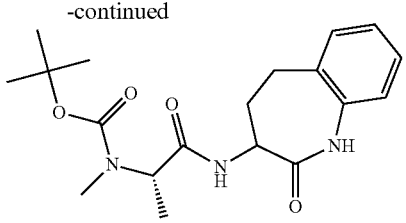

In a similar manner to that described for Example 5 Step 1, 3-amino-1,3,4,5-tetrahydro-benzo[b]azepin-2-one (0.75 g, 4.26 mmol) and BOC-N-Me-Ala-OH (1.04 g, 5.11 mmol) was converted to the title compound and used as a mixture of diastereomers (1.68 g, 100%). MS m/z (384.0 M+Na)

In a similar manner to that described for Example 5 Step 2 where the conditions can be varied so that the temperature can range from 50° C.-70° C. and the reaction time can range from 2-24 h and NaI can be optionally omitted, and in a similar manner to that described for Example 10 Step 3 except the reaction time can range from 30 min. to 24 h, the diastereomic mixture of methyl-[(S)-1-(2-oxo-2,3,4,5-tetrahydro-1H-benzo[b]azepin-3-ylcarbamoyl)-ethyl]-carbamic acid tert-butyl ester can be converted to the following compounds obtained as mixtures of diastereomers.

TABLE 7

| Example | Final Product | m/z (MH+) |
|---------|---------------|-----------|
| 55a | | 428.0 |
| 55b | | 428.0 |
| 55c | | 419.0 |
| 55d | | 442.0 |
| 55e | | 352.0 |

TABLE 7-continued

| Example | Final Product | m/z (MH⁺) |
|---|---|---|
| 55f | | 428.0 |
| 55g | | 366.0 |
| 55h | | 380.1 |

Example 56

(S)—N—((S)-1-((3-Cyclopropylquinolin-4-yl)methyl)-2-oxo-2,3,4,5-tetrahydro-1H-benzo[b]azepin-3-yl)-2-(methylamino)propanamide dihydrochloride

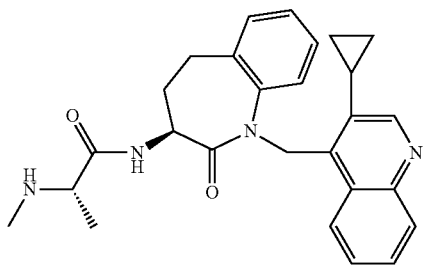 [SMILES: CN[C@@H](C)C(=O)N[C@H]1CCc2ccccc2N(Cc2c(C3CC3)cnc3ccccc23)C1=O]

Step 1: A mixture of methyl-[(S)-1-((S)-2-oxo-2,3,4,5-tetrahydro-1H-benzo[b]azepin-3-ylcarbamoyl)-ethyl]-carbamic acid tert-butyl ester (55.4 mg, 153 µmol, Eq: 0.8), (3-cyclopropylquinolin-4-yl)methyl methanesulfonate (53.1 mg, 191 µmol, Eq: 1.00) and Cs₂CO₃ (156 mg, 479 µmol, Eq: 2.5) in DMF (3.00 mL) was heated to 50° C. for 1 h, cooled, diluted with brine and extracted with EtOAc. The combined extracts were washed with brine, dried over Na₂SO₄ and concentrated. The residue was purified by flash chromatography to afford tert-butyl (S)-1-((S)-1-((3-cyclopropylquinolin-4-yl)methyl)-2-oxo-2,3,4,5-tetrahydro-1H-benzo[b]azepin-3-ylamino)-1-oxopropan-2-yl(methyl)carbamate (52.0 mg, 50.0%) MS m/z 543.2 (MH⁺).

Step 2: 2.0 M HCl in Et₂O (3 mL, 6.00 mmol, Eq: 62.6) was added to a solution of tert-butyl (S)-1-((S)-1-((3-cyclopropylquinolin-4-yl)methyl)-2-oxo-2,3,4,5-tetrahydro-1H-benzo[b]azepin-3-ylamino)-1-oxopropan-2-yl(methyl)carbamate (52 mg, 95.8 µmol, Eq: 1.00) in MeOH (1.5 mL). After 90 min the mixture was concentrated, the residue taken up in MeCN/H₂O and lyophilized to afford the title compound (42.2, 85.4%, mg, off-white solid). MS m/z 443.1 (MH⁺).

Example 57

(S)—N—((S)-1-((2,6-Bis(trifluoromethyl)quinolin-4-yl)methyl)-2-oxo-2,3,4,5-tetrahydro-1H-benzo[b]azepin-3-yl)-2-(methylamino)propanamide hydrochloride

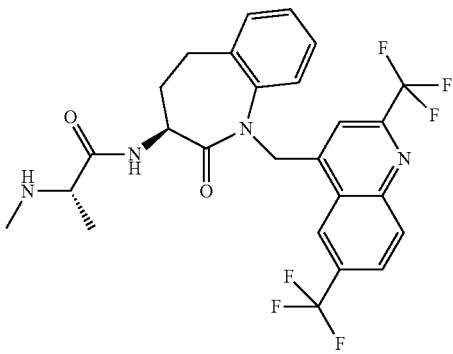 [SMILES: CN[C@@H](C)C(=O)N[C@H]1CCc2ccccc2N(Cc2cc(C(F)(F)F)nc3ccc(C(F)(F)F)cc23)C1=O]

In a similar manner to that described for Example 56, methyl-[(S)-1-((S)-2-oxo-2,3,4,5-tetrahydro-1H-benzo[b]azepin-3-ylcarbamoyl)-ethyl]-carbamic acid tert-butyl ester (49.0 mg, 135 µmol, Eq: 0.8) and (2,6-bis(trifluoromethyl)quinolin-4-yl)methyl methanesulfonate (63.2 mg, 169 µmol, Eq: 1.00) were converted to the title compound (5.5 mg, 74.5%, light yellow solid). MS m/z 539.0 (MH$^+$).

Example 58

(S)—N—((S)-1-((6-Bromo-2-methoxynaphthalen-1-yl)methyl)-2-oxo-2,3,4,5-tetrahydro-1H-benzo[b]azepin-3-yl)-2-(methylamino)butanamide trifluoroacetate

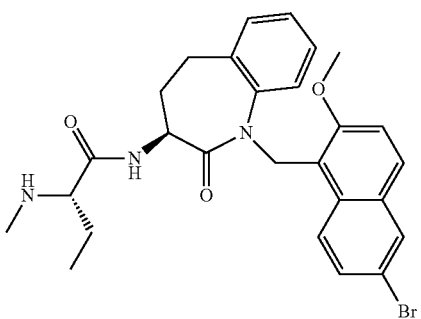 [SMILES: CC[C@H](NC)C(=O)N[C@H]1CCc2ccccc2N(Cc2c(OC)ccc3cc(Br)ccc23)C1=O]

Step 1: A mixture of tert-butyl methyl((S)-1-oxo-1-((S)-2-oxo-2,3,4,5-tetrahydro-1H-benzo[b]azepin-3-ylamino)butan-2-yl)carbamate (121 mg, 322 µmol, Eq: 1.00), 6-bromo-1-(chloromethyl)-2-methoxynaphthalene (138 mg, 483 µmol, Eq: 1.5), NaI (72.5 mg, 483 µmol, Eq: 1.5) and Cs$_2$CO$_3$ (158 mg, 483 µmol, Eq: 1.5) in DMF (4 mL) was heated to 60° C. After 3 h, the mixture was cooled, diluted with EtOAc and washed with brine. The combined extracts were dried over Na$_2$SO$_4$ and concentrated. The residue was purified by flash chromatography to afford tert-butyl (S)-1-((S)-1-((6-bromo-2-methoxynaphthalen-1-yl)methyl)-2-oxo-2,3,4,5-tetrahydro-1H-benzo[b]azepin-3-ylamino)-1-oxobutan-2-yl(methyl)carbamate (88.0 mg, 43.7%) MS m/z 625.9 (MH$^+$).

Step 2: TFA (592 mg, 0.4 mL, 5.19 mmol, Eq: 36.8) was added to a solution of tert-butyl (S)-1-((S)-1-((6-bromo-2-methoxynaphthalen-1-yl)methyl)-2-oxo-2,3,4,5-tetrahydro-1H-benzo[b]azepin-3-ylamino)-1-oxobutan-2-yl(methyl)carbamate (88 mg, 141 µmol, Eq: 1.00) in DCM (2 mL). After 30 min the mixture was concentrated, the residue dissolved in MeCN/H$_2$O and lyophilized to afford the title compound (76.5 mg, 85.0%, white solid). MS m/z 525.9 (MH$^+$)

Example 59

(S)—N—((S)-1-((6-Bromo-2-methoxynaphthalen-1-yl)methyl)-2-oxo-2,3,4,5-tetrahydro-1H-benzo[b]azepin-3-yl)-2-(propylamino)propanamide

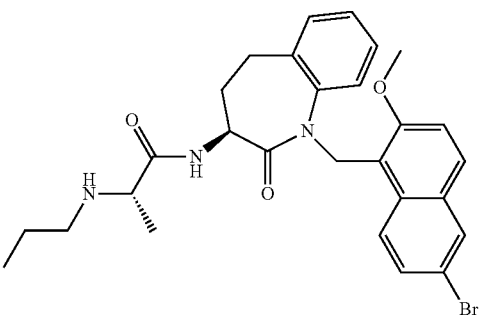 [SMILES: CCCN[C@@H](C)C(=O)N[C@H]1CCc2ccccc2N(Cc2c(OC)ccc3cc(Br)ccc23)C1=O]

Step 1: HBTU (1.08 g, 2.86 mmol, Eq: 1.2) and HOBT.H$_2$O (438 mg, 2.86 mmol, Eq: 1.2) in 8 mL DMF were added to a mixture of (S)-3-amino-4,5-dihydro-1H-benzo[b]azepin-2(3H)-one (0.42 g, 2.38 mmol, Eq: 1.00), (S)-2-(tert-butoxycarbonylamino)propanoic acid (451 mg, 2.38 mmol, Eq: 1.00) and TEA (724 mg, 997 µL, 7.15 mmol, Eq: 3) in DMF (8 mL). After 2 h, the mixture was diluted with EtOAc and washed with a 1:1 mixture of sat. NaHCO$_3$/brine and brine. The organic solution was dried over Na$_2$SO$_4$, concentrated and the residue purified by flash chromatography to give tert-butyl (S)-1-oxo-1-((S)-2-oxo-2,3,4,5-tetrahydro-1H-benzo[b]azepin-3-ylamino)propan-2-ylcarbamate (0.88 g, 70%, white foam). MS m/z 348 (MH$^+$)

Step 2: Cs$_2$CO$_3$ (1.24 g, 3.8 mmol, Eq: 1.50) and NaI (570 mg, 3.8 mmol, Eq: 1.50) were added to a mixture of tert-butyl (S)-1-oxo-1-((S)-2-oxo-2,3,4,5-tetrahydro-1H-benzo[b]azepin-3-ylamino)propan-2-ylcarbamate (0.88 g, 2.53 mmol, Eq: 1.00) and 6-bromo-1-(chloromethyl)-2-methoxynaphthalene (1.09 g, 3.8 mmol, Eq: 1.50) in DMF (20 mL) and the mixture was stirred at 65° C. for 4.5 h. The mixture was cooled, diluted with brine and extracted with EtOAc. The combined extracts were washed with brine, dried over Na$_2$SO$_4$ and concentrated. The residue was purified by flash chromatography to afford tert-butyl (S)-1-((S)-1-((6-bromo-2-methoxynaphthalen-1-yl)methyl)-2-oxo-2,3,4,5-tetrahydro-1H-benzo[b]azepin-3-ylamino)-1-oxopropan-2-ylcarbamate (0.7689 g, white foam). MS m/z 597.75 (MH$^+$)

Step 3: TFA (5.92 g, 4 mL, 51.9 mmol, Eq: 46.2) was added to a solution of tert-butyl (S)-1-((S)-1-((6-bromo-2-methoxynaphthalen-1-yl)methyl)-2-oxo-2,3,4,5-tetrahydro-1H-benzo[b]azepin-3-ylamino)-1-oxopropan-2-ylcarbamate (0.67 g, 1.12 mmol, Eq: 1.00) in DCM (25 mL). After 1.5 h, the mixture was concentrated, poured into 1 M NaOH and extracted with DCM. The extracts were washed with 1 M NaOH and H₂O. The extracts were dried over Na₂SO₄ and concentrated afford (S)-2-amino-N—((S)-1-(6-bromo-2-methoxynaphthalen-1-yl)methyl)-2-oxo-2,3,4,5-tetrahydro-1H-benzo[b]azepin-3-yl)propanamide (0.5027 g, light yellow foam). MS m/z 498.0 (MH⁺)

Step 4: Acetic acid (9.07 mg, 8.65 µL, 151 µmol, Eq: 1.00) and sodium cyanoborohydride (14.2 mg, 227 µmol, Eq: 1.5) were added to a solution of (S)-2-amino-N—((S)-1-((6-bromo-2-methoxynaphthalen-1-yl)methyl)-2-oxo-2,3,4,5-tetrahydro-1H-benzo[b]azepin-3-yl)propanamide (75 mg, 151 µmol, Eq: 1.00) and propionaldehyde (9.65 mg, 12.0 µL, 166 µmol, Eq: 1.1) in MeOH (2 mL). After stirring overnight, the mixture was diluted with 1 N HCl, made basic with 1 N NaOH and extracted with DCM. The extracts were dried over Na₂SO₄ and concentrated. The residue was purified by flash chromatography to give a material that was lyophilized from MeCN/H₂O to give the title compound (41.6 mg, 51.1, white solid). MS m/z 539.9 (MH⁺)

Example 60

(S)—N—((S)-1-((6-Bromo-2-methoxynaphthalen-1-yl)methyl)-2-oxo-2,3,4,5-tetrahydro-1H-benzo[b]azepin-3-yl)-2-(isobutylamino)propanamide

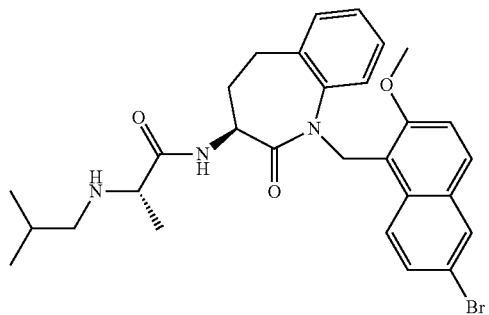 [SMILES: COc1ccc2cc(Br)ccc2c1CN1C(=O)[C@@H](NC(=O)[C@H](C)NCC(C)C)CCc2ccccc21]

In a similar manner to that described for Example 59 Step 4, (S)-2-amino-N—((S)-1-((6-bromo-2-methoxynaphthalen-1-yl)methyl)-2-oxo-2,3,4,5-tetrahydro-1H-benzo[b]azepin-3-yl)propanamide (75 mg, 151 µmol, Eq: 1.00) and isobutyraldehyde (11.4 mg, 14.5 µL, 159 µmol, Eq: 1.05) were converted to the title compound (46.1 mg. 55.2, white solid). MS m/z 554.0 (MH⁺).

Example 61

(S)—N—((S)-1-((6-Bromo-2-methoxynaphthalen-1-yl)methyl)-2-oxo-2,3,4,5-tetrahydro-1H-benzo[b]azepin-3-yl)-2-(ethylamino)propanamide hydrochloride

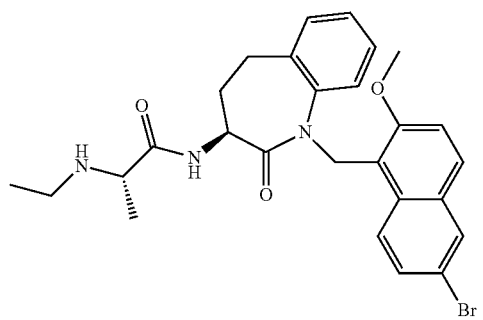 [SMILES: CCN[C@@H](C)C(=O)N[C@H]1CCc2ccccc2N(Cc2c(OC)ccc3cc(Br)ccc23)C1=O]

Step 1: In a similar manner to that described for Example 59 step 1, (S)-2-(tert-butoxycarbonyl(ethyl)amino)propanoic acid (Peptides: Struct. Funct., Proc. Am. Pept. Symp. 1983, 8, 143-6, 0.25 g, 1.15 mmol, Eq: 1.00) and (S)-3-amino-4,5-dihydro-1H-benzo[b]azepin-2(3H)-one (203 mg, 1.15 mmol, Eq: 1.00) were converted to tert-butyl ethyl((S)-1-oxo-1-((S)-2-oxo-2,3,4,5-tetrahydro-1H-benzo[b]azepin-3-ylamino)propan-2-yl)carbamate (0.2048 g, 47.4, white foam). MS m/z 398.1 (MH⁺)

Step 2: In a similar manner to that described for Example 59 Step 2 except the NaI was omitted and the reaction was heated for 15 h, tert-butyl ethyl((S)-1-oxo-1-((S)-2-oxo-2,3,4,5-tetrahydro-1H-benzo[b]azepin-3-ylamino)propan-2-yl)carbamate (0.2048 g, 545 µmol, Eq: 1.00) and 6-bromo-1-(chloromethyl)-2-methoxynaphthalene (234 mg, 818 µmol, Eq: 1.50) were converted to tert-butyl (S)-1-((S)-1-((6-bromo-2-methoxynaphthalen-1-yl)methyl)-2-oxo-2,3,4,5-tetrahydro-1H-benzo[b]azepin-3-ylamino)-1-oxopropan-2-yl(ethyl)carbamate (0.2563 g, 75.2, white foam). MS m/z 625.8 (MH⁺)

Step 3: In a similar manner to that described for Example 56 Step 2, tert-butyl (S)-1-((S)-1-((6-bromo-2-methoxynaphthalen-1-yl)methyl)-2-oxo-2,3,4,5-tetrahydro-1H-benzo[b]azepin-3-ylamino)-1-oxopropan-2-yl(ethyl)carbamate (0.2563 g, 410 µmol) was converted to the title compound (0.2061 g, 89.5, light yellow solid). MS m/z 525.8 (MH⁺)

Example 62

(S)-2-(Azetidin-3-ylamino)-N—((S)-1-((6-bromo-2-methoxy naphthalen-1-yl)methyl)-2-oxo-2,3,4,5-tetrahydro-1H-benzo[13]azepin-3-yl)propanamide dihydrochloride

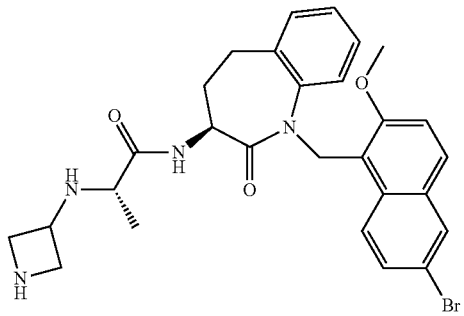 [SMILES: COc1ccc2cc(Br)ccc2c1CN1C(=O)[C@@H](NC(=O)[C@H](C)NC2CNC2)CCc2ccccc21]

Step 1: Sodium triacetoxyborohydride (122 mg, 574 µmol, Eq: 1.5) was added to a mixture of (S)-2-amino-N—((S)-1-((6-bromo-2-methoxynaphthalen-1-yl)methyl)-2-oxo-2,3,4,5-tetrahydro-1H-benzo[b]azepin-3-yl)propanamide (190 mg, 383 µmol, Eq: 1.00), tert-butyl 3-oxoazetidine-1-carboxylate (72.1 mg, 421 µmol, Eq: 1.1) and acetic acid (23.0 mg, 21.9 µL, 383 µmol, Eq: 1.00) in DCM (5 mL). After 24 h, the mixture was poured into sat. NaHCO₃, and extracted with DCM. The extracts were washed with H₂O, brine, dried over Na₂SO₄ and concentrated. The residue was purified by flash chromatography tert-butyl 3-((S)-1-((S)-1-((6-bromo-2-methoxynaphthalen-1-yl)methyl)-2-oxo-2,3,4,5-tetrahydro-1H-benzo[b]azepin-3-ylamino)-1-oxopropan-2-ylamino)azetidine-1-carboxylate to afford (63.3 mg, 25.4, white foam). MS m/z 651.2 (MH⁺)

Step 2: In a similar manner to that described for Example 56 Step 2, tert-butyl 3-((S)-1-((S)-1-((6-bromo-2-methoxynaphthalen-1-yl)methyl)-2-oxo-2,3,4,5-tetrahydro-1H-benzo[b]azepin-3-ylamino)-1-oxopropan-2-ylamino)azetidine-1-carboxylate (63.3 mg, 97.1 μmol) was converted to the title compound (51.2 mg, 84.4, white solid). MS m/z 552.9 (MH⁺)

Example 63

(S)—N—((S)-1-((6-Bromo-2-methoxynaphthalen-1-yl)methyl)-2-oxo-2,3,4,5-tetrahydro-1H-benzo[b]azepin-3-yl)-2-(ethylamino)butanamide hydrochloride

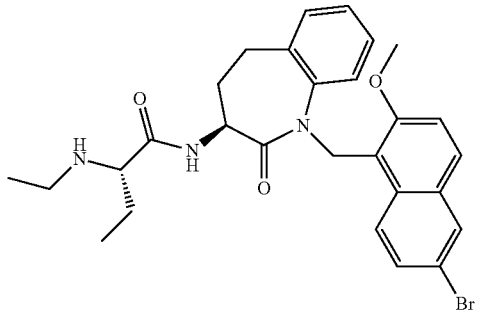 [SMILES: CCN[C@@H](CC)C(=O)N[C@H]1CCc2ccccc2N(Cc2c(OC)ccc3cc(Br)ccc23)C1=O]

Step 1: NaH (886 mg, 22.1 mmol, Eq: 3) was added in portions to a mixture of (S)-2-(tert-butoxycarbonylamino)butanoic acid (1.5 g, 7.38 mmol, Eq: 1.00) and iodoethane (9.21 g, 4.72 mL, 59.0 mmol, Eq: 8) in THF (25.0 mL) at 0° C. The mixture was heated at 55° C. overnight, cooled and ice and H₂O were added. The mixture was extracted with Et₂O. The aqueous layer was acidified with sat. KHSO₄ and extracted with Et₂O. The combined extracts washed with brine dried over Na₂SO₄ and concentrated to afford (S)-2-(tert-butoxycarbonyl(ethyl)amino)butanoic acid (0.9595 g, yellow oil) which was used without purification.

Step 2: In a similar manner to that described for Example 59 Step 1, (S)-3-amino-4,5-dihydro-1H-benzo[b]azepin-2(3H)-one (130 mg, 737 μmol, Eq: 1.2) and (S)-2-(tert-butoxycarbonyl(ethyl)amino)butanoic acid (0.142 g, 614 μmol, Eq: 1.00) were converted to tert-butyl ethyl((S)-1-oxo-1-((S)-2-oxo-2,3,4,5-tetrahydro-1H-benzo[b]azepin-3-ylamino)butan-2-yl)carbamate (90.7 mg, 37.9, white foam). MS m/z 390.2 (MH⁺)

Step 3: In a similar manner to that described for Example 59 Step 2 except the NaI was omitted and the mixture was heated for 2.5 h, tert-butyl ethyl((S)-1-oxo-1-((S)-2-oxo-2,3,4,5-tetrahydro-1H-benzo[b]azepin-3-ylamino)butan-2-yl)carbamate (90.7 mg, 233 μmol, Eq: 1.00) and 6-bromo-1-(chloromethyl)-2-methoxynaphthalene (99.7 mg, 349 μmol, Eq: 1.50) were converted to tert-butyl (S)-1-((S)-1-((6-bromo-2-methoxynaphthalen-1-yl)methyl)-2-oxo-2,3,4,5-tetrahydro-1H-benzo[b]azepin-3-ylamino)-1-oxobutan-2-yl(ethyl)carbamate (129.4 mg, 87.0, white foam). MS m/z 639.9 (MH⁺)

Step 4: In a similar manner to that described for Example 56 Step 2, tert-butyl (S)-1-((S)-1-((6-bromo-2-methoxynaphthalen-1-yl)methyl)-2-oxo-2,3,4,5-tetrahydro-1H-benzo[b]azepin-3-ylamino)-1-oxobutan-2-yl(ethyl)carbamate (129.4 mg, 203 μmol) was converted to the title compound (107.9 mg, 92.6%, off-white solid). MS m/z 540.1 (MH⁺)

Example 64

(S)—N—((S)-1-((5-Fluoro-2-methoxynaphthalen-1-yl)methyl)-2-oxo-2,3,4,5-tetrahydro-1H-benzo[b]azepin-3-yl)-2-(methylamino)propanamide hydrochloride

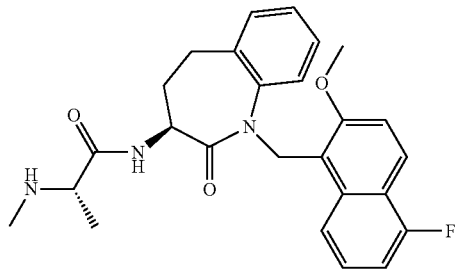 [SMILES: CN[C@@H](C)C(=O)N[C@H]1CCc2ccccc2N(Cc2c(OC)ccc3c(F)cccc23)C1=O]

In a similar manner to that described for Example 56 except in Step 1 the mixture was heated at 50° C. for 1.5 h, methyl-[(S)-1-((S)-2-oxo-2,3,4,5-tetrahydro-1H-benzo[b]azepin-3-ylcarbamoyl)-ethyl]-carbamic acid tert-butyl ester (40.2 mg, 111 μmol, Eq: 0.9) and (5-fluoro-2-methoxynaphthalen-1-yl)methyl methanesulfonate (35.1 mg, 123 μmol, Eq: 1.00) were converted to the title compound (34.5 mg, 86.3%, white solid). MS m/z 450.1 (MH⁺)

Example 65

(S)—N—((S)-1-((6-Fluoro-2-methoxynaphthalen-1-yl)methyl)-2-oxo-2,3,4,5-tetrahydro-1H-benzo[b]azepin-3-yl)-2-(methylamino)propanamide hydrochloride

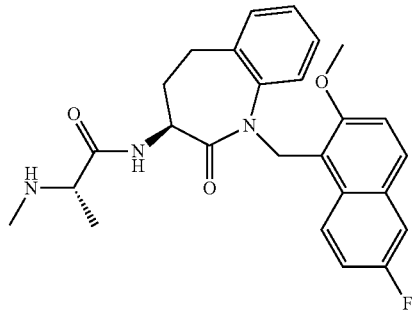 [SMILES: CN[C@@H](C)C(=O)N[C@H]1CCc2ccccc2N(Cc2c(OC)ccc3cc(F)ccc23)C1=O]

Step 1: In a similar manner to that described for Example 56 Step 1 except the mixture was heated at 50° C. for 15 h, methyl-[(S)-1-((S)-2-oxo-2,3,4,5-tetrahydro-1H-benzo[b]azepin-3-ylcarbamoyl)-ethyl]-carbamic acid tert-butyl ester (56.6 mg, 157 μmol, Eq: 0.9) and (6-fluoro-2-methoxynaphthalen-1-yl)methyl methanesulfonate (49.5 mg, 174 μmol, Eq: 1.00) were converted to a material that was purified by flash chromatography. The resulting material was purified by HPLC to afford tert-butyl (S)-1-((S)-1-((6-fluoro-2-methoxynaphthalen-1-yl)methyl)-2-oxo-2,3,4,5-tetrahydro-1H-benzo[b]azepin-3-ylamino)-1-oxopropan-2-yl(methyl)carbamate (44 mg, 46.0%, white solid). MS m/z 550.2 (MH⁺)

Step 2: 2.0 M HCl in Et₂O (3 mL, 6.00 mmol, Eq: 74.9) was added to a solution of tert-butyl (S)-1-((S)-1-((6-fluoro- 2-methoxynaphthalen-1-yl)methyl)-2-oxo-2,3,4,5-tetrahydro-1H-benzo[b]azepin-3-ylamino)-1-oxopropan-2-yl(methyl)carbamate (44 mg, 80.1 μmol, Eq: 1.00) in MeOH (1 mL). After 2 h, the mixture was concentrated, the residue partitioned between 1 N NaOH and EtOAc. The organic layer was separated, washed with H₂O, filtered, added to 1 mL 1 M HCl in Et₂O and the mixture concentrated. The residue was lyophilized from MeCN/H₂O to afford the title compound (31.0 mg, 79.9%, off-white solid). MS m/z 450.1 (MH⁺)

Example 66

(S)—N—((S)-1-((6-Chloro-2-methoxynaphthalen-1-yl)methyl)-2-oxo-2,3,4,5-tetrahydro-1H-benzo[b]azepin-3-yl)-2-(methylamino)propanamide hydrochloride

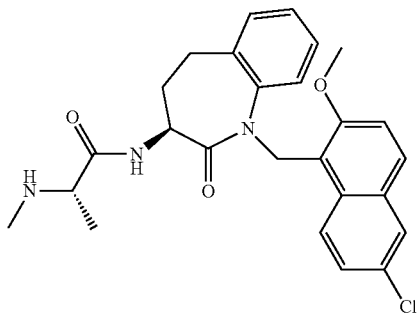 [SMILES: CN[C@@H](C)C(=O)N[C@H]1CCc2ccccc2N(Cc2c(OC)ccc3cc(Cl)ccc23)C1=O]

In a similar manner to that described for Example 56 except in Step 1 the mixture was heated at 50° C. for 15 h, methyl-[(S)-1-((S)-2-oxo-2,3,4,5-tetrahydro-1H-benzo[b]azepin-3-ylcarbamoyl)-ethyl]-carbamic acid tert-butyl ester (41.2 mg, 114 μmol, Eq: 0.9) and (6-chloro-2-methoxynaphthalen-1-yl)methyl methanesulfonate (38.1 mg, 127 μmol, Eq: 1.00) were converted to the title compound (36.1 mg, 86.0%, white solid). MS m/z 465.95 (MH⁺)

Example 67

(S)—N—((S)-1-((6-Bromo-2-methoxynaphthalen-1-yl)methyl)-2-oxo-2,3,4,5-tetrahydro-1H-benzo[b]azepin-3-yl)-2-(cyclopropylmethylamino)propanamide

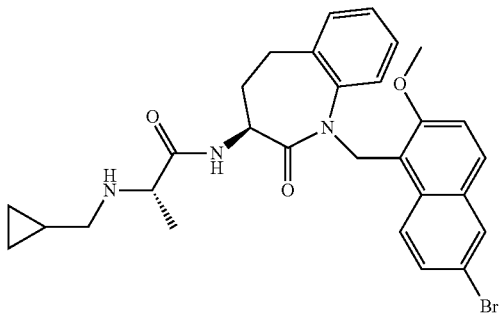 [SMILES: COc1ccc2cc(Br)ccc2c1CN1C(=O)[C@@H](NC(=O)[C@H](C)NCC2CC2)CCc2ccccc21]

In a similar manner to that described for Example 59 Step 4, (S)-2-amino-N—((S)-1-((6-bromo-2-methoxynaphthalen-1-yl)methyl)-2-oxo-2,3,4,5-tetrahydro-1H-benzo[b]azepin-3-yl)propanamide (75 mg, 151 μmol, Eq: 1.00) and cyclopropanecarbaldehyde (11.6 mg, 12.4 μL, 166 μmol, Eq: 1.1) were converted to the title compound (39.8 mg, 47.9%, white solid). MS m/z 552.0 (MH⁺).

Example 68

(S)—N—((S)-1-((2-Methoxy-5-(1H-tetrazol-5-yl)naphthalen-1-yl)methyl)-2-oxo-2,3,4,5-tetrahydro-1H-benzo[b]azepin-3-yl)-2-(methylamino)propanamide hydrochloride

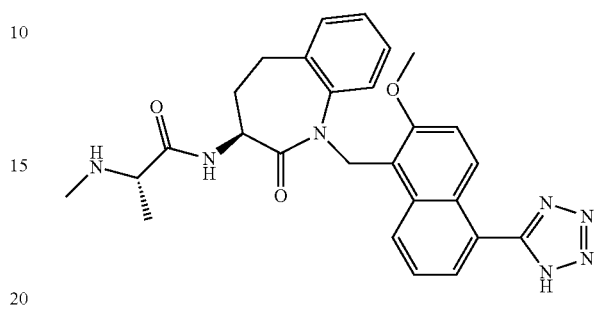

Step 1: TMS-N₃ (98.0 mg, 113 μL, 808 μmol, Eq: 3) was added to a mixture of tert-butyl (S)-1-((S)-1-((5-cyano-2-methoxynaphthalen-1-yl)methyl)-2-oxo-2,3,4,5-tetrahydro-1H-benzo[b]azepin-3-ylamino)-1-oxopropan-2-yl(methyl)carbamate (150 mg, 269 μmol, Eq: 1.00) and copper(I) oxide (7.71 mg, 53.9 μmol, Eq: 0.2) in DMF (900 μL) and MeOH. After 10 min the mixture was heated to 80° C. After 18 h, the mixture was cooled to RT and an additional portion of the TMS-N₃ was added and the mixture heated to 80° C. After 18 h, the mixture was diluted with EtOAc and washed with 1 M HCl. The extracts were dried over Na₂SO₄ and concentrated to give a material that was purified by preparative HPLC. The resulting material was dissolved in MeCN/H₂O and lyophilized to afford tert-butyl (S)-1-((S)-1-((2-methoxy-6-(1H-tetrazol-5-yl)naphthalen-1-yl)methyl)-2-oxo-2,3,4,5-tetrahydro-1H-benzo[b]azepin-3-ylamino)-1-oxopropan-2-yl(methyl)carbamate (21.0 mg, 13%, white solid).

Step 2: In a similar manner to that described for Example 45 except the mixture was stirred 1.5 h, tert-butyl (S)-1-((S)-1-((2-methoxy-5-(1H-tetrazol-5-yl)naphthalen-1-yl)methyl)-2-oxo-2,3,4,5-tetrahydro-1H-benzo[b]azepin-3-ylamino)-1-oxopropan-2-yl(methyl)carbamate (21 mg, 35.0 μmol) was converted to the title compound (16.5 mg, 88%, white solid). MS m/z 500.1 (MO.

Example 69

(S)-2-Methylamino-N—{(S)-2-oxo-1-[5-(1H-tetrazol-5-yl)-naphthalen-1-ylmethyl]-2,3,4,5-tetrahydro-1H-benzo[b]azepin-3-yl}-propionamide hydrochloride

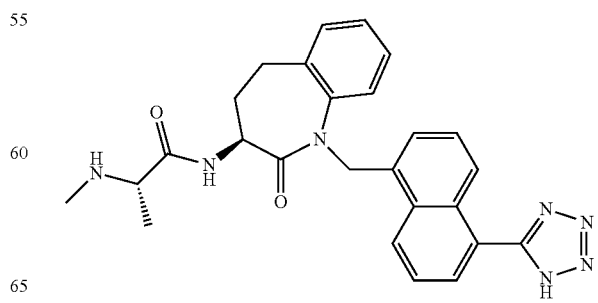

In a similar manner to that described for Example 39 except the product of Step 1 was used without purification, tert-butyl (S)-1-((S)-1-((5-cyanonaphthalen-1-yl)methyl)-2-oxo-2,3,4,5-tetrahydro-1H-benzo[b]azepin-3-ylamino)-1-oxopropan-2-yl(methyl)carbamate (0.25 g, 475 µmol) was converted to the title compound (37.2 mg, 92%, yellow solid). MS m/e 470.0 (M+H⁺).

Example 70

(S)—N—((S)-1-((5-Acetyl-2-methoxynaphthalen-1-yl)methyl)-2-oxo-2,3,4,5-tetrahydro-1H-benzo[b]azepin-3-yl)-2-(methylamino)propanamide hydrochloride

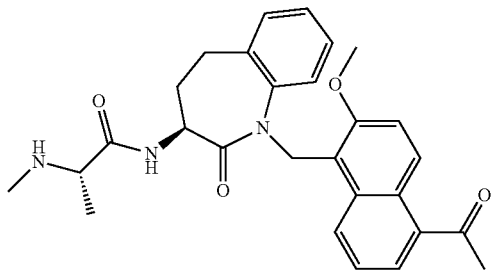 [SMILES: CN[C@@H](C)C(=O)N[C@H]1CCc2ccccc2N(Cc2c(OC)ccc3c(C(C)=O)cccc23)C1=O]

Step 1: A mixture of tert-butyl (S)-1-((S)-1-((5-bromo-2-methoxynaphthalen-1-yl)methyl)-2-oxo-2,3,4,5-tetrahydro-1H-benzo[b]azepin-3-ylamino)-1-oxopropan-2-yl(methyl)carbamate (0.125 g, 205 µmol, Eq: 1.00), 1-(vinyloxy)butane (51.3 mg, 64.9 µL, 512 µmol, Eq: 2.5), palladium(II) acetate (2.76 mg, 12.3 µmol, Eq: 0.06) 1,1'-bis(diphenylphosphino)ferrocene (13.6 mg, 24.6 µmol, Eq: 0.12) and $K_2CO_3$ (34.0 mg, 246 µmol, Eq: 1.2) in DMF (1 mL) and water (0.1 mL) was heated to 80° C. After 18 h, the mixture was cooled, diluted with 1 M HCl and extracted with DCM. The extracts were washed with brine, dried over $Na_2SO_4$ and concentrated. The residue was purified by flash chromatography, the resulting material taken up in $MeCN/H_2O$ and lyophilized to afford tert-butyl (S)-1-((S)-1-((5-(1-butoxyvinyl)-2-methoxynaphthalen-1-yl)methyl)-2-oxo-2,3,4,5-tetrahydro-1H-benzo[b]azepin-3-ylamino)-1-oxopropan-2-yl (methyl)carbamate (72.0 mg, 56%, white solid).

Step 2: In a similar manner to that described for Example 45 Step 3, tert-butyl (S)-1-((S)-1-((5-(1-butoxyvinyl)-2-methoxynaphthalen-1-yl)methyl)-2-oxo-2,3,4,5-tetrahydro-1H-benzo[b]azepin-3-ylamino)-1-oxopropan-2-yl(methyl)carbamate (63.9 mg, 101 µmol) was converted to the title compound (37.2 mg, white solid, 72%). MS m/z 474.0 (MH⁺)

Example 71

Biochemical Assays

TR-FRET Assay for BIR2 and BIR3

The ability of a test compound to inhibit the binding of BIR2 and/or BIR3 domains of the XIAP protein to Peptide A (a SMAC-derived peptide described below) evidences that the test compound acts as a SMAC-mimetic resulting in reactivation of a cell's apoptotic pathway.

The peptide AVPIAQKSEK-(ε-biotin)-OH (SEQ ID NO: 1) 1:2 TFA ("Peptide A") was identified as a substrate for the TR-FRET assay by screening the 6× Histidine-tagged (SEQ ID NO: 2) BIR2 domain and BIR3 domain of XIAP against a set of 29 peptides synthesized based on sequences reported by Sweeny et al. (*Biochemistry*, 2006, 45, 14740 14748). The peptides were labeled with the fluorescent tags FITC or TAMRA and Kd values were determined by fluorescence polarization assay. The sequence AVPIAQKSEK (SEQ ID NO: 3) was identified as optimal for using in an assay. The peptide sequence was derivatized with biotin to provide AVPIAQKSEK-(ε-biotin)-OH (SEQ ID NO: 1) 1:2 TFA as the substrate for the TR-FRET assay.

The XIAP protein sequence was obtained from the SWISS-PROT protein sequence database and the BIR2 and BIR3 domains were derived from that. The sequence of the BIR2 domain used for the TR-FRET assay is MRHHHH-HHRDHFALDRPSETHADYLLRTGQVVDISDTIYPRN-PAMYSEEARLKSFQNW PDYAHLTPRELASAGLYYT-GIGDQVQCFACGGKLKNWEPGDRAWSEHRRHFPN-CFFVL GRNLNIRSE (SEQ ID NO: 4).

The sequence of the BIR3 domain used for the TR-FRET assay is MRHHHHHHRSDAVSSDRNFPNSTNLPRNPS-MADYEARIFTFGTWIYSVNKEQLARAGF YALGEGD-KVKCFHCGGGLTDWKPSEDPWEQHAKWYPGCKYL-LEQKGQEYINNIHLTH SLEECLVRTT (SEQ ID NO: 5).

Ten nanomolar of 6× Histidine-tagged (SEQ ID NO: 2) BIR2 domain, corresponding to amino acids 124-240 of XIAP, or BIR3 domain, corresponding to amino acids 241-356 of XIAP, was mixed with 20 nM of the peptide AVPIAQKSEK-(ε-biotin)-OH (SEQ ID NO: 1) 1:2 TFA, in the presence of 50 mM Tris-Cl, pH 7.5, 100 mM NaCl, 1 mM dithiothreitol (DTT) and 0.1 mg/niL bovine serum albumin (BSA). Following a 45 min. incubation at 37° C., Europium-Streptavidin and Allophycocyanin conjugated anti-Histidine antibody were added to a final concentration of 1.5 nM and 15 nM, respectively. Time-resolved fluorescence resonance energy transfer (TR-FRET) signals were measured 1 hour later at room temperature. Test compound potency was assessed at 10 serially diluted concentrations. Percentage of inhibition at each concentration was determined to generate an $IC_{50}$ value for each test compound. These values are listed below in Table 8.

TABLE 8

| Ex. | Name | BIR2 $IC_{50}$ (µM) | BIR3 $IC_{50}$ (µM) |
|---|---|---|---|
| 1a | (S)-N-[(S)-1-(5-Fluoro-2-methoxy-benzyl)-2-oxo-2,3,4,5-tetrahydro-1H-benzo[b]azepin-3-yl]-2-methylamino-propionamide hydrochloride | 1.700 | >54.8 |
| 2a | (S)-2-(Methylamino)-N-((S)-2-oxo-1-(thiophen-2-ylmethyl)-2,3,4,5-tetrahydro-1H-benzo[b]azepin-3-yl)propanamide hydrochloride | 1.087 | >51.5 |
| 3 | (S)-2-Amino-N-((S)-1-((3-methoxyquinolin-4-yl)methyl)-2-oxo-2,3,4,5-tetrahydro-1H-benzo[b]azepin-3-yl)butanamide | 0.032 | 49.91 |

TABLE 8-continued

| Ex. | Name | BIR2 IC$_{50}$ (µM) | BIR3 IC$_{50}$ (µM) |
|---|---|---|---|
| 4 | (S)-2-(2-Hydroxyethylamino)-N-((S)-1-((3-methoxyquinolin-4-yl)methyl)-2-oxo-2,3,4,5-tetrahydro-1H-benzo[b]azepin-3-yl)butanamide | 0.060 | >54.8 |
| 5a | (S)-2-Amino-N-[(R)-1-(6-bromo-2-methoxy-naphthalen-1-ylmethyl)-2-oxo-2,3,4,5-tetrahydro-1H-benzo[b]azepin-3-yl]-butyramide hydrochloride | 12.420 | >54.8 |
| 5b | (S)-2-Amino-N-[(S)-1-(6-bromo-2-methoxy-naphthalen-1-ylmethyl)-2-oxo-2,3,4,5-tetrahydro-1H-benzo[b]azepin-3-yl]-butyramide | 0.095 | |
| 6 | (S)-N-((S)-1-((6-Bromo-2-methoxynaphthalen-1-yl)methyl)-2-oxo-2,3,4,5-tetrahydro-1H-benzo[b]azepin-3-yl)-2-(2-hydroxyethylamino)butanamide | 0.022 | 39.68 |
| 7 | (S)-N-((S)-1-((6-Bromo-2-methoxynaphthalen-1-yl)methyl)-2-oxo-2,3,4,5-tetrahydro-1H-benzo[b]azepin-3-yl)-2-(cyclobutylamino)butanamide | 0.194 | >54.8 |
| 8 | (S)-2-(Benzylamino)-N-((S)-1-((6-bromo-2-methoxynaphthalen-1-yl)methyl)-2-oxo-2,3,4,5-tetrahydro-1H-benzo[b]azepin-3-yl)butanamide | 2.366 | >54.8 |
| 9 | (S)-N-((S)-1-((6-Bromo-2-methoxynaphthalen-1-yl)methyl)-2-oxo-2,3,4,5-tetrahydro-1H-benzo[b]azepin-3-yl)-2-(oxetan-3-ylamino)butanamide | 0.231 | >54.8 |
| 10 | (2S,3S)-2-Amino-N-((S)-1-((6-bromo-2-methoxynaphthalen-1-yl)methyl)-2-oxo-2,3,4,5-tetrahydro-1H-benzo[b]azepin-3-yl)-3-hydroxybutanamide hydrochloride | 0.104 | >54.8 |
| 11 | (2S,3R)-2-Amino-N-((S)-1-((6-bromo-2-methoxynaphthalen-1-yl)methyl)-2-oxo-2,3,4,5-tetrahydro-1H-benzo[b]azepin-3-yl)-3-hydroxybutanamide hydrochloride | 3.884 | >54.8 |
| 12 | (S)-2-Amino-N-[(S)-1-(6-bromo-2-methoxy-naphthalen-1-ylmethyl)-2-oxo-2,3,4,5-tetrahydro-1H-benzo[b]azepin-3-yl]-3-hydroxy-propionamide hydrochloride | 0.345 | >54.8 |
| 13 | {(S)-1-[(S)-1-(6-Bromo-2-methoxy-naphthalen-1-ylmethyl)-2-oxo-2,3,4,5-tetrahydro-1H-benzo[b]azepin-3-ylcarbamoyl]-2-hydroxy-ethyl}-carbamic acid tert-butyl ester hydrochloride | 0.463 | >54.8 |
| 14 | (S)-N-{(S)-1-[2-(3-Hydroxy-oxetan-3-ylethynyl)-naphthalen-1-ylmethyl]-2-oxo-2,3,4,5-tetrahydro-1H-benzo[b]azepin-3-yl}-2-methylamino-propionamide | 0.122 | >54.8 |
| 15 | (S)-2-Methylamino-N-[(S)-2-oxo-1-(2-propoxy-naphthalen-1-ylmethyl)-2,3,4,5-tetrahydro-1H-benzo[b]azepin-3-yl]-propionamide hydrochloride | 0.616 | >54.8 |
| 16 | (S)-N-[(S)-1-(2-Allyloxy-naphthalen-1-ylmethyl)-2-oxo-2,3,4,5-tetrahydro-1H-benzo[b]azepin-3-yl]-2-methylamino-propionamide | 0.746 | >54.8 |
| 17 | (S)-N-[(S)-1-(2-Hydroxy-naphthalen-1-ylmethyl)-2-oxo-2,3,4,5-tetrahydro-1H-benzo[b]azepin-3-yl]-2-methylamino-propionamide hydrochloride | 1.138 | >54.8 |
| 18 | (S)-N-[(S)-8-Benzyloxy-1-(2-methyl-naphthalen-1-ylmethyl)-2-oxo-2,3,4,5-tetrahydro-1H-benzo[b]azepin-3-yl]-2-methylamino-propionamide hydrochloride | 1.340 | >54.8 |
| 19 | (S)-N-[(S)-1-(5-Bromo-benzo[b]thiophen-3-ylmethyl)-2-oxo-2,3,4,5-tetrahydro-1H-benzo[b]azepin-3-yl]-2-methylamino-propionamide hydrochloride | 1.066 | 27.37 |
| 20 | (S)-N-((S)-1-Benzo[b]thiophen-3-ylmethyl-2-oxo-2,3,4,5-tetrahydro-1H-benzo[b]azepin-3-yl)-2-methylamino-propionamide | 1.820 | >57.6 |
| 21 | (S)-2-Methylamino-N-[(S)-1-(2-methyl-naphthalen-1-ylmethyl)-2-oxo-8-phenyl-2,3,4,5-tetrahydro-1H-benzo[b]azepin-3-yl]-propionamide hydrochloride | 2.069 | >57.6 |
| 22 | (S)-N-((S)-1-Benzyl-8-benzyloxy-2-oxo-2,3,4,5-tetrahydro-1H-benzo[b]azepin-3-yl)-2-methylamino-propionamide hydrochloride | 3.248 | >57.6 |
| 23 | (S)-N-((S)-1-Benzyl-2-oxo-8-phenethyloxy-2,3,4,5-tetrahydro-1H-benzo[b]azepin-3-yl)-2-methylamino-propionamide hydrochloride | 5.121 | >54.0 |
| 24 | (S)-N-((S)-1-Benzyl-8-methoxy-2-oxo-2,3,4,5-tetrahydro-1H-benzo[b]azepin-3-yl)-2-methylamino-propionamide hydrochloride | 16.810 | >54.2 |
| 25 | (S)-N-[(S)-1-Benzyl-2-oxo-8-(3-phenyl-propoxy)-2,3,4,5-tetrahydro-1H-benzo[b]azepin-3-yl]-2-methylamino-propionamide hydrochloride | 6.335 | >54.0 |
| 26 | (S)-N-(1-Benzyl-8-bromo-2-oxo-2,3,4,5-tetrahydro-1H-benzo[b]azepin-3-yl)-2-methylamino-propionamide hydrochloride | 15.905 | >54.8 |

TABLE 8-continued

| Ex. | Name | BIR2 IC$_{50}$ (μM) | BIR3 IC$_{50}$ (μM) |
|---|---|---|---|
| 27 | (R)-N-[(S)-1-(6-Bromo-2-methoxy-naphthalen-1-ylmethyl)-2-oxo-2,3,4,5-tetrahydro-1H-benzo[b]azepin-3-yl]-2-methylamino-propionamide hydrochloride | 1.912 | >54.8 |
| 28 | (S)-2-Methylamino-N-{(S)-2-oxo-1-[7-(1H-tetrazol-5-yl)-naphthalen-1-ylmethyl]-2,3,4,5-tetrahydro-1H-benzo[b]azepin-3-yl}-propionamide | 6.570 | >54.8 |
| 29 | (S)-N-[(S)-1-(6-Bromo-2-methoxy-naphthalen-1-ylmethyl)-2-oxo-2,3,4,5-tetrahydro-1H-benzo[b]azepin-3-yl]-2-methylamino-propionamide hydrochloride | 0.194 | |
| 30 | (S)-N-{(S)-1-[2-Methoxy-6-(4-methyl-thiazol-2-yl)-naphthalen-1-ylmethyl]-2-oxo-2,3,4,5-tetrahydro-1H-benzo[b]azepin-3-yl}-2-methylamino-propionamide hydrochloride | 0.213 | >54.8 |
| 31 | (S)-N-{(S)-1-[2-Methoxy-6-(5-oxo-4,5-dihydro-[1,2,4]oxadiazol-3-yl)-naphthalen-1-ylmethyl]-2-oxo-2,3,4,5-tetrahydro-1H-benzo[b]azepin-3-yl}-2-methylamino-propionamide hydrochloride | 0.056 | 45.025 |
| 32 | (S)-N-[(S)-1-(2-Methoxy-6-[1,2,4]oxadiazol-3-yl-naphthalen-1-ylmethyl)-2-oxo-2,3,4,5-tetrahydro-1H-benzo[b]azepin-3-yl]-2-methylamino-propionamide hydrochloride | 0.199 | >54.8 |
| 33 | (S)-N-{(S)-1-[6-(N-Aminocarbamimidoyl)-2-methoxy-naphthalen-1-ylmethyl]-2-oxo-2,3,4,5-tetrahydro-1H-benzo[b]azepin-3-yl}-2-methylamino-propionamide dihydrochloride | 0.454 | >54.8 |
| 34 | (S)-N-{(S)-1-[2-Methoxy-6-(5-oxo-4,5-dihydro-1H-[1,2,4]triazol-3-yl)-naphthalen-1-ylmethyl]-2-oxo-2,3,4,5-tetrahydro-1H-benzo[b]azepin-3-yl}-2-methylamino-propionamide hydrochloride | 0.127 | >54.8 |
| 35 | (S)-N-{(S)-1-[6-(5,6-Dioxo-1,4,5,6-tetrahydro-[1,2,4]triazin-3-yl)-2-methoxy-naphthalen-1-ylmethyl]-2-oxo-2,3,4,5-tetrahydro-1H-benzo[b]azepin-3-yl}-2-methylamino-propionamide hydrochloride | 0.066 | >54.8 |
| 36 | (S)-N-{(S)-1-[2-Methoxy-6-(5-trifluoromethyl-4H-[1,2,4]triazol-3-yl)-naphthalen-1-ylmethyl]-2-oxo-2,3,4,5-tetrahydro-1H-benzo[b]azepin-3-yl}-2-methylamino-propionamide | 0.131 | >54.8 |
| 37 | (S)-N-[(S)-1-(2-Methoxy-6-[1,2,4]triazin-3-yl-naphthalen-1-ylmethyl)-2-oxo-2,3,4,5-tetrahydro-1H-benzo[b]azepin-3-yl]-2-methylamino-propionamide hydrochloride | 0.243 | >54.8 |
| 38 | (S)-N-{(S)-1-[2-Methoxy-6-(1H-[1,2,4]triazol-3-yl)-naphthalen-1-ylmethyl]-2-oxo-2,3,4,5-tetrahydro-1H-benzo[b]azepin-3-yl}-2-methylamino-propionamide dihydrochloride | 0.591 | >54.8 |
| 39 | (S)-N-{(S)-1-[2-Methoxy-6-(1H-tetrazol-5-yl)-naphthalen-1-ylmethyl]-2-oxo-2,3,4,5-tetrahydro-1H-benzo[b]azepin-3-yl}-2-methylamino-propionamide hydrochloride | 0.093 | >54.8 |
| 40 | (S)-N-{(S)-1-[2-Methoxy-6-(2-methyl-2H-tetrazol-5-yl)-naphthalen-1-ylmethyl]-2-oxo-2,3,4,5-tetrahydro-1H-benzo[b]azepin-3-yl}-2-methylamino-propionamide hydrochloride | 0.253 | >54.8 |
| 41 | (S)-N-{(S)-1-[2-Methoxy-6-(1-methyl-1H-tetrazol-5-yl)-naphthalen-1-ylmethyl]-2-oxo-2,3,4,5-tetrahydro-1H-benzo[b]azepin-3-yl}-2-methylamino-propionamide hydrochloride | 1.141 | >54.8 |
| 42 | (S)-N-[(S)-1-(6-Acetylamino-2-methoxy-naphthalen-1-ylmethyl)-2-oxo-2,3,4,5-tetrahydro-1H-benzo[b]azepin-3-yl]-2-methylamino-propionamide hydrochloride | 0.294 | >54.8 |
| 43 | (S)-N-{(S)-1-[2-Methoxy-6-(1H-pyrazol-4-yl)-naphthalen-1-ylmethyl]-2-oxo-2,3,4,5-tetrahydro-1H-benzo[b]azepin-3-yl}-2-methylamino-propionamide hydrochloride | 0.442 | >54.8 |
| 44 | (S)-N-[(S)-1-(2-Methoxy-5,6,7,8-tetrahydro-naphthalen-1-ylmethyl)-2-oxo-2,3,4,5-tetrahydro-1H-benzo[b]azepin-3-yl]-2-methylamino-propionamide hydrochloride | 1.478 | >57.6 |
| 45 | (S)-N-[(S)-1-(6-Acetyl-2-methoxy-naphthalen-1-ylmethyl)-2-oxo-2,3,4,5-tetrahydro-1H-benzo[b]azepin-3-yl]-2-methylamino-propionamide hydrochloride | 0.197 | >54.8 |
| 46 | (S)-N-[(S)-1-(2-Methoxy-6-vinyl-naphthalen-1-ylmethyl)-2-oxo-2,3,4,5-tetrahydro-1H-benzo[b]azepin-3-yl]-2-methylamino-propionamide hydrochloride | 0.310 | >54.8 |
| 47a | (S)-N-{(S)-1-[6-(1-Hydroxy-ethyl)-2-methoxy-naphthalen-1-ylmethyl]-2-oxo-2,3,4,5-tetrahydro-1H-benzo[b]azepin-3-yl}-2-methylamino-propionamide trifluoroacetate | 0.260 | >54.8 |
| 48 | (S)-2-Methylamino-N-[(S)-2-oxo-1-(1-oxy-quinolin-4-ylmethyl)-2,3,4,5-tetrahydro-1H-benzo[b]azepin-3-yl]-propionamide hydrochloride | 0.499 | >54.8 |

TABLE 8-continued

| Ex. | Name | BIR2 IC$_{50}$ (μM) | BIR3 IC$_{50}$ (μM) |
|---|---|---|---|
| 49a | (S)-N-[(S)-1-(5-Furan-2-yl-2-methoxy-naphthalen-1-ylmethyl)-2-oxo-2,3,4,5-tetrahydro-1H-benzo[b]azepin-3-yl]-2-methylamino-propionamide | 0.097 | >54.8 |
| 50 | 6-Methoxy-5-[(S)-3-((S)-2-methylamino-propionylamino)-2-oxo-2,3,4,5-tetrahydro-benzo[b]azepin-1-ylmethyl]-naphthalene-2-carboxylic acid methyl ester hydrochloride | 0.263 | >54.8 |
| 51 | 6-Methoxy-5-[(S)-3-((S)-2-methylamino-propionylamino)-2-oxo-2,3,4,5-tetrahydro-benzo[b]azepin-1-ylmethyl]-naphthalene-2-carboxylic acid | 0.061 | >54.8 |
| 52a | (S)-N-[(S)-1-(6-Methanesulfonylaminocarbonyl-2-methoxy-naphthalen-1-ylmethyl)-2-oxo-2,3,4,5-tetrahydro-1H-benzo[b]azepin-3-yl]-2-methylamino-propionamide | 0.048 | 45.045 |
| 53 | (S)-N-[(S)-1-(5-Cyano-2-methoxy-naphthalen-1-ylmethyl)-2-oxo-2,3,4,5-tetrahydro-1H-benzo[b]azepin-3-yl]-2-methylamino-propionamide hydrochloride | 0.171 | >54.8 |
| 54a | 5-[(S)-3-((S)-2-Methylamino-propionylamino)-2-oxo-2,3,4,5-tetrahydro-benzo[b]azepin-1-ylmethyl]-naphthalene-1-carboxylic acid amide | 0.391 | >54.8 |
| 56 | (S)-N-((S)-1-((3-Cyclopropylquinolin-4-yl)methyl)-2-oxo-2,3,4,5-tetrahydro-1H-benzo[b]azepin-3-yl)-2-(methylamino)propanamide dihydrochloride | 0.057 | 40.3 |
| 57 | (S)-N-((S)-1-((2,6-Bis(trifluoromethyl)quinolin-4-yl)methyl)-2-oxo-2,3,4,5-tetrahydro-1H-benzo[b]azepin-3-yl)-2-(methylamino)propanamide hydrochloride | 2.304 | 45.44 |
| 58 | (S)-N-((S)-1-((6-Bromo-2-methoxynaphthalen-1-yl)methyl)-2-oxo-2,3,4,5-tetrahydro-1H-benzo[b]azepin-3-yl)-2-(methylamino)butanamide trifluoroacetate | 0.044 | 31.64 |
| 59 | (S)-N-((S)-1-((6-Bromo-2-methoxynaphthalen-1-yl)methyl)-2-oxo-2,3,4,5-tetrahydro-1H-benzo[b]azepin-3-yl)-2-(propylamino)propanamide | 0.152 | >50.0 |
| 60 | (S)-N-((S)-1-((6-Bromo-2-methoxynaphthalen-1-yl)methyl)-2-oxo-2,3,4,5-tetrahydro-1H-benzo[b]azepin-3-yl)-2-(isobutylamino)propanamide | 0.903 | >50.0 |
| 61 | (S)-N-((S)-1-((6-Bromo-2-methoxynaphthalen-1-yl)methyl)-2-oxo-2,3,4,5-tetrahydro-1H-benzo[b]azepin-3-yl)-2-(ethylamino)propanamide hydrochloride | 0.081 | >54.8 |
| 62 | (S)-2-(Azetidin-3-ylamino)-N-((S)-1-((6-bromo-2-methoxynaphthalen-1-yl)methyl)-2-oxo-2,3,4,5-tetrahydro-1H-benzo[b]azepin-3-yl)propanamide dihydrochloride | 2.383 | >54.8 |
| 63 | (S)-N-((S)-1-((6-Bromo-2-methoxynaphthalen-1-yl)methyl)-2-oxo-2,3,4,5-tetrahydro-1H-benzo[b]azepin-3-yl)-2-(ethylamino)butanamide hydrochloride | 0.050 | |
| 64 | (S)-N-((S)-1-((5-Fluoro-2-methoxynaphthalen-1-yl)methyl)-2-oxo-2,3,4,5-tetrahydro-1H-benzo[b]azepin-3-yl)-2-(methylamino)propanamide hydrochloride | 0.053 | >54.8 |
| 65 | (S)-N-((S)-1-((6-Fluoro-2-methoxynaphthalen-1-yl)methyl)-2-oxo-2,3,4,5-tetrahydro-1H-benzo[b]azepin-3-yl)-2-(methylamino)propanamide hydrochloride | 0.075 | >54.8 |
| 66 | (S)-N-((S)-1-((6-Chloro-2-methoxynaphthalen-1-yl)methyl)-2-oxo-2,3,4,5-tetrahydro-1H-benzo[b]azepin-3-yl)-2-(methylamino)propanamide hydrochloride | 0.044 | >54.8 |
| 67 | (S)-N-((S)-1-((6-Bromo-2-methoxynaphthalen-1-yl)methyl)-2-oxo-2,3,4,5-tetrahydro-1H-benzo[b]azepin-3-yl)-2-(cyclopropylmethylamino)propanamide | 0.223 | >54.8 |
| 68 | (S)-N-((S)-1-((2-Methoxy-5-(1H-tetrazol-5-yl)naphthalene-1-yl)methyl)-2-oxo-2,3,4,5-tetrahydro-1H-benzo[b]azepin-3-yl)-2-(methylamino)propanamide hydrochloride | 0.072 | >54.8 |
| 69 | (S)-2-Methylamino-N-{(S)-2-oxo-1-[5-(1H-tetrazol-5-yl)-naphthalen-1-ylmethyl]-2,3,4,5-tetrahydro-1H-benzo[b]azepin-3-yl}-propionamide hydrochloride | 0.181 | >54.8 |
| 70 | (S)-N-((S)-1-((5-Acetyl-2-methoxynaphthalen-1-yl)methyl)-2-oxo-2,3,4,5-tetrahydro-1H-benzo[b]azepin-3-yl)-2-(methylamino)propanamide hydrochloride | 0.186 | >54.8 |
| 1b | (S)-2-Methylamino-N-[(S)-1-(1-methyl-1H-indazol-3-ylmethyl)-2-oxo-2,3,4,5-tetrahydro-1H-benzo[b]azepin-3-yl]-propionamide hydrochloride | 0.403 | >54.8 |
| 1c | (S)-N-[(S)-1-(2-Methoxy-5-trifluoromethyl-benzyl)-2-oxo-2,3,4,5-tetrahydro-1H-benzo[b]azepin-3-yl]-2-methylamino-propionamide hydrochloride | 1.329 | >54.8 |
| 1d | (S)-N-[(S)-1-(4,5-Difluoro-2-methoxy-benzyl)-2-oxo-2,3,4,5-tetrahydro-1H-benzo[b]azepin-3-yl]-2-methylamino-propionamide hydrochloride | 1.532 | >54.8 |
| 1e | (S)-N-[(S)-1-(5-Bromo-2-methoxy-benzyl)-2-oxo-2,3,4,5-tetrahydro-1H-benzo[b]azepin-3-yl]-2-methylamino-propionamide hydrochloride | 0.387 | >54.8 |

TABLE 8-continued

| Ex. | Name | BIR2 IC$_{50}$ (μM) | BIR3 IC$_{50}$ (μM) |
|---|---|---|---|
| 1f | (S)-N-[(S)-1-(5-Chloro-2-methoxy-benzyl)-2-oxo-2,3,4,5-tetrahydro-1H-benzo[b]azepin-3-yl]-2-methylamino-propionamide hydrochloride | 0.349 | >54.8 |
| 1g | (S)-N-[(S)-1-(2,5-Difluoro-benzyl)-2-oxo-2,3,4,5-tetrahydro-1H-benzo[b]azepin-3-yl]-2-methylamino-propionamide hydrochloride | 1.255 | >54.8 |
| 1h | (S)-2-Methylamino-N-((S)-2-oxo-1-pentafluorophenylmethyl-2,3,4,5-tetrahydro-1H-benzo[b]azepin-3-yl)-propionamide hydrochloride | 1.055 | >54.8 |
| 1i | (S)-N-[(S)-1-(4-Chloro-2-methoxy-benzyl)-2-oxo-2,3,4,5-tetrahydro-1H-benzo[b]azepin-3-yl]-2-methylamino-propionamide hydrochloride | 1.658 | >54.8 |
| 1j | (S)-N-[(S)-1-(4-Bromo-2-methoxy-benzyl)-2-oxo-2,3,4,5-tetrahydro-1H-benzo[b]azepin-3-yl]-2-methylamino-propionamide hydrochloride | 1.043 | >54.8 |
| 1k | (S)-N-((S)-1-Benzo[d]isoxazol-3-ylmethyl-2-oxo-2,3,4,5-tetrahydro-1H-benzo[b]azepin-3-yl)-2-methylamino-propionamide hydrochloride | 0.317 | >54.8 |
| 1l | (S)-N-[(S)-1-(2,5-Dichloro-benzyl)-2-oxo-2,3,4,5-tetrahydro-1H-benzo[b]azepin-3-yl]-2-methylamino-propionamide hydrochloride | 0.491 | >54.8 |
| 1m | (S)-N-[(S)-1-(5-Chloro-2-fluoro-benzyl)-2-oxo-2,3,4,5-tetrahydro-1H-benzo[b]azepin-3-yl]-2-methylamino-propionamide hydrochloride | 0.591 | >51.5 |
| 1n | (S)-N-[(S)-1-(5-Iodo-2-methoxy-benzyl)-2-oxo-2,3,4,5-tetrahydro-1H-benzo[b]azepin-3-yl]-2-methylamino-propionamide hydrochloride | 0.533 | 43.03 |
| 1o | (S)-N-[(S)-1-(5-Isopropyl-2-methoxy-benzyl)-2-oxo-2,3,4,5-tetrahydro-1H-benzo[b]azepin-3-yl]-2-methylamino-propionamide hydrochloride | 6.02 | >51.5 |
| 2b | (S)-2-Methylamino-N-((S)-2-oxo-1-thiophen-3-ylmethyl-2,3,4,5-tetrahydro-1H-benzo[b]azepin-3-yl)-propionamide hydrochloride | 2.446 | >51.5 |
| 2c | (S)-2-Methylamino-N-((S)-2-oxo-1-thiazol-5-ylmethyl-2,3,4,5-tetrahydro-1H-benzo[b]azepin-3-yl)-propionamide hydrochloride | 2.898 | >51.5 |
| 2d | (S)-2-Methylamino-N-((S)-2-oxo-1-thiazol-2-ylmethyl-2,3,4,5-tetrahydro-1H-benzo[b]azepin-3-yl)-propionamide hydrochloride | 1.597 | >54.8 |
| 2e | (S)-2-Methylamino-N-((S)-1-oxazol-5-ylmethyl-2-oxo-2,3,4,5-tetrahydro-1H-benzo[b]azepin-3-yl)-propionamide hydrochloride | 19.38 | >54.8 |
| 2f | (S)-2-Methylamino-N-((S)-2-oxo-1-pyridin-3-ylmethyl-2,3,4,5-tetrahydro-1H-benzo[b]azepin-3-yl)-propionamide hydrochloride | 3.948 | >51.5 |
| 2g | (S)-2-Methylamino-N-((S)-2-oxo-1-pyridin-2-ylmethyl-2,3,4,5-tetrahydro-1H-benzo[b]azepin-3-yl)-propionamide hydrochloride | 11.85 | >54.8 |
| 2h | (S)-2-Methylamino-N-((S)-2-oxo-1-pyridin-4-ylmethyl-2,3,4,5-tetrahydro-1H-benzo[b]azepin-3-yl)-propionamide hydrochloride | 6.048 | >54.8 |
| 2i | (S)-2-Methylamino-N-[(S)-1-(3-methyl-3H-imidazol-4-ylmethyl)-2-oxo-2,3,4,5-tetrahydro-1H-benzo[b]azepin-3-yl]-propionamide hydrochloride | 2.714 | >54.8 |
| 47b | (S)-2-Methylamino-N-[(S)-1-(2-methyl-naphthalen-1-ylmethyl)-2-oxo-2,3,4,5-tetrahydro-1H-benzo[b]azepin-3-yl]-propionamide hydrochloride | 0.486 | >54.8 |
| 47c | (S)-N-[(S)-1-(2-Methoxy-naphthalen-1-ylmethyl)-2-oxo-2,3,4,5-tetrahydro-1H-benzo[b]azepin-3-yl]-2-methylamino-propionamide hydrochloride | 0.249 | >54.0 |
| 47d | (S)-2-Methylamino-N-((S)-2-oxo-1-quinolin-4-ylmethyl-2,3,4,5-tetrahydro-1H-benzo[b]azepin-3-yl)-propionamide hydrochloride | 0.280 | >54.8 |
| 47e | (S)-2-Methylamino-N-((S)-2-oxo-1-quinolin-5-ylmethyl-2,3,4,5-tetrahydro-1H-benzo[b]azepin-3-yl)-propionamide hydrochloride | 0.388 | >54.8 |
| 47f | (S)-2-Methylamino-N-[(S)-1-(4-methyl-naphthalen-1-ylmethyl)-2-oxo-2,3,4,5-tetrahydro-1H-benzo[b]azepin-3-yl]-propionamide hydrochloride | 0.702 | >54.8 |
| 47g | (S)-N-[(S)-1-(4-Bromo-naphthalen-1-ylmethyl)-2-oxo-2,3,4,5-tetrahydro-1H-benzo[b]azepin-3-yl]-2-methylamino-propionamide hydrochloride | 0.878 | >54.8 |
| 47h | (S)-2-Methylamino-N-((S)-1-naphthalen-1-ylmethyl-2-oxo-2,3,4,5-tetrahydro-1H-benzo[b]azepin-3-yl)-propionamide hydrochloride | 1.470 | >54.2 |

TABLE 8-continued

| Ex. | Name | BIR2 IC$_{50}$ (µM) | BIR3 IC$_{50}$ (µM) |
|---|---|---|---|
| 47i | (S)-N-[(S)-1-(2-Ethynyl-naphthalen-1-ylmethyl)-2-oxo-2,3,4,5-tetrahydro-1H-benzo[b]azepin-3-yl]-2-methylamino-propionamide hydrochloride | 0.035 | >54.8 |
| 47j | (S)-N-[(S)-1-(3-Ethynyl-quinolin-4-ylmethyl)-2-oxo-2,3,4,5-tetrahydro-1H-benzo[b]azepin-3-yl]-2-methylamino-propionamide hydrochloride | 0.049 | 37.190 |
| 47k | (S)-N-[(S)-1-(2-Cyclopropyl-naphthalen-1-ylmethyl)-2-oxo-2,3,4,5-tetrahydro-1H-benzo[b]azepin-3-yl]-2-methylamino-propionamide hydrochloride | 0.055 | >54.8 |
| 47l | (S)-N-[(S)-1-(2-Methoxy-6-trifluoromethyl-naphthalen-1-ylmethyl)-2-oxo-2,3,4,5-tetrahydro-1H-benzo[b]azepin-3-yl]-2-methylamino-propionamide hydrochloride | 0.060 | 40.360 |
| 47m | (S)-N-[(S)-1-(3-Methoxy-[1,8]naphthyridin-4-ylmethyl)-2-oxo-2,3,4,5-tetrahydro-1H-benzo[b]azepin-3-yl]-2-methylamino-propionamide hydrochloride | 0.062 | >54.8 |
| 47n | (S)-N-[(S)-1-(2-Chloro-3-methyl-quinolin-4-ylmethyl)-2-oxo-2,3,4,5-tetrahydro-1H-benzo[b]azepin-3-yl]-2-methylamino-propionamide hydrochloride | 0.065 | 44.850 |
| 47o | (S)-N-[(S)-1-(5-Bromo-2-methoxy-naphthalen-1-ylmethyl)-2-oxo-2,3,4,5-tetrahydro-1H-benzo[b]azepin-3-yl]-2-methylamino-propionamide hydrochloride | 0.058 | >54.8 |
| 47p | (S)-2-Methylamino-N-{(S)-2-oxo-1-[2-(2,2,2-trifluoro-ethoxy)-naphthalen-1-ylmethyl]-2,3,4,5-tetrahydro-1H-benzo[b]azepin-3-yl}-propionamide hydrochloride | 0.085 | 52.580 |
| 47q | (S)-2-Methylamino-N-[(S)-1-(3-methyl-quinolin-4-ylmethyl)-2-oxo-2,3,4,5-tetrahydro-1H-benzo[b]azepin-3-yl]-propionamide hydrochloride | 0.086 | >54.8 |
| 47r | (S)-N-[(S)-1-(3-Chloro-[1,8]naphthyridin-4-ylmethyl)-2-oxo-2,3,4,5-tetrahydro-1H-benzo[b]azepin-3-yl]-2-methylamino-propionamide hydrochloride | 0.102 | 40.200 |
| 47s | (S)-N-[(S)-1-(2-Fluoro-naphthalen-1-ylmethyl)-2-oxo-2,3,4,5-tetrahydro-1H-benzo[b]azepin-3-yl]-2-methylamino-propionamide hydrochloride | 0.105 | >54.8 |
| 47t | (S)-2-Methylamino-N-{(S)-2-oxo-1-[3-(2,2,2-trifluoro-ethoxy)-quinolin-4-ylmethyl]-2,3,4,5-tetrahydro-1H-benzo[b]azepin-3-yl}-propionamide hydrochloride | 0.122 | >54.8 |
| 47u | (S)-2-Methylamino-N-[(S)-1-(3-methyl-isoquinolin-4-ylmethyl)-2-oxo-2,3,4,5-tetrahydro-1H-benzo[b]azepin-3-yl]-propionamide hydrochloride | 0.126 | 41.180 |
| 47v | (S)-N-[(S)-1-(7-Bromo-2-methoxy-naphthalen-1-ylmethyl)-2-oxo-2,3,4,5-tetrahydro-1H-benzo[b]azepin-3-yl]-2-methylamino-propionamide hydrochloride | 0.221 | |
| 47x | (S)-N-[(S)-1-(2-Chloro-naphthalen-1-ylmethyl)-2-oxo-2,3,4,5-tetrahydro-1H-benzo[b]azepin-3-yl]-2-methylamino-propionamide hydrochloride | 0.290 | 52.100 |
| 47y | (S)-N-[(S)-1-(2-Ethoxy-naphthalen-1-ylmethyl)-2-oxo-2,3,4,5-tetrahydro-1H-benzo[b]azepin-3-yl]-2-methylamino-propionamide hydrochloride | 0.356 | >54.8 |
| 47z | (S)-N-((S)-1-Isoquinolin-4-ylmethyl-2-oxo-2,3,4,5-tetrahydro-1H-benzo[b]azepin-3-yl)-2-methylamino-propionamide hydrochloride | 0.357 | >54.8 |
| 47aa | (S)-N-((S)-1-Cinnolin-4-ylmethyl-2-oxo-2,3,4,5-tetrahydro-1H-benzo[b]azepin-3-yl)-2-methylamino-propionamide hydrochloride | 0.378 | >54.8 |
| 47bb | (S)-N-[(S)-1-(2,4-Dimethyl-naphthalen-1-ylmethyl)-2-oxo-2,3,4,5-tetrahydro-1H-benzo[b]azepin-3-yl]-2-methylamino-propionamide hydrochloride | 0.471 | >54.0 |
| 47cc | (S)-2-Methylamino-N-((S)-1-[1,8]naphthyridin-4-ylmethyl-2-oxo-2,3,4,5-tetrahydro-1H-benzo[b]azepin-3-yl)-propionamide hydrochloride | 0.608 | >54.8 |
| 47dd | (S)-N-[(S)-1-(2-Isopropoxy-naphthalen-1-ylmethyl)-2-oxo-2,3,4,5-tetrahydro-1H-benzo[b]azepin-3-yl]-2-methylamino-propionamide hydrochloride | 0.719 | >54.8 |
| 47ee | (S)-N-((S)-1-Anthracen-1-ylmethyl-2-oxo-2,3,4,5-tetrahydro-1H-benzo[b]azepin-3-yl)-2-methylamino-propionamide hydrochloride | 1.191 | >54.8 |
| 47ff | (S)-N-[(S)-1-(7-Bromo-naphthalen-1-ylmethyl)-2-oxo-2,3,4,5-tetrahydro-1H-benzo[b]azepin-3-yl]-2-methylamino-propionamide hydrochloride | 1.347 | 47.540 |
| 47gg | (S)-N-[(S)-1-(3-Bromo-naphthalen-1-ylmethyl)-2-oxo-2,3,4,5-tetrahydro-1H-benzo[b]azepin-3-yl]-2-methylamino-propionamide hydrochloride | 1.933 | >54.8 |
| 47hh | (S)-N-[(S)-1-(8-Bromo-naphthalen-1-ylmethyl)-2-oxo-2,3,4,5-tetrahydro-1H-benzo[b]azepin-3-yl]-2-methylamino-propionamide hydrochloride | 5.400 | >54.8 |

TABLE 8-continued

| Ex. | Name | BIR2 IC$_{50}$ (μM) | BIR3 IC$_{50}$ (μM) |
|---|---|---|---|
| 47ii | (S)-N-[(S)-1-(3-Methoxy-quinolin-4-ylmethyl)-2-oxo-2,3,4,5-tetrahydro-1H-benzo[b]azepin-3-yl]-2-methylamino-propionamide hydrochloride | 0.032 | 44.930 |
| 47jj | (S)-N-((S)-1-Benzo[b]thiophen-7-ylmethyl-2-oxo-2,3,4,5-tetrahydro-1H-benzo[b]azepin-3-yl)-2-methylamino-propionamide hydrochloride | 1.127 | >54.8 |
| 47kk | (S)-N-[(S)-1-(4-Cyano-naphthalen-1-ylmethyl)-2-oxo-2,3,4,5-tetrahydro-1H-benzo[b]azepin-3-yl]-2-methylamino-propionamide hydrochloride | 1.585 | >54.8 |
| 47ll | (S)-2-Methylamino-N-[(S)-2-oxo-1-(2,3,5,6-tetramethyl-benzyl)-2,3,4,5-tetrahydro-1H-benzo[b]azepin-3-yl]-propionamide hydrochloride | 1.783 | >57.6 |
| 47mm | (S)-N-[(S)-1-(2,3-Dimethyl-benzyl)-2-oxo-2,3,4,5-tetrahydro-1H-benzo[b]azepin-3-yl]-2-methylamino-propionamide hydrochloride | 3.868 | >57.6 |
| 47nn | (S)-2-Methylamino-N-((S)-1-naphthalen-2-ylmethyl-2-oxo-2,3,4,5-tetrahydro-1H-benzo[b]azepin-3-yl)-propionamide hydrochloride | 4.314 | >54.2 |
| 47oo | (S)-N-[(S)-1-(2-Chloro-benzyl)-2-oxo-2,3,4,5-tetrahydro-1H-benzo[b]azepin-3-yl]-2-methylamino-propionamide hydrochloride | 4.340 | >54.8 |
| 47pp | (S)-N-[(S)-1-(2,6-Dimethyl-benzyl)-2-oxo-2,3,4,5-tetrahydro-1H-benzo[b]azepin-3-yl]-2-methylamino-propionamide hydrochloride | 5.085 | >54.8 |
| 47qq | (S)-N-((S)-1-Benzyl-2-oxo-2,3,4,5-tetrahydro-1H-benzo[b]azepin-3-yl)-2-methylamino-propionamide hydrochloride | 5.489 | >54.2 |
| 47rr | (S)-N-[(S)-1-(2,4-Dimethyl-benzyl)-2-oxo-2,3,4,5-tetrahydro-1H-benzo[b]azepin-3-yl]-2-methylamino-propionamide hydrochloride | 7.172 | >54.8 |
| 47ss | (S)-2-Methylamino-N-[(S)-1-(2-methyl-benzyl)-2-oxo-2,3,4,5-tetrahydro-1H-benzo[b]azepin-3-yl]-propionamide hydrochloride | 9.394 | >57.6 |
| 47tt | (S)-N-[(S)-1-(5-Bromo-naphthalen-1-ylmethyl)-2-oxo-2,3,4,5-tetrahydro-1H-benzo[b]azepin-3-yl]-2-methylamino-propionamide hydrochloride | 0.548 | >54.8 |
| 49b | (S)-N-[(S)-1-(6-Furan-2-yl-2-methoxy-naphthalen-1-ylmethyl)-2-oxo-2,3,4,5-tetrahydro-1H-benzo[b]azepin-3-yl]-2-methylamino-propionamide hydrochloride | 0.118 | 54.130 |
| 49c | (S)-N-[(S)-1-(5-Furan-3-yl-2-methoxy-naphthalen-1-ylmethyl)-2-oxo-2,3,4,5-tetrahydro-1H-benzo[b]azepin-3-yl]-2-methylamino-propionamide hydrochloride | 0.128 | >54.8 |
| 49d | (S)-N-[(S)-1-(6-Cyclopropyl-2-methoxy-naphthalen-1-ylmethyl)-2-oxo-2,3,4,5-tetrahydro-1H-benzo[b]azepin-3-yl]-2-methylamino-propionamide hydrochloride | 0.496 | >54.8 |
| 49e | (S)-N-[(S)-1-(5-Cyclopropyl-naphthalen-1-ylmethyl)-2-oxo-2,3,4,5-tetrahydro-1H-benzo[b]azepin-3-yl]-2-methylamino-propionamide hydrochloride | 0.547 | >54.8 |
| 49f | (S)-N-[(S)-1-(4-Benzyl-naphthalen-1-ylmethyl)-2-oxo-2,3,4,5-tetrahydro-1H-benzo[b]azepin-3-yl]-2-methylamino-propionamide hydrochloride | 0.559 | >54.0 |
| 49g | (S)-N-[(S)-1-(3-Cyclopropyl-naphthalen-1-ylmethyl)-2-oxo-2,3,4,5-tetrahydro-1H-benzo[b]azepin-3-yl]-2-methylamino-propionamide hydrochloride | 0.873 | >54.8 |
| 49h | (S)-2-Methylamino-N-[(S)-2-oxo-1-(4-phenethyl-naphthalen-1-ylmethyl)-2,3,4,5-tetrahydro-1H-benzo[b]azepin-3-yl]-propionamide hydrochloride | 0.956 | >54.0 |
| 49i | (S)-N-[(S)-1-(6-Benzyl-2-methoxy-naphthalen-1-ylmethyl)-2-oxo-2,3,4,5-tetrahydro-1H-benzo[b]azepin-3-yl]-2-methylamino-propionamide hydrochloride | 1.074 | >54.8 |
| 49j | (S)-N-[(S)-1-(3-Benzyl-naphthalen-1-ylmethyl)-2-oxo-2,3,4,5-tetrahydro-1H-benzo[b]azepin-3-yl]-2-methylamino-propionamide hydrochloride | 1.075 | |
| 49k | (S)-N-[(S)-1-(5-Benzyl-naphthalen-1-ylmethyl)-2-oxo-2,3,4,5-tetrahydro-1H-benzo[b]azepin-3-yl]-2-methylamino-propionamide hydrochloride | 1.247 | >54.8 |
| 49l | (S)-N-[(S)-1-(4-Isopropoxymethyl-naphthalen-1-ylmethyl)-2-oxo-2,3,4,5-tetrahydro-1H-benzo[b]azepin-3-yl]-2-methylamino-propionamide hydrochloride | 1.883 | >54.8 |
| 49m | (S)-N-[(S)-1-(4-Cyclopropyl-naphthalen-1-ylmethyl)-2-oxo-2,3,4,5-tetrahydro-1H-benzo[b]azepin-3-yl]-2-methylamino-propionamide hydrochloride | 1.937 | >54.8 |
| 49n | (S)-2-Methylamino-N-[(S)-2-oxo-1-(5-piperazin-1-ylmethyl-naphthalen-1-ylmethyl)-2,3,4,5-tetrahydro-1H-benzo[b]azepin-3-yl]-propionamide hydrochloride | 2.236 | >54.8 |

TABLE 8-continued

| Ex. | Name | BIR2 IC$_{50}$ (μM) | BIR3 IC$_{50}$ (μM) |
|---|---|---|---|
| 49o | (S)-2-Methylamino-N-[(S)-1-(4-morpholin-4-ylmethyl-naphthalen-1-ylmethyl)-2-oxo-2,3,4,5-tetrahydro-1H-benzo[b]azepin-3-yl]-propionamide hydrochloride | 2.980 | >54.8 |
| 49p | (S)-N-{(S)-1-[6-(3,5-Dimethyl-isoxazol-4-ylmethyl)-2-methoxy-naphthalen-1-ylmethyl]-2-oxo-2,3,4,5-tetrahydro-1H-benzo[b]azepin-3-yl}-2-methylamino-propionamide hydrochloride | 3.645 | 43.993 |
| 49q | (S)-2-Methylamino-N-[(S)-2-oxo-1-(4-piperidin-1-ylmethyl-naphthalen-1-ylmethyl)-2,3,4,5-tetrahydro-1H-benzo[b]azepin-3-yl]-propionamide hydrochloride | 4.560 | >54.8 |
| 49r | (S)-N-[(S)-1-(2-Methoxy-6-piperazin-1-ylmethyl-naphthalen-1-ylmethyl)-2-oxo-2,3,4,5-tetrahydro-1H-benzo[b]azepin-3-yl]-2-methylamino-propionamide hydrochloride | 5.109 | >54.8 |
| 49s | (S)-2-Methylamino-N-[(S)-2-oxo-1-(4-piperazin-1-ylmethyl-naphthalen-1-ylmethyl)-2,3,4,5-tetrahydro-1H-benzo[b]azepin-3-yl]-propionamide hydrochloride | 5.277 | >54.8 |
| 49t | (S)-N-[(S)-1-(8-Cyclopropyl-naphthalen-1-ylmethyl)-2-oxo-2,3,4,5-tetrahydro-1H-benzo[b]azepin-3-yl]-2-methylamino-propionamide hydrochloride | 29.115 | >54.8 |
| 49u | (S)-N-[(S)-1-(2-Methoxy-6-phenyl-naphthalen-1-ylmethyl)-2-oxo-2,3,4,5-tetrahydro-1H-benzo[b]azepin-3-yl]-2-methylamino-propionamide hydrochloride | 0.389 | >54.8 |
| 52b | (S)-N-{(S)-1-[2-Methoxy-5-(propane-1-sulfonylaminocarbonyl)-naphthalen-1-ylmethyl]-2-oxo-2,3,4,5-tetrahydro-1H-benzo[b]azepin-3-yl}-2-methylamino-propionamide hydrochloride | 0.039 | >54.8 |
| 52c | (S)-N-[(S)-1-(5-Methanesulfonylaminocarbonyl-2-methoxy-naphthalen-1-ylmethyl)-2-oxo-2,3,4,5-tetrahydro-1H-benzo[b]azepin-3-yl]-2-methylamino-propionamide hydrochloride | 0.054 | >54.8 |
| 52d | (S)-N-{(S)-1-[2-Methoxy-6-(propane-1-sulfonylaminocarbonyl)-naphthalen-1-ylmethyl]-2-oxo-2,3,4,5-tetrahydro-1H-benzo[b]azepin-3-yl}-2-methylamino-propionamide hydrochloride | 0.058 | |
| 52e | 6-Methoxy-5-[(S)-3-((S)-2-methylamino-propionylamino)-2-oxo-2,3,4,5-tetrahydro-benzo[b]azepin-1-ylmethyl]-naphthalene-1-carboxylic acid methyl ester hydrochloride | 0.181 | >54.8 |
| 52f | 5-[(S)-3-((S)-2-Methylamino-propionylamino)-2-oxo-2,3,4,5-tetrahydro-benzo[b]azepin-1-ylmethyl]-naphthalene-1-carboxylic acid hydrochloride | 0.196 | >54.8 |
| 52g | 5-[(S)-3-((S)-2-Methylamino-propionylamino)-2-oxo-2,3,4,5-tetrahydro-benzo[b]azepin-1-ylmethyl]-naphthalene-1-carboxylic acid methyl ester hydrochloride | 0.649 | >54.8 |
| 52h | 7-Methoxy-8-[(S)-3-((S)-2-methylamino-propionylamino)-2-oxo-2,3,4,5-tetrahydro-benzo[b]azepin-1-ylmethyl]-naphthalene-2-carboxylic acid methyl ester hydrochloride | 10.110 | >54.8 |
| 54b | 6-Methoxy-5-[(S)-3-((S)-2-methylamino-propionylamino)-2-oxo-2,3,4,5-tetrahydro-benzo[b]azepin-1-ylmethyl]-naphthalene-2-carboxylic acid amide hydrochloride | 0.542 | >54.8 |
| 54c | (S)-N-[(S)-1-(7-Cyano-2-methoxy-naphthalen-1-ylmethyl)-2-oxo-2,3,4,5-tetrahydro-1H-benzo[b]azepin-3-yl]-2-methylamino-propionamide hydrochloride | 0.273 | >54.8 |
| 54d | (S)-N-[(S)-1-(6-Cyano-2-methoxy-naphthalen-1-ylmethyl)-2-oxo-2,3,4,5-tetrahydro-1H-benzo[b]azepin-3-yl]-2-methylamino-propionamide hydrochloride | 0.773 | >54.8 |
| 54e | (S)-N-[(S)-1-(5-Cyano-naphthalen-1-ylmethyl)-2-oxo-2,3,4,5-tetrahydro-1H-benzo[b]azepin-3-yl]-2-methylamino-propionamide hydrochloride | 0.799 | >54.8 |
| 54f | (S)-N-[(S)-1-(7-Cyano-naphthalen-1-ylmethyl)-2-oxo-2,3,4,5-tetrahydro-1H-benzo[b]azepin-3-yl]-2-methylamino-propionamide hydrochloride | 1.390 | >54.8 |
| 54g | 8-[(S)-3-((S)-2-Methylamino-propionylamino)-2-oxo-2,3,4,5-tetrahydro-benzo[b]azepin-1-ylmethyl]-naphthalene-2-carboxylic acid amide hydrochloride | 5.130 | >54.8 |
| 54h | (S)-N-[(S)-1-(8-Cyano-naphthalen-1-ylmethyl)-2-oxo-2,3,4,5-tetrahydro-1H-benzo[b]azepin-3-yl]-2-methylamino-propionamide hydrochloride | 13.210 | >54.8 |
| 55a | (S)-N-(1-Biphenyl-2-ylmethyl-2-oxo-2,3,4,5-tetrahydro-1H-benzo[b]azepin-3-yl)-2-methylamino-propionamide hydrochloride | 4.947 | >54.2 |
| 55b | (S)-N-(1-Biphenyl-3-ylmethyl-2-oxo-2,3,4,5-tetrahydro-1H-benzo[b]azepin-3-yl)-2-methylamino-propionamide hydrochloride | 4.994 | 31.8325 |
| 55c | (S)-2-Methylamino-N-[2-oxo-1-(3-phenyl-isoxazol-5-ylmethyl)-2,3,4,5-tetrahydro-1H-benzo[b]azepin-3-yl]-propionamide hydrochloride | 7.524 | >54.2 |

TABLE 8-continued

| Ex. | Name | BIR2 IC$_{50}$ (μM) | BIR3 IC$_{50}$ (μM) |
|---|---|---|---|
| 55d | (S)-2-Methylamino-N-[1-(6-methyl-biphenyl-3-ylmethyl)-2-oxo-2,3,4,5-tetrahydro-1H-benzo[b]azepin-3-yl]-propionamide hydrochloride | 8.451 | 33.53 |
| 55e | (S)-N-(1-Benzyl-2-oxo-2,3,4,5-tetrahydro-1H-benzo[b]azepin-3-yl)-2-methylamino-propionamide hydrochloride | 9.852 | >54.2 |
| 55f | (S)-N-(1-Biphenyl-4-ylmethyl-2-oxo-2,3,4,5-tetrahydro-1H-benzo[b]azepin-3-yl)-2-methylamino-propionamide hydrochloride | 12.571 | >54.2 |
| 55g | (S)-2-Methylamino-N-(2-oxo-1-phenethyl-2,3,4,5-tetrahydro-1H-benzo[b]azepin-3-yl)-propionamide hydrochloride | 13.830 | >54.2 |
| 55h | (S)-2-Methylamino-N-[2-oxo-1-(3-phenyl-propyl)-2,3,4,5-tetrahydro-1H-benzo[b]azepin-3-yl]-propionamide hydrochloride | 18.260 | >54.2 |

The invention claimed is:
1. A compound of Formula 1:

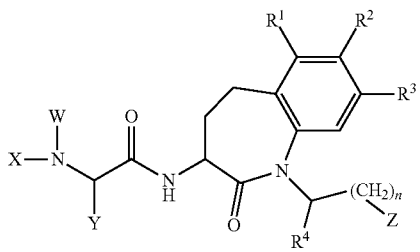

wherein:
W and X are the same or different and each is independently selected from the group
  a) H,
  b) alkyl that optionally may be substituted with $OR^5$, aryl, alkenyl, alkynyl and cycloalkyl,
  c) cycloalkyl, and
  d) heterocycle,
  or alternatively, X and W together with the nitrogen to which they are bound can form a $C_2$-$C_9$ heterocycle, or W together with the nitrogen to which it is bound and Y together with the carbon to which it is bound can form a $C_3$-$C_9$ heterocycle;
Y is selected from the group
  a) alkyl that optionally may be substituted with $OR^5$ and cycloalkyl, and
  b) cycloalkyl;
Z is selected from the group
  a) lower alkyl that optionally may be substituted with aryl,
  b) aryl that optionally may be substituted with
    1) lower alkyl that optionally may be substituted with $OR^5$, aryl and heterocyclyl,
    2) $OR^5$,
    3) halogen,
    4) $COOR^5$,
    5) $CONR^6R^7$,
    6) $NR^4C(O)R^5$,
    7) $C(O)R^5$,
    8) $CF_3$,
    9) alkenyl
    10) alkynyl that optionally may be substituted with heterocycle that optionally may be substituted with $OR^5$,
    11) heterocycle that optionally may be substituted with lower alkyl, oxo and $OR^5$,
    12) $NH_2C$=$N$—$NH_2$,
    13) $CONR^5SO_2R^4$,
    14) cyano,
    15) cycloalkyl,
    16) aryl,
    17) heteroaryl that optionally may be substituted with lower alkyl, oxo and $CF_3$,
  c) aryl fused with cycloalkyl, wherein the aryl may be substituted with $OR^5$,
  d) heteroaryl that optionally may be substituted with lower alkynyl, $OR^5$, halogen, $COOR^5$, $CONR^6R^7$, oxo, $CF_3$, cycloalkyl, cyano and aryl, and
  e) heterocyclyl;
$R^1$, $R^2$ and $R^3$ are the same or different and each is independently selected from the group
  a) H,
  b) halogen,
  c) alkyl that optionally may be substituted with aryl,
  d) cyano,
  e) aryl,
  f) $C(O)R^5$,
  g) $OR^5$,
  h) N-acyl,
  i) N-sulfonyl, and
  j) $OR^5$;
$R^4$ is selected from the group
  a) H, and
  h) alkyl;
$R^5$ is selected from the group
  a) H,
  b) lower alkyl that optionally may be substituted with aryl, cycloalkyl, and $CF_3$,
  c) cycloalkyl,
  d) alkenyl,
  e) aryl that optionally may be substituted with $NR^5R^7$, $C(O)R^7$, $CR^1OR^7$, $NO_2$ and $OR^7$,
  f) heterocyclyl,
  g) $CR^4F_2$, and
  h) $CR^6R^7$;
$R^6$ and $R^7$ are the same or different and each is independently selected from the group
  a) H, and
  b) alkyl that optionally may be substituted with aryl, heteroaryl and cycloalkyl; and
n is 0, 1 or 2;
or a pharmaceutically acceptable salt thereof.

2. The compound of claim 1 wherein W and X are independently selected from H, $C_{3-7}$-cycloalkyl, and $C_{1-6}$-alkyl that optionally may be substituted with $OR^5$, aryl, and $C_{3-7}$-cycloalkyl, or a pharmaceutically acceptable salt thereof.

3. The compound according to claim 1 wherein Z is lower alkyl that optionally may be substituted with aryl, or a pharmaceutically acceptable salt thereof.

4. The compound according to claim 2 wherein Z is lower alkyl that optionally may be substituted with aryl, or a pharmaceutically acceptable salt thereof.

5. The compound according to claim 1 wherein Z is aryl, or a pharmaceutically acceptable salt thereof.

6. The compound according to claim 2 wherein Z is aryl, or a pharmaceutically acceptable salt thereof.

7. The compound of claim 5 wherein the aryl is not phenyl, or a pharmaceutically acceptable salt thereof.

8. The compound of claim 6 wherein the aryl is not phenyl, or a pharmaceutically acceptable salt thereof.

9. The compound of claim 5 wherein the aryl is naphthelynyl, or a pharmaceutically acceptable salt thereof.

10. The compound of claim 6 wherein the aryl is naphthelynyl, or a pharmaceutically acceptable salt thereof.

11. The compound according to claim 5 wherein the aryl group optionally may be substituted with $C_{1-6}$-alkyl, $OR^5$, halogen, $CF_3$, heterocycle and cyano, or a pharmaceutically acceptable salt thereof.

12. The compound according to claim 6 wherein the aryl group optionally may be substituted with $C_{1-6}$-alkyl, $OR^5$, halogen, $CF_3$, heterocycle and cyano, or a pharmaceutically acceptable salt thereof.

13. The compound according to claim 1 wherein Z is heteroaryl that optionally may be substituted with $C_{1-6}$-alkyl, $OR^5$, halogen, oxo, $CF_3$, $C_{3-7}$-cycloalkyl and cyano, or a pharmaceutically acceptable salt thereof.

14. The compound according to claim 2 wherein Z is heteroaryl that optionally may be substituted with $C_{1-6}$-alkyl, $OR^5$, halogen, oxo, $CF_3$, $C_{3-7}$-cycloalkyl and cyano, or a pharmaceutically acceptable salt thereof.

15. The compound according to claim 13 wherein the heteroaryl is bicyclic, or a pharmaceutically acceptable salt thereof.

16. The compound according to claim 13 wherein the heteroaryl is selected from quinolinyl, isoquinolinyl, benzo[b]thiophenyl, indazolyl, isoxazolyl, naphthyridinyl and cynnolinyl, or a pharmaceutically acceptable salt thereof.

17. The compound according to claim 1 wherein $R^1$ and $R^2$ are H, or a pharmaceutically acceptable salt thereof.

18. The compound according to claim 2 wherein $R^1$ and $R^2$ are H, or a pharmaceutically acceptable salt thereof.

19. The compound according to claim 3 wherein $R^1$ and $R^2$ are H, or a pharmaceutically acceptable salt thereof.

20. The compound according to claim 5 wherein $R^1$ and $R^2$ are H, or a pharmaceutically acceptable salt thereof.

21. The compound according to claim 11 wherein $R^1$ and $R^2$ are H, or a pharmaceutically acceptable salt thereof.

22. The compound according to claim 13 wherein $R^1$ and $R^2$ are H, or a pharmaceutically acceptable salt thereof.

23. The compound according to claim 15 wherein $R^1$ and $R^2$ are H, or a pharmaceutically acceptable salt thereof.

24. The compound according to claim 16 wherein $R^1$ and $R^2$ are H, or a pharmaceutically acceptable salt thereof.

25. The compound according to claim 1 wherein $R^3$ is H, phenyl, halogen, cyano or $OR^5$, or a pharmaceutically acceptable salt thereof.

26. The compound according to claim 1 wherein $R^4$ is H, or a pharmaceutically acceptable salt thereof.

27. The compound according to claim 1 wherein $R^5$ is selected from H, alkenyl and lower alkyl that optionally may be substituted with aryl and $CF_3$, or a pharmaceutically acceptable salt thereof.

28. The compound according to claim 1 wherein $R^6$ and $R^7$ are the same or different and each is independently selected from H and lower alkyl, or a pharmaceutically acceptable salt thereof.

29. The compound according to claim 1 wherein n is 0, or a pharmaceutically acceptable salt thereof.

30. The compound of claim 1, wherein X is H or methyl, W is H, Y is methyl or ethyl, $R^1$, $R^2$, $R^3$ and $R^4$ are H, n is 0, and Z is phenyl that may be substituted with lower alkyl, $OCH_3$, F, Cl, Br, I or $CF_3$, or a pharmaceutically acceptable salt thereof.

31. The compound of claim 1, wherein X is H or methyl, W is H, Y is methyl or ethyl, $R^1$, $R^2$, $R^3$ and $R^4$ are H, n is 0, and Z is naphthalenyl that may be substituted with $OR^5$, halogen, lower alkyl that optionally is substituted with aryl or heterocyclyl, $CF_3$, alkynyl, alkenyl, heterocycle, $C(O)CH_3$, $COOR^5$, cyano, cycloalkyl, $CONHSO_2R^4$, and $CONH_2$, or a pharmaceutically acceptable salt thereof.

32. The compound of claim 1, wherein X is H or methyl, W is H, Y is methyl or ethyl, $R^1$, $R^2$, $R^3$ and $R^4$ are H, n is 0, and Z is quinolinyl or isoquinolinyl that optionally may be substituted with $C_{1-6}$-alkyl, $OR^5$, oxo, $C_{3-7}$-cycloalkyl, $CF_3$, cyano, and halogen, or a pharmaceutically acceptable salt thereof.

33. The compound of claim 1, wherein X is H or methyl, W is H, Y is methyl or ethyl, $R^1$, $R^2$, $R^3$ and $R^4$ are H, n is 0, and Z is selected from cinnolinyl, thiophenyl, benzothiophenyl, benzo[d]isoxazolyl, tetrahydronaphthalenyl, indazolyl, oxazolyl, thiazolyl, pyridinyl, imidazolyl or naphthyridinyl, each of which may be substituted as defined in claim 1, or a pharmaceutically acceptable salt thereof.

34. The compound of claim 1, wherein Z is $C_{1-6}$-alkyl, said compound being selected from the group consisting of:
(S)-2-Methylamino-N-(2-oxo-1-phenethyl-2,3,4,5-tetrahydro-1H-benzo[b]azepin-3-yl)-propionamide hydrochloride; and
(S)-2-Methylamino-N-[2-oxo-1-(3-phenyl-propyl)-2,3,4,5-tetrahydro-1H-benzo[b]azepin-3-yl]-propionamide hydrochloride.

35. A compound, selected from the group consisting of:
(S)-2-Amino-N—[(R)-1-(6-bromo-2-methoxy-naphthalen-1-ylmethyl)-2-oxo-2,3,4,5-tetrahydro-1H-benzo[b]azepin-3-yl]-butyramide hydrochloride;
(S)-2-Amino-N—[(S)-1-(6-bromo-2-methoxy-naphthalen-1-ylmethyl)-2-oxo-2,3,4,5-tetrahydro-1H-benzo[b]azepin-3-yl]-butyramide or a pharmaceutically acceptable salt thereof;
(S)—N—((S)-1-((6-Bromo-2-methoxynaphthalen-1-yl)methyl)-2-oxo-2,3,4,5-tetrahydro-1H-benzo[b]azepin-3-yl)-2-(2-hydroxyethylamino)butanamide or a pharmaceutically acceptable salt thereof;
(S)—N—((S)-1-((6-Bromo-2-methoxynaphthalen-1-yl)methyl)-2-oxo-2,3,4,5-tetrahydro-1H-benzo[b]azepin-3-yl)-2-(cyclobutylamino)butanamide or a pharmaceutically acceptable salt thereof;
(S)-2-(Benzylamino)-N—((S)-1-((6-bromo-2-methoxynaphthalen-1-yl)methyl)-2-oxo-2,3,4,5-tetrahydro-1H-benzo[b]azepin-3-yl)butanamide or a pharmaceutically acceptable salt thereof;
(S)—N—((S)-1-((6-Bromo-2-methoxynaphthalen-1-yl)methyl)-2-oxo-2,3,4,5-tetrahydro-1H-benzo[b]azepin-3-yl)-2-(oxetan-3-ylamino)butanamide or a pharmaceutically acceptable salt thereof;
(2S,3S)-2-Amino-N—((S)-1-((6-bromo-2-methoxynaphthalen-1-yl)methyl)-2-oxo-2,3,4,5-tetrahydro-1H-benzo[b]azepin-3-yl)-3-hydroxybutanamide hydrochloride;
(2S,3R)-2-Amino-N—((S)-1-((6-bromo-2-methoxynaphthalen-1-yl)methyl)-2-oxo-2,3,4,5-tetrahydro-1H-benzo[b]azepin-3-yl)-3-hydroxybutanamide hydrochloride;
(S)-2-Amino-N—[(S)-1-(6-bromo-2-methoxy-naphthalen-1-ylmethyl)-2-oxo-2,3,4,5-tetrahydro-1H-benzo[b]azepin-3-yl]-3-hydroxy-propionamide hydrochloride;
{(S)-1-[(S)-1-(6-Bromo-2-methoxy-naphthalen-1-ylmethyl)-2-oxo-2,3,4,5-tetrahydro-1H-benzo[b]azepin-3-ylcarbamoyl]-2-hydroxy-ethyl}-carbamic acid tert-butyl ester hydrochloride;
(S)—N—{(S)-1-[2-(3-Hydroxy-oxetan-3-ylethynyl)-naphthalen-1-ylmethyl]-2-oxo-2,3,4,5-tetrahydro-1H-benzo[b]azepin-3-yl}-2-methylamino-propionamide or a pharmaceutically acceptable salt thereof;
(S)-2-Methylamino-N—[(S)-2-oxo-1-(2-propoxy-naphthalen-1-ylmethyl)-2,3,4,5-tetrahydro-1H-benzo[b]azepin-3-yl]-propionamide hydrochloride;
(S)—N—[(S)-1-(2-Allyloxy-naphthalen-1-ylmethyl)-2-oxo-2,3,4,5-tetrahydro-1H-benzo[b]azepin-3-yl]-2-methylamino-propionamide or a pharmaceutically acceptable salt thereof;
(S)—N—[(S)-1-(2-Hydroxy-naphthalen-1-ylmethyl)-2-oxo-2,3,4,5-tetrahydro-1H-benzo[b]azepin-3-yl]-2-methylamino-propionamide hydrochloride;
(S)—N—[(S)-8-Benzyloxy-1-(2-methyl-naphthalen-1-ylmethyl)-2-oxo-2,3,4,5-tetrahydro-1H-benzo[b]azepin-3-yl]-2-methylamino-propionamide hydrochloride;
(S)-2-Methylamino-N—[(S)-1-(2-methyl-naphthalen-1-ylmethyl)-2-oxo-8-phenyl-2,3,4,5-tetrahydro-1H-benzo[b]azepin-3-yl]-propionamide hydrochloride;

(R)—N—[(S)-1-(6-Bromo-2-methoxy-naphthalen-1-yl-methyl)-2-oxo-2,3,4,5-tetrahydro-1H-benzo[b]azepin-3-yl]-2-methylamino-propionamide hydrochloride;

(S)-2-Methylamino-N—{(S)-2-oxo-1-[7-(1H-tetrazol-5-yl)-naphthalen-1-ylmethyl]-2,3,4,5-tetrahydro-1H-benzo[b]azepin-3-yl}-propionamide or a pharmaceutically acceptable salt thereof;

(S)—N—[(S)-1-(6-Bromo-2-methoxy-naphthalen-1-yl-methyl)-2-oxo-2,3,4,5-tetrahydro-1H-benzo[b]azepin-3-yl]-2-methylamino-propionamide hydrochloride;

(S)—N—{(S)-1-[2-Methoxy-6-(4-methyl-thiazol-2-yl)-naphthalen-1-ylmethyl]-2-oxo-2,3,4,5-tetrahydro-1H-benzo[b]azepin-3-yl}-2-methylamino-propionamide hydrochloride;

(S)—N—{(S)-1-[2-Methoxy-6-(5-oxo-4,5-dihydro-[1,2,4]oxadiazol-3-yl)-naphthalen-1-ylmethyl]-2-oxo-2,3,4,5-tetrahydro-1H-benzo[b]azepin-3-yl}-2-methyl-amino-propionamide hydrochloride;

(S)—N—[(S)-1-(2-Methoxy-6-[1,2,4]oxadiazol-3-yl-naphthalen-1-ylmethyl)-2-oxo-2,3,4,5-tetrahydro-1H-benzo[b]azepin-3-yl]-2-methylamino-propionamide hydrochloride;

(S)—N—{(S)-1-[6-(N-Aminocarbamimidoyl)-2-methoxy-naphthalen-1-ylmethyl]-2-oxo-2,3,4,5-tetrahydro-1H-benzo[b]azepin-3-yl}-2-methylamino-propionamide dihydrochloride;

(S)—N—{(S)-1-[2-Methoxy-6-(5-oxo-4,5-dihydro-1H-[1,2,4]triazol-3-yl)-naphthalen-1-ylmethyl]-2-oxo-2,3,4,5-tetrahydro-1H-benzo[b]azepin-3-yl}-2-methyl-amino-propionamide hydrochloride;

(S)—N—{(S)-1-[6-(5,6-Dioxo-1,4,5,6-tetrahydro-[1,2,4]triazin-3-yl)-2-methoxy-naphthalen-1-ylmethyl]-2-oxo-2,3,4,5-tetrahydro-1H-benzo[b]azepin-3-yl}-2-methylamino-propionamide hydrochloride;

(S)—N—{(S)-1-[2-Methoxy-6-(5-trifluoromethyl-4H-[1,2,4]triazol-3-yl)-naphthalen-1-ylmethyl]-2-oxo-2,3,4,5-tetrahydro-1H-benzo[b]azepin-3-yl}-2-methyl-amino-propionamide hydrochloride;

(S)—N—[(S)-1-(2-Methoxy-6-[1,2,4]triazin-3-yl-naphthalen-1-ylmethyl)-2-oxo-2,3,4,5-tetrahydro-1H-benzo[b]azepin-3-yl]-2-methylamino-propionamide hydrochloride;

(S)—N—{(S)-1-[2-Methoxy-6-(1H-[1,2,4]triazol-3-yl)-naphthalen-1-ylmethyl]-2-oxo-2,3,4,5-tetrahydro-1H-benzo[b]azepin-3-yl}-2-methylamino-propionamide dihydrochloride;

(S)—N—{(S)-1-[2-Methoxy-6-(1H-tetrazol-5-yl)-naphthalen-1-ylmethyl]-2-oxo-2,3,4,5-tetrahydro-1H-benzo[b]azepin-3-yl}-2-methylamino-propionamide hydrochloride;

(S)—N—{(S)-1-[2-Methoxy-6-(2-methyl-2H-tetrazol-5-yl)-naphthalen-1-ylmethyl]-2-oxo-2,3,4,5-tetrahydro-1H-benzo[b]azepin-3-yl}-2-methylamino-propionamide hydrochloride;

(S)—N-{f(S)-1-[2-Methoxy-6-(1-methyl-1H-tetrazol-5-yl)-naphthalen-1-ylmethyl]-2-oxo-2,3,4,5-tetrahydro-1H-benzo[b]azepin-3-yl}-2-methylamino-propionamide hydrochloride;

(S)—N—[(S)-1-(6-Acetylamino-2-methoxy-naphthalen-1-ylmethyl)-2-oxo-2,3,4,5-tetrahydro-1H-benzo[b]azepin-3-yl]-2-methylamino-propionamide hydrochloride;

(S)—N—{(S)-1-[2-Methoxy-6-(1H-pyrazol-4-yl)-naphthalen-1-ylmethyl]-2-oxo-2,3,4,5-tetrahydro-1H-benzo[b]azepin-3-yl}-2-methylamino-propionamide hydrochloride;

(S)—N—[(S)-1-(6-Acetyl-2-methoxy-naphthalen-1-ylmethyl)-2-oxo-2,3,4,5-tetrahydro-1H-benzo[b]azepin-3-yl]-2-methylamino-propionamide hydrochloride;

(S)—N—[(S)-1-(2-Methoxy-6-vinyl-naphthalen-1-ylmethyl)-2-oxo-2,3,4,5-tetrahydro-1H-benzo[b]azepin-3-yl]-2-methylamino-propionamide hydrochloride;

(S)—N—{(S)-1-[6-(1-Hydroxy-ethyl)-2-methoxy-naphthalen-1-ylmethyl]-2-oxo-2,3,4,5-tetrahydro-1H-benzo[b]azepin-3-yl}-2-methylamino-propionamide trifluoroacetate;

(S)-2-Methylamino-N—[(S)-1-(2-methyl-naphthalen-1-ylmethyl)-2-oxo-2,3,4,5-tetrahydro-1H-benzo[b]azepin-3-yl]-propionamide hydrochloride;

(S)—N—[(S)-1-(2-Methoxy-naphthalen-1-ylmethyl)-2-oxo-2,3,4,5-tetrahydro-1H-benzo[b]azepin-3-yl]-2-methylamino-propionamide hydrochloride;

(S)-2-Methylamino-N-[(S)-1-(4-methyl-naphthalen-1-ylmethyl)-2-oxo-2,3,4,5-tetrahydro-1H-benzo[b]azepin-3-yl]-propionamide hydrochloride;

(S)—N—[(S)-1-(4-Bromo-naphthalen-1-ylmethyl)-2-oxo-2,3,4,5-tetrahydro-1H-benzo[b]azepin-3-yl]-2-methylamino-propionamide hydrochloride;

(S)-2-Methylamino-N—((S)-1-naphthalen-1-ylmethyl-2-oxo-2,3,4,5-tetrahydro-1H-benzo[b]azepin-3-yl)-propionamide hydrochloride;

(S)—N—[(S)-1-(2-Ethynyl-naphthalen-1-ylmethyl)-2-oxo-2,3,4,5-tetrahydro-1H-benzo[b]azepin-3-yl]-2-methylamino-propionamide hydrochloride;

(S)—N—[(S)-1-(2-Cyclopropyl-naphthalen-1-ylmethyl)-2-oxo-2,3,4,5-tetrahydro-1H-benzo[b]azepin-3-yl]-2-methylamino-propionamide hydrochloride;

(S)—N—[(S)-1-(2-Methoxy-6-trifluoromethyl-naphthalen-1-ylmethyl)-2-oxo-2,3,4,5-tetrahydro-1H-benzo[b]azepin-3-yl]-2-methylamino-propionamide hydrochloride;

(S)—N—[(S)-1-(5-Bromo-2-methoxy-naphthalen-1-ylmethyl)-2-oxo-2,3,4,5-tetrahydro-1H-benzo[b]azepin-3-yl]-2-methylamino-propionamide hydrochloride;

(S)-2-Methylamino-N—{(S)-2-oxo-1-[2-(2,2,2-trifluoro-ethoxy)-naphthalen-1-ylmethyl]-2,3,4,5-tetrahydro-1H-benzo[b]azepin-3-yl}-propionamide hydrochloride;

(S)—N—[(S)-1-(2-Fluoro-naphthalen-1-ylmethyl)-2-oxo-2,3,4,5-tetrahydro-1H-benzo[b]azepin-3-yl]-2-methylamino-propionamide hydrochloride;

(S)—N—[(S)-1-(7-Bromo-2-methoxy-naphthalen-1-ylmethyl)-2-oxo-2,3,4,5-tetrahydro-1H-benzo[b]azepin-3-yl]-2-methylamino-propionamide hydrochloride;

(S)—N—[(S)-1-(2-Chloro-naphthalen-1-ylmethyl)-2-oxo-2,3,4,5-tetrahydro-1H-benzo[b]azepin-3-yl]-2-methylamino-propionamide hydrochloride;

(S)—N—-[(S)-1-(2-Ethoxy-naphthalen-1-ylmethyl)-2-oxo-2,3,4,5-tetrahydro-1H-benzo[b]azepin-3-yl]-2-methylamino-propionamide hydrochloride;

(S)—N—[(S)-1-(2,4-Dimethyl-naphthalen-1-ylmethyl)-2-oxo-2,3,4,5-tetrahydro-1H-benzo[b]azepin-3-yl]-2-methylamino-propionamide hydrochloride;

(S)—N—[(S)-1-(2-Isopropoxy-naphthalen-1-ylmethyl)-2-oxo-2,3,4,5-tetrahydro-1H-benzo[b]azepin-3-yl]-2-methylamino-propionamide hydrochloride;

(S)—N—((S)-1-Anthracen-1-yl methyl-2-oxo-2,3,4,5-tetrahydro-1H-benzo[b]azepin-3-yl)-2-methylamino-propionamide hydrochloride;

(S)—N—[(S)-1-(7-Bromo-naphthalen-1-ylmethyl)-2-oxo-2,3,4,5-tetrahydro-1H-benzo[b]azepin-3-yl]-2-methylamino-propionamide hydrochloride;

(S)—N—[(S)-1-(3-Bromo-naphthalen-1-ylmethyl)-2-oxo-2,3,4,5-tetrahydro-1H-benzo[b]azepin-3-yl]-2-methylamino-propionamide hydrochloride;
(S)—N—[(S)-1-(8-Bromo-naphthalen-1-ylmethyl)-2-oxo-2,3,4,5-tetrahydro-1H-benzo[b]azepin-3-yl]-2-methylamino-propionamide hydrochloride;
(S)—N—[(S)-1-(4-Cyano-naphthalen-1-ylmethyl)-2-oxo-2,3,4,5-tetrahydro-1H-benzo[b]azepin-3-yl]-2-methylamino-propionamide hydrochloride;
(S)-2-Methylamino-N—((S)-1-naphthalen-2-ylmethyl-2-oxo-2,3,4,5-tetrahydro-1H-benzo[b]azepin-3-yl)-propionamide hydrochloride;
(S)—N—[(S)-1-(5-Bromo-naphthalen-1-ylmethyl)-2-oxo-2,3,4,5-tetrahydro-1H-benzo[b]azepin-3-yl]-2-methylamino-propionamide hydrochloride;
(S)—N—[(S)-1-(5-Furan-2-yl-2-methoxy-naphthalen-1-ylmethyl)-2-oxo-2,3,4,5-tetrahydro-1H-benzo[b]azepin-3-yl]-2-methylamino-propionamide or a pharmaceutically acceptable salt thereof;
(S)—N—[(S)-1-(6-Furan-2-yl-2-methoxy-naphthalen-1-ylmethyl)-2-oxo-2,3,4,5-tetrahydro-1H-benzo[b]azepin-3-yl]-2-methylamino-propionamide hydrochloride;
(S)—N—[(S)-1-(5-Furan-3-yl-2-methoxy-naphthalen-1-ylmethyl)-2-oxo-2,3,4,5-tetrahydro-1H-benzo[b]azepin-3-yl]-2-methylamino-propionamide hydrochloride;
(S)—N—[(S)-1-(6-Cyclopropyl-2-methoxy-naphthalen-1-ylmethyl)-2-oxo-2,3,4,5-tetrahydro-1H-benzo[b]azepin-3-yl]-2-methylamino-propionamide hydrochloride;
(S)—N—[(S)-1-(5-Cyclopropyl-naphthalen-1-ylmethyl)-2-oxo-2,3,4,5-tetrahydro-1H-benzo[b]azepin-3-yl]-2-methylamino-propionamide hydrochloride;
(S)—N—[(S)-1-(4-Ben yl-naphthalen-1-ylmethyl)-2-oxo-2,3,4,5-tetrahydro-1H-benzo[b]azepin-3-yl]-2-methylamino-propionamide hydrochloride;
(S)—N—[(S)-1-(3-Cyclopropyl-naphthalen-1-ylmethyl)-2-oxo-2,3,4,5-tetrahydro-1H-benzo[b]azepin-3-yl]-2-methylamino-propionamide hydrochloride;
(S)-2-Methylamino-N—[(S)-2-oxo-1-(4-phenethyl-naphthalen-1-ylmethyl)-2,3,4,5-tetrahydro-1H-benzo[b]azepin-3-yl]-propionamide hydrochloride;
(S)—N—[(S)-1-(6-Benzyl-2-methoxy-naphthalen-1-ylmethyl)-2-oxo-2,3,4,5-tetrahydro-1H-benzo[b]azepin-3-yl]-2-methylamino-propionamide hydrochloride;
(S)—N—[(S)-1-(3-Benzyl-naphthalen-1-ylmethyl)-2-oxo-2,3,4,5-tetrahydro-1H-benzo[b]azepin-3-yl]-2-methylamino-propionamide hydrochloride;
(S)—N—[(S)-1-(5-Benzyl-naphthalen-1-ylmethyl)-2-oxo-2,3,4,5-tetrahydro-1H-benzo[b]azepin-3-yl]-2-methylamino-propionamide hydrochloride;
(S)—N—[(S)-1-(4-Isopropoxymethyl-naphthalen-1-ylmethyl)-2-oxo-2,3,4,5-tetrahydro-1H-benzo[b]azepin-3-yl]-2-methylamino-propionamide hydrochloride;
(S)—N—[(S)-1-(4-Cyclopropyl-naphthalen-1-ylmethyl)-2-oxo-2,3,4,5-tetrahydro-1H-benzo[b]azepin-3-yl]-2-methylamino-propionamide hydrochloride;
(S)-2-Methylamino-N—[(S)-2-oxo-1-(5-piperazin-1-yl-methyl-naphthalen-1-ylmethyl)-2,3,4,5-tetrahydro-1H-benzo[b]azepin-3-yl]-propionamide hydrochloride;
(S)-2-Methylamino-N—[(S)-1-(4-morpholin-4-ylmethyl-naphthalen-1-ylmethyl)-2-oxo-2,3,4,5-tetrahydro-1H-benzo[b]azepin-3-yl]-propionamide hydrochloride;
(S)—N—{(S)-1-[6-(3,5-Dimethyl-isoxazol-4-ylmethyl)-2-methoxy-naphthalen-1-ylmethyl]-2-oxo-2,3,4,5-tetrahydro-1H-benzo[b]azepin-3-yl}-2-methylamino-propionamide hydrochloride;
(S)-2-Methylamino-N—[(S)-2-oxo-1-(4-piperidin-1-yl-methyl-naphthalen-1-ylmethyl)-2,3,4,5-tetrahydro-1H-benzo[b]azepin-3-yl]-propionamide hydrochloride;
(S)—N—[(S)-1-(2-Methoxy-6-piperazin-1-ylmethyl-naphthalen-1-ylmethyl)-2-oxo-2,3,4,5-tetrahydro-1H-benzo[b]azepin-3-yl]-2-methylamino-propionamide hydrochloride;
(S)-2-Methylamino-N—[(S)-2-oxo-1-(4-piperazin-1-yl-methyl-naphthalen-1-ylmethyl)-2,3,4,5-tetrahydro-1H-benzo[b]azepin-3-yl]-propionamide hydrochloride;
(S)—N—[(S)-1-(8-Cyclopropyl-naphthalen-1-ylmethyl)-2-oxo-2,3,4,5-tetrahydro-1H-benzo[b]azepin-3-yl]-2-methylamino-propionamide hydrochloride;
(S)—N—[(S)-1-(2-Methoxy-6-phenyl-naphthalen-1-ylmethyl)-2-oxo-2,3,4,5-tetrahydro-1H-benzo[b]azepin-3-yl]-2-methylamino-propionamide hydrochloride;
6-Methoxy-5-[(S)-3-((S)-2-methylamino-propionylamino)-2-oxo-2,3,4,5-tetrahydro-benzo[b]azepin-1-ylmethyl]-naphthalene-2-carboxylic acid methyl ester hydrochloride;
6-Methoxy-5-[(S)-3-((S)-2-methylamino-propionylamino)-2-oxo-2,3,4,5-tetrahydro-benzo[b]azepin-1-ylmethyl]-naphthalene-2-carboxylic acid or a pharmaceutically acceptable salt thereof;
(S)—N—[(S)-1-(6-Methanesulfonylaminocarbonyl-2-methoxy-naphthalen-1-ylmethyl)-2-oxo-2,3,4,5-tetrahydro-1H-benzo[b]azepin-3-yl]-2-methylamino-propionamide or a pharmaceutically acceptable salt thereof;
(S)—N—{(S)-1-[2-Methoxy-5-(propane-1-sulfonylaminocarbonyl)-naphthalen-1-ylmethyl]-2-oxo-2,3,4,5-tetrahydro-1H-benzo[b]azepin-3-yl}-2-methylamino-propionamide hydrochloride;
(S)—N—[(S)-1-(5-Methanesulfonylaminocarbonyl-2-methoxy-naphthalen-1-ylmethyl)-2-oxo-2,3,4,5-tetrahydro-1H-benzo[b]azepin-3-yl]-2-methylamino-propionamide hydrochloride;
(S)—N—{(S)-1-[2-Methoxy-6-(propane-1-sulfonylaminocarbonyl)-naphthalen-1-ylmethyl]-2-oxo-2,3,4,5-tetrahydro-1H-benzo[b]azepin-3-yl}-2-methylamino-propionamide hydrochloride;
6-Methoxy-5-[(S)-3-((S)-2-methylamino-propionylamino)-2-oxo-2,3,4,5-tetrahydro-benzo[b]azepin-1-ylmethyl]-naphthalene-1-carboxylic acid methyl ester hydrochloride;
5-[(S)-3-((S)-2-Methylami no-propionylamino)-2-oxo-2,3,4,5-tetrahydro-benzo[b]azepin-1-ylmethyl]-naphthalene-1-carboxylic acid hydrochloride;
5-[(S)-3-((S)-2-Methylamino-propionylamino)-2-oxo-2,3,4,5-tetrahydro-benzo[b]azepin-1-ylmethyl]-naphthalene-1-carboxylic acid methyl ester hydrochloride;
7-Methoxy-8-[(S)-3-((S)-2-methylamino-propionylamino)-2-oxo-2,3,4,5-tetrahydro-benzo[b]azepin-1-ylmethyl]-naphthalene-2-carboxylic acid methyl ester hydrochloride;
(S)—N—[(S)-1-(5-Cyano-2-methoxy-naphthalen-1-ylmethyl)-2-oxo-2,3,4,5-tetrahydro-1H-benzo[b]azepin-3-yl]-2-methylamino-propionamide hydrochloride;
5-[(S)-3-((S)-2-Methylamino-propionylamino)-2-oxo-2,3,4,5-tetrahydro-benzo[b]azepin-1-ylmethyl]-naphthalene-1-carboxylic acid amide or a pharmaceutically acceptable salt thereof;
6-Methoxy-5-[(S)-3-((S)-2-methylamino-propionylamino)-2-oxo-2,3,4,5-tetrahydro-benzo[b]azepin-1-ylmethyl]-naphthalene-2-carboxylic acid amide hydrochloride;

(S)—N—[(S)-1-(7-Cyano-2-methoxy-naphthalen-1-ylm-ethyl)-2-oxo-2,3,4,5-tetrahydro-1H-benzo[b]azepin-3-yl]-2-methylamino-propionamide hydrochloride;
(S)—N—[(S)-1-(6-Cyano-2-methoxy-naphthalen-1-ylm-ethyl)-2-oxo-2,3,4,5-tetrahydro-1H-benzo[b]azepin-3-yl]-2-methylamino-propionamide hydrochloride;
(S)—N—[(S)-1-(5-Cyano-naphthalen-1-ylmethyl)-2-oxo-2,3,4,5-tetrahydro-1H-benzo[b]azepin-3-yl]-2-methylamino-propionamide hydrochloride;
(S)—N—[(S)-1-(7-Cyano-naphthalen-1-ylmethyl)-2-oxo-2,3,4,5-tetrahydro-1H-benzo[b]azepin-3-yl]-2-methylamino-propionamide hydrochloride;
8-[(S)-3-((S)-2-Methylamino-propionylamino)-2-oxo-2,3,4,5-tetrahydro-benzo[b]azepin-1-ylmethyl]-naphtha-lene-2-carboxylic acid amide hydrochloride;
(S)—N—[(S)-1-(8-Cyano-naphthalen-1-ylmethyl)-2-oxo-2,3,4,5-tetrahydro-1H-benzo[b]azepin-3-yl]-2-methylamino-propionamide hydrochloride;
(S)—N—((S)-1-((6-Bromo-2-methoxynaphthalen-1-yl)methyl)-2-oxo-2,3,4,5-tetrahydro-1H-(benzo[b]aze-pin-3-yl)-2-(methylamino)butanamide trifluoroacetate;
(S)—N—((S)-1-((6-Bromo-2-methoxynaphthalen-1-yl)methyl)-2-oxo-2,3,4,5-tetrahydro-1H-benzo[b]azepin-3-yl)-2-(propylamino)propanamide or a pharmaceuti-cally acceptable salt thereof;
(S)—N—[(S)-1-((6-Bromo-2-methoxynaphthalen-1-yl)methyl)-2-oxo-2,3,4,5-tetrahydro-1H-benzo[b]azepin-3-yl)-2-(isobutylamino)propanamide or a pharmaceuti-cally acceptable salt thereof;
(S)—N—((S)-1-((6-Bromo-2-methoxynaphthalen-1-yl)methyl)-2-oxo-2,3,4,5-tetrahydro-1H-benzo[b]azepin-3-yl)-2-(ethylamino)propanamide hydrochloride;
(S)-2-(Azetidin-3-ylamino)-N—((S)-1-((6-bromo-2-methoxynaphthalen-1-yl)methyl)-2-oxo-2,3,4,5-tetra-hydro-1H-benzo[b]azepin-3-yl)propanamide dihydro-chloride;
(S)—N—((S)-1-((6-Bromo-2-methoxynaphthalen-1-yl)methyl)-2-oxo-2,3,4,5-tetrahydro-1H-benzo[b]azepin-3-yl)-2-(ethylamino)butanamide hydrochloride;
(S)—N—((S)-1-((5-Fluoro-2-methoxynaphthalen-1-yl)methyl)-2-oxo-2,3,4,5-tetrahydro-1H-benzo[b]azepin-3-yl)-2-(methylamino)propanamide hydrochloride;
(S)—N—((S)-1-((6-Fluoro-2-methoxynaphthalen-1-yl)methyl)-2-oxo-2,3,4,5-tetrahydro-1H-benzo[b]azepin-3-yl)-2-(methylamino)propanamide hydrochloride;
(S)—N—((S)-1-((6-Chloro-2-methoxynaphthalen-1-yl)methyl)-2-oxo-2,3,4,5-tetrahydro-1H-benzo[b]azepin-3-yl)-2-(methylamino)propanamide hydrochloride;
(S)—N—((S)-1-((6-Bromo-2-methoxynaphthalen-1-yl)methyl)-2-oxo-2,3,4,5-tetrahydro-1H-benzo[b]azepin-3-yl)-2-(cyclopropylmethylamino)propanamide or a pharmaceutically acceptable salt thereof;
(S)-2-Methylamino-N—{(S)-2-oxo-1-[5-(1H-tetrazol-5-yl)-naphthalen-1-ylmethyl]-2,3,4,5-tetrahydro-1H-benzo[b]azepin-3-yl})-propionamide hydrochloride; and
(S)—N—((S)-1-((5-Acetyl-2-methoxynaphthalen-1-yl)methyl)-2-oxo-2,3,4,5-tetrahydro-1H-benzo[b]azepin-3-yl)-2-(methylamino)propanamide hydrochloride.

36. The compound of claim 1 wherein Z is phenyl, said compound being selected from the group consisting of:
(S)—N—[(S)-1-(5-Fluoro-2-methoxy-benzyl)-2-oxo-2,3,4,5-tetrahydro-1H-benzo[b]azepin-3-yl]-2-methyl-amino-propionamide hydrochloride;
(S)—N—[(S)-1-(2-Methoxy-5-trifluoromethyl-benzyl)-2-oxo-2,3,4, 5-tetrahydro-1H-benzo[b]azepin-3-yl]-2-methylamino-propionamide hydrochloride;
(S)—N—[(S)-1-(4,5-Difluoro-2-methoxy-benzyl)-2-oxo-2,3,4,5-tetrahydro-1H-benzo[b]azepin-3-yl]-2-methylamino-propionamide hydrochloride;
(S)—N—[(S)-1-(5-Bromo-2-methoxy-benzyl)-2-oxo-2,3,4,5-tetrahydro-1H-benzo[b]azepin-3-yl]-2-methyl-amino-propionamide hydrochloride;
(S)—N—[(S)-1-(5-Chloro-2-methoxy-benzyl)-2-oxo-2,3,4,5-tetrahydro-1H-benzo[b]azepin-3-yl]-2-methyl-amino-propionamide hydrochloride;
(S)—N—[(S)-1-(2,5-Difluoro-benzyl)-2-oxo-2,3,4,5-tet-rahydro-1H-benzo[b]azepin-3-yl]-2-methylamino-pro-pionamide hydrochloride;
(S)-2-Methylamino-N—((S)-2-oxo-1-pentafluorophenyl-methyl-2,3,4,5-tetrahydro-1H-benzo[b]azepin-3-yl)-propionamide hydrochloride;
(S)—N—[(S)-1-(4-Chloro-2-methoxy-benzyl)-2-oxo-2,3,4,5-tetrahydro-1H-benzo[b]azepin-3-yl]-2-methyl-amino-propionamide hydrochloride;
(S)—N—[(S)-1-(4-Bromo-2-methoxy-benzyl)-2-oxo-2,3,4,5-tetrahydro-1H-benzo[b]azepin-3-yl]-2-methyl-amino-propionamide hydrochloride;
(S)—N—[(S)-1-(2,5-Dichloro-benzyl)-2-oxo-2,3,4,5-tet-rahydro-1H-benzo[b]azepin-3-yl]-2-methylamino-pro-pionamide hydrochloride;
(S)—N—[(S)-1-(5-Chloro-2-fluoro-benzyl)-2-oxo-2,3,4,5-tetrahydro-1H-benzo[b]azepin-3-yl]-2-methyl-amino-propionamide hydrochloride;
(S)—N—[(S)-1-(5-Iodo-2-methoxy-benzyl)-2-oxo-2,3,4,5-tetrahydro-1H-benzo[b]azepin-3-yl]-2-methyl-amino-propionamide hydrochloride;
(S)—N—[(S)-1-(5-Isopropyl-2-methoxy-benzyl)-2-oxo-2,3,4,5-tetrahydro-1H-benzo[b]azepin-3-yl]-2-methyl-amino-propionamide hydrochloride;
(S)—N—((S)-1-Benzyl-8-benzyloxy-2-oxo-2,3,4,5-tet-rahydro-1H-benzo[b]azepin-3-yl)-2-methylamino-pro-pionamide hydrochloride;
(S)—N—((S)-1-Benzyl-2-oxo-8-phenethyloxy-2,3,4,5-tetrahydro-1H-benzo[b]azepin-3-yl)-2-methylamino-propionamide hydrochloride;
(S)—N—((S)-1-Benzyl-8-methoxy-2-oxo-2,3,4,5-tetra-hydro-1H-benzo[b]azepin-3-yl)-2-methylamino-pro-pionamide hydrochloride;
(S)—N—[(S)-1-Benzyl-2-oxo-8-(3-phenyl-propoxy)-2,3,4,5-tetrahydro-1H-benzo[b]azepin-3-yl]-2-methyl-amino-propionamide hydrochloride;
(S)—N-(1-Benzyl-8-bromo-2-oxo-2,3,4,5-tetrahydro-1H-benzo[b]azepin-3-yl)-2-methylamino-propiona-mide hydrochloride;
(S)-2-Methylamino-N—[(S)-2-oxo-1-(2,3,5,6-tetram-ethyl-benzyl)-2,3,4,5-tetrahydro-1H-benzo[b]azepin-3-yl]-propionamide hydrochloride;
(S)—N—[(S)-1-(2,3-Dimethyl-benzyl)-2-oxo-2,3,4,5-tetrahydro-1H-benzo[b]azepin-3-yl]-2-methylamino-propionamide hydrochloride;
(S)—N—[(S)-1-(2-Chloro-benzyl)-2-oxo-2,3,4,5-tetra-hydro-1H-benzo[b]azepin-3-yl]-2-methylamino-pro-pionamide hydrochloride;
(S)—N—[(S)-1-(2,6-Dimethyl-benzyl)-2-oxo-2,3,4,5-tetrahydro-1H-benzo[b]azepin-3-yl]-2-methylamino-propionamide hydrochloride;
(S)—N—((S)-1-Benzyl-2-oxo-2,3,4,5-tetrahydro-1H-benzo[b]azepin-3-yl)-2-methylamino-propionamide hydrochloride;
(S)—N—[(S)-1-(2,4-Dimethyl-benzyl)-2-oxo-2,3,4,5-tetrahydro-1H-benzo[b]azepin-3-yl]-2-methylamino-propionamide hydrochloride;

(S)-2-Methylamino-N—[(S)-1-(2-methyl-benzyl)-2-oxo-2,3,4,5-tetrahydro-1H-benzo[b]azepin-3-yl]-propionamide hydrochloride;
(S)—N-(1-Biphenyl-2-ylmethyl-2-oxo-2,3,4,5-tetrahydro-1H-benzo[b]azepin-3-yl)-2-methylamino-propionamide hydrochloride;
(S)—N-(1-Biphenyl-3-ylmethyl-2-oxo-2,3,4,5-tetrahydro-1H-benzo[b]azepin-3-yl)-2-methylamino-propionamide hydrochloride;
(S)-2-Methylamino-N-[1-(6-methyl-biphenyl-3-ylmethyl)-2-oxo-2,3,4,5-tetrahydro-1H-benzo[b]azepin-3-yl]-propionamide hydrochloride;
(S)—N-(1-Benzyl-2-oxo-2,3,4,5-tetrahydro-1H-benzo[b]azepin-3-yl)-2-methylamino-propionamide hydrochloride; and
(S)—N-(1-Biphenyl-4-ylmethyl-2-oxo-2,3,4,5-tetrahydro-1H-benzo[b]azepin-3-yl)-2-methylamino-propionamide hydrochloride.

37. The compound of claim 1 wherein Z is aryl fused with cycloalkyl, said compound being:
(S)—N—[(S)-1-(2-Methoxy-5,6,7,8-tetrahydro-naphthalen-1 ylmethyl)-2-oxo-2,3,4,5-tetrahydro-1H-benzo[b]azepin-3-yl]-2-methylamino-propionamide hydrochloride.

38. The compound of claim 1 wherein Z is heteroaryl, said compound being selected from the group consisting of:
(S)-2-Methylamino-N—[(S)-1-(1-methyl-1H-indazol-3-ylmethyl)-2-oxo-2,3,4,5-tetrahydro-1H-benzo[b]azepin-3-yl]-propionamide hydrochloride;
(S)—N—((S)-1-Benzo[d]isoxazol-3-ylmethyl-2-oxo-2,3,4,5-tetrahydro-1H-benzo[b]azepin-3-yl)-2-methylamino-propionamide hydrochloride;
(S)-2-(Methylamino)-N—((S)-2-oxo-1-(thiophen-2-ylmethyl)-2,3,4,5-tetrahydro-1H-benzo[b]azepin-3-yl)propanamide hydrochloride;
(S)-2-Methylamino-N—((S)-2-oxo-1-thiophen-3-ylmethyl-2,3,4,5-tetrahydro-1H-benzo[b]azepin-3-yl)-propionamide hydrochloride;
(S)-2-Methylamino-N—((S)-2-oxo-1-thiazol-5-ylmethyl-2,3,4,5-tetrahydro-1H-benzo[b]azepin-3-yl)-propionamide hydrochloride;
(S)-2-Methylamino-N—((S)-2-oxo-1-thiazol-2-ylmethyl-2,3,4,5-tetrahydro-1H-benzo[b]azepin-3-yl)-propionamide hydrochloride;
(S)-2-Methylamino-N—((S)-1-oxazol-5-ylmethyl-2-oxo-2,3,4,5-tetrahydro-1H-benzo[b]azepin-3-yl)-propionamide hydrochloride;
(S)-2-Methylamino-N—((S)-2-oxo-1-pyridin-3-ylmethyl-2,3,4,5-tetrahydro-1H-benzo[b]azepin-3-yl)-propionamide hydrochloride;
(S)-2-Methylamino-N—((S)-2-oxo-1-pyridin-2-ylmethyl-2,3,4,5-tetrahydro-1H-benzo[b]azepin-3-yl)-propionamide hydrochloride;
(S)-2-Methylamino-N—((S)-2-oxo-1-pyridin-4-ylmethyl-2,3,4,5-tetrahydro-1H-benzo[b]azepin-3-yl)-propionamide hydrochloride;
(S)-2-Methylamino-N—[(S)-1-(3-methyl-3H-imidazol-4-ylmethyl)-2-oxo-2,3,4,5-tetrahydro-1H-benzo[b]azepin-3-yl]-propionamide hydrochloride;
(S)-2-Amino-N—((S)-1-((3-methoxyquinolin-4-yl)methyl)-2-oxo-2,3,4,5-tetrahydro-1H-benzo[b]azepin-3-yl)butanamide or a pharmaceutically acceptable salt thereof;
(S)-2-(2-Hydroxyethylamino)-N—((S)-1-((3-methoxyquinolin-4yl)methyl)-2-oxo-2,3,4,5-tetrahydro-1H-benzo[b]azepin-3-yl)butanamide or a pharmaceutically acceptable salt thereof;
(S)—N—[(S)-1-(5-Bromo-benzo[b]thiophen-3-ylmethyl)-2-oxo-2,3,4,5-tetrahydro-1H-benzo[b]azepin-3-yl]-2-methylamino-propionamide hydrochloride;
(S)—N—((S)-1-Benzo[b]thiophen-3-ylmethyl-2-oxo-2,3,4,5-tetrahydro-1H-benzo[b]azepin-3-yl)-2-methylamino-propionamide or a pharmaceutically acceptable salt thereof;
(S)-2-Methylamino-N—((S)-2-oxo-1-quinolin-4-ylmethyl-2,3,4,5-tetrahydro-1H-benzo[b]azepin-3-yl)-propionamide hydrochloride;
(S)-2-Methylamino-N—((S)-2-oxo-1-quinolin-5-ylmethyl-2,3,4,5-tetrahydro-1H-benzo[b]azepin-3-yl)-propionamide hydrochloride;
(S)—N—[(S)-1-(3-Ethynyl-quinolin-4-ylmethyl)-2-oxo-2,3,4,5-tetrahydro-1H-benzo[b]azepin-3-yl]-2-methylamino-propionamide hydrochloride;
(S)—N—[(S)-1-(3-Methoxy-[1,8]naphthyridin-4-ylmethyl)-2-oxo-2,3,4,5-tetrahydro-1H-benzo[b]azepin-3-yl]-2-methylamino-propionamide hydrochloride;
(S)—N—[(S)-1-(2-Chloro-3-methyl-quinolin-4-ylmethyl)-2-oxo-2,3,4,5-tetrahydro-1H-benzo[b]azepin-3-yl]-2-methylamino-propionamide hydrochloride;
(S)-2-Methylamino-N—[(S)-1-(3-methyl-quinolin-4-ylmethyl)-2-oxo-2,3,4,5-tetrahydro-1H-benzo[b]azepin-3-yl]-propionamide hydrochloride;
(S)—N—[(S)-1-(3-Chloro-[1,8]naphthyridin-4-ylmethyl)-2-oxo-2,3,4,5-tetrahydro-1H-benzo[b]azepin-3-yl]-2-methylamino-propionamide hydrochloride;
(S)-2-Methylamino-N—{(S)-2-oxo-1-[3-(2,2,2-trifluoroethoxy)-quinolin-4-ylmethyl]-2,3,4,5-tetrahydro-1H-benzo[b]azepin-3-yl}-propionamide hydrochloride;
(S)-2-Methylamino-N—[(S)-1-(3-methyl-isoquinolin-4-ylmethyl)-2-oxo-2,3,4,5-tetrahydro-1H-benzo[b]azepin-3-yl]-propionamide hydrochloride;
(S)—N—((S)-1-Isoquinolin-4-ylmethyl-2-oxo-2,3,4,5-tetrahydro-1H-benzo[b]azepin-3-yl)-2-methylamino-propionamide hydrochloride;
(S)—N—((S)-1-quinolin-4-ylmethyl-2-oxo-2,3,4,5-tetrahydro-1H-benzo[b]azepin-3-yl)-2-methylamino-propionamide hydrochloride;
(S)-2-Methylamino-N—((S)-1-[1,8]naphthyridin-4-ylmethyl-2-oxo-2,3,4,5-tetrahydro-1H-benzo[b]azepin-3-yl)-propionamide hydrochloride;
(S)—N—[(S)-1-(3-Methoxy-quinolin-4-ylmethyl)-2-oxo-2,3,4,5-tetrahydro-1H-benzo[b]azepin-3-yl]-2-methylamino-propionamide hydrochloride;
(S)—N—((S)-1-Benzo[b]thiophen-7-ylmethyl-2-oxo-2,3,4,5-tetrahydro-1H-benzo[b]azepin-3-yl)-2-methylamino-propionamide hydrochloride;
(S)-2-Methylamino-N—[(S)-2-oxo-1-(1-oxy-quinolin-4-ylmethyl)-2,3,4,5-tetrahydro-1H-benzo[b]azepin-3-yl]-propionamide hydrochloride;
(S)-2-Methylamino-N-[2-oxo-1-(3-phenyl-isoxazol-5-ylmethyl)-2,3,4,5-tetrahydro-1H-benzo[b]azepin-3-yl]-propionamide hydrochloride;
(S)—N—((S)-1-((3-Cyclopropylquinolin-4-yl)methyl)-2-oxo-2,3,4,5-tetrahydro-1H-benzo[b]azepin-3-yl)-2-(methylamino)propanamide dihydrochioride; and
(S)—N—((S)-1-((2,6-Bis(trifluoromethyl)quinolin-4-yl)methyl)-2-oxo-2,3,4,5-tetrahydro-1H-benzo[b]azepin-3-yl)-2-(methylamino)propanamide hydrochloride.

39. A compound selected from the group consisting of:
(S)—N—[(S)-1-(6-Bromo-2-methoxy-naphthalen-1-ylmethyl)-2-oxo-2,3,4,5-tetrahydro-1H-benzo[b]azepin-3-yl]-2-methylamino-propionamide hydrochloride;

(S)—N—[(S)-1-(2-Ethoxy-naphthalen-1-ylmethyl)-2-oxo-2,3,4,5-tetrahydro-1H-benzo[b]azepin-3-yl]-2-methylamino-propionamide hydrochloride;

(S)—N—[(S)-1-(5-Bromo-2-methoxy-naphthalen-1-ylmethyl)-2-oxo-2,3,4,5-tetrahydro-1H-benzo[b]azepin-3-yl]-2-methylamino-propionamide hydrochloride;

(S)—N—[(S)-1-(5-Cyano-2-methoxy-naphthalen-1-ylmethyl)-2-oxo-2,3,4,5-tetrahydro-1H-benzo[b]azepin-3-yl]-2-methylamino-propionamide hydrochloride;

(S)-2-Methylamino-N—{(S)-2-oxo-1-[2-(2,2,2-trifluoro-ethoxy)-naphthalen-1-ylmethyl]-2,3,4,5-tetrahydro-1H-benzo[b]azepin-3-yl}-propionamide hydrochloride;

(S)—N—[(S)-1-(2-Methoxy-6-trifluoromethyl-naphthalen-1-ylmethyl)-2-oxo-2,3,4,5-tetrahydro-1H-benzo[b]azepin-3-yl]-2-methylamino-propionamide hydrochloride;

(S)—N—[(S)-1-(2-Chloro-naphthalen-1-ylethyl)-2-oxo-2,3,4,5-tetrahydro-1H-benzo[b]azepin-3-yl]-2-methylamino-propionamide hydrochloride;

(S)—N—((S)-1-((5-Fluoro-2-methoxynaphthalen-1-yl)methyl)-2-oxo-2,3,4,5-tetrahydro-1H-benzo[b]azepin-3-yl)-2-(methylamino)propanamide or a pharmaceutically acceptable salt thereof;

(S)—N—((S)-1-((6-Fluoro-2-methoxynaphthalen-1-yl)methyl)-2-oxo-2,3,4,5-tetrahydro-1H-benzo[b]azepin-3-yl)-2-(methylamino)propanamide or a pharmaceutically acceptable salt thereof; and (S)—N—((S)-1-(((6-Chloro-2-methoxynaphthalen-1-yl)methyl)-2-oxo-2,3,4,5-tetrahydro-1H-benzo[b]azepin-3-yl)-2-(methylamino)propanamide hydrochloride.

40. A compound selected from the group consisting of:

(S)-2-Methylamino-N—((S)-2-oxo-1-quinolin-4-ylmethyl-2,3,4,5-tetrahydro-1H-benzo[b]azepin-3-yl)-propionamide hydrochloride;

(S)-2-Methylamino-N—((S)-2-oxo-1-quinolin-5-ylmethyl-2,3,4,5-tetrahydro-1H-benzo[b]azepin-3-yl)-propionamide hydrochloride;

(S)—N—[(S)-1-(3-Methoxy-quinolin-4-ylmethyl)-2-oxo-2,3,4,5-tetrahydro-1H-benzo[b]azepin-3-yl]-2-methylamino-propionamide hydrochloride;

(S)—N—((S)-1-Isoquinolin-4-ylmethyl-2-oxo-2,3,4,5-tetrahydro-1H-benzo[b]azepin-3-yl)-2-methylamino-propionamide hydrochloride;

(S)-2-Methylamino-N—{(S)-2-oxo-1-[3-(2,2,2-trifluoro-ethoxy)-quinolin-4-ylmethyl]-2,3,4,5-tetrahydro-1H-benzo[b]azepin-3-yl}-propionamide hydrochloride;

(S)-2-Methylamino-N—[(S)-1-(3-methyl-quinolin-4-ylmethyl)-2-oxo-2,3,4,5-tetrahydro-1H-benzo[b]azepin-3-yl]-propionamide hydrochloride;

(S)—N—[(S)-1-(3-Ethynyl-quinolin-4-ylmethyl)-2-oxo-2,3,4,5-tetrahydro-1H-benzo[b]azepin-3-yl]-2-methylamino-propionamide hydrochloride;

(S)-2-Methylamino-N—[(S)-1-(3-methyl-isoquinolin-4-ylmethyl)-2-oxo-2,3,4,5-tetrahydro-1H-benzo[b]azepin-3-yl]-propionamide hydrochloride;

(S)—N—[(S)-1-(2-Chloro-3-methyl-quinolin-4-ylmethyl)-2-oxo-2,3,4,5-tetrahydro-1H-benzo[b]azepin-3-yl]-2-methylamino-propionamide hydrochloride; and (S)—N—((S)-1-((3-Cyclopropylquinolin-4-yl)methyl)-2-oxo-2,3,4,5-tetrahydro-1H-benzo[b]azepin-3-yl)-2-(methylamino)propanamide dihydrochioride.

41. A compound selected from the group consisting of:

(S)-2-Methylamino-N—[(S)-1-(1-methyl-1H-indazol-3-ylmethyl)-2-oxo-2,3,4,5-tetrahydro-1H-benzo[b]azepin-3-yl]-propionamide hydrochloride;

(S)—N—((S)-1-Cinnolin-4-ylmethyl-2-oxo-2,3,4,5-tetrahydro-H-benzo[b]azepin-3-yl)-2-methylamino-propionamide hydrochloride;

(S)-2-Methylamino-N—((S)-1-[1,8]naphthyridin-4-ylmethyl-2-oxo-2,3,4,5-tetrahydro-1H-benzo[b]azepin-3-yl)-propionamide hydrochloride;

(S)—N—[(S)-1-(3-Methoxy-[1,8]naphthyridin-4-ylmethyl)-2-oxo-2,3,4,5-tetrahydro-1H-benzo[b]azepin-3-yl]-2-methylamino-propionamide hydrochloride;

(S)—N—[(S)-1-(3-Chloro-[1,8]naphthyridin-4-ylmethyl)-2-oxo-2,3,4,5-tetrahydro-1H-benzo[b]azepin-3-yl]-2-methylamino-propionamide hydrochloride;

(S)—N—((S)-1-Benzo[d]isoxazol-3-ylmethyl-2-oxo-2,3,4,5-tetrahydro-1H-benzo[b]azepin-3-yl)-2-methylamino-propionamide hydrochloride; and (S)—N—((S)-1-Benzo[b]thiophen-3-ylmethyl-2-oxo-2,3,4,5-tetrahydro-1H-benzo[b]azepin-3-yl)-2-methylamino-propionamide.

42. A pharmaceutical composition comprising the compounds according to claim 1, or a pharmaceutically acceptable salt thereof, as an active ingredient together with a pharmaceutically acceptable carrier or excipient.

* * * * *

SEQUENCE LISTING

```
<160> NUMBER OF SEQ ID NOS: 5

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term Epsilon-biotin-OH

<400> SEQUENCE: 1

Ala Val Pro Ile Ala Gln Lys Ser Glu Lys
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 2

His His His His His His
1               5

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Val Pro Ile Ala Gln Lys Ser Glu Lys
1               5                   10

<210> SEQ ID NO 4
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 4

Met Arg His His His His His Arg Asp His Phe Ala Leu Asp Arg
1               5                   10                  15

Pro Ser Glu Thr His Ala Asp Tyr Leu Leu Arg Thr Gly Gln Val Val
            20                  25                  30

Asp Ile Ser Asp Thr Ile Tyr Pro Arg Asn Pro Ala Met Tyr Ser Glu
        35                  40                  45

Glu Ala Arg Leu Lys Ser Phe Gln Asn Trp Pro Asp Tyr Ala His Leu
    50                  55                  60

Thr Pro Arg Glu Leu Ala Ser Ala Gly Leu Tyr Tyr Thr Gly Ile Gly
65                  70                  75                  80

Asp Gln Val Gln Cys Phe Ala Cys Gly Gly Lys Leu Lys Asn Trp Glu
                85                  90                  95

Pro Gly Asp Arg Ala Trp Ser Glu His Arg Arg His Phe Pro Asn Cys
            100                 105                 110

Phe Phe Val Leu Gly Arg Asn Leu Asn Ile Arg Ser Glu
        115                 120                 125

<210> SEQ ID NO 5
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Arg His His His His His Arg Ser Asp Ala Val Ser Ser Asp
1               5                   10                  15

Arg Asn Phe Pro Asn Ser Thr Asn Leu Pro Arg Asn Pro Ser Met Ala
            20                  25                  30

Asp Tyr Glu Ala Arg Ile Phe Thr Phe Gly Thr Trp Ile Tyr Ser Val
        35                  40                  45

Asn Lys Glu Gln Leu Ala Arg Ala Gly Phe Tyr Ala Leu Gly Glu Gly
    50                  55                  60

Asp Lys Val Lys Cys Phe His Cys Gly Gly Gly Leu Thr Asp Trp Lys
65                  70                  75                  80

Pro Ser Glu Asp Pro Trp Glu Gln His Ala Lys Trp Tyr Pro Gly Cys
                85                  90                  95

Lys Tyr Leu Leu Glu Gln Lys Gly Gln Glu Tyr Ile Asn Asn Ile His
            100                 105                 110

Leu Thr His Ser Leu Glu Glu Cys Leu Val Arg Thr Thr
        115                 120                 125
```